US011767355B2

(12) United States Patent
Seidel, III et al.

(10) Patent No.: US 11,767,355 B2
(45) Date of Patent: *Sep. 26, 2023

(54) METHODS FOR MODULATING AN IMMUNE RESPONSE

(71) Applicant: Cue Biopharma, Inc., Boston, MA (US)

(72) Inventors: Ronald D. Seidel, III, Cambridge, MA (US); Rodolfo J. Chaparro, Cambridge, MA (US)

(73) Assignee: Cue Biopharma, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/961,001

(22) Filed: Oct. 6, 2022

(65) Prior Publication Data

US 2023/0109980 A1 Apr. 13, 2023

Related U.S. Application Data

(63) Continuation of application No. 16/830,831, filed on Mar. 26, 2020, now Pat. No. 11,479,595, which is a continuation of application No. 16/489,586, filed as application No. PCT/US2018/022492 on Mar. 14, 2018, now abandoned.

(60) Provisional application No. 62/521,009, filed on Jun. 16, 2017, provisional application No. 62/471,832, filed on Mar. 15, 2017.

(51) Int. Cl.
| | |
|---|---|
| *A61K 47/68* | (2017.01) |
| *A61P 37/06* | (2006.01) |
| *C07K 14/55* | (2006.01) |
| *C07K 14/79* | (2006.01) |
| *C12N 15/62* | (2006.01) |
| *A61P 35/00* | (2006.01) |
| *C07K 14/74* | (2006.01) |
| *A61K 47/64* | (2017.01) |
| *A61K 9/00* | (2006.01) |
| *C07K 16/28* | (2006.01) |

(52) U.S. Cl.
CPC ...... *C07K 14/70539* (2013.01); *A61K 9/0019* (2013.01); *A61K 47/644* (2017.08); *A61K 47/68* (2017.08); *A61P 37/06* (2018.01); *C07K 14/55* (2013.01); *C07K 14/79* (2013.01); *C07K 16/2818* (2013.01); *C07K 16/2827* (2013.01); *C12N 15/62* (2013.01)

(58) Field of Classification Search
CPC .. C07K 14/70539; C07K 14/55; C07K 14/79; C07K 16/2827; A61K 9/0019; A61K 47/68; A61P 37/06; C12N 15/62
USPC ..................................................... 424/185.1
See application file for complete search history.

(56) References Cited

U.S. PATENT DOCUMENTS

| | | |
|---|---|---|
| 5,635,363 A | 6/1997 | Altman et al. |
| 6,197,302 B1 | 3/2001 | Hirsch et al. |
| 6,211,342 B1 | 4/2001 | Hirsch et al. |
| 6,268,411 B1 | 7/2001 | Schneck et al. |
| 6,322,789 B1 | 11/2001 | Vitiello et al. |
| 6,696,304 B1 | 2/2004 | Parker |
| 7,098,306 B2 | 8/2006 | Economou et al. |
| 7,186,804 B2 | 3/2007 | Gillies et al. |
| 7,432,351 B1 | 10/2008 | Chen |
| 7,670,595 B2 | 3/2010 | Gillies et al. |
| 8,992,937 B2 | 3/2015 | Hansen et al. |
| 9,284,349 B2 | 3/2016 | Tsunoda et al. |
| 9,359,424 B2 | 6/2016 | Maoult et al. |
| 9,494,588 B2 | 11/2016 | Springer et al. |
| 10,272,042 B2 | 4/2019 | Daftarian et al. |
| 10,501,521 B2 | 12/2019 | Georges et al. |
| 10,927,158 B2 | 2/2021 | Seidel, III et al. |
| 10,927,161 B2 | 2/2021 | Seidel, III et al. |
| 11,104,712 B2 | 8/2021 | Seidel, III et al. |
| 11,117,945 B2 | 9/2021 | Seidel, III et al. |
| 11,370,821 B2 | 6/2022 | Seidel et al. |
| 11,377,478 B2 | 7/2022 | Seidel, III et al. |
| 11,380,821 B2 | 7/2022 | Jia et al. |
| 11,401,314 B2 | 8/2022 | Seidel, III et al. |
| 11,479,595 B2 | 10/2022 | Seidel et al. |
| 2002/0006664 A1 | 1/2002 | Sabatini |
| 2002/0031520 A1 | 3/2002 | Economou et al. |
| 2004/0038349 A1 | 2/2004 | Hilbert et al. |
| 2004/0132977 A1 | 7/2004 | Gantier et al. |

(Continued)

FOREIGN PATENT DOCUMENTS

| | | |
|---|---|---|
| CN | 1791675 | 6/2006 |
| CN | 101384621 | 3/2009 |

(Continued)

OTHER PUBLICATIONS

Stauber et al.; "Crystal structure of the IL-2 signaling complex: Paradigm for a heterotrimeric cytokine receptor"; Proc. Natl. Acad. Sci.; vol. 103, No. 8, pp. 2788-2793 (Feb. 21, 2006).

Bresson, et al; "Anti-CD3 and nasal proinsulin combination therapy enhances remission from recent-onset autoimmune diabetes by inducing Tregs"; The Journal of Clinical Investigation; vol. 116, No. 5, pp. 1371-1381 (May 2006).

(Continued)

*Primary Examiner* — Yan Xiao
(74) *Attorney, Agent, or Firm* — Bozicevic, Field & Francis LLP; Paula A. Borden

(57) ABSTRACT

The present disclosure provides methods of modulating an immune response in an individual. The present disclosure provides methods of treatment. The present disclosure provides methods comprising administering a multimeric polypeptide (synTac) and an immune checkpoint inhibitor to an individual. The present disclosure provides methods comprising administering a multimeric polypeptide (synTac) to an individual who is undergoing treatment with immune checkpoint inhibitor.

28 Claims, 97 Drawing Sheets

Specification includes a Sequence Listing.

(56) References Cited

U.S. PATENT DOCUMENTS

| | | |
|---|---|---|
| 2004/0161817 A1 | 8/2004 | Benton et al. |
| 2004/0209363 A1 | 10/2004 | Watts et al. |
| 2005/0003431 A1 | 1/2005 | Wucherpfennig et al. |
| 2005/0009012 A1 | 1/2005 | Holzberg et al. |
| 2005/0100926 A1 | 5/2005 | Hedley et al. |
| 2005/0142142 A1 | 6/2005 | Burrows et al. |
| 2006/0034865 A1 | 2/2006 | Hildebrand et al. |
| 2006/0269515 A1 | 11/2006 | Deniz-Mize et al. |
| 2007/0036752 A1 | 2/2007 | Gillies et al. |
| 2007/0148162 A1 | 6/2007 | Bhardwaj et al. |
| 2007/0286843 A1 | 12/2007 | Pfizenmaier et al. |
| 2008/0199485 A1 | 8/2008 | Kundig et al. |
| 2008/0219947 A1 | 9/2008 | Linette et al. |
| 2008/0269070 A1 | 10/2008 | Ramseier et al. |
| 2010/0159594 A1 | 6/2010 | Hansen et al. |
| 2011/0002956 A1 | 1/2011 | Weiner et al. |
| 2011/0268737 A1 | 11/2011 | Favier et al. |
| 2011/0318380 A1 | 12/2011 | Brix et al. |
| 2012/0003220 A1 | 1/2012 | Chen |
| 2012/0121577 A1 | 5/2012 | Weidanz et al. |
| 2012/0177595 A1 | 7/2012 | Wong et al. |
| 2012/0264161 A1 | 10/2012 | Scholler et al. |
| 2013/0017199 A1 | 1/2013 | Langermann |
| 2013/0149305 A1 | 6/2013 | Ostrand-Rosenberg |
| 2014/0046026 A1 | 2/2014 | Garcia et al. |
| 2014/0162293 A1 | 6/2014 | Springer et al. |
| 2014/0242077 A1 | 8/2014 | Choi et al. |
| 2015/0071987 A1 | 3/2015 | Selvaraj |
| 2015/0224186 A1 | 8/2015 | Nakagawa |
| 2015/0232532 A1 | 8/2015 | Ostrand-Rosenberg |
| 2015/0374788 A1 | 12/2015 | Paulsen et al. |
| 2016/0011204 A1 | 1/2016 | Almo et al. |
| 2016/0083477 A1 | 3/2016 | Klein et al. |
| 2016/0090407 A1 | 3/2016 | Hosse et al. |
| 2016/0114019 A1 | 4/2016 | Sumitomo |
| 2016/0152725 A1 | 6/2016 | Cheung et al. |
| 2016/0175397 A1 | 6/2016 | Umana et al. |
| 2016/0304580 A1 | 10/2016 | Ellmark et al. |
| 2016/0362465 A1 | 12/2016 | Nishimura et al. |
| 2017/0044229 A1 | 2/2017 | Garcia et al. |
| 2017/0058015 A1 | 3/2017 | Seidel, III et al. |
| 2017/0334951 A1 | 11/2017 | O'Reilly et al. |
| 2018/0064795 A1 | 3/2018 | Sugiyama |
| 2018/0086832 A1 | 3/2018 | Vogelstein et al. |
| 2018/0127481 A1 | 5/2018 | Santamaria |
| 2018/0208626 A1 | 7/2018 | Scheinberg et al. |
| 2018/0282392 A1 | 10/2018 | Seidel, III et al. |
| 2018/0339030 A1 | 11/2018 | Scheinberg |
| 2019/0046648 A1 | 2/2019 | Seidel, III et al. |
| 2019/0062400 A1 | 2/2019 | Seidel, III et al. |
| 2019/0106476 A1 | 4/2019 | Seidel, III et al. |
| 2019/0119377 A1 | 4/2019 | Spirig et al. |
| 2020/0140519 A1 | 5/2020 | Seidel, III et al. |
| 2020/0172595 A1 | 6/2020 | Seidel, III et al. |
| 2020/0317747 A1 | 10/2020 | Seidel, III et al. |
| 2021/0284712 A1 | 9/2021 | Seidel, III et al. |
| 2022/0017596 A1 | 1/2022 | Cemerski et al. |
| 2022/0017597 A1 | 1/2022 | Seidel, III et al. |
| 2022/0089680 A1 | 3/2022 | Seidel, III et al. |
| 2022/0089681 A1 | 3/2022 | Seidel, III et al. |
| 2022/0105162 A1 | 4/2022 | Seidel, III et al. |
| 2022/0106378 A1 | 4/2022 | Seidel, III et al. |
| 2022/0112252 A1 | 4/2022 | Seidel, III et al. |
| 2022/0119483 A1 | 4/2022 | Seidel, III et al. |
| 2022/0143063 A1 | 5/2022 | Seidel, III et al. |
| 2022/0162314 A1 | 5/2022 | Yeung et al. |
| 2022/0251202 A1 | 8/2022 | Djuretic et al. |

FOREIGN PATENT DOCUMENTS

| | | |
|---|---|---|
| CN | 101418309 | 4/2009 |
| CN | 101448951 | 6/2009 |
| CN | 101688213 | 3/2010 |
| CN | 105121715 | 12/2015 |
| CN | 108431022 | 11/2016 |
| EP | 3596118 | 1/2020 |
| JP | 2000515363 | 11/2000 |
| JP | 2004501364 | 1/2004 |
| JP | 2005506058 | 3/2005 |
| JP | 2007530021 | 11/2007 |
| JP | 2009537175 | 10/2009 |
| JP | 2010524506 | 7/2010 |
| JP | 2012516854 | 7/2012 |
| JP | 2015537043 | 12/2015 |
| WO | WO 1997/028191 | 8/1997 |
| WO | WO 2001/090747 | 11/2001 |
| WO | WO 2002/072631 | 9/2002 |
| WO | WO 2002/087613 | 11/2002 |
| WO | WO 2002/093129 | 11/2002 |
| WO | WO 2002/102299 | 12/2002 |
| WO | WO 2003/048334 | 6/2003 |
| WO | WO 2004/029197 | 4/2004 |
| WO | WO 2004/111190 | 12/2004 |
| WO | WO 2007/136778 | 11/2007 |
| WO | WO 2008/019888 | 2/2008 |
| WO | WO 2008/113970 | 9/2008 |
| WO | WO 2008/116468 | 10/2008 |
| WO | WO 2008/134461 | 11/2008 |
| WO | WO 2010/037395 | 4/2010 |
| WO | WO 2010/085495 | 7/2010 |
| WO | WO 2010/091122 | 8/2010 |
| WO | WO 2011/066342 | 6/2011 |
| WO | WO 2011/066389 | 6/2011 |
| WO | WO 2012/007951 | 1/2012 |
| WO | WO 2012/127464 | 9/2012 |
| WO | WO 2012/175508 | 12/2012 |
| WO | WO 2013/003761 | 1/2013 |
| WO | WO 2013/079174 | 6/2013 |
| WO | WO 2014/083004 | 6/2014 |
| WO | WO 2014/093118 | 6/2014 |
| WO | WO 2014/145806 | 9/2014 |
| WO | WO 2015/007903 | 1/2015 |
| WO | WO 2015/112541 | 7/2015 |
| WO | WO 2015/164815 | 10/2015 |
| WO | WO 2015/195531 | 12/2015 |
| WO | WO 2016/000619 | 1/2016 |
| WO | WO 2016/014428 | 1/2016 |
| WO | WO 2016/025642 | 2/2016 |
| WO | WO 2016/029043 | 2/2016 |
| WO | WO 2016/030350 | 3/2016 |
| WO | WO 2016/141357 | 9/2016 |
| WO | WO 2016/164937 | 10/2016 |
| WO | WO 2016/168771 | 10/2016 |
| WO | WO 2016/198932 | 12/2016 |
| WO | WO 2017/008844 | 1/2017 |
| WO | WO 2017/023779 | 2/2017 |
| WO | WO 2017/059819 | 4/2017 |
| WO | WO 2017/120222 | 7/2017 |
| WO | WO 2017/151818 | 9/2017 |
| WO | WO 2017/151940 | 9/2017 |
| WO | WO 2017/201131 | 11/2017 |
| WO | WO 2017/201210 | 11/2017 |
| WO | WO 2018/119114 | 6/2018 |
| WO | WO 2018/170168 | 9/2018 |
| WO | WO 2019/051126 | 3/2019 |
| WO | WO 2019/051127 | 3/2019 |
| WO | WO 2019/139896 | 7/2019 |
| WO | WO 2020/243315 | 12/2020 |
| WO | WO 2020/247843 | 12/2020 |
| WO | WO 2020/257191 | 12/2020 |
| WO | WO 2021/081239 | 4/2021 |
| WO | WO 2022/087458 | 4/2022 |
| WO | WO 2022/125694 | 6/2022 |
| WO | WO 2022/125711 | 6/2022 |

OTHER PUBLICATIONS

Casares, et al.; "A Peptide-Major Histocompatibility Complex II Chimera Favors Survival of Pancreatic β-Islets Grafted in Type 1 Diabetic Mice"; Transplantation; vol. 85, No. 12, pp. 1717-1725 (Jun. 27, 2008).

Durinovic-Bello, et al.; "DRB1*0401-restricted human T cell clone specific for the major proinsulin73-90 epitope expresses a down-

(56) References Cited

OTHER PUBLICATIONS regulatory T helper 2 phenotype"; PNAS; vol. 103, No. 31, pp. 11683-11688 (Aug. 1, 2006).
Gojanovich, et al.; "The Use of Peptide-Major-Histocompatibility-Complex Multimers in Type 1 Diabetes Mellitus"; Journal of Diabetes Science and Technology; vol. 6, No. 3, pp. 515-524 (May 2012).
Li, et al.; "Suppression of Ongoing T Cell-Mediated Autoimmunity by Peptide-MHC Class II Dimer Vaccination"; The Journal of Immunology; vol. 183, pp. 4809-4816 (Sep. 14, 2009).
Lin, et al.; "Reversal of type 1 diabetes by a new MHC II-peptide chimera: "Single-epitope-mediated suppression" to stabilize a polyclonal autoimmune T-cell process"; Eur. J. Immunol.; vol. 40, pp. 2277-2288 (2010).
Michels, et al.; "Islet-Derived CD4 T Cells Targeting Proinsulin in Human Autoimmune Diabetes"; Diabetes; vol. 66, pp. 722-734 (Mar. 2017).
Preda, et al.; "Soluble, dimeric HLA DR4-peptide chimeras: An approach for detection and immunoregulation of human type-1 diabetes"; Eur. J. Immunol.; vol. 35, pp. 2763-2776 (Aug. 16, 2005).
Sang, et al.; "Long-term silencing of autoimmune diabetes and improved life expectancy by a soluble pHLA-DR4 chimera in a newly-humanized NOD-DR4/B7 mouse"; Human Vaccines & Immunotherapeutics; vol. 10, No. 3, pp. 693-699 (Mar. 2014).
Tan, et al.; "Type 1 diabetes induction in humanized mice"; PNAS; vol. 114, No. 41, pp. 10954-10959 (Oct. 10, 2017).
Woodham, et al.; "In vivo detection of antigen-specific CD8T cells by immuno-positron emission tomography"; Nat Methods.; vol. 17, No. 10, pp. 1025-1032 (Oct. 2020).
Zhang, et al.; "Monoclonal antibody blocking the recognition of an insulin peptide-MHC complex modulates type 1 diabetes"; PNAS; vol. 111, No. 7, pp. 2656-2661 (Feb. 18, 2014).
Accession No. 1 IRL_A chain A Interleukin-2; 1 page (Aug. 25, 1995).
Ackerman, et al.; "Highly Avid Magnetic Bead Capture: An Efficient Selection Method for de novo Protein Engineering Utilizing yeast Surface Display"; Biotechnol. Prog.; vol. 25, No. 3, pp. 774-783 (2009).
Aina, et al.; "Identification of novel targeting peptides for human ovarian cancer cells using 'one-bead one-compound' combinatorial libraries"; Mol. Cancer Ther.; vol. 4, No. 5, 8 pages (May 2005).
Arduin, et al.; "Highly reduced binding to high and low affinity mouse Fc gamma receptors by L234A/L235A and N297A Fc mutations engineered into mouse IgG2a"; Molecular Immunology; vol. 63, pp. 456-463 (Feb. 2015).
Azuma, et al.; "B7-H1 is a ubiquitous antiapoptotic receptor on cancer cells"; Immunobiology; vol. 111, No. 7, pp. 3635-3643 (Apr. 1, 2008).
Baldi, et al.; "Recombinant protein production by large-scale transient gene expression in mammalian cells: state of the art and future perspectives"; Biotechnol. Lett.; vol. 29, pp. 677-684 (2007).
Bowers, et al.; "Coupling mammalian cell surface display with somatic hypermutation for the discovery and maturation of human antibodies"; PNAS; vol. 108, No. 51, pp. 20455-20460 (Dec. 20, 2011).
Brophy, et al.; "A yeast display system for engineering functional peptide-MHC complexes"; Journal of Immunological Methods; vol. 272, pp. 235-246 (2003).
Buonaguro, et al.; "Translating Tumor Antigens into Cancer Vaccines"; Clinical and Vaccine Immunology; vol. 18, No. 1, pp. 23-24 (Jan. 2011).
Büttner; "Cell-based assays for high-throughput screening"; Expert Opin. Drug Discov . . . ; vol. 1, No. 4, pp. 301-306 (Sep. 2006).
Card, et al.; "A soluble single-chain T-cell receptor IL-2 fusion protein retains MHC-restricted peptide specificity and IL-2 bioactivity"; Cancer Immunol Immunother; vol. 53, pp. 345-357 (Nov. 11, 2003).
Cafri, et al.; "Development of novel genetic cancer vaccines based on membrane-attached β2 microglobulin"; Ann. N.Y. Acad. Sci.; vol. 1283, pp. 87-90 (2013).

Carey, et al.; "A soluble divalent class I MHC/IgG1 fusion protein activates $CD8_+$ T cells in vivo"; Clinical Immunology; vol. 116, pp. 65-76 (2005).
Cebecauer, et al.; "Soluble MHC-Peptide Complexes Induce Rapid Death of $CD8_+$ CTL"; The Journal of Immunology; vol. 174, pp. 6809-6819 (2005).
Celis, et al.; "Identification of Potential CTL Epitopes of Tumor-Associated Antigen Mage-1 for Five Common HLA-A Alleles"; Molecular Immunology; vol. 31, No. 18, pp. 1423-1430 (1994).
Center for Disease Control and Prevention; "How Many Cancers are Linked with HPV Each Year?"; 4 pages (2016).
Chames, et al.; "Bispecific antibodies for cancer therapy; The light at the end of the tunnel?" mAbs; vol. 1, No. 6, pp. 539-547 (Nov.-Dec. 2009).
Cheever, et al.; "The Prioritization of Cancer Antigens: A National Cancer Institute Pilot Project for the Acceleration of Translational Research"; Clinical Cancer Research; vol. 15, No. 17, pp. 5324-5337 (Sep. 1, 2009).
Crawford, et al.; "Use of baculovirus MHC/ peptide display libraries to characterize T-cell receptor ligands"; Immunological Reviews; vol. 210, pp. 156-170 (2006).
Crisci, et al.; "Virus-like particles: The new frontier of vaccines for animal viral infections"; Veterinary Immunology and Immunopathology; vol. 148, pp. 211-225 (2012).
Czajkowsky, et al.; "Fc-fusion proteins: new developments and future perspectives"; EMBO Mol. Med.; vol. 4, pp. 1015-1028 (2012).
Das, et al.; "Generation of murine tumor cell lines deficient in MHC molecule surface expression using the CRISPR/Cas9 system"; PLoS One; vol. 12, No. 3, 19 pages (Mar. 16, 2017).
De Charette, et al.; "Turning tumour cells into antigen presenting cells: The next step to improve cancer immunotherapy?"; European Journal of Cancer; vol. 68, pp. 134-147 (Oct. 2016).
Desmond, et al.; "A systematic review of T-cell epitopes in hepatitis B virus: identification, genotypic variation and relevance to antiviral therapeutics"; Antiviral Therapy; vol. 13, pp. 161-175 (2008).
Dimasi, et al.; "The design and characterization of oligospecific antibodies for simultaneous targeting of multiple disease mediators"; Journal of Molecular Biology; 393(3): p. 672-692 (2009).
Doussal, et al.; "Phage display of peptide /major histocompatibility complex"; Journal of Immunological Methods; vol. 241, pp. 147-158 (2000).
Dulberger, et al.; "Human leukocyte antigen F (HLA-F) presents peptides and regulates immunity through interactions with NK-cell receptors"; Immunity; vol. 46, No. 6, pp. 1018-1027 (Jun. 20, 2017).
Emboss Needle; 2 pages (Feb. 10, 2022).
Edwards, et al.; "The Remarkable Flexibility of the Human Antibody Repertoire; Isolation of Over One Thousand Different Antibodies to a Single Protein, BLyS"; J. Mol. Biol.; vol. 334, pp. 103-118 (2003).
Engelhard; "Structure of peptides associated with MHC class I molecules"; Current Opinion in Immunology; vol. 6, pp. 13-23 (1994).
Engler, et al.; "Peptide vaccines against hepatitis B virus: from animal model to human studies"; Molecular Immunology; vol. 38, pp. 457-465 (Dec. 2001).
GenBank:AEV43323.1; "Fc IgG1 heavy chain constant region, partial [*Homo sapiens*]"; 2 pages (Jul. 25, 2016).
GenBank:NP_068693.1; "programmed cell death 1 ligand 1 precursor [*Mus musculus*]"; 3 pages (Jun. 9, 2021).
GenBank:NP_001009066.1; 2 pages (2003).
GenBank:NP_001300958.1; "programmed cell death 1 ligand 1 isoform c precursor [*Homo sapiens*]"; 3 pages (Jun. 9, 2021).
GenCore AEE04235; 4 pages (2005).
Goel, et al.; "Plasticity within the Antigen-Combining Site May Manifest as Molecufar Mimicry in the Humoral Immune Response"; The Journal of Immunology; vol. 173, pp. 7358-7367 (2004).
Gough, et al.; "The HLA Region and Autoimmune Disease: Associations and Mechanisms of Action"; Current Genomics; vol. 8, pp. 453-465 (2007).

(56) References Cited

OTHER PUBLICATIONS

Greten, et al.; "Peptide-β2-microglobulin-MHC fusion molecules bind antigen-specific T cells and can be used for multivalent MHC-Ig complexes"; Journal of Immunological Methods; vol. 271, pp. 125-135 (2002).
Grupp, et al.; "Adoptive Cellular Therapy"; Curr Top Microbiol Immunol.; 344: p. 149-172 (2011).
Guo, et al.; "Different length peptides bind to HLA-Aw68 similarly at their ends but bulge out in the middle"; Nature; vol. 360, pp. 364-366 (Nov. 26, 1992).
Hansen, et al.; "Phage display of peptide/major histocompatibility class I complexes"; Eur. J. Immunol.; vol. 31, pp. 32-38 (2001).
HLA Nomenclature; "HLA Alleles Numbers"; 2 pages (Mar. 17, 2015).
Huang, et al.; "Bone regeneration in a rat cranial defect with delivery of PEI-condensed plasmid DNA encoding for bone morphogenetic protein-4 (BMP-4)"; Gene Therapy; vol. 12, No. 5, p. 418 (2005).
Huang, et al.; "Cancer immunotherapy using a DNA vaccine encoding a single-chain trimer of MHC class I linked to an HPV-16 E6 immunodominant CTL epitope"; Gene Ther.; vol. 12, No. 15, pp. 1180-1186 (Aug. 2005).
Hug, et al.; "T-cadherin is a receptor for hexameric and high-molecular-weight forms of Acrp30/adiponectin"; PNAS; vol. 101, No. 28, pp. 10308-10313 (Jul. 13, 2004).
Hugues, et al.; "Generation and use of alternative multimers of peptide/MHC complexes"; Journal of Immunological Methods; vol. 268, pp. 83-92 (2002).
Judkowski, et al.; "Identification of MHC Class II-Restricted Peptide Ligands, Including a Glutamic Acid Decarboxylase 65 Sequence, that Stimulate Diabetogenic T Cells from Transgenic BDC2.5 Nonobese Diabetic Mice"; The Journal of Immunology; vol. 166, pp. 908-917 (2001).
Karaki, et al.; "Is There Still Room for Cancer Vaccines at the Era of Checkpoint Inhibitors"; Vaccines; vol. 4, No. 37, 24 pages (2016).
Karin, et al.; "Reversal of Experimental Autoimmune Encephalomyelitis by a Soluble Peptide Variant of a Myelin Basic Protein Epitope: T Cell Receptor Antagonism and Reduction of Interferon γ and Tumor Necrosis Factor α Production"; J. Exp. Med.; vol. 180, pp. 2227-2237 (Dec. 1994).
Khan, et al.; "Adjustable Locks and Flexible Keys: Plasticity of Epitope-Paratope Interactions in Germline Antibodies"; The Journal of Immunology; vol. 192, pp. 5398-5405 (2014).
Kim, et al.; "Single chain MHC I trimer-based DNA vaccines for protection against *Listeria monocytogenes* infection"; Vaccine; vol. 30, pp. 2178-2186 (2012).
Krautwurst, et al.; "Identification of Ligands for Olfactory Receptors by Functional Expression of a Receptor Library"; Cell; vol. 95, pp. 917-926 (Dec. 23, 1998).
Kreiter, et al.; "Increased Antigen Presentation Efficiency by Coupling Antigens to MHC Class I Trafficking Signals"; The Journal of Immunology; vol. 180, No. 1, pp. 309-318 (Jan. 1, 2008).
Kushnir, et al.; "Virus-like particles as a highly efficient vaccine platform: Diversity of targets and production systems and advances in clinical development"; Vaccine; vol. 31, pp. 58-83 (2012).
Lazar-Molnar, et al.; "Crystal structure of the complex between programmed death-1 (PD-1) and its ligand PD-L2"; PNAS; vol. 105, No. 30, pp. 10483-10488 (Jul. 29, 2008).
Lazar-Molnar, et al.; "The PD-1/PD-L costimulatory pathway critically affects host resistance to the pathogenic fungus *Histoplasma capsulatum*"; PNAS; vol. 105, No. 7, pp. 2658-2663 (Feb. 19, 2008).
Lenormand, et al.;"HLA-DQA2 and HLA-DQB2 Genes are Specifically Expressed in Human Langerhans Cells and Encode a New HLA Class II Molecule"; The Journal of Immunology; vol. 199, No. 8, pp. 3903-3911 (Apr. 15, 2012).
Liao, et al.; "Interleukin-2 at the Crossroads of Effector Responses, Tolerance, and Immunotherapy"; Immunity; vol. 38, No. 1, pp. 13-25 (Jan. 1, 2013).
Lin, et al.; "The PD-1/PD-L1 complex resembles the antigen-binding Fv domains of antibodies and T cell receptors"; PNAS; vol. 105, No. 8, pp. 3011-3016 (Feb. 26, 2008).
Liu, et al.; "Attaining High Transient Titers in CHO Cells"; Genetic Engineering & Biotechnology News; vol. 35, No. 17, 3 pages (Oct. 1, 2015).
Liu, et al.; "Major Histocompatibility Complex: Interaction with Peptides"; eLS; 12 pages (Aug. 15, 2011).
Lloyd, et al.; "Modelling the human immune response: performance of a 1011 human antibody repertoire against a broad panel of therapeutically relevant antigens"; Protein Engineering, Design & Selection; vol. 22, No. 3, pp. 159-168 (2009).
Mallone, et al.; "T Cell Recognition of Autoantigens in Human Type 1 Diabetes: Clinical Perspectives"; Clinical and Developmental Immunology; vol. 2011, 16 pages (2011).
Margalit, et al.; "Induction of Antitumor Immunity by CTL Epitopes Genetically Linked to Membrane-Anchored β2-Microglobulin"; The Journal of Immunology; vol. 176, pp. 217-224 (2006).
Martin-Orozco, et al.; "Melanoma Cells Express ICOS Ligand to Promote the Activation and Expansion of T-Regulatory Cells"; Cancer Research; vol. 70, No. 23, pp. 9581-9590 (2010).
McAllister, et al.; "Adaptation of Recombinant HEK-293 Cells to Growth in Serum Free Suspension"; Animal Cell Technology: Products from Cells, Cells as Products; 3 pages (1999).
McNally, et al.; "$CD4^+CD25^+$ regulatory T cells control $CD8^+$ T-cell effector differentiation by modulating IL-2 homeostasis"; PNAS; vol. 108, No. 18, pp. 7529-7534 (May 3, 2011).
Medina, et al.; "PD-1 Pathway Inhibitors: Immuno-Onology Agents for Restoring Anititumor Immune Responses"; Pharmacotherapy; vol. 36, No. 3, pp. 317-334 (Mar. 2016).
Miao, et al.; "Transient expression of fluorescent fusion proteins in protoplasts of suspension cultured cells"; Nature Protocols; vol. 2, No. 10, pp. 2348-2353 (2007).
Mizukoshi, et al.; "Identification of a-fetoprotein-derived peptides recognized by cytotoxic T lymphocytes in HLA-A24+ patients with hepatocellular carcinoma"; Int. J. Cancer; vol. 118, pp. 1194-1204 (2006).
Mott, et al.; "The Solution Structure of the F42A Mutant of Human Interleukin 2"; J. Mol. Biol.; vol. 247, pp. 979-994 (1995).
Mottez, et al.; "Cells Expressing a Major Histocompatibility Complex Class I Molecule with a Single Covalently Bound Peptide are Highly Immunogenic"; J. Exp. Med.; vol. 181, pp. 493-502 (Feb. 1995).
Motz, et al.; "Tumor Endothelium FasL Establishes a Selective Immune Barrier Promoting Tolerance in Tumors"; Nat. Med.; vol. 20, No. 6, pp. 607-615 (Jun. 2014).
Muller, et al.; "Random peptide libraries displayed on adeno-associated virus to select for targeted gene therapy vectors"; Nature Biotechnology; vol. 21, No. 9, pp. 1040-1046 (Sep. 2003).
Naidoo, et al.; "Toxicities of the anti-PD-1 and anti-PD-L1 immune checkpoint antibodies"; Annals of Oncology; vol. 26, pp. 2375-2391 (Sep. 2015).
Nielsen, et al.; "MHC Class II epitope predictive algorithms"; Immunology; vol. 130, pp. 319-328 (2010).
Oates, et al.; "ImmTACs: Novel bi-specific agents for targeted cancer therapy"; OncoImmunology; vol. 2, No. 2, 3 pages (Feb. 2013).
Obermann, et al.; "Peptide-β2-microglobulin-major histocompatibility complex expressing cells are potent antigen-presenting cells that can generate specific T cells"; Immunology; vol. 122, pp. 90-97 (2007).
Ochoa-Garay, et al.; "The Ability of Peptides to Induce Cytotoxic T Cells In Vitro Does Not Strongly Correlate with Their Affinity for the $H-2L^d$ Molecule: Implications for Vaccine Design and Immunotherapy"; Molecular Immunology; vol. 34, No. 3, pp. 273-281 (1997).
Oka, et al.; "Induction of WT1 (Wilms' tumor gene)-specific cytotoxic T lymphocytes by WT1 peptide vaccine and the resultant cancer regression"; PNAS; vol. 101, No. 38, pp. 13885-13890 (Sep. 21, 2004).
Oliveira, et al.; "Design, Immune Responses and Anti-Tumor Potential of an HPV16 E6E7 Multi-Epitope Vaccine"; PLoS One; vol. 10, No. 9, 13 pages (Sep. 21, 2015).

(56) References Cited

OTHER PUBLICATIONS

PDB:1I8L_A; "Chain A, T Lymphocyte Activation Antigen Cd80" 2 pages (Dec. 27, 2012).
Peach, et al.; "Both Extracellular Immunoglobin-like Domains of CD80 Contain Residues Critical for Binding T Cell Surface Receptors CTLA-4 and CD28*"; The Journal of Biological Chemistry; vol. 270, No. 36, pp. 21181-21187 (1995).
Ponstingl, et al.; "The Rule of Antibody Structure: The Primary Structure of a Monoclonal IgG1 Immunoglobulin (Myeloma Protein Nie)"; Hoppe Seylers Z Physiol Chem.; vol. 357, No. 11, pp. 1571-1604 (Nov. 1976). [English translation of Abstract Only].
Poosarla, et al.; "Computational De Novo Design of Antibodies Binding to a Peptide With High Affinity"; Biotechnology & Bioengineering; vol. 114, No. 6, pp. 1331-1342 (Jun. 2017).
Quayle, et al.; "CUE-101, a Novel HPV16 E7-pHLA-IL-2-Fc Fusion Protein, Enhances Tumor Antigen Specific T Cell Activation for the Treatment of HPV16-Driven Malignancies"; Clinical Cancer Research; vol. 26, No. 8, pp. 1953-1964 (Jan. 21, 2020).
Quayle, et al.; "Immuno-STAT(TM) (Selective Targeting and Alteration of T cells) Platform: Targeting Tumor Heterogeneity and Tumor Escape Mechanisms"; DOI:10.1158/1078-0432.CCR-19-3354; URL:https://www.cuebiopharma.com/our-appro ch/scien ific-presentations-publications/; 1 page (Jan. 21, 2020).
Rabu, et al.; "Production of recombinant human trimeric CD137L (4-1BBL). Cross-linking is essential to its T cell co-stimulation activity"; The Journal of Biological Chemistry; vol. 280, No. 50, pp. 41472-41481 (Dec. 16, 2005).
Ramani, et al.; "A secreted protein microarray platform for extracellular protein interaction discovery"; Analytical Biochemistry; vol. 420, pp. 127-138 (2012).
Reche, et al.; "Sequence Variability Analysis of Human Class I and Class II MHC Molecules: Functional and Structural Correlates of Amino Acid Polymorphisms"; Journal of Molecular Biology; vol. 331, No. 3, pp. 623-641 (Aug. 15, 2003).
Repana, et al.; "The Network of Cancer Genes (NCG): a comprehensive catalogue of known and candidate cancer genes from cancer sequencing screens"; Genome Biology; vol. 20, No. 1, 12 pages (2019).
Ressing, et al.; "Human CTL epitopes encoded by human papillomavirus type 16 E6 and E7 identified through in vivo and in vitro immunogenicity studies of HLA-A*0201-binding peptides"; The Journal of Immunology; vol. 154, pp. 5934-5943 (1995).
Rocha-Zavaleta, et al.; "Interleukin-2 (IL-2) receptor-βγ signalling is activated by c-Kit in the absence of IL-2, or by exogenous IL-2 via JAK3/STAT5 in human papillomavirus-associated cervical cancer"; Cellular Signalling; vol. 16, pp. 1239-1247 (2004).
Schmittnaegel, et al.; "A New Class of Bifunctional Major Histocompatibility Class I Antibody Fusion Molecules to Redirect CD8 T Cells"; Molecular Cancer Therapeutics; vol. 15, No. 9, pp. 2130-2142 (Sep. 2016).
Schumacher, et al.; "Neoantigens in cancer immunotherapy"; Science; vol. 348, No. 6230, pp. 69-74 (Apr. 2, 2015).
Seidel, et al.; "Peptide-HLA-based immunotherapeutics platforms for direct modulation of antigen-specific T cells"; Scientific Reports; vol. 11, No. 19220, 8 pages (Sep. 2021).
Shah, et al.; "Bio-layer Interferometry for Measuring Kinetics of Protein-protein Interactions and Allosteric Ligand Effects"; Journal of Visualized Experiments; vol. 84, 11 pages (2014).
Sharma, et al.; "A synthetic chimeric peptide harboring human papillomavirus 16 cytotoxic T lymphocyte epitopes shows therapeutic potential in a murine model of cervical cancer"; Immunologic Research; 58(1): p. 132-138 (2014).
Solinas, et al.; "The rationale behind targeting the ICOS-ICOS ligand costimulatory pathway in cancer immunotherapy"; ESMO Open; vol. 5, 7 pages (Jan. 2020).
Spang, et al.; "Heterodimeric Barnase-Barstar Vaccine Molecules: Influence of One versus Two Targeting Units Specific for Antigen Presenting Cells"; PLoS One; vol. 7, No. 9, 11 pages (Sep. 2012).

Stadinski, et al.; "Diabetogenic T cells recognize insulin bound to IAg7 in an unexpected, weakly binding register"; PNAS; vol. 107, No. 24, pp. 10978-10983 (Jun. 15, 2010).
Stamper, et al.; "Crystal structure of the B7-1/CTLA-4 complex that inhibits human immune responses"; Nature; vol. 410, pp. 608-611 (Mar. 29, 2001).
Strohl; "Optimization of Fc-mediated effector functions of monoclonal antibodies"; Current Opinion in Biotechnology; vol. 20, pp. 685-691 (2009).
Tafuro, et al.; "Reconstitution of antigen presentation in HLA class I-negative cancer cells with peptide-β2m fusion molecules"; Eur. J. Immunol.; vol. 31, pp. 440-449 (2001).
Taube, et al.; "Lentivirus Display: Stable Expression of Human Antibodies on the Surface of Human Cells and Virus Particles"; PLoS One; vol. 3, No. 9, 12 pages (Sep. 2008).
Tham, et al.; "Activation of antigen-specific T cells by artificial cell constructs having immobilized multimeric peptide-class I complexes and recombinant B7-Fc proteins"; Journal of Immunological Methods; vol. 249, pp. 111-119 (2001).
Torres, et al.; "The immunoglobulin constant region contributes to affinity and specificity"; Trends in Immunology; vol. 29, No. 2, pp. 91-97 (Jan. 10, 2008).
Toukam, et al.; "Targeting Antibody Responses to the Membrane Proximal External Region of the Envelope Glycoprotein of Human Immunodeficiency Virus"; PLoS One; vol. 7, No. 5, 10 pages (May 2012).
Trolle, et al.; "The length distribution of class I restricted T cell epitopes is determined by both peptide supply and MHC allele specific binding preference"; J Immunol; vol. 196, No. 4, pp. 1480-1487 (Feb. 15, 2016).
Van Der Burg, et al.; "An HLA Class I Peptide-Binding Assay Based on Competition for Binding to Class I Molecules on Intact Human B Cells Identification of Conserved HIV-1 Polymerase Peptides Binding to HLA-A*0301"; Hum. Immunol.; vol. 44, No. 4, pp. 189-198 (Dec. 1995).
Venkatakrishnan, et al.; "The Structural Biology of Hepatitis B Virus: Form and Function"; Annu. Rev. Virol.; vol. 3, No. 1, pp. 429-451 (Sep. 29, 2016).
Vitello, et al.; "Neoantigen prediction and the need for validation"; Nature Biotechnology; vol. 35, No. 9, pp. 815-817 (Sep. 2017).
Wang, et al.; "Molecular Modeling and Functional Mapping of B7-H1 and B7-DC Uncouple Costimulatory Function from PD-1 Interaction"; J. Exp. Med.; vol. 197, No. 9, pp. 1083-1091 (May 5, 2003).
Wang, et al.; "Using a baculovirus display library to identify MHC class I mimotopes"; PNAS; vol. 102, No. 7, pp. 2476-2481 (Feb. 15, 2005).
Wen, et al.; "Construction and screening of an antigen-derived peptide library displayed on yeast cell surface for CD4+ T cell epitope identification"; Methods Mol. Biol.; vol. 1061, pp. 245-264 (2013).
White, et al.; "Soluble Class I MHC with β2-MicroglobulinCovalently Linked Peptides: Specific Binding to a T Cell Hybridoma"; J Immunol; vol. 162, pp. 2671-2676 (1999).
Whitehead, et al.; "Optimization of affinity, specificity and function of designed influenza inhibitors using deep sequencing"; Nat. Biotechnol.; vol. 30, No. 6, pp. 543-548 (Apr. 29, 2013).
Wieczorek, et al.; "Major Histocompatibility Complex (MHC) Class I and MHC Class II Proteins: Conformational Plasticity in Antigen Presentation"; Frontiers in Immunology; vol. 8, No. 292, pp. 1-16 (Mar. 2017).
Won, et al.; "The structure of the trimer of human 4-1BB ligand is unique among members of the tumor necrosis factor superfamily"; J Biol Chem; vol. 285, No. 12, pp. 9202-9210 (Mar. 19, 2010).
Wu, et al.; "Simultaneous targeting of multiple disease mediators by a dual-variable-domain immunoglobulin"; Nature Biotechnology; 25: p. 1290-1297 (2007).
Xu, et al.; "Cytokine release syndrome in cancer immunotherapy with chimeric antigen receptor engineered T cells"; Cancer Letters; 343(2): p. 172-178 (2014).
Zheng, et al.; "B7-CTLA4 interaction enhances both production of antitumor cytotoxic T lymphocytes and resistance to tumor challenge"; PNAS; vol. 95, pp. 6284-6289 (May 1998).

(56) References Cited

OTHER PUBLICATIONS

Ziauddin, et al.; "Microarrays of cells expressing defined cDNAs"; Nature; vol. 411, pp. 107-110 (May 3, 2011).

Burtness, et al.; "Pembrolizumab alone or with chemotherapy versus cetuximab with chemotherapy for recurrent or metastatic squamous cell carcinoma of the head and neck (KEYNOTE-048): a randomised, open-label, phase 3 study"; The Lancet; vol. 19, 14 pages (Oct. 31, 2019).

Burtness, et al.; "Supplementary to: Pembrolizumab alone or with chemotherapy versus cetuximab with chemotherapy for recurrent or metastatic squamous cell carcinoma of the head and neck (KEYNOTE-048): a randomised, open-label, phase 3 study"; The Lancet; vol. 19, 14 pages (Oct. 31, 2019).

Chung, et al.; "A phase 1 dose-escalation and expansion study of CUE-101, a novel HPV16 E7-pHLA-IL2-Fc fusion protein, given alone and in combination with pembrolizumab in patients with recurrent/metastatic HPV16$_+$ head and neck cancer."; ASCO; poster, 1 page (2022).

Chung, et al.; "# 681 A phase 1 study of CUE-101, a novel HPV16 E7-pHLA-IL2-Fc fusion protein, as monotherapy and in combination with pembrolizumab in patients with recurrent/metastatic HPV16$_+$ head and neck cancer"; Society for Immunotherapy of Cancer (SITC) Annual Meeting; poster, 1 pages (Nov. 8, 2022).

Quayle, et al.; "CUE-101, a Novel E7-pHLA-IL2-Fc Fusion Protein, Enhances Tumor Antigen-Specific T-Cell Activation for the Treatment of HPV16-Driven Malignancies"; Clinical Cancer Research; vol. 26, No. 8, pp. 1953-1964 (Jan. 21, 2020).

Unverdorben, et al.; "Pharmacokinetic properties of IgG and various Fc fusion proteins in mice"; MABS; vol. 8, No. 1, pp. 120-128 (Oct. 29, 2015).

Fellner; "Ipilimumab (Yervoy) Prolongs Survival in Advanced Melanoma"; Drug Forecast; vol. 37, No. 9, pp. 503-530 (Sep. 2012).

FIG. 2A

IL2 – *Homo sapiens*

APTSSSTKKT QLQLEHLLLD LQMILNGINN YKNPKLTRML TFKFYMPKKA TELKHLQCLE
EELKPLEEVL NLAQSKNFHL RPRDLISNIN VIVLELKGSE TTFMCEYADE TATIVEFLNR
WITFCQSIIS TLT (SEQ ID NO:1)

APTSSSTKKT QLQLEHLLLD LQMILNGINN YKNPKLTRML TXKFYMPKKA TELKHLQCLE
EELKPLEEVL NLAQSKNFHL RPRDLISNIN VIVLELKGSE TTFMCEYADE TATIVEFLNR
WITFCQSIIS TLT (SEQ ID NO:2)

APTSSSTKKT QLQLEHLLLX LQMILNGINN YKNPKLTRML TFKFYMPKKA TELKHLQCLE
EELKPLEEVL NLAQSKNFHL RPRDLISNIN VIVLELKGSE TTFMCEYADE TATIVEFLNR
WITFCQSIIS TLT (SEQ ID NO:3)

APTSSSTKKT QLQLXHLLLD LQMILNGINN YKNPKLTRML TFKFYMPKKA TELKHLQCLE
EELKPLEEVL NLAQSKNFHL RPRDLISNIN VIVLELKGSE TTFMCEYADE TATIVEFLNR
WITFCQSIIS TLT (SEQ ID NO:4)

APTSSSTKKT QLQLEXLLLD LQMILNGINN YKNPKLTRML TFKFYMPKKA TELKHLQCLE
EELKPLEEVL NLAQSKNFHL RPRDLISNIN VIVLELKGSE TTFMCEYADE TATIVEFLNR
WITFCQSIIS TLT (SEQ ID NO:5)

APTSSSTKKT QLQLEHLLLD LQMILNGINN YKNPKLTRML TFKFXMPKKA TELKHLQCLE
EELKPLEEVL NLAQSKNFHL RPRDLISNIN VIVLELKGSE TTFMCEYADE TATIVEFLNR
WITFCQSIIS TLT (SEQ ID NO:6)

APTSSSTKKT QLQLEHLLLD LQMILNGINN YKNPKLTRML TFKFYMPKKA TELKHLQCLE
EELKPLEEVL NLAQSKNFHL RPRDLISNIN VIVLELKGSE TTFMCEYADE TATIVEFLNR
WITFCXSIIS TLT (SEQ ID NO:7)

APTSSSTKKT QLQLEXLLLD LQMILNGINN YKNPKLTRML TXKFYMPKKA TELKHLQCLE
EELKPLEEVL NLAQSKNFHL RPRDLISNIN VIVLELKGSE TTFMCEYADE TATIVEFLNR
WITFCQSIIS TLT (SEQ ID NO:8)

APTSSSTKKT QLQLEHLLLX LQMILNGINN YKNPKLTRML TXKFYMPKKA TELKHLQCLE
EELKPLEEVL NLAQSKNFHL RPRDLISNIN VIVLELKGSE TTFMCEYADE TATIVEFLNR
WITFCQSIIS TLT (SEQ ID NO:9)

APTSSSTKKT QLQLXHLLLX LQMILNGINN YKNPKLTRML TXKFYMPKKA TELKHLQCLE
EELKPLEEVL NLAQSKNFHL RPRDLISNIN VIVLELKGSE TTFMCEYADE TATIVEFLNR
WITFCQSIIS TLT (SEQ ID NO:10)

APTSSSTKKT QLQLEXLLLX LQMILNGINN YKNPKLTRML TXKFYMPKKA TELKHLQCLE
EELKPLEEVL NLAQSKNFHL RPRDLISNIN VIVLELKGSE TTFMCEYADE TATIVEFLNR
WITFCQSIIS TLT (SEQ ID NO:11)

APTSSSTKKT QLQLEHLLLX LQMILNGINN YKNPKLTRML TXKFYMPKKA TELKHLQCLE
EELKPLEEVL NLAQSKNFHL RPRDLISNIN VIVLELKGSE TTFMCEYADE TATIVEFLNR
WITFCXSIIS TLT (SEQ ID NO:12)

APTSSSTKKT QLQLEHLLLX LQMILNGINN YKNPKLTRML TXKFXMPKKA TELKHLQCLE
EELKPLEEVL NLAQSKNFHL RPRDLISNIN VIVLELKGSE TTFMCEYADE TATIVEFLNR
WITFCQSIIS TLT (SEQ ID NO:13)

APTSSSTKKT QLQLEXLLLX LQMILNGINN YKNPKLTRML TXKFXMPKKA TELKHLQCLE
EELKPLEEVL NLAQSKNFHL RPRDLISNIN VIVLELKGSE TTFMCEYADE TATIVEFLNR
WITFCQSIIS TLT (SEQ ID NO:14)

APTSSSTKKT QLQLEHLLLX LQMILNGINN YKNPKLTRML TXKFXMPKKA TELKHLQCLE
EELKPLEEVL NLAQSKNFHL RPRDLISNIN VIVLELKGSE TTFMCEYADE TATIVEFLNR
WITFCXSIIS TLT (SEQ ID NO:15)

APTSSSTKKT QLQLEXLLLX LQMILNGINN YKNPKLTRML TXKFXMPKKA TELKHLQCLE
EELKPLEEVL NLAQSKNFHL RPRDLISNIN VIVLELKGSE TTFMCEYADE TATIVEFLNR
WITFCXSIIS TLT (SEQ ID NO:16)

APTSSSTKKT QLQLEXLLLD LQMILNGINN YKNPKLTRML TXKFYMPKKA TELKHLQCLE
EELKPLEEVL NLAQSKNFHL RPRDLISNIN VIVLELKGSE TTFMCEYADE TATIVEFLNR
WITFCXSIIS TLT (SEQ ID NO: 17)

FIG. 3A

IL2R-alpha chain
*Homo sapiens*

```
  1 MDSYLLMWGL LTFIMVPGCQ AELCDDDPPE IPHATFKAMA YKEGTMLNCE CKRGFRRIKS
 61 GSLYMLCTGN SSHSSWDNQC QCTSSATRNT TKQVTPQPEE QKERKTTEMQ SPMQPVDQAS
121 LPGHCREPPP WENEATERIY HFVVGQMVYY QCVQGYRALH RGPAESVCKM THGKTRWTQP
181 QLICTGEMET SQFPGEEKPQ ASPEGRPESE TSCLVTTTDF QIQTEMAATM ETSIFTTEYQ
241 VAVAGCVFLL ISVLLLSGLT WQRRQRKSRR TI   (SEQ ID NO:18)
```

Mature = amino acids 22-272

FIG. 3B

IL2R-beta chain
*Homo sapiens*

```
  1 MAAPALSWRL PLLILLLPLA TSWASAAVNG TSQFTCFYNS RANISCVWSQ DGALQDTSCQ
 61 VHAWPDRRRW NQTCELLPVS QASWACNLIL GAPDSQKLTT VDIVTLRVLC REGVRWRVMA
121 IQDFKPFENL RLMAPISLQV VHVETHRCNI SWEISQASHY FERHLEFEAR TLSPGHTWEE
181 APLLTLKQKQ EWICLETLTP DTQYEFQVRV KPLQGEFTTW SPWSQPLAFR TKPAALGKDT
241 IPWLGHLLVG LSGAFGFIIL VYLLINCRNT GPWLKKVLKC NTPDPSKFFS QLSSEHGGDV
301 QKWLSSPFPS SSFSPGGLAP EISPLEVLER DKVTQLLLQQ DKVPEPASLS SNHSLTSCFT
361 NQGYFFFHLP DALEIEACQV YFTYDPYSEE DPDEGVAGAP TGSSPQPLQP LSGEDDAYCT
421 FPSRDDLLLF SPSLLGGPSP PSTAPGGSGA GEERMPPSLQ ERVPRDWDPQ PLGPPTPGVP
481 DLVDFQPPPE LVLREAGEEV PDAGPREGVS FPWSRPPGQG EFRALNARLP LNTDAYLSLQ
541 ELQGQDPTHL V (SEQ ID NO:19)
```

Mature = amino acids 27-551

FIG. 3C

IL2R-gamma chain
*Homo sapiens*

```
  1 MLKPSLPFTS LLFLQLPLLG VGLNTTILTP NGNEDTTADF FLTTMPTDSL SVSTLPLPEV
 61 QCFVFNVEYM NCTWNSSSEP QPTNLTLHYW YKNSDNDKVQ KCSHYLFSEE ITSGCQLQKK
121 EIHLYQTFVV QLQDPREPRR QATQMLKLQN LVIPWAPENL TLHKLSESQL ELNWNNRFLN
181 HCLEHLVQYR TDWDHSWTEQ SVDYRHKFSL PSVDGQKRYT FRVRSRFNPL CGSAQHWSEW
241 SHPIHWGSNT SKENPFLFAL EAVVISVGSM GLIISLLCVY FWLERTMPRI PTLKNLEDLV
301 TEYHGNFSAW SGVSKGLAES LQPDYSERLC LVSEIPPKGG ALGEGPGASP CNQHSPYWAP
361 PCYTLKPET (SEQ ID NO:20)
```

Mature = amino acids 23-369

FIG. 4A

GenBank 3S7G_A

*Homo sapiens* IgG1 Fc (SEQ ID NO:21)

227 aa

```
  1 dkthtcppcp apellggpsv flfppkpkdt lmisrtpevt cvvvdvshed pevkfnwyvd
 61 gvevhnaktk preeqynsty rvvsvltvlh qdwlngkeyk ckvsnkalpa piektiskak
121 gqprepqvyt lppsrdeltk nqvsltclvk gfypsdiave wesngqpenn ykttppvlds
181 dgsfflyskl tvdksrwqqg nvfscsvmhe alhnhytqks lslspgk
```

GenBank AAN76044

*Homo sapiens* IgG2 Fc (amino acids 99-325) (SEQ ID NO:22)

227 aa

```
  1 stkgpsvfpl apcsrstses taalgclvkd yfpepvtvsw nsgaltsgvh tfpavlqssg
 61 lyslssvvtv pssnfgtqty tcnvdhkpsn tkvdktverk ccvecppcpa ppvagpsvfl
121 fppkpkdtlm isrtpevtcv vvdvshedpe vqfnwyvdgv evhnaktkpr eeqfnstfrv
181 vsvltvvhqd wlngkeykck vsnkglpapi ektisktkgq prepqvytlp psreemtknq
241 vsltclvkgf ypsdiavewe sngqpennyk ttppmldsdg sfflyskltv dksrwqqgnv
301 fscsvmheal hnhytqksls lspgk
```

GenBank AAW65947

*Homo sapiens* IgG3 Fc (amino acids 19-246) (SEQ ID NO:23)

238 aa

```
  1 hkpsntkvdk rvelktplgd tthtcppcpa pellggpsvf lfppkpkdtl misrtpevtc
 61 vvvdvshedp evkfnwyvdg vevhnaktkp reeqynstyr vvsvltvlhq dwlngkeykc
121 kvsnkalpap iektiskakg qprepqvytl ppsrdeltkn qvsltclvkg fypsdiavew
181 esngqpenny kttppvldsd gsfflysklt vdksrwqqgn vfscsvmhea lhnhytqksl
241 slspgk
```

FIG. 4B

GenBank AAA52770
*Homo sapiens* IgD Fc (amino acids 162-383) (SEQ ID NO: 24)
222 aa

```
  1 ptkapdvfpi isgcrhpkdn spvvlaclit gyhptsvtvt wymgtqsqpq rtfpeiqrrd
 61 syymtssqls tplqqwrqge ykcvvqhtas kskkeifrwp espkaqassv ptaqpqaegs
121 lakattapat trntgrggee kkkekekeeq eeretktpec pshtqplgvy lltpavqdlw
181 lrdkatftcf vvgsdlkdah ltwevagkvp tggveeglle rhsngsqsqh srltlprslw
241 nagtsvtctl nhpslppqrl malrepaaga pvklslnlla ssdppeaasw llcevsgfsp
301 pnillmwled qrevntsgfa parpppqprs ttfwawsvlr vpappspqpa tytcvvshed
361 srtllnasrs levsyvtdhg pmk
```

GenBank O308221A
*Homo sapiens* IgM Fc (SEQ ID NO: 25)
276 aa

```
  1 vtstltikzs dwlgesmftc rvdhrqltfq qnassmcvpd qdtairvfai ppsfasiflt
 61 kstkltclvt dlttybsvti swtreengav kthtnisesh pnatfsavge asicedbdws
121 gerftctvth tdlpsplkqt isrpkgvalh rpbvyllppa rzzlnlresa titclvtgfs
181 padvfvewmq rgeplspqky vtsapmpepq apgryfahsi ltvseeewnt ggtytcvvah
241 ealpnrvter tvdkstgkpt lynvslvmsd tagtcy
```

FIG. 4C

GenBank P01876
*Homo sapiens* IgA Fc (amino acids 120-353) (SEQ ID NO: 26)
234 aa

```
  1 asptspkvfp lslcstqpdg nvviaclvqg ffpqeplsvt wsesgqgvta rnfppsqdas
 61 gdlyttssql tlpatqclag ksvtchvkhy tnpsqdvtvp cpvpstpptp spstpptpsp
121 scchprlslh rpaledlllg seanltctlt glrdasgvtf twtpssgksa vqgpperdlc
181 gcysvssvlp gcaepwnhgk tftctaaype sktpltatls ksgntfrpev hllpppseel
241 alnelvtltc largfspkdv lvrwlqgsqe lprekyltwa srqepsqgtt tfavtsilrv
301 aaedwkkgdt fscmvgheal plaftqktid rlagkpthvn vsvvmaevdg tcy
```

GenBank 1F6A_B
*Homo sapiens* IgE Fc (amino acids 6-222) (SEQ ID NO: 27)
212 aa

```
  1 adpcdsnprg vsaylsrpsp fdlfirkspt itclvvdlap skgtvnltws rasgkpvnhs
 61 trkeekqrng tltvtstlpv gtrdwieget yqcrvthphl pralmrsttk tsgpraapev
121 yafatpewpg srdkrtlacl iqnfmpedis vqwlhnevql pdarhsttqp rktkgsgffv
181 fsrlevtrae weqkdeficr avheaaspsq tvqravsvnp gk
```

GenBank P01861
*Homo sapiens* IgG4 Fc (amino acids 100-327) (SEQ ID NO: 28)
228 aa

```
  1 astkgpsvfp lapcsrstse staalgclvk dyfpepvtvs wnsgaltsgv htfpavlqss
 61 glyslssvvt vpssslgtkt ytcnvdhkps ntkvdkrves kygppcpscp apeflggpsv
121 flfppkpkdt lmisrtpevt cvvvdvsqed pevqfnwyvd gvevhnaktk preeqfnsty
181 rvvsvltvlh qdwlngkeyk ckvsnkglps siektiskak gqprepqvyt lppsqeemtk
241 nqvsltclvk gfypsdiave wesngqpenn ykttppvlds dgsfflysrl tvdksrwqeg
301 nvfscsvmhe alhnhytqks lslslgk
```

FIG. 5A

*Homo sapiens*
GenBank NP_001229687
HLA-A
Amino acids 25-365 (SEQ ID NO:29)

```
  1 mavmaprtll lllsgalalt qtwagshsmr yfftsvsrpg rgeprfiavg yvddtqfvrf
 61 dsdaasqkme prapwieqeg peywdqetrn mkahsqtdra nlgtlrgyyn qsedgshtiq
121 imygcdvgpd grflrgyrqd aydgkdyial nedlrswtaa dmaaqitkrk weavhaaeqr
181 rvylegrcvd glrrylengk etlqrtdppk thmthhpisd heatlrcwal gfypaeitlt
241 wqrdgedqtq dtelvetrpa gdgtfqkwaa vvvpsgeeqr ytchvqhegl pkpltlrwel
301 ssqptipivg iiaglvllga vitgavvaav mwrrkssdrk ggsytqaass dsaqgsdvsl
361 tackv
```

FIG. 5B

*Homo sapiens*
GenBank NP_005505
HLA-B
Amino acids 25-362 (SEQ ID NO:30)

```
  1 mlvmaprtvl lllsaalalt etwagshsmr yfytsvsrpg rgeprfisvg yvddtqfvrf
 61 dsdaaspree prapwieqeg peywdrntqi ykaqaqtdre slrnlrgyyn qseagshtlq
121 smygcdvgpd grllrghdqy aydgkdyial nedlrswtaa dtaaqitqrk weaareaeqr
181 raylegecve wlrrylengk dkleradppk thvthhpisd heatlrcwal gfypaeitlt
241 wqrdgedqtq dtelvetrpa gdrtfqkwaa vvvpsgeeqr ytchvqhegl pkpltlrwep
301 ssqstvpivg ivaglavlav vvigavvaav mcrrkssggk ggsysqaacs dsaqgsdvsl
361 ta
```

FIG. 5C

*Homo sapiens*
GenBank NP_001229971
HLA-C
Amino acids 25-366 (SEQ ID NO:31)

```
  1 mrvmaprall llsgglalt etwacshsmr yfdtavsrpg rgeprfisvg yvddtqfvrf
 61 dsdaasprge prapwveqeg peywdretqn ykrqaqadrv slrnlrgyyn qsedgshtlq
121 rmygcdlgpd grllrgydqs aydgkdyial nedlrswtaa dtaaqitqrk leaaraaeql
181 raylegtcve wlrrylengk etlqraeppk thvthhplsd heatlrcwal gfypaeitlt
241 wqrdgedqtq dtelvetrpa gdgtfqkwaa vvvpsgqeqr ytchmqhegl qepltlswep
301 ssqptipimg ivaglavlvv lavlgavvta mmcrrkssgg kggscsqaac snsaqgsdes
361 litcka
```

FIG. 6

| | |
|---|---|
| NP_004039.1 | MSRSVALAVLALLSLSGLEAIQRTPKIQVYSRHPAENGKSNFLNCYVSGFHPSDIEVDLL 60 |
| NP_001009066.1 | MSRSVALAVLALLSLSGLEAIQRTPKIQVYSRHPAENGKSNFLNCYVSGFHPSDIEVDLL 60 |
| NP_001040602.1 | MSRSVALAVLALLSLSGLEAIQRTPKIQVYSRHPPENGKPNFLNCYVSGFHPSDIEVDLL 60 |
| NP_776318.1 | MARFVALVLLGLLSLSGLDAIQRPPKIQVYSRHPPEDGKPNYLNCYVYGFHPPQIEIDLL 60 |
| NP_033865.2 | MARSVTLVFLVLVSLTGLYAIQKTPQIQVYSRHPPENGKPNILNCYVTQFHPPHTEIQML 60 |
| | *:*  *.*:. *  *:.**  :** :***** :**:*:********   *:** |

| | |
|---|---|
| NP_004039.1 | KNGERIEKVEHSDLSFSKDWSFYLLYYTEFTPTEKDEYACRVNHVTLSQPKIVKWDRDM 119 |
| NP_001009066.1 | KNGERIEKVEHSDLSFSKDWSFYLLYYTEFTPTEKDEYACRVNHVTLSQPKIVKWDRDM 119 |
| NP_001040602.1 | KNGEKMGKVEHSDLSFSKDWSFYLLYYTEFTPNEKDEYACRVNHVTLSGPRTVKWDRDM 119 |
| NP_776318.1 | KNGEKI-KSEQSDLSFSKDWSFYLLSHAEFTPNSKDQYSCRVKHVTLEQPRIVKWDRDL 118 |
| NP_033865.2 | KNGKKIPKVEMSDMSFSKDWSFYILAHTEFTPTETDTYACRVKHASMAEPKTVWWDRDM 119 |
| | ****.:  *  :************     * *:. .* : ****** |

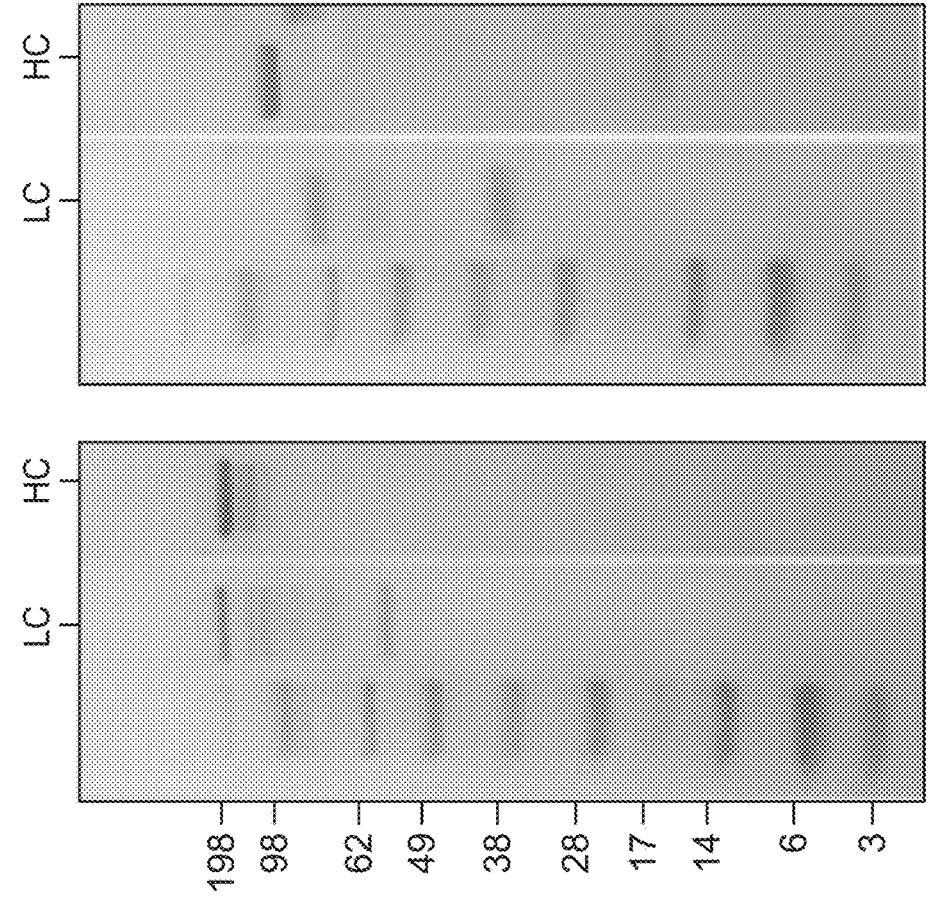
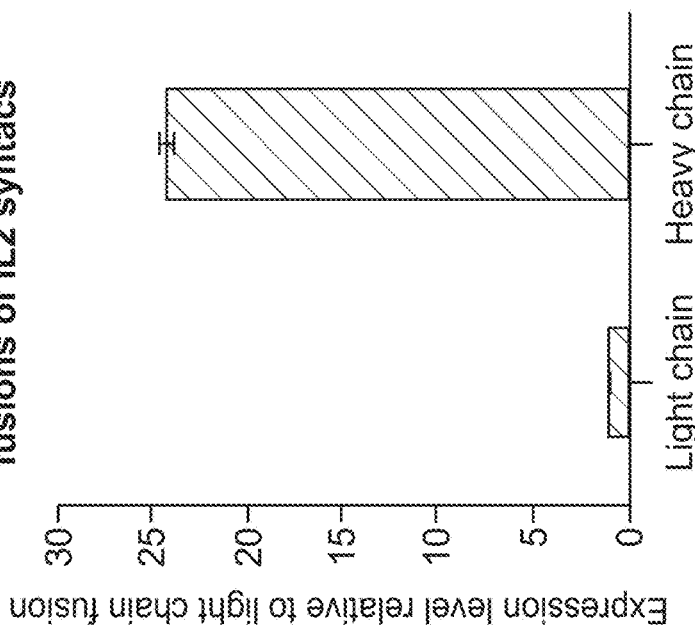
FIG. 8A
FIG. 8B

FIG. 12
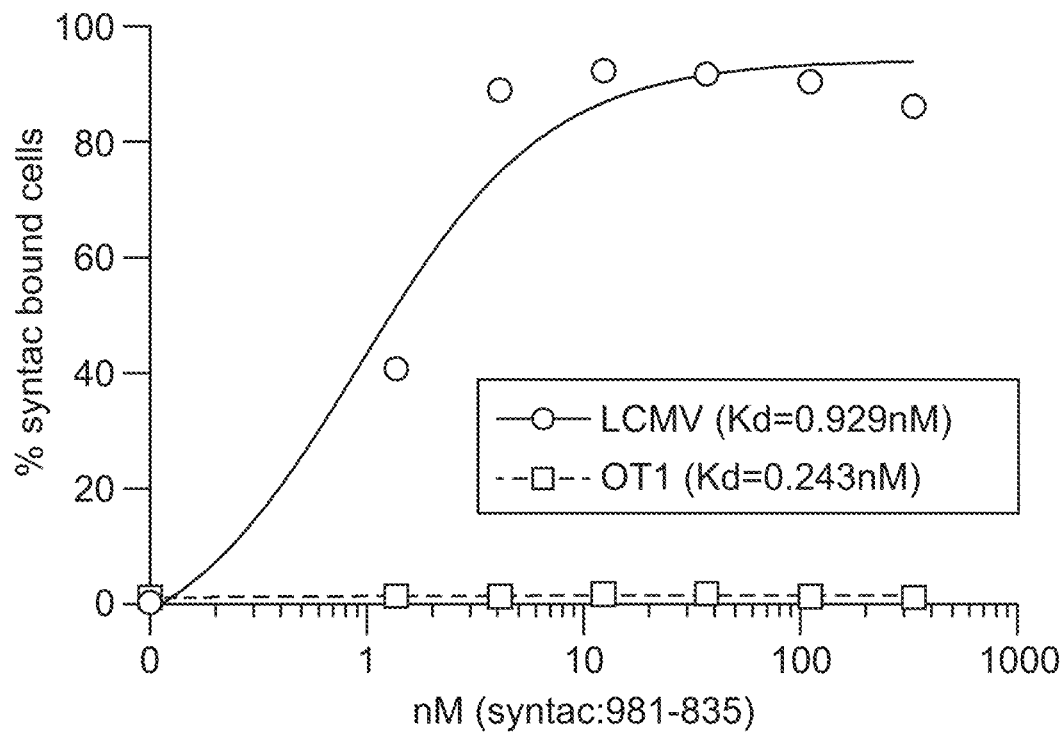
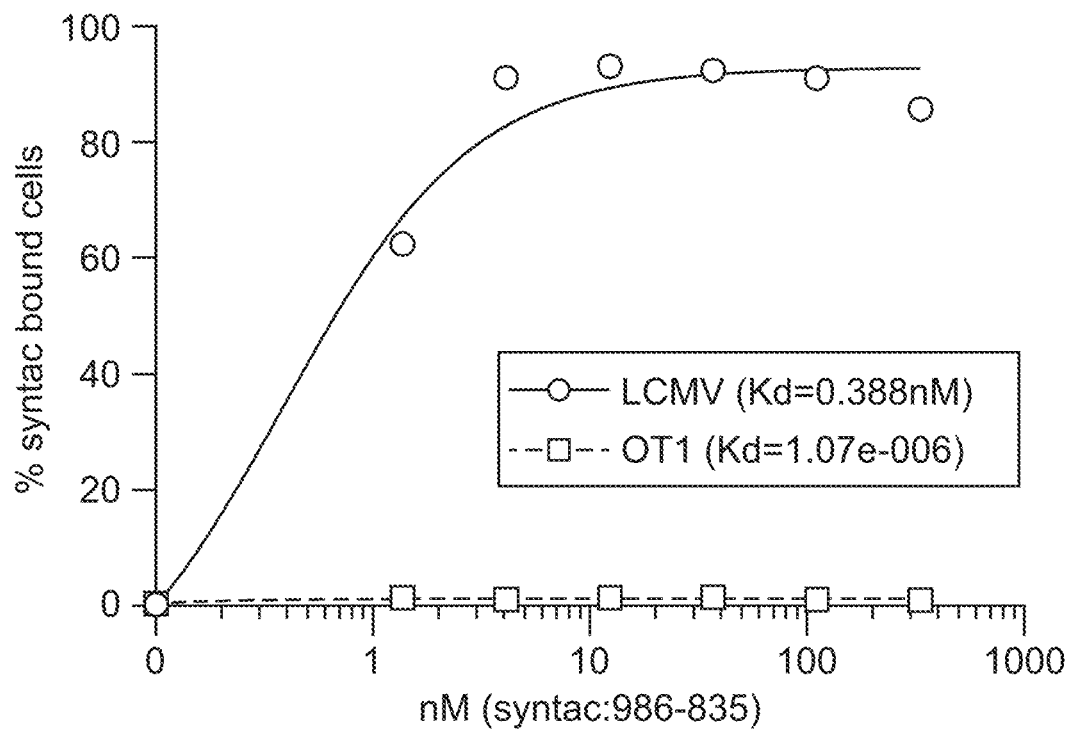

FIG. 13

Number of IL-2 Repeats versus Mutations

LCMV-1xhIL2

971-835 (1X-hIL2, F42A)

F42A

- LCMV (EC50=11)
- BL6 (EC50=334)

975-835 (1X-hIL2, F42A, H16A)

F42A, H16A

- LCMV (EC50=78)
- BL6 (EC50=1129)

Number of IL-2 Repeats versus Mutations

LCMV-2xhIL2

FIG. 13 (Cont.)
Number of IL-2 Repeats versus Mutations
LCMV-3xhIL2
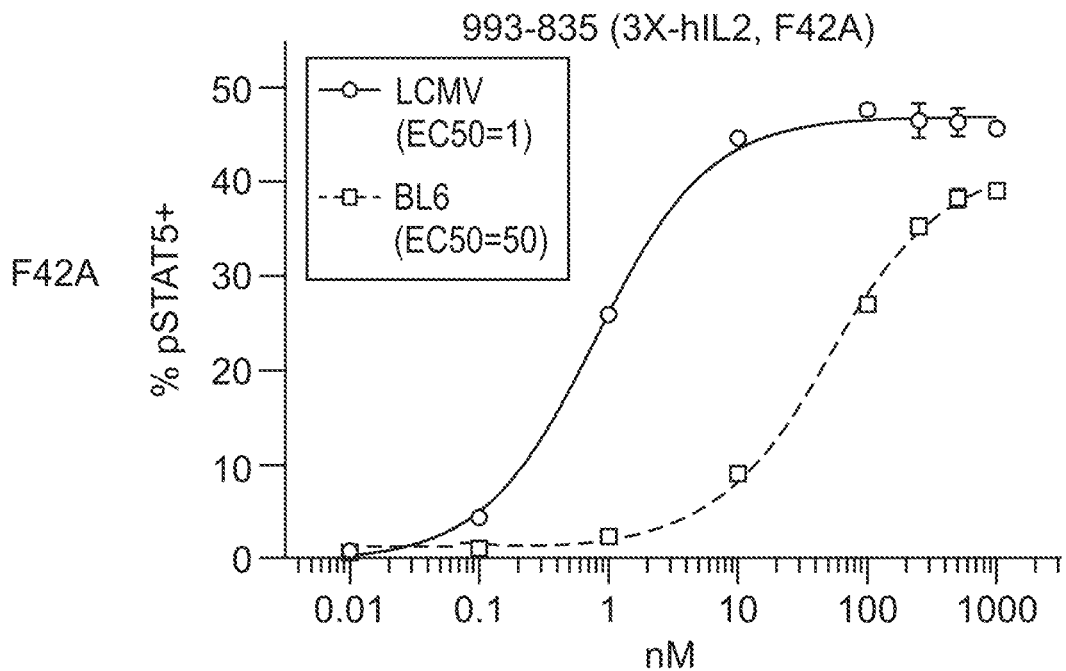
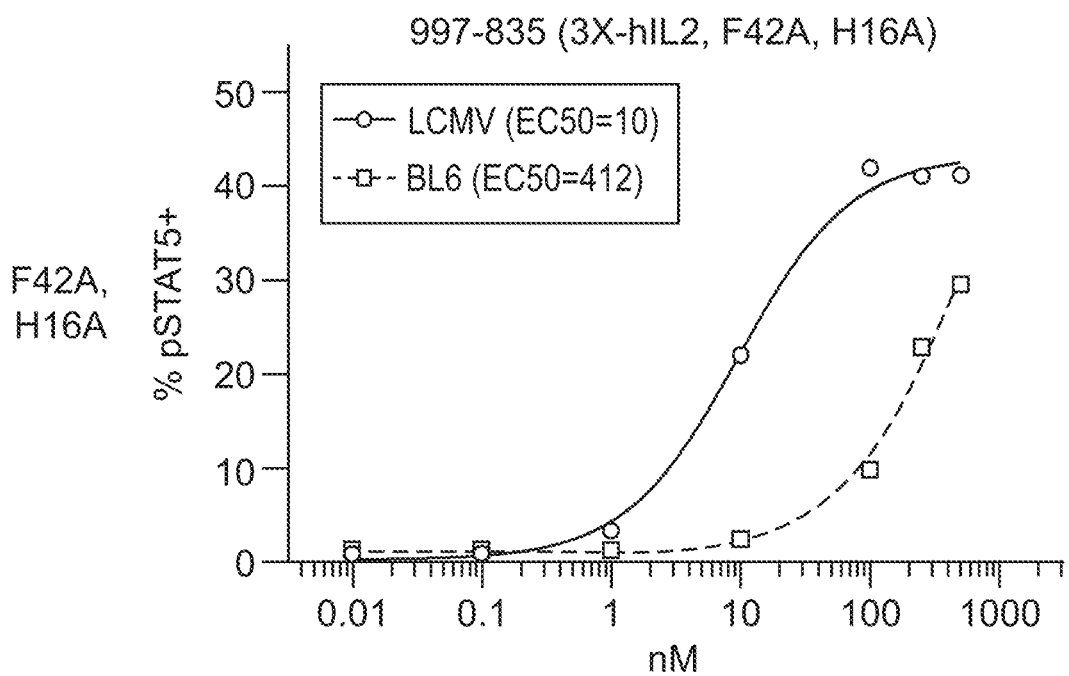

FIG. 14A
One copy of IL-2
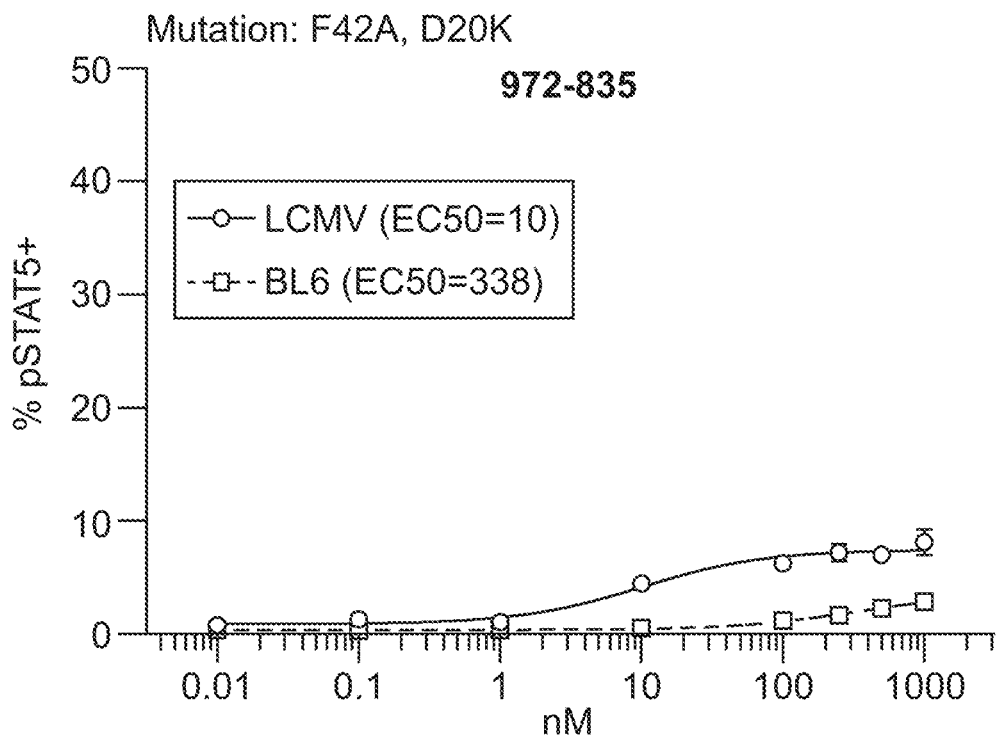
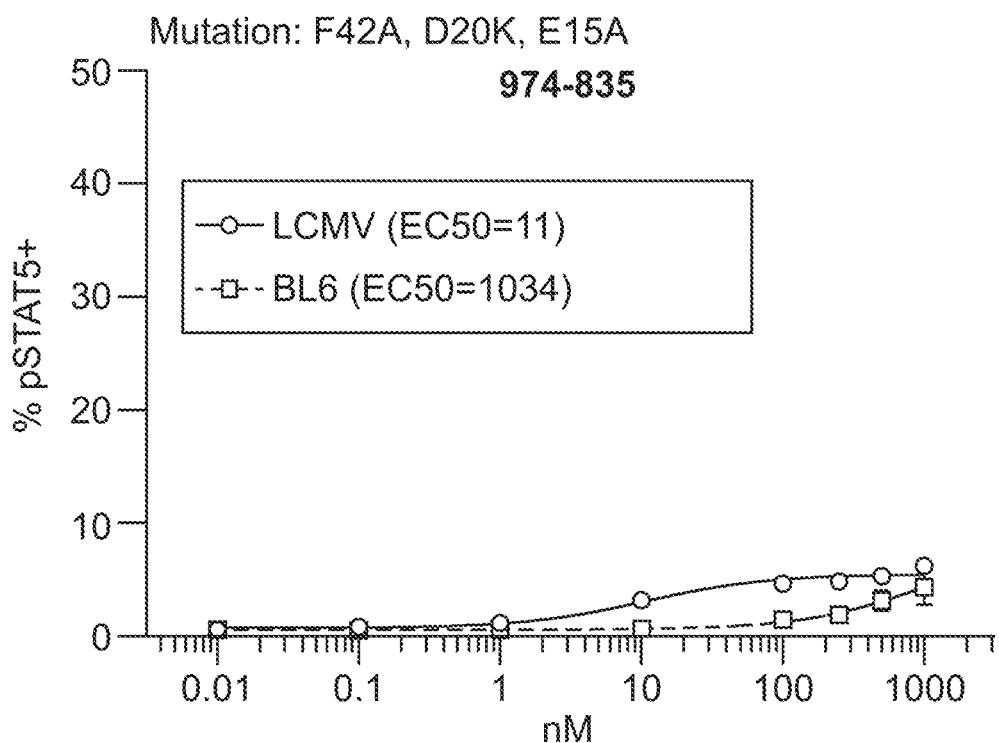

FIG. 14A (Cont.)
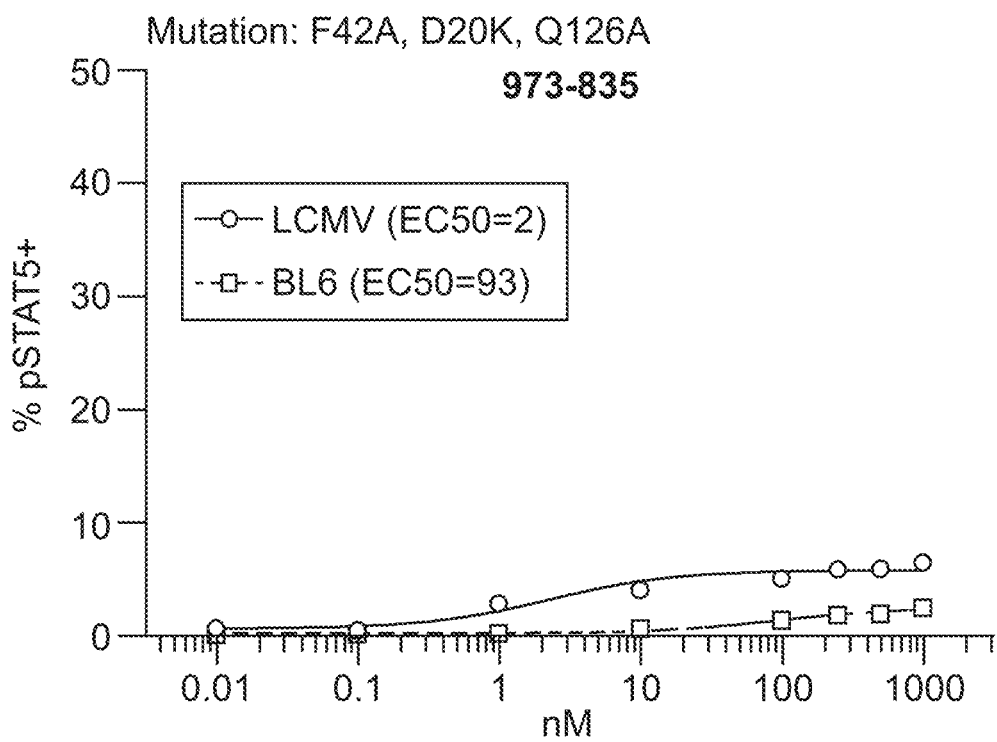
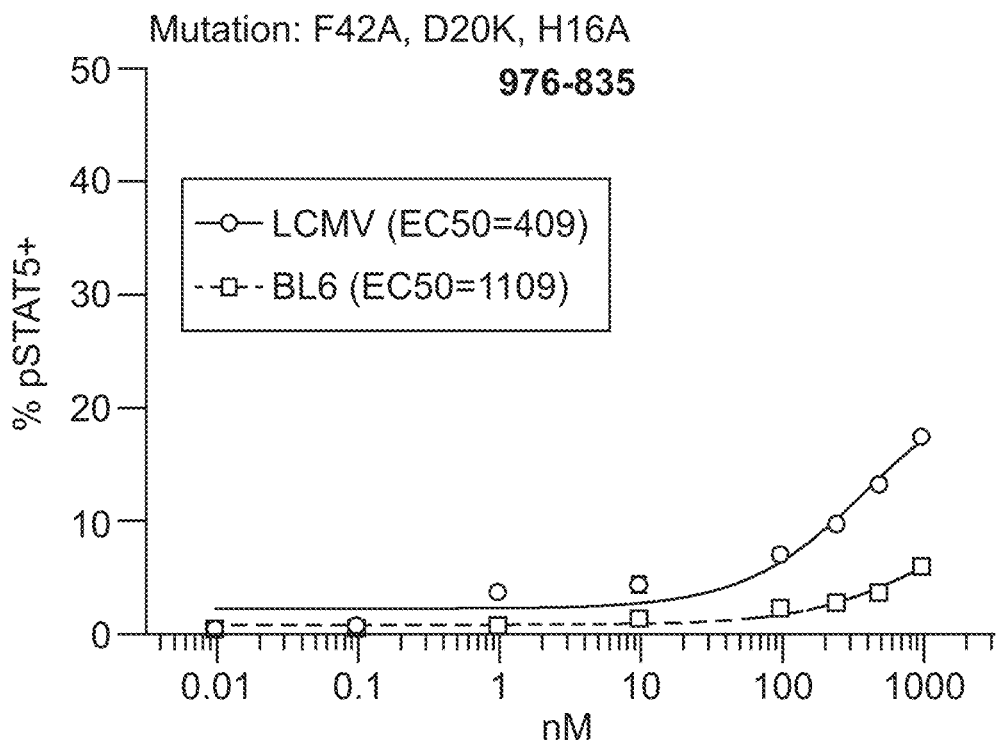

FIG. 14B
One copy of IL-2
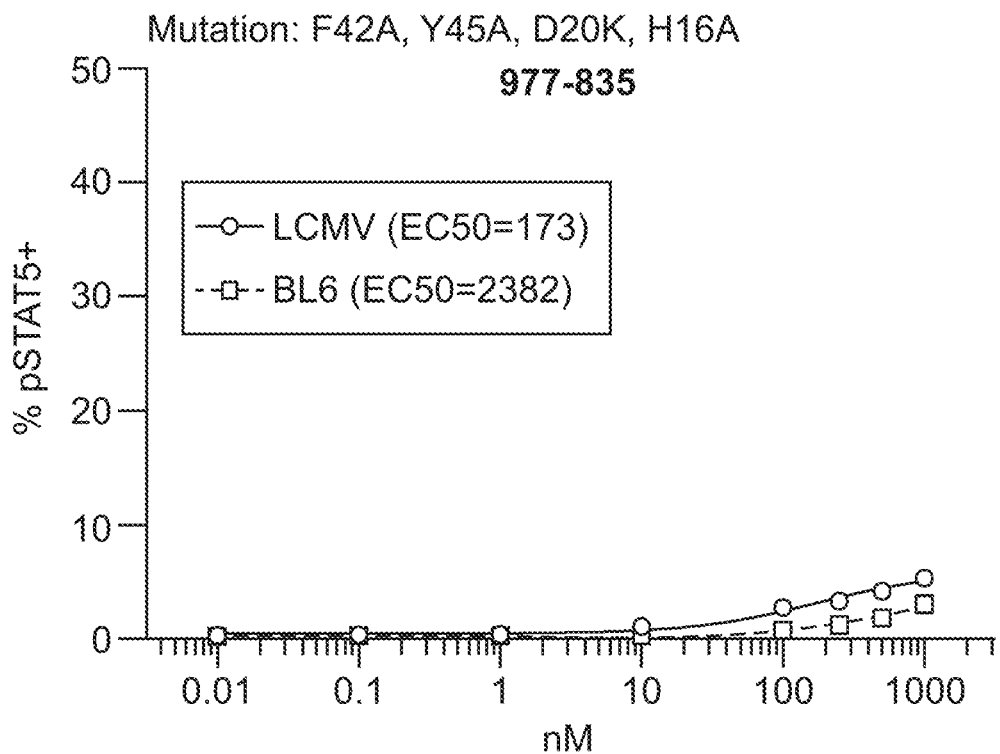
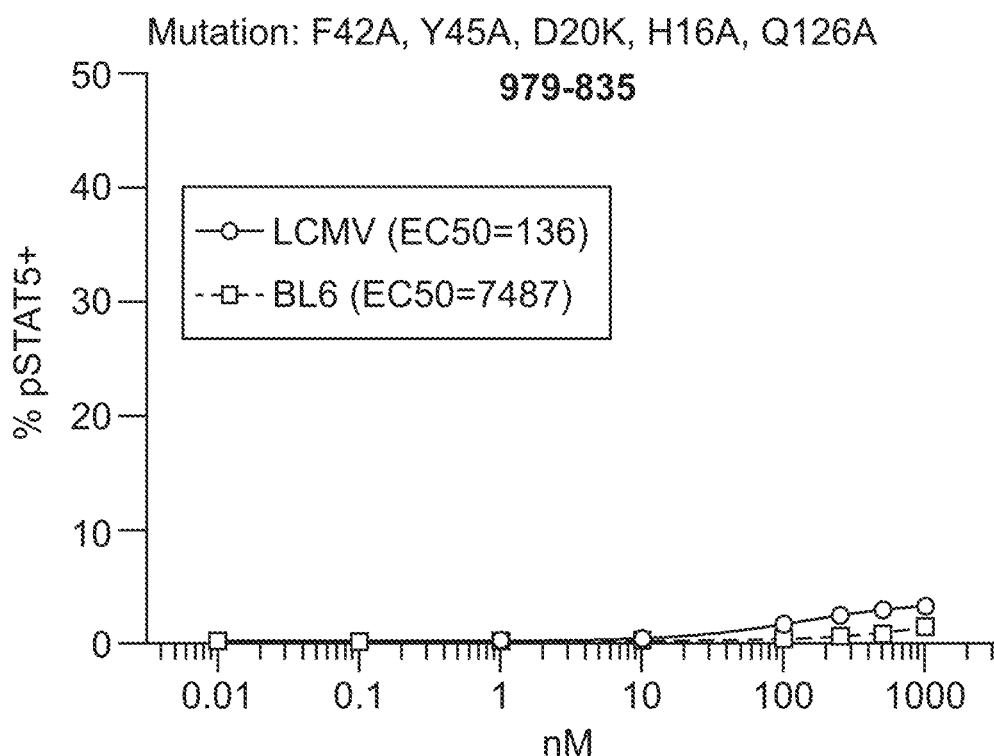

FIG. 14B (Cont.)
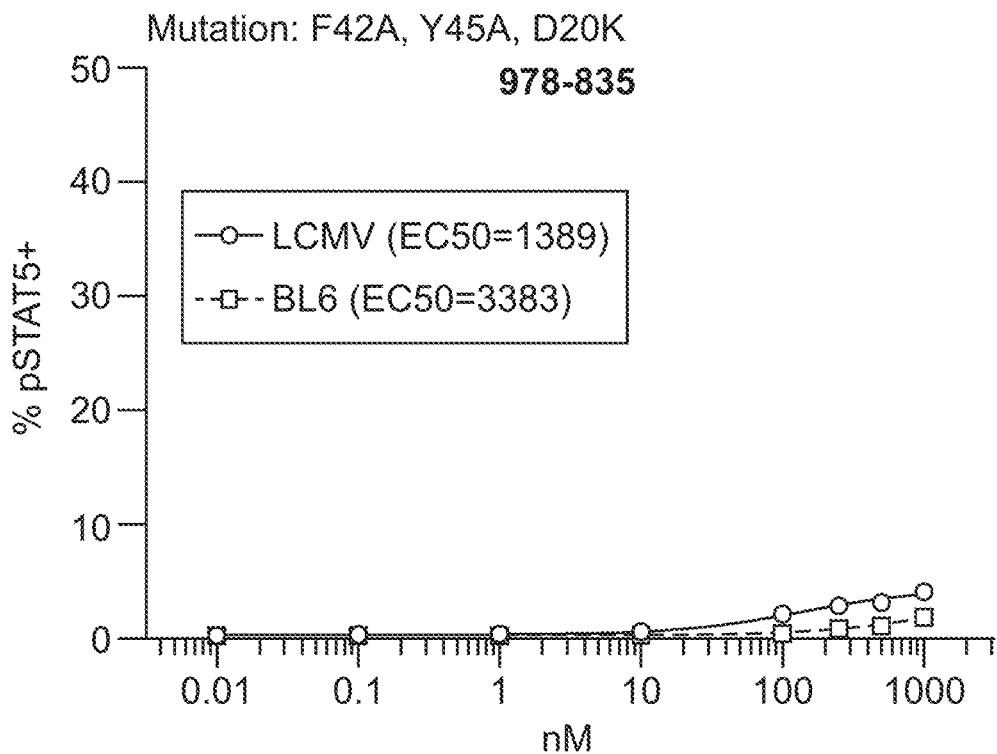
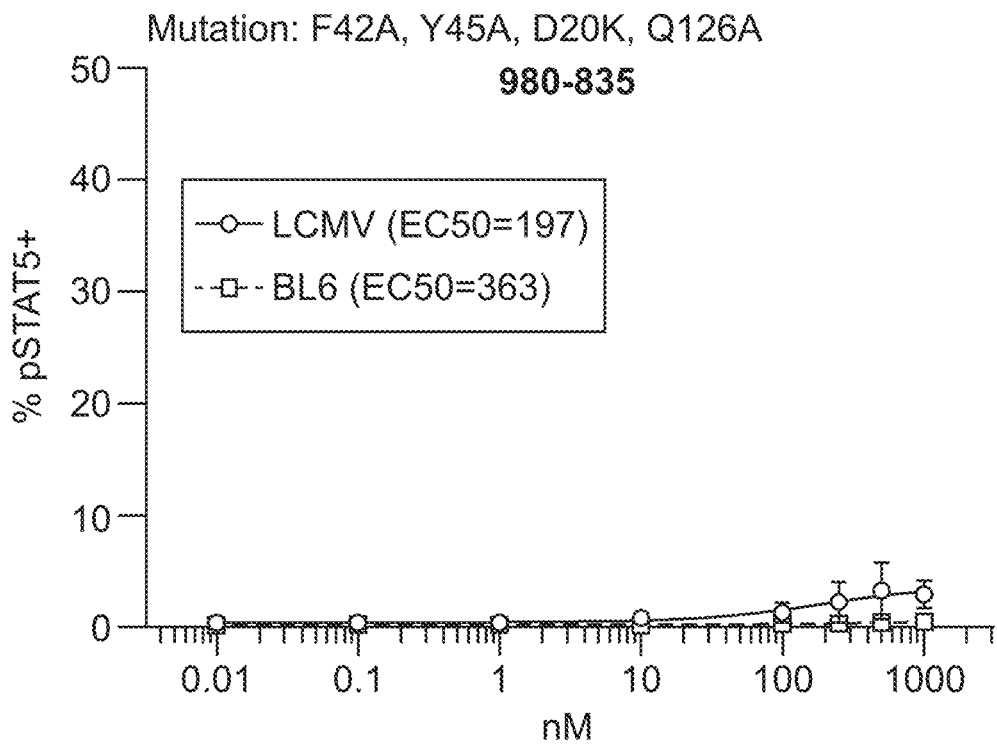

FIG. 14C
Two copies of IL-2
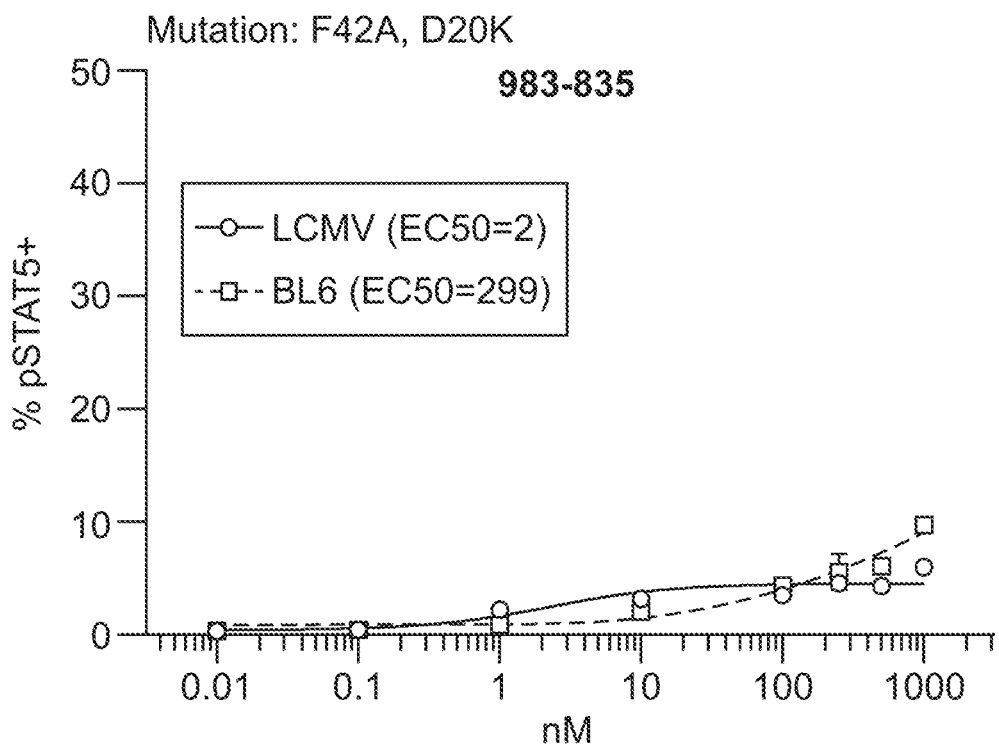
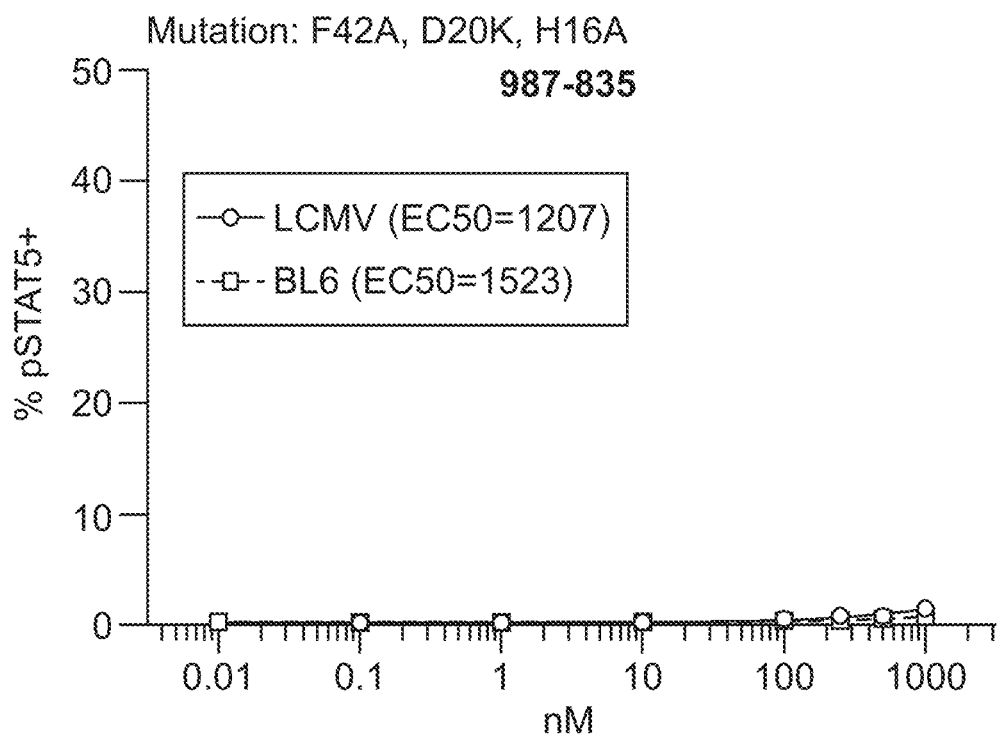

FIG. 14D
Two copies of IL-2
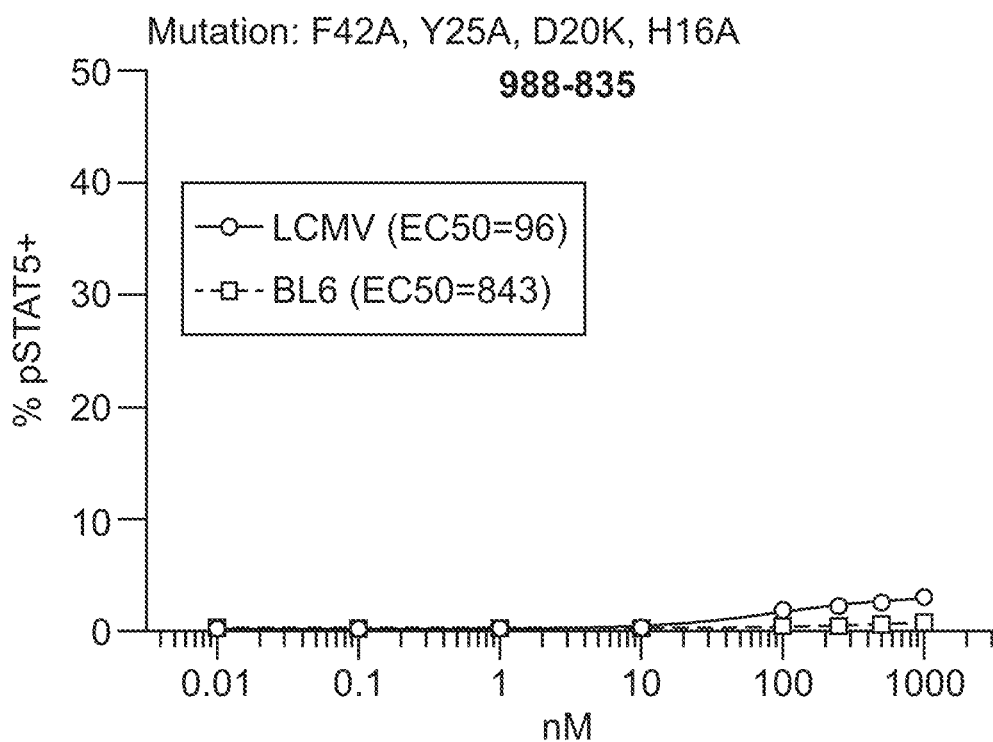
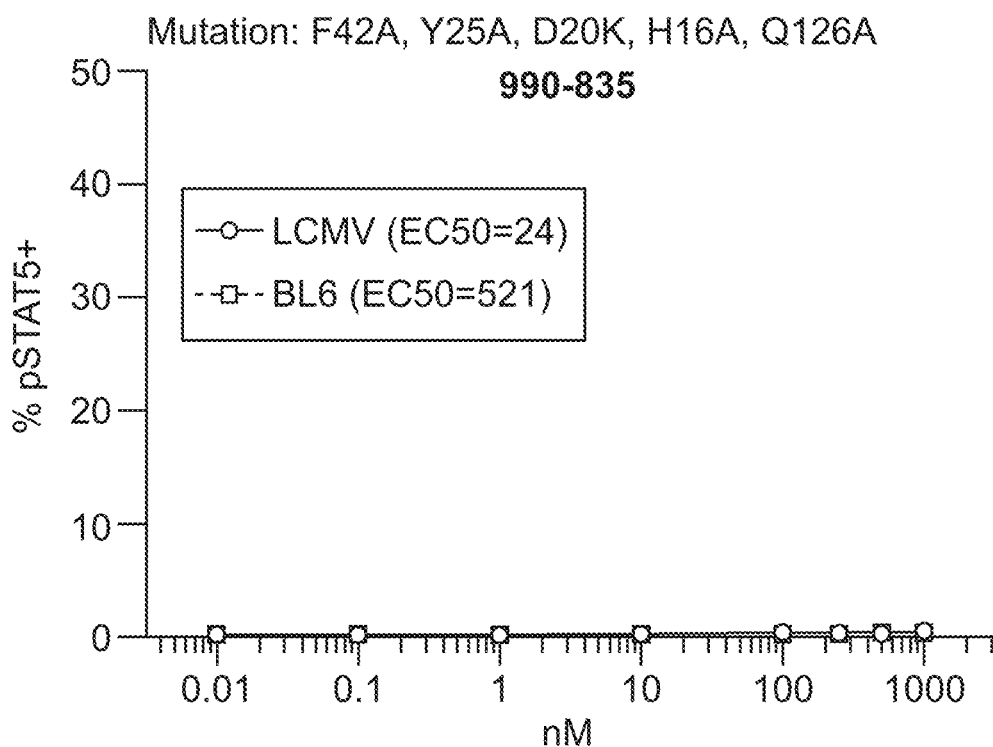

FIG. 14D (Cont.)
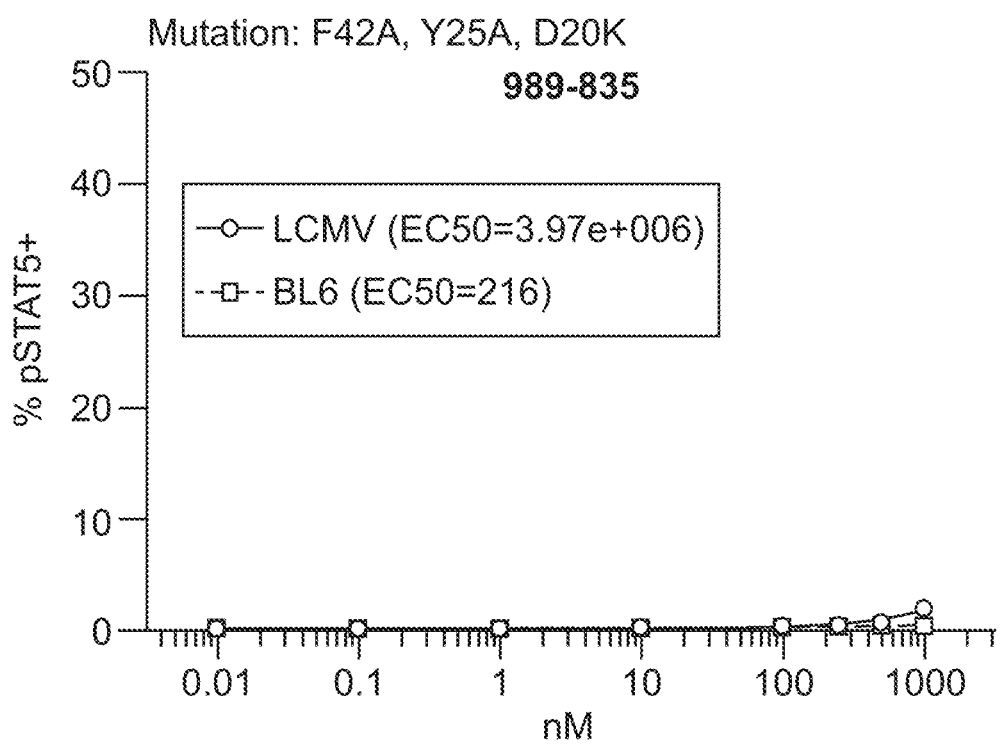
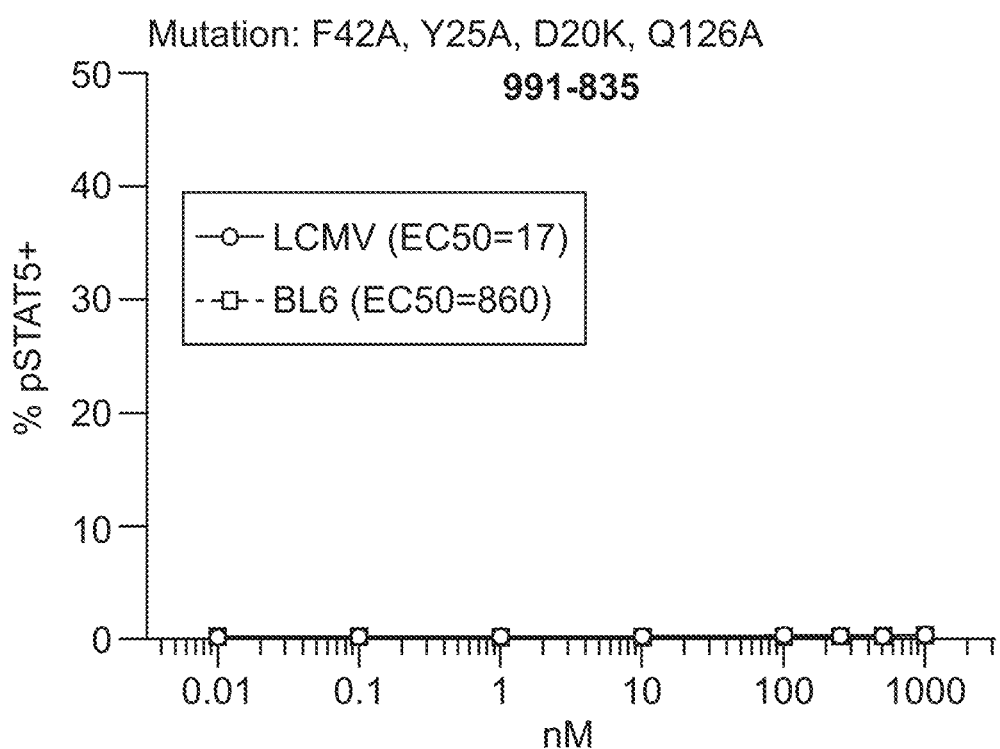

FIG. 14E
Three copies of IL-2
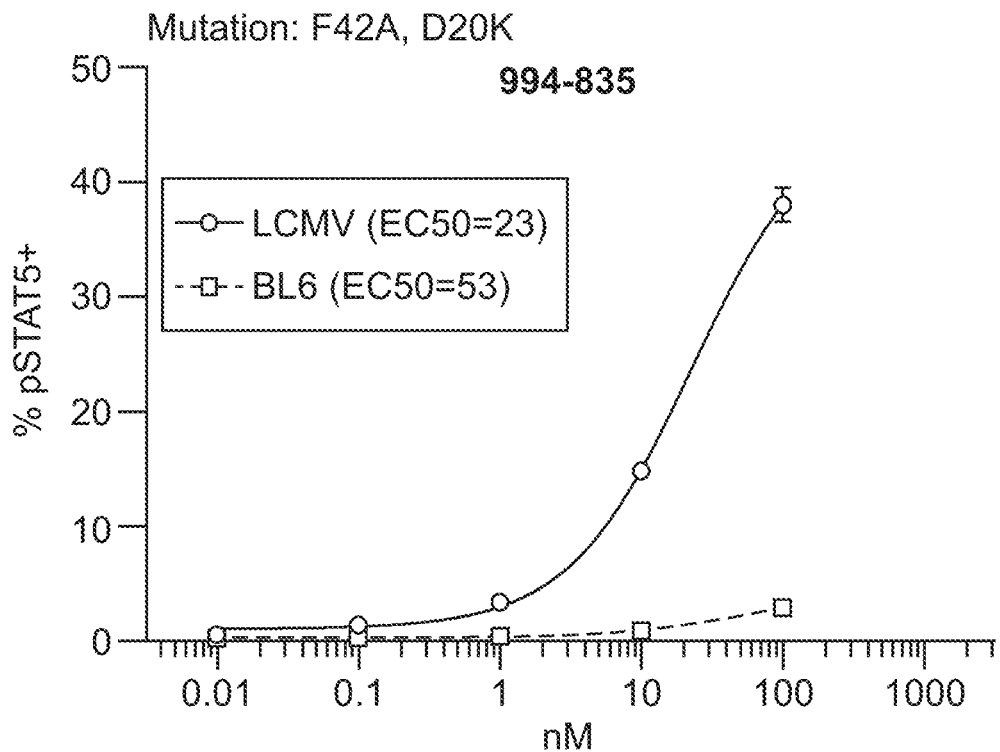
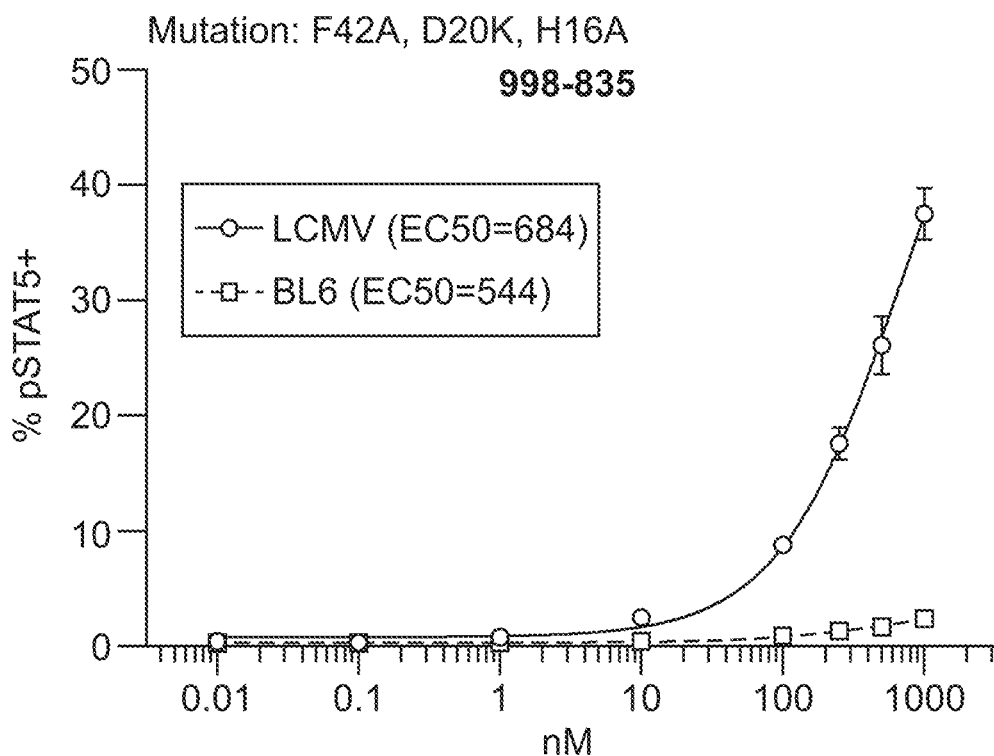

FIG. 14F
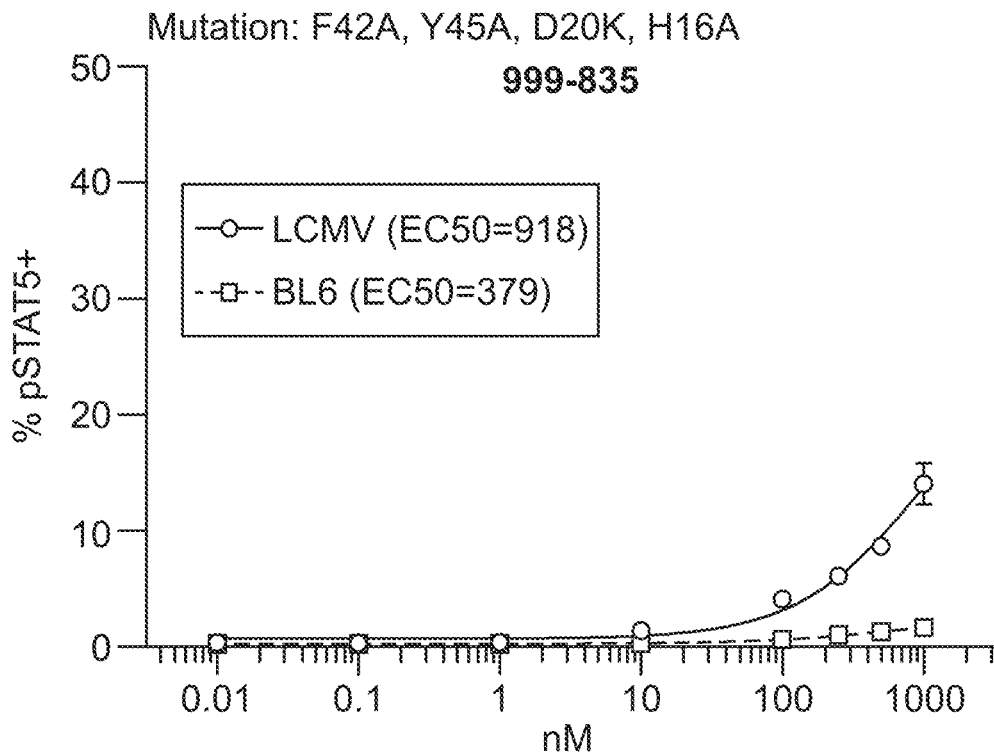
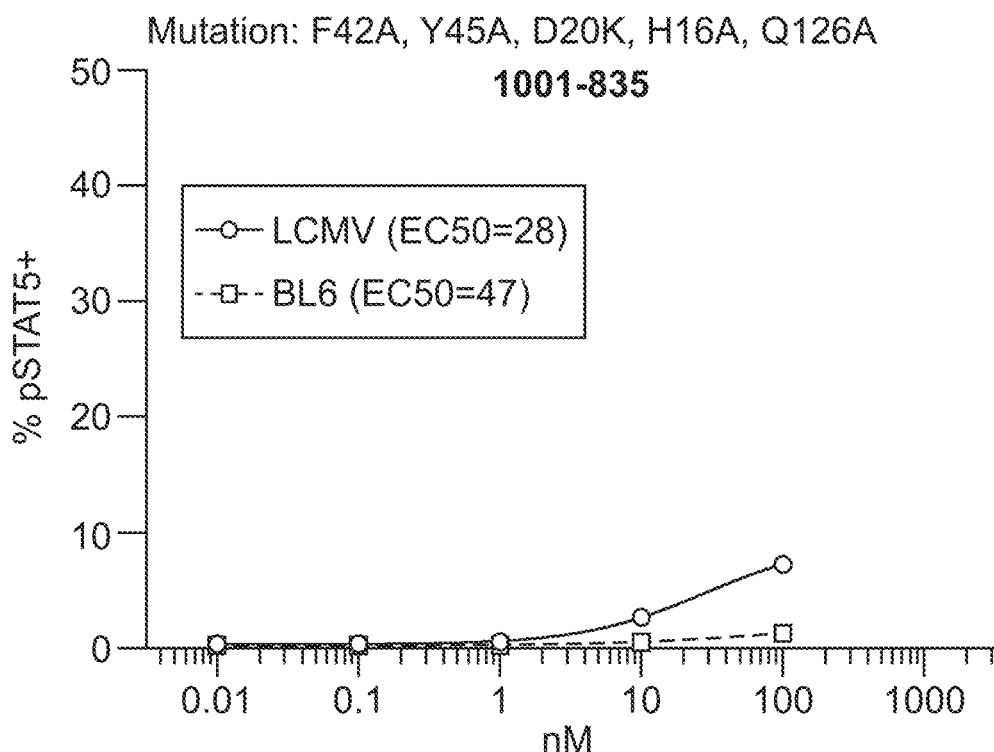

FIG. 14F (Cont.)
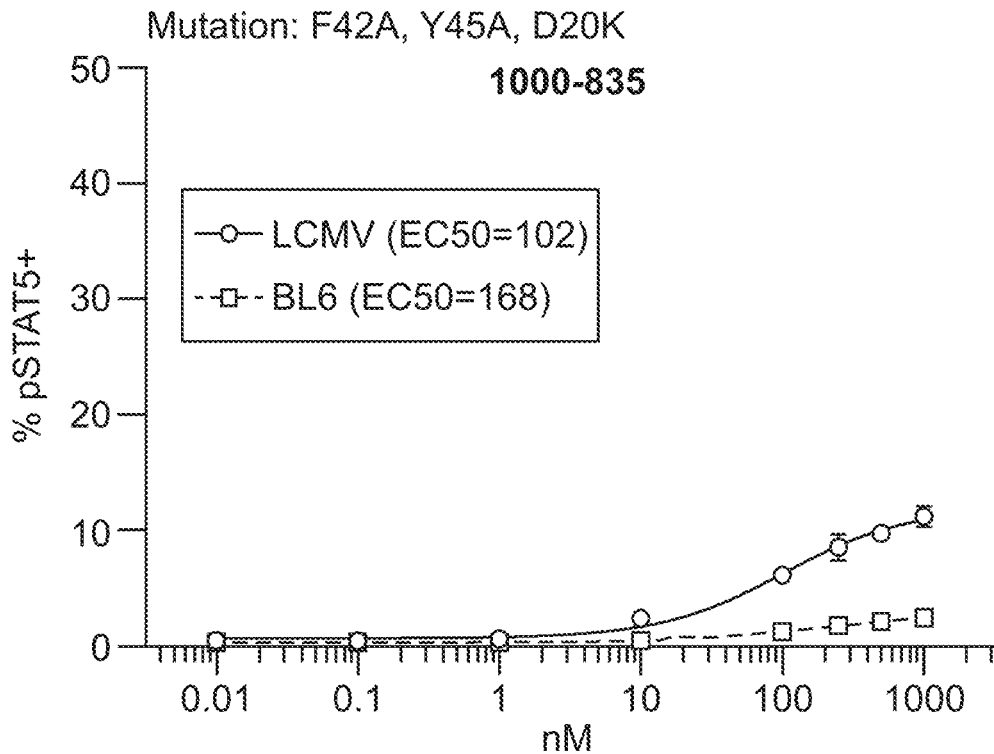
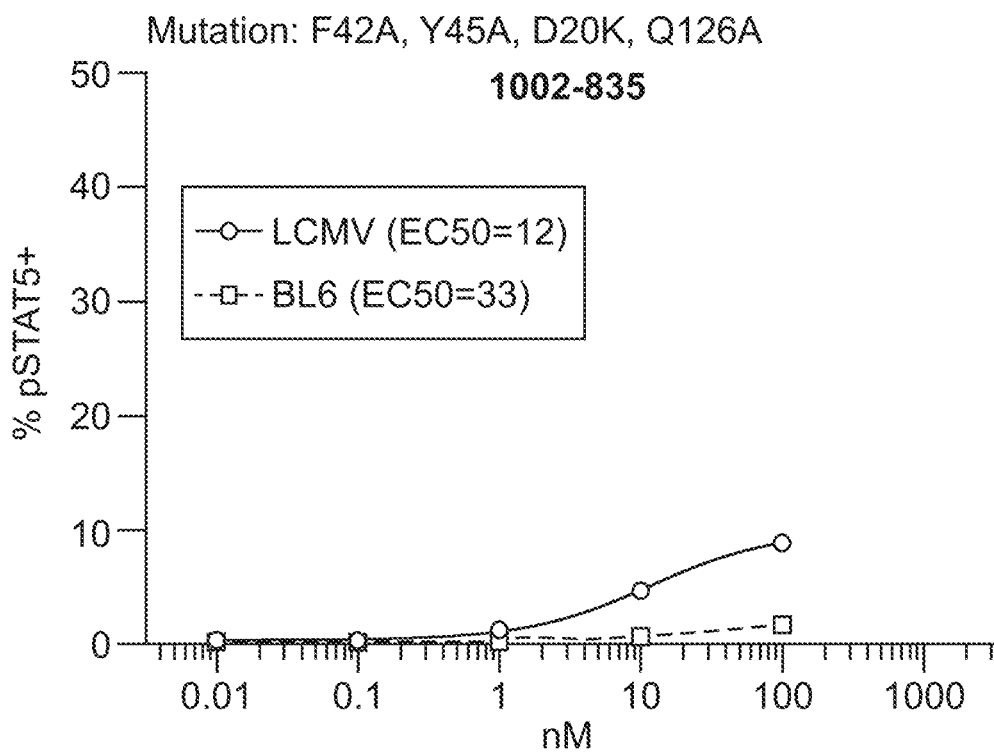

FIG. 15
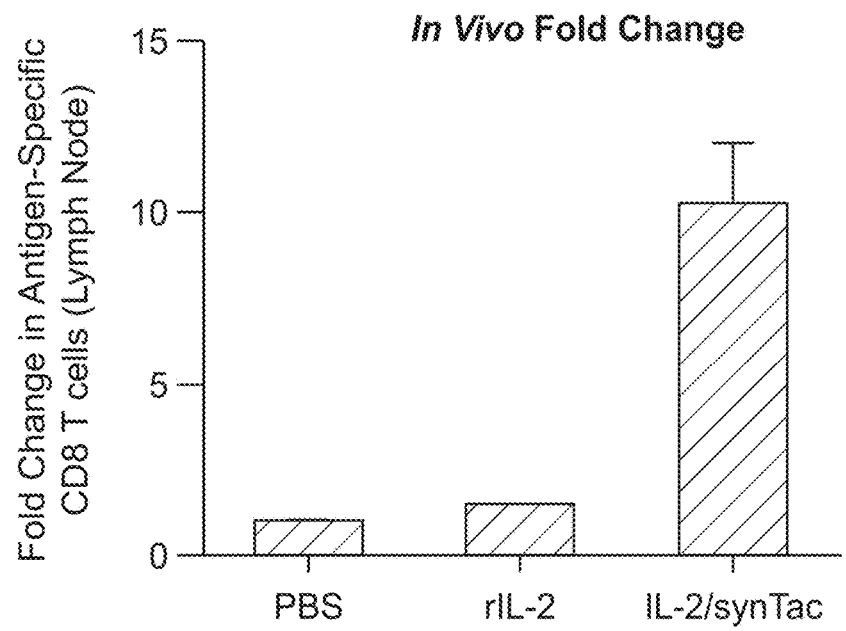
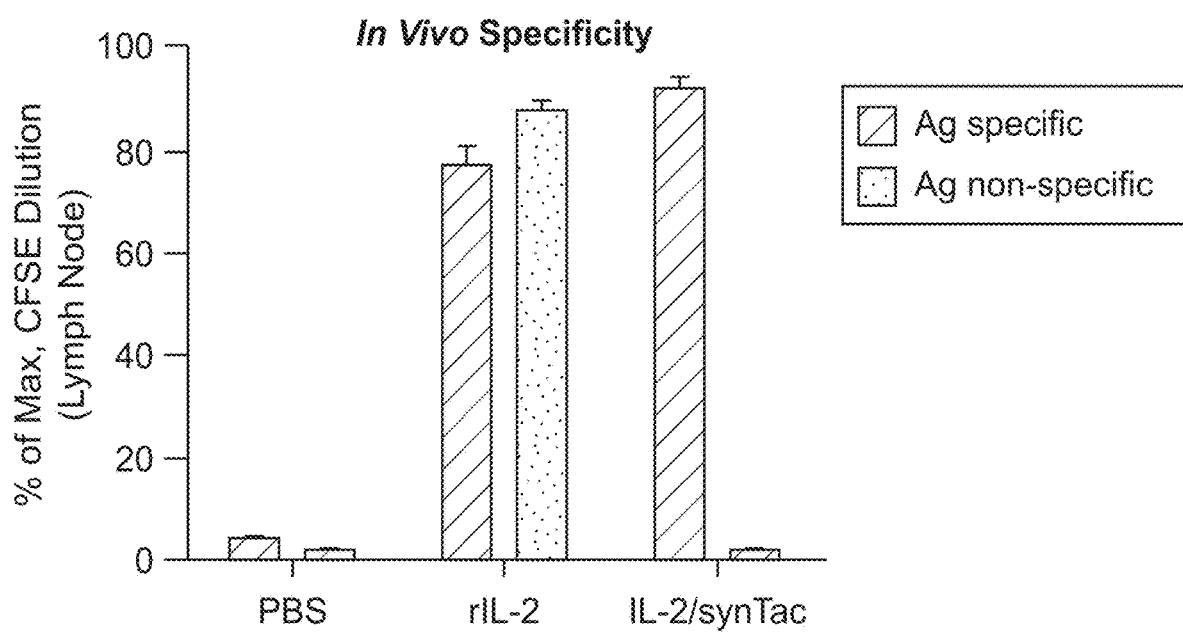

FIG. 21

(SEQ ID NO:32)

CUE101-N297A with leader peptide

*MYRMQLLSCIALSLALVTNS*APTSSSTKKTQLQLEALLL**DLQMILNGINNYKNPKLTRML
TAKFYMPKKATELKHLQCLEEELKPLEEVLNLAQSKNFHLRPRDLISNINVIVLELKGSE
TTFMCEYADETATIVEFLNRWITFCQSIISTLTGGGGSGGGGSGGGGSGGGGSAPTSSST
KKTQLQLEALLLDLQMILNGINNYKNPKLTRMLTAKFYMPKKATELKHLQCLEEELKPLE
EVLNLAQSKNFHLRPRDLISNINVIVLELKGSETTFMCEYADETATIVEFLNRWITFCQS
IISTLT**GGGGSGGGGSGGGGSGGGGSGSHSMRYFFTSVSRPGRGEPRFIAVGYVDDTQFV
RFDSDAASQRMEPRAPWIEQEGPEYWDGETRKVKAHSQTHRVDLGTLRGAYNQSEAGSHT
VQRMYGCDVGSDWRFLRGYHQYAYDGKDYIALKEDLRSWTAADMAAQTTKHKWEAAHVAE
QLRAYLEGTCVEWLRRYLENGKETLQRTDAPKTHMTHHAVSDHEATLRCWALSFYPAEIT
LTWQRDGEDQTQDTELVETRPCGDGTFQKWAAVVVPSGQEQRYTCHVQHEGLPKPLTLRW
EAAAGG**DKTHTCPPCPAPELLGGPSVFLFPPKPDTLMISRTPEVTCVVVDVSHEDPEVK
FNWYVDGVEVHNAKTKPREEQYASTYRVVSVLTVLHQDWLNGKEYKCKVSNKALPAPIEK
TISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK

Human IL2 Leader sequence – italics
IL-2 (H16A/F42A) – bold (with H16 and F42 underlined)
(G4S)4 Linkers – single underlined
MHC H chain Y84A; A236C– double underlined (with Y84A and A236C in bold)
AAAGG linker – single underlined
Human IgG1 Fc; N297A – (bold and underlined, with N297A unbolded)

FIG. 22

(SEQ ID NO:33)
CUE101-N297A without leader peptide

APTSSSTKKTQLQLE<u>A</u>LLLDLQMILNGINNYKNPKLTRML
TAKFYMPKKATELKHLQCLEEELKPLEEVLNLAQSK<u>N</u>FHLRPRDLISNINVIVLELKGSE
TTFMCEYADETATIVEFLNRWITFCQSIISTLT<u>GGGGSGGGGSGGGGSGGGGS</u>APTSSST
KKTQLQLE<u>A</u>LLLDLQMILNGINNYKNPKLTRMLTAKFYMPKKATELKHLQCLEEELKPLE
EVLNLAQSK<u>N</u>FHLRPRDLISNINVIVLELKGSETTFMCEYADETATIVEFLNRWITFCQS
IISTLT<u>GGGGSGGGGSGGGGSGGGGS</u><u><u>GSHSMRYFFTSVSRPGRGEPRFIAVGYVDDTQFV
RFDSDAASQRMEPRAPWIEQEGPEYWDGETRKVKAHSQTHRVDLGTLRGAYNQSEAGSHT
VQRMYGCDVGSDWRFLRGYHQYAYDGKDYIALKEDLRSWTAADMAAQTTKHKWEAAHVAE
QLRAYLEGTCVEWLRRYLENGKETLQRTDAPKTHMTHHAVSDHEATLRCWALSFYPAEIT
LTWQRDGEDQTQDTELVETRPCGDGTFQKWAAVVVPSGQEQRYTCHVQHEGLPKPLTLRW
E</u></u><u>AAAGG</u>
<u><u>FNWYVDGVEVHNAKTKPREEQYASTYRVVSVLTVLHQDWLNGKEYKCKVSNKALPAPIEK
TISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK</u></u>

IL-2 (H16A/F42A) – bold (with H16 and F42 underlined)
(G4S)4 Linkers – single underlined
MHC H chain Y84A; A236C– double underlined (with Y84A and A236C in bold)
AAAGG linker – single underlined
Human IgG1 Fc; N297A – (bold and underlined, with N297A unbolded)

FIG. 23A (SEQ ID NO:34)
CUE101-N297A
1360:

*ATGTACAGGATGCAACTCCTGTCTTGCATTGCACTAAGTCTTGCACTTGTCACAAACAGT*GCACCTACTTC
AAGTTCTACAAAGAAAACACAGCTACAACTGGAG GCA TTACTGCTGGATTTACAGATGATTTTGAATG
GAATTAATAATTACAAGAATCCCAAACTCACCAGGATGCTCACA GCA AAGTTTTACATGCCCAAGAAG
GCCACAGAACTGAAACATCTTCAGTGTCTAGAAGAAGAACTCAAACCTCTGGAGGAAGTGCTAAATTT
AGCTCAAAGCAAAAACTTTCACTTAAGACCCAGGGACTTAATCAGCAATATCAACGTAATAGTTCTGGA
ACTAAAGGGATCTGAAACAACATTCATGTGTGAATATGCTGATGAGACAGCAACCATTGTAGAATTTC
TGAACAGATGGATTACCTTTTGTCAAAGCATCATCTCAACACTGACTGGAGGCGGAGGATCTGGTGGTG
GAGGTTCTGGTGGTGGGGGATCTGGAGGCGGAGGATCTGCACCTACTTCAAGTTCTACAAAGAAAACA
CAGCTACAACTGGAG GCA TTACTGCTGGATTTACAGATGATTTTGAATGGAATTAATAATTACAAGAAT
CCCAAACTCACCAGGATGCTCACA GCA AAGTTTTACATGCCCAAGAAGGCCACAGAACTGAAACATCTT
CAGTGTCTAGAAGAAGAACTCAAACCTCTGGAGGAAGTGCTAAATTTAGCTCAAAGCAAAAACTTTCA
CTTAAGACCCAGGGACTTAATCAGCAATATCAACGTAATAGTTCTGGAACTAAAGGGATCTGAAACAA
CATTCATGTGTGAATATGCTGATGAGACAGCAACCATTGTAGAATTTCTGAACAGATGGATTACCTTTT
GTCAAAGCATCATCTCAACACTGACTGGAGGCGGAGGATCTGGTGGTGGAGGTTCTGGTGGTGGGGGA
TCTGGAGGCGGAGGATCTGGCTCTCACTCCATGAGGTATTTCTTCACATCCGTGTCCCGGCCCGGCCGCG
GGGAGCCCCGCTTCATCGCAGTGGGCTACGTGGACGACACGCAGTTCGTGCGGTTCGACAGCGACGCCG
CGAGCCAGAGGATGGAGCCGCGGGCGCCGTGGATAGAGCAGGAGGGTCCGGAGTATTGGGACGGGGA
GACACGGAAAGTGAAGGCCCACTCACAGACTCACCGAGTGGACCTGGGGACCCTGCGCGGCGCCTACA
ACCAGAGCGAGGCCGGTTCTCACACCGTCCAGAGGATGTATGGCTGCGACGTGGGGTCGGACTGGCGC
TTCCTCCGCGGGTACCACCAGTACGCCTACGACGGCAAGGATTACATCGCCCTGAAAGAGGACCTGCGCT
CTTGGACCGCGGCGGACATGGCAGCTCAGACCACCAAGCACAAGTGGGAGGCGGCCCATGTGGCGGAG
CAGTTGAGAGCCTACCTGGAGGGCACGTGCGTGGAGTGGCTCCGCAGATACCTGGAGAACGGGAAGGA
GACGCTGCAGCGCACGGACGCCCCCAAAACGCATATGACTCACCACGCTGTCTCTGACCATGAAGCCACC
CTGAGGTGCTGGGCCCTGAGCTTCTACCCTGCGGAGATCACACTGACCTGGCAGCGGGATGGGGAGGA
CCAGACCCAGGACACGGAGCTCGTGGAGACCAGGCCTTGCGGGGATGGAACCTTCCAGAAGTGGGCGG
CTGTGGTGGTGCCTTCTGGACAGGAGCAGAGATACACCTGCCATGTGCAGCATGAGGGTTTGCCCAAGC
CCCTCACCCTGAGATGGGAGGCAGCTGCGGGTGGC**GACAAAACTCACACATGCCCACCGTGCCCAGCA
CCTGAACTCCTGGGGGGACCGTCAGTCTTCCTCTTCCCCCCAAAACCCAAGGACACCCTCATGATCTCCC
GGACCCCTGAGGTCACATGCGTGGTGGTGGACGTGAGCCACGAAGACCCTGAGGTCAAGTTCAACTG**

FIG. 23A (Cont.)

<u>GTACGTGGACGGCGTGGAGGTGCATAATGCCAAGACAAAGCCGCGGGAGGAGCAGTAC</u>GCA<u>AGCAC</u>
<u>GTACCGTGTGGTCAGCGTCCTCACCGTCCTGCACCAGGACTGGCTGAATGGCAAGGAGTACAAGTGCA</u>
<u>AGGTCTCCAACAAAGCCCTCCCAGCCCCCATCGAGAAAACCATCTCCAAAGCCAAAGGGCAGCCCCGA</u>
<u>GAACCACAGGTGTACACCCTGCCCCCATCCCGGGAGGAGATGACCAAGAACCAGGTCAGCCTGACCTG</u>
<u>CCTGGTCAAAGGCTTCTATCCCAGCGACATCGCCGTGGAGTGGGAGAGCAATGGGCAGCCGGAGAAC</u>
<u>AACTACAAGACCACGCCTCCCGTGCTGGACTCCGACGGCTCCTTCTTCCTCTACAGCAAGCTCACCGTGG</u>
<u>ACAAGAGCAGATGGCAGCAGGGGAACGTCTTCTCATGCTCCGTGATGCACGAGGCTCTGCACAACCAC</u>
<u>TACACGCAGAAGTCCCTCTCCCTGTCTCCGGGTAAA</u>TAGTGA

FIG. 23B

Human IL2 Leader sequence – italics
Human IL2; H16A=<u>GCA</u>; F42A=<u>GCA</u> – bold (with GCA underlined)
(G4S)4 linker – single underlined
Human A0201; Y84A=<u>GCC</u>; A236C=<u>TGC</u>
AAAGG linker – single underlined
Human IgG1 Fc; N297A= <u>*GCA*</u>; AGG to <u>AGA</u> (still R) and AGC to <u>TCC</u> (still S) – (bold and underlined, with GCA italicized)
Stop codons (TAGTGA)

FIG. 24

(SEQ ID NO:35)
CUE101-LALA with leader peptide

*MYRMQLLSCIALSLALVTNS*APTSSSTKKTQLQLEALLLDLQMILNGINNYKNPKLTRML
TAKFYMPKKATELKHLQCLEEELKPLEEVLNLAQSKNFHLRPRDLISNINVIVLELKGSE
TTFMCEYADETATIVEFLNRWITFCQSIISTLTGGGGSGGGGSGGGGSGGGGSAPTSSST
KKTQLQLEALLLDLQMILNGINNYKNPKLTRMLTAKFYMPKKATELKHLQCLEEELKPLE
EVLNLAQSKNFHLRPRDLISNINVIVLELKGSETTFMCEYADETATIVEFLNRWITFCQS
IISTLTGGGGSGGGGSGGGGSGGGGSGSHSMRYFFTSVSRPGRGEPRFIAVGYVDDTQFV
RFDSDAASQRMEPRAPWIEQEGPEYWDGETRKVKAHSQTHRVDLGTLRGAYNQSEAGSHT
VQRMYGCDVGSDWRFLRGYHQYAYDGKDYIALKEDLRSWTAADMAAQTTKHKWEAAHVAE
QLRAYLEGTCVEWLRRYLENGKETLQRTDAPKTHMTHHAVSDHEATLRCWALSFYPAEIT
LTWQRDGEDQTQDTELVETRCGDGTFQKWAAVVVPSGQEQRYTCHVQHEGLPKPLTLRW
EAAAGGDKTHTCPPCPAPEAAGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIEK
TISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK

Leader peptide – italics
IL-2 (H16A/F42A) – bold (with H16 and F42 underlined)
(G4S)4 Linkers – single underlined
MHC H chain Y84A; A236C – double underlined (with Y84A and A236C in bold)
AAAGG linker – single underlined
Human IgG1 Fc; L234A; L235A – (bold and underlined, with L234A and L235A unbolded)

FIG. 25

(SEQ ID NO:36)
CUE101-LALA without leader peptide

APTSSSTKKTQLQLEALLLDLQMILNGINNYKNPKLTRML
TAKFYMPKKATELKHLQCLEEELKPLEEVLNLAQSKNFHLRPRDLISNINVIVLELKGSE
TTFMCEYADETATIVEFLNRWITFCQSIISTLT<u>GGGGSGGGGSGGGGSGGGGS</u>APTSSST
KKTQLQLEALLLDLQMILNGINNYKNPKLTRMLTAKFYMPKKATELKHLQCLEEELKPLE
EVLNLAQSKNFHLRPRDLISNINVIVLELKGSETTFMCEYADETATIVEFLNRWITFCQS
IISTLT<u>GGGGSGGGGSGGGGSGGGGS</u>G<u>SHSMRYFFTSVSRPGRGEPRFIAVGYVDDTQFV</u>
<u>RFDSDAASQRMEPRAPWIEQEGPEYWDGETRKVKAHSQTHRVDLGTLRGAYNQSEAGSHT</u>
<u>VQRMYGCDVGSDWRFLRGYHQYAYDGKDYIALKEDLRSWTAADMAAQTTKHKWEAAHVAE</u>
<u>QLRAYLEGTCVEWLRRYLENGKETLQRTDAPKTHMTHHAVSDHEATLRCWALSFYPAEIT</u>
<u>LTWQRDGEDQTQDTELVETRPCGDGTFQKWAAVVVPSGQEQRYTCHVQHEGLPKPLTLRW</u>
EAAAGGDKTHTCPPCPAPEAAGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIEK
TISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK

IL-2 (H16A/F42A) – bold (with H16 and F42 underlined)
(G4S)4 Linkers – single underlined
MHC H chain Y84A; A236C – double underlined (with Y84A and A236C in bold)
AAAGG linker – single underlined
Human IgG1 Fc; L234A; L235A – (bold and underlined, with L234A and L235A unbolded)

FIG. 26A (SEQ ID NO:37)
CUE101-LALA: nucleotide sequence encoding CUE101-LALA with leader peptide

*ATGTACAGGATGCAACTCCTGTCTTGCATTGCACTAAGTCTTGCACTTGTCACAAACAGT*GCACCTACTTC
AAGTTCTACAAAGAAAACACAGCTACAACTGGAGGCATTACTGCTGGATTTACAGATGATTTTGAATG
GAATTAATAATTACAAGAATCCCAAACTCACCAGGATGCTCACAGCAAAGTTTTACATGCCCAAGAAG
GCCACAGAACTGAAACATCTTCAGTGTCTAGAAGAAGAACTCAAACCTCTGGAGGAAGTGCTAAATTT
AGCTCAAAGCAAAAACTTTCACTTAAGACCCAGGGACTTAATCAGCAATATCAACGTAATAGTTCTGGA
ACTAAAGGGATCTGAAACAACATTCATGTGTGAATATGCTGATGAGACAGCAACCATTGTAGAATTTC
TGAACAGATGGATTACCTTTTGTCAAAGCATCATCTCAACACTGACTGGAGGCGGAGGATCTGGTGGTG
GAGGTTCTGGTGGTGGGGGATCTGGAGGCGGAGGATCT GCACCTACTTCAAGTTCTACAAAGAAAACA
CAGCTACAACTGGAGGCATTACTGCTGGATTTACAGATGATTTTGAATGGAATTAATAATTACAAGAAT
CCCAAACTCACCAGGATGCTCACAGCAAAGTTTTACATGCCCAAGAAGGCCACAGAACTGAAACATCTT
CAGTGTCTAGAAGAAGAACTCAAACCTCTGGAGGAAGTGCTAAATTTAGCTCAAAGCAAAAACTTTCA
CTTAAGACCCAGGGACTTAATCAGCAATATCAACGTAATAGTTCTGGAACTAAAGGGATCTGAAACAA
CATTCATGTGTGAATATGCTGATGAGACAGCAACCATTGTAGAATTTCTGAACAGATGGATTACCTTTT
GTCAAAGCATCATCTCAACACTGACTGGAGGCGGAGGATCTGGTGGTGGAGGTTCTGGTGGTGGGGGA
TCTGGAGGCGGAGGATCTGGCTCTCACTCCATGAGGTATTTCTTCACATCCGTGTCCCGGCCCGGCCGCG
GGGAGCCCCGCTTCATCGCAGTGGGCTACGTGGACGACACGCAGTTCGTGCGGTTCGACAGCGACGCCG
CGAGCCAGAGGATGGAGCCGCGGGCGCCGTGGATAGAGCAGGAGGGTCCGGAGTATTGGGACGGGGA
GACACGGAAAGTGAAGGCCCACTCACAGACTCACCGAGTGGACCTGGGGACCCTGCGCGGCGCCTACA
ACCAGAGCGAGGCCGGTTCTCACACCGTCCAGAGGATGTATGGCTGCGACGTGGGGTCGGACTGGCGC
TTCCTCCGCGGGTACCACCAGTACGCCTACGACGGCAAGGATTACATCGCCCTGAAAGAGGACCTGCGCT
CTTGGACCGCGGCGGACATGGCAGCTCAGACCACCAAGCACAAGTGGGAGGCGGCCCATGTGGCGGAG
CAGTTGAGAGCCTACCTGGAGGGCACGTGCGTGGAGTGGCTCCGCAGATACCTGGAGAACGGGAAGGA
GACGCTGCAGCGCACGGACGCCCCCAAAACGCATATGACTCACCACGCTGTCTCTGACCATGAAGCCACC
CTGAGGTGCTGGGCCCTGAGCTTCTACCCTGCGGAGATCACACTGACCTGGCAGCGGGATGGGGAGGA
CCAGACCCAGGACACGGAGCTCGTGGAGACCAGGCCTTGCGGGGATGGAACCTTCCAGAAGTGGGCGG
CTGTGGTGGTGCCTTCTGGACAGGAGCAGAGATACACCTGCCATGTGCAGCATGAGGGTTTGCCCAAGC
CCCTCACCCTGAGATGGGAGGCAGCTGCGGGTGGCGACAAAACTCACACATGCCCACCGTGCCCAGCA
CCTGAAGCCGCCGGGGGACCGTCAGTCTTCCTCTTCCCCCCAAAACCCAAGGACACCCTCATGATCTCCC
GGACCCCTGAGGTCACATGCGTGGTGGTGGACGTGAGCCACGAAGACCCTGAGGTCAAGTTCAACTG

FIG. 26A (Cont.)

GTACGTGGACGGCGTGGAGGTGCATAATGCCAAGACAAAGCCGCGGGAGGAGCAGTACAACAGCAC
GTACCGTGTGGTCAGCGTCCTCACCGTCCTGCACCAGGACTGGCTGAATGGCAAGGAGTACAAGTGCA
AGGTCTCCAACAAAGCCCTCCCAGCCCCCATCGAGAAAACCATCTCCAAAGCCAAAGGGCAGCCCCGA
GAACCACAGGTGTACACCCTGCCCCCATCCCGGGAGGAGATGACCAAGAACCAGGTCAGCCTGACCTG
CCTGGTCAAAGGCTTCTATCCCAGCGACATCGCCGTGGAGTGGGAGAGCAATGGGCAGCCGGAGAAC
AACTACAAGACCACGCCTCCCGTGCTGGACTCCGACGGCTCCTTCTTCCTCTACAGCAAGCTCACCGTGG
ACAAGAGCAGATGGCAGCAGGGGAACGTCTTCTCATGCTCCGTGATGCACGAGGCTCTGCACAACCAC
TACACGCAGAAGTCCCTCTCCCTGTCTCCGGGTAAATAGTGA

FIG. 26B

Human IL2 Leader sequence – italics
Human IL2; H16A=GCA; F42A=GCA – bold (with GCA underlined)
(G4S)4 linker – single underlined
Human A0201; Y84A=GCC; A236C=TGC – double underlined (with GCC and TGC in bold)
AAAGG linker – single underlined
Human IgG1 Fc; L234A, L235A = GCCGCC
    N297= AAC; AGG to AGA (still R) and AGC to TCC (still S) – (bold and underlined, with GCCGCC italicized)
Stop codons (TAGTGA)

FIG. 27

(SEQ ID NO:38)
CUE101-TM with leader peptide

*MYRMQLLSCIALSLALVTNS***APTSSSTKKTQLQLEALLLDLQMILNGINNYKNPKLTRML
TAKFYMPKKATELKHLQCLEEELKPLEEVLNLAQSKNFHLRPRDLISNINVIVLELKGSE
TTFMCEYADETATIVEFLNRWITFCQSIISTLTGGGGSGGGGSGGGGSGGGGSAPTSSST
KKTQLQLEALLLDLQMILNGINNYKNPKLTRMLTAKFYMPKKATELKHLQCLEEELKPLE
EVLNLAQSKNFHLRPRDLISNINVIVLELKGSETTFMCEYADETATIVEFLNRWITFCQS
IISTLT**GGGGSGGGGSGGGGSGGGGS<ins>GSHSMRYFFTSVSRPGRGEPRFIAVGYVDDTQFV
RFDSDAASQRMEPRAPWIEQEGPEYWDGETRKVKAHSQTHRVDLGTLRGAYNQSEAGSHT
VQRMYGCDVGSDWRFLRGYHQYAYDGKDYIALKEDLRSWTAADMAAQTTKHKWEAAHVAE
QLRAYLEGTCVEWLRRYLENGKETLQRTDAPKTHMTHHAVSDHEATLRCWALSFYPAEIT
LTWQRDGEDQTQDTELVETRPCGDGTFQKWAAVVVPSGQEQRYTCHVQHEGLPKPLTLRW
E</ins>AAAGGDKTHTCPPCPAPEF**EGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPASIEK
TISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK**

Leader peptide – italics
IL-2 (H16A/F42A) – bold (with H16 and F42 underlined)
(G4S)4 Linkers – single underlined
MHC H chain Y84A; A236C– double underlined (with Y84A and A236C in bold)
AAAGG linker – single underlined
Human IgG1 Fc; L234F; L235E; P331S – (bold and underlined, with L234F, L235E, and P331S unbolded)

FIG. 28

(SEQ ID NO:39)
CUE101-TM without leader peptide

APTSSSTKKTQLQLEALLLDLQMILNGINNYKNPKLTRML
TAKFYMPKKATELKHLQCLEEELKPLEEVLNLAQSKNFHLRPRDLISNINVIVLELKGSE
TTFMCEYADETATIVEFLNRWITFCQSIISTLTGGGGSGGGGSGGGGSGGGGSAPTSSST
KKTQLQLEALLLDLQMILNGINNYKNPKLTRMLTAKFYMPKKATELKHLQCLEEELKPLE
EVLNLAQSKNFHLRPRDLISNINVIVLELKGSETTFMCEYADETATIVEFLNRWITFCQS
IISTLTGGGGSGGGGSGGGGSGGGGSGSHSMRYFFTSVSRPGRGEPRFIAVGYVDDTQFV
RFDSDAASQRMEPRAPWIEQEGPEYWDGETRKVKAHSQTHRVDLGTLRGAYNQSEAGSHT
VQRMYGCDVGSDWRFLRGYHQYAYDGKDYIALKEDLRSWTAADMAAQTTKHKWEAAHVAE
QLRAYLEGTCVEWLRRYLENGKETLQRTDAPKTHMTHHAVSDHEATLRCWALSFYPAEIT
LTWQRDGEDQTQDTELVETRPCGDGTFQKWAAVVVPSGQEQRYTCHVQHEGLPKPLTLRW
EAAAGG DKTHTCPPCPAPEFEGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPASIEK
TISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK

IL-2 (H16A/F42A) — bold (with H16 and F42 underlined)
(G4S)4 Linkers — single underlined
MHC H chain Y84A; A236C — double underlined (with Y84A and A236C in bold)
AAAGG linker — single underlined
Human IgG1 Fc; L234F; L235E; P331S — (bold and underlined, with L234F, L235E, and P331S unbolded)

FIG. 29A (SEQ ID NO:40)

CUE101-TM: nucleotide sequence encoding CUE101-TM with leader sequence

*ATGTACAGGATGCAACTCCTGTCTTGCATTGCACTAAGTCTTGCACTTGTCACAAACAGT*GCACCTACTTC
AAGTTCTACAAAGAAAACACAGCTACAACTGGAGGCATTACTGCTGGATTTACAGATGATTTTGAATG
GAATTAATAATTACAAGAATCCCAAACTCACCAGGATGCTCACAGCAAAGTTTTACATGCCCAAGAAG
GCCACAGAACTGAAACATCTTCAGTGTCTAGAAGAAGAACTCAAACCTCTGGAGGAAGTGCTAAATTT
AGCTCAAAGCAAAAACTTTCACTTAAGACCCAGGGACTTAATCAGCAATATCAACGTAATAGTTCTGGA
ACTAAAGGGATCTGAAACAACATTCATGTGTGAATATGCTGATGAGACAGCAACCATTGTAGAATTTC
TGAACAGATGGATTACCTTTTGTCAAAGCATCATCTCAACACTGACTGGAGGCGGAGGATCTGGTGGTG
GAGGTTCTGGTGGTGGGGGATCTGGAGGCGGAGGATCTGCACCTACTTCAAGTTCTACAAAGAAAACA
CAGCTACAACTGGAGGCATTACTGCTGGATTTACAGATGATTTTGAATGGAATTAATAATTACAAGAAT
CCCAAACTCACCAGGATGCTCACAGCAAAGTTTTACATGCCCAAGAAGGCCACAGAACTGAAACATCTT
CAGTGTCTAGAAGAAGAACTCAAACCTCTGGAGGAAGTGCTAAATTTAGCTCAAAGCAAAAACTTTCA
CTTAAGACCCAGGGACTTAATCAGCAATATCAACGTAATAGTTCTGGAACTAAAGGGATCTGAAACAA
CATTCATGTGTGAATATGCTGATGAGACAGCAACCATTGTAGAATTTCTGAACAGATGGATTACCTTTT
GTCAAAGCATCATCTCAACACTGACTGGAGGCGGAGGATCTGGTGGTGGAGGTTCTGGTGGTGGGGGA
TCTGGAGGCGGAGGATCTGGCTCTCACTCCATGAGGTATTTCTTCACATCCGTGTCCCGGCCCGGCCGCG
GGGAGCCCCGCTTCATCGCAGTGGGCTACGTGGACGACACGCAGTTCGTGCGGTTCGACAGCGACGCCG
CGAGCCAGAGGATGGAGCCGCGGGCGCCGTGGATAGAGCAGGAGGGTCCGGAGTATTGGGACGGGGA
GACACGGAAAGTGAAGGCCCACTCACAGACTCACCGAGTGGACCTGGGGACCCTGCGCGGCGCCTACA
ACCAGAGCGAGGCCGGTTCTCACACCGTCCAGAGGATGTATGGCTGCGACGTGGGGTCGGACTGGCGC
TTCCTCCGCGGGTACCACCAGTACGCCTACGACGGCAAGGATTACATCGCCCTGAAAGAGGACCTGCGCT
CTTGGACCGCGGCGGACATGGCAGCTCAGACCACCAAGCACAAGTGGGAGGCGGCCCATGTGGCGGAG
CAGTTGAGAGCCTACCTGGAGGGCACGTGCGTGGAGTGGCTCCGCAGATACCTGGAGAACGGGAAGGA
GACGCTGCAGCGCACGGACGCCCCCAAAACGCATATGACTCACCACGCTGTCTCTGACCATGAAGCCACC
CTGAGGTGCTGGGCCCTGAGCTTCTACCCTGCGGAGATCACACTGACCTGGCAGCGGGATGGGGAGGA
CCAGACCCAGGACACGGAGCTCGTGGAGACCAGGCCTGCGGGGATGGAACCTTCCAGAAGTGGGCGG
CTGTGGTGGTGCCTTCTGGACAGGAGCAGAGATACACCTGCCATGTGCAGCATGAGGGTTTGCCCAAGC
CCCTCACCCTGAGATGGGAGGCAGCTGCGGGTGGCGACAAAACTCACACATGCCCACCGTGCCCAGCA
CCTGAA*TTC*GAGGGGGGACCGTCAGTCTTCCTCTTCCCCCCAAAACCCAAGGACACCCTCATGATCTCCC
GGACCCCTGAGGTCACATGCGTGGTGGTGGACGTGAGCCACGAAGACCCTGAGGTCAAGTTCAACTG

FIG. 29A (Cont.)

GTACGTGGACGGCGTGGAGGTGCATAATGCCAAGACAAAGCCGCGGGAGGAGCAGTACAACAGCAC
GTACCGTGTGGTCAGCGTCCTCACCGTCCTGCACCAGGACTGGCTGAATGGCAAGGAGTACAAGTGCA
AGGTCTCCAACAAAGCCCTCCCAGCCAGCATCGAGAAAACCATCTCCAAAGCCAAAGGGCAGCCCCGA
GAACCACAGGTGTACACCCTGCCCCCATCCCGGGAGGAGATGACCAAGAACCAGGTCAGCCTGACCTG
CCTGGTCAAAGGCTTCTATCCCAGCGACATCGCCGTGGAGTGGGAGAGCAATGGGCAGCCGGAGAAC
AACTACAAGACCACGCCTCCCGTGCTGGACTCCGACGGCTCCTTCTTCCTCTACAGCAAGCTCACCGTGG
ACAAGAGCAGATGGCAGCAGGGGAACGTCTTCTCATGCTCCGTGATGCACGAGGCTCTGCACAACCAC
TACACGCAGAAGTCCCTCTCCCTGTCTCCGGGTAAATAGTGA

FIG. 29B

Human IL2 Leader sequence – italics
Human IL2; H16A=GCA; F42A=GCA – bold (with GCA underlined)
(G4S)4 linker – single underlined
Human A0201; Y84A=GCC; A236C=TGC – double underlined (with GCC and TGC in bold)
AAAGG linker – single underlined
Human IgG1 Fc; L234F=TTC; L235E=GAG; P331S=AGC
    N297= AAC; AGG to AGA (still R) and AGC to TCC (still S) – (bold and underlined, with TTC, GAG, AAC, and AGC italicized)
Stop codons (TAGTGA)

FIG. 30

(SEQ ID NO:41)
1274:

*MSRSVALAVLALLSLSGLEA*YMLDLQPETT<u>GGGGSGGGGSGGGGS</u><u><u>IQRTPKIQVYSCHPA
ENGKSNFLNCYVSGFHPSDIEVDLLKNGERIEKVEHSDLSFSKDWSFYLLYYTEFTPTEK
DEYACRVNHVTLSQPKIVKWDRDM</u></u>

Human β2M leader sequence -- italics
E7(11-20) – bold and underlined
(G4S)3 linker – single underlined
Human β2M; R12C– double underlined (R12C bolded)

FIG. 31

(SEQ ID NO:42)
1274 without leader peptide
<u>YMLDLQPETT</u><u>GGGGSGGGGSGGGGS</u>IQ<u><u>YMLDLQPETT</u></u><u>GGGGSGGGGSGGGGS</u><u><u>IQRTPKIQVYSCH
PAENGKSNFLNCYVSGFHPSDIEVDLLKNGERIEKVEHSDLSFSKDWSFYLLYYTEFTPTEKDEY
ACRVNHVTLSQPKIVKWDRDMRTPKIQVYSCHPAENGKSNFLNCYVSGFHPSDIEVDLLKNGERI
EKVEHSDLSFSKDWSFYLLYYTEFTPTEKDEYACRVNHVTLSQPKIVKWDRDM</u></u>

E7(11-20) – bold and underlined (YMLDLQPETT; SEQ ID NO:77)
(G4S)3 linker – single underlined (GGGGSGGGGSGGGGS (SEQ ID NO: 207)
Human β2M; R12C – double underlined

FIG. 32

(SEQ ID NO:43)

1274 nucleotide sequence encoding 1274 with leader peptide

*ATGTCTCGCTCCGTGGCCTTAGCTGTGCTCGCGCTACTCTCTCTTTCTGGCCTGGAGGCC*<u>TACATGCTCGA</u>
<u>TTTGCAGCCCGAAACGACG</u><u>GGTGGAGGTGGTTCTGGAGGAGGCGGTTCGGGCGGAGGTGGTAGT</u><u>ATC</u>
<u>CAGCGTACTCCAAAGATTCAGGTTTACTCATGCCATCCAGCAGAGAATGGAAAGTCAAATTTCCTGAATT</u>
<u>GCTATGTGTCTGGGTTTCATCCATCCGACATTGAAGTTGACTTACTGAAGAATGGAGAGAGAATTGAAAA</u>
<u>AGTGGAGCATTCAGACTTGTCTTTCAGCAAGGACTGGTCTTTCTATCTCTTGTATTATACTGAATTCACCCC</u>
<u>CACTGAAAAAGATGAGTATGCCTGCCGTGTGAACCACGTGACTTTGTCACAGCCCAAGATAGTTAAGTG</u>
<u>GGATCGAGACATG</u>TAGTGA

Human β2M leader sequence -- italics
E7(11-20) – bold and underlined
(G4S)3 linker – single underlined
Human β2M; R12C=<u>TGC</u> – double underlined (TGC in bold)
Stop codons TAGTGA

FIG. 33A (SEQ ID NO:44)

<u>WT Human IgG1 Fc Sequence:</u>

DKTHTCPPCPAPE<u>LL</u>GGPSVFLFPPKPKDTLMISRTPEVTCVVVDVSHEDPEVKFNWYVDGVE
VHNAKTKPREEQY<u>N</u>STYRVVSVLTVLHQDWLNGKEYKCKVSNKALPA<u>P</u>IEKTISKAKGQPREP
QVYTLPPSREEMTKNQVSLTCLVKGFYPSDIAVEWESNGQPENNYKTTPPVLDSDGSFFLYSK
LTVDKSRWQQGNVFSCSVMHEALHNHYTQKSLSLSPGK

FIG. 33B

(SEQ ID NO:45)

Human IgG1 Fc Mutant: L234F/L235E/P331S (Triple Mutant "TM")

DKTHTCPPCPAPEFEGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPASIEKTISKAKGQPREP
QVYTLPPSREEMTKNQVSLTCLVKGFYPSDIAVEWESNGQPENNYKTTPPVLDSDGSFFLYSK
LTVDKSRWQQGNVFSCSVMHEALHNHYTQKSLSLSPGK

FIG. 33C

(SEQ ID NO:46)

Human IgG1 Fc Mutant: N297A

DKTHTCPPCPAPELLGGPSVFLFPPKPKDTLMISRTPEVTCVVVDVSHEDPEVKFNWYVDGVE
VHNAKTKPREEQYASTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGSFFLYSK
LTVDKSRWQQGNVFSCSVMHEALHNHYTQKSLSLSPGK

FIG. 33D

(SEQ ID NO:47)

Human IgG1 Fc Mutant: L234A/L235A ("LALA")

DKTHTCPPCPAPEAAGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGSFFLYSK
LTVDKSRWQQGNVFSCSVMHEALHNHYTQKSLSLSPGK

Residue numbered according to EU index (Kabat Numbering)

FIG. 34A (SEQ ID NO:48)

B2M R12C

IQRTPKIQVYSCHPAENGKSNFLNCYVSGFHPSDIEVDLLKNGERIEKVEHSDLSFSKDWSFYLL
YYTEFTPTEKDEYACRVNHVTLSQPKIVKWDRDM

FIG. 34B (SEQ ID NO:49)

IL-2 (H16A; F42A)

APTSSSTKKTQLQLEALLLDLQMILNGINNYKNPKLTRMLTAKFYMPKKATELKHLQCLEEELKP
LEEVLNLAQSKNFHLRPRDLISNINVIVLELKGSETTFMCEYADETATIVEFLNRWITFCQSIIS
TLT

FIG. 34C (SEQ ID NO:50)

Class I MHC-H chain A0201 (Y84A; A236C)

GSHSMRYFFTSVSRPGRGEPRFIAVGYVDDTQFVRFDSDAASQRMEPRAPWIEQEGPEYWDGETR
KVKAHSQTHRVDLGTLRGAYNQSEAGSHTVQRMYGCDVGSDWRFLRGYHQYAYDGKDYIALKEDL
RSWTAADMAAQTTKHKWEAAHVAEQLRAYLEGTCVEWLRRYLENGKETLQRTDAPKTHMTHHAVS
DHEATLRCWALSFYPAEITLTWQRDGEDQTQDTELVETRPCGDGTFQKWAAVVVPSGQEQRYTCH
VQHEGLPKPLTLRWE

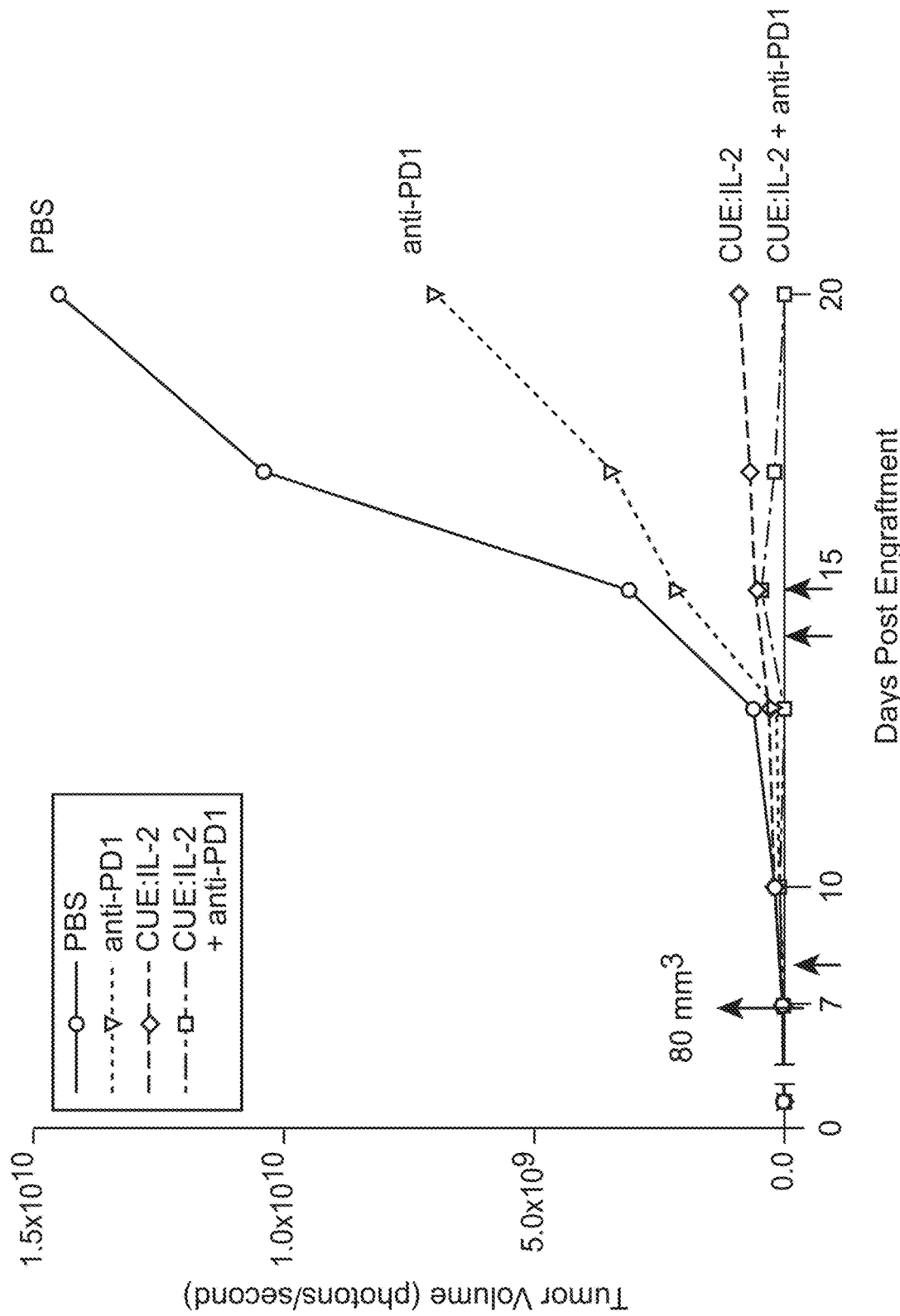

FIG. 36A

4-1-BBL
*Homo sapiens*
GenBank NP_003802
Cytoplasmic domain = 1-25
Transmembrane domain = 26-48
Ectodomain = 49-254
TNF homology domain = 80-254, 81-254, or 80-246

```
  1 MEYASDASLD PEAPWPPAPR ARACRVLPWA LVAGLLLLLL LAAACAVFLA CPWAVSGARA
 61 SPGSAASPRL REGPELSPDD PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:99)
```

FIG. 36B

K127
```
 81            PAGLLDLRQG MFAQLVAQNV LLIDGPLSWY SDPGLAGVSL
121 TGGLSYXEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:100)
```

FIG. 36C

K127
```
 81            PAGLLDLRQG MFAQLVAQNV LLIDGPLSWY SDPGLAGVSL
121 TGGLSYAEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:101)
```

FIG. 36D

Q227
```
 81            PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWXLTQ GATVLGLFRV
241 TPEIPAGLPS PRSE (SEQ ID NO:102)
```

FIG. 36E

M91
```
 81                      PAGLLDLRQG XFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:103)
```

FIG. 36F

F92
```
 81                      PAGLLDLRQG MXAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:104)
```

FIG. 36G

Q94
```
 81                      PAGLLDLRQG MFAXLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:105)
```

FIG. 36H

L95
```
 81                      PAGLLDLRQG MFAQXVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:106)
```

FIG. 36I

V96
```
 81                      PAGLLDLRQG MFAQLXAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:107)
```

FIG. 36J

Q98
```
 81            PAGLLDLRQG MFAQLVAXNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:108)
```

FIG. 36K

N99
```
 81            PAGLLDLRQG MFAQLVAQXV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:109)
```

FIG. 36L

V100
```
 81            PAGLLDLRQG MFAQLVAQNX LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:110)
```

FIG. 36M

L101
```
 81            PAGLLDLRQG MFAQLVAQNV XLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:111)
```

FIG. 36N

L102
```
 81            PAGLLDLRQG MFAQLVAQNV LXIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:112)
```

FIG. 36O

I103
 81                       PAGLLDLRQG MFAQLVAQNV LLXDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:113)

FIG. 36P

D104
 81                       PAGLLDLRQG MFAQLVAQNV LLIXGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:114)

FIG. 36Q

G105
 81                       PAGLLDLRQG MFAQLVAQNV LLIDXPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:115)

FIG. 36R

P106
 81                       PAGLLDLRQG MFAQLVAQNV LLIDGXLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:116)

FIG. 36S

L107
 81                       PAGLLDLRQG MFAQLVAQNV LLIDGPXSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:117)

FIG. 36T

S108
```
 81                      PAGLLDLRQG MFAQLVAQNV LLIDGPLXWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:118)
```

FIG. 36U

W109
```
 81                      PAGLLDLRQG MFAQLVAQNV LLIDGPLSXY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:119)
```

FIG. 36V

Y110
```
 81                      PAGLLDLRQG MFAQLVAQNV LLIDGPLSWX SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:120)
```

FIG. 36W

S111
```
 81                      PAGLLDLRQG MFAQLVAQNV LLIDGPLSWY XDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:121)
```

FIG. 36X

D112
```
 81                      PAGLLDLRQG MFAQLVAQNV LLIDGPLSWY SXPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:122)
```

P113
FIG. 36Y

```
 81            PAGLLDLRQG MFAQLVAQNV LLIDGPLSWY SDXGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:123)
```

G114
FIG. 36Z

```
 81            PAGLLDLRQG MFAQLVAQNV LLIDGPLSWY SDPXLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:124)
```

L115
FIG. 36AA

```
 81            PAGLLDLRQG MFAQLVAQNV LLIDGPLSWY SDPGXAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:125)
```

G117
FIG. 36BB

```
 81            PAGLLDLRQG MFAQLVAQNV LLIDGPLSWY SDPGLAXVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:126)
```

V118
FIG. 36CC

```
 81            PAGLLDLRQG MFAQLVAQNV LLIDGPLSWY SDPGLAGXSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:127)
```

```
 81                     PAGLLDLRQG MFAQLVAQNV LLIDGPLSWY SDPGLAGVXL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:128)
```

```
 81                     PAGLLDLRQG MFAQLVAQNV LLIDGPLSWY SDPGLAGVSX
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:129)
```

```
 81                     PAGLLDLRQG MFAQLVAQNV LLIDGPLSWY SDPGLAGVSL
121 XGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:130)
```

```
 81                     PAGLLDLRQG MFAQLVAQNV LLIDGPLSWY SDPGLAGVSL
121 TXGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:131)
```

```
 81                     PAGLLDLRQG MFAQLVAQNV LLIDGPLSWY SDPGLAGVSL
121 TGXLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:132)
```

FIG. 36II

L124
```
 81                       PAGLLDLRQG MFAQLVAQNV LLIDGPLSWY SDPGLAGVSL
121 TGGXSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:133)
```

FIG. 36JJ

S125
```
 81                       PAGLLDLRQG MFAQLVAQNV LLIDGPLSWY SDPGLAGVSL
121 TGGLXYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:134)
```

FIG. 36KK

Y126
```
 81                       PAGLLDLRQG MFAQLVAQNV LLIDGPLSWY SDPGLAGVSL
121 TGGLSXKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:135)
```

FIG. 36LL

E128
```
 81                       PAGLLDLRQG MFAQLVAQNV LLIDGPLSWY SDPGLAGVSL
121 TGGLSYKXDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:136)
```

FIG. 36MM

D129
```
 81                       PAGLLDLRQG MFAQLVAQNV LLIDGPLSWY SDPGLAGVSL
121 TGGLSYKEXT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:137)
```

FIG. 36NN

T130
```
 81                       PAGLLDLRQG MFAQLVAQNV LLIDGPLSWY SDPGLAGVSL
121 TGGLSYKEDX KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:138)
```

FIG. 36OO

K131
```
 81                       PAGLLDLRQG MFAQLVAQNV LLIDGPLSWY SDPGLAGVSL
121 TGGLSYKEDT XELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:139)
```

FIG. 36PP

E132
```
 81                       PAGLLDLRQG MFAQLVAQNV LLIDGPLSWY SDPGLAGVSL
121 TGGLSYKEDT KXLVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:140)
```

FIG. 36QQ

F144
```
 81                       PAGLLDLRQG MFAQLVAQNV LLIDGPLSWY SDPGLAGVSL
121 TGGLSYKEDT KELVVAKAGV YYVXFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:141)
```

FIG. 36RR

F145
```
 81                       PAGLLDLRQG MFAQLVAQNV LLIDGPLSWY SDPGLAGVSL
121 TGGLSYKEDT KELVVAKAGV YYVFXQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:142)
```

FIG. 36SS

Q146
```
 81                     PAGLLDLRQG MFAQLVAQNV LLIDGPLSWY SDPGLAGVSL
121 TGGLSYKEDT KELVVAKAGV YYVFFXLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:143)
```

FIG. 36TT

L147
```
 81                     PAGLLDLRQG MFAQLVAQNV LLIDGPLSWY SDPGLAGVSL
121 TGGLSYKEDT KELVVAKAGV YYVFFQXELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:144)
```

FIG. 36UU

E148
```
 81                     PAGLLDLRQG MFAQLVAQNV LLIDGPLSWY SDPGLAGVSL
121 TGGLSYKEDT KELVVAKAGV YYVFFQLXLR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:145)
```

FIG. 36VV

L149
```
 81                     PAGLLDLRQG MFAQLVAQNV LLIDGPLSWY SDPGLAGVSL
121 TGGLSYKEDT KELVVAKAGV YYVFFQLEXR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:146)
```

FIG. 36WW

R150
```
 81                     PAGLLDLRQG MFAQLVAQNV LLIDGPLSWY SDPGLAGVSL
121 TGGLSYKEDT KELVVAKAGV YYVFFQLELX RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:147)
```

```
 81                     PAGLLDLRQG MFAQLVAQNV LLIDGPLSWY SDPGLAGVSL
121 TGGLSYKEDT KELVVAKAGV YYVFFQLELR XVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:148)
```

```
 81                     PAGLLDLRQG MFAQLVAQNV LLIDGPLSWY SDPGLAGVSL
121 TGGLSYKEDT KELVVAKAGV YYVFFQLELR RXVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:149)
```

```
 81                     PAGLLDLRQG MFAQLVAQNV LLIDGPLSWY SDPGLAGVSL
121 TGGLSYKEDT KELVVAKAGV YYVFFQLELR RVXAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:150)
```

```
 81                     PAGLLDLRQG MFAQLVAQNV LLIDGPLSWY SDPGLAGVSL
121 TGGLSYKEDT KELVVAKAGV YYVFFQLELR RVVAXEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:151)
```

```
 81                     PAGLLDLRQG MFAQLVAQNV LLIDGPLSWY SDPGLAGVSL
121 TGGLSYKEDT KELVVAKAGV YYVFFQLELR RVVAGXGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:152)
```

FIG. 36CCC

G157
```
 81                     PAGLLDLRQG MFAQLVAQNV LLIDGPLSWY SDPGLAGVSL
121 TGGLSYKEDT KELVVAKAGV YYVFFQLELR RVVAGEXSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:153)
```

FIG. 36DDD

S158
```
 81                     PAGLLDLRQG MFAQLVAQNV LLIDGPLSWY SDPGLAGVSL
121 TGGLSYKEDT KELVVAKAGV YYVFFQLELR RVVAGEGXGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:154)
```

FIG. 36EEE

D184
```
 81                     PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVXLPPASS EARNSAFGFQ GRLLHLSAGQ RLGVHLHTEA RARHAWQLTQ GATVLGLFRV
241 TPEIPAGLPS PRSE (SEQ ID NO:155)
```

FIG. 36FFF

L185
```
 81                     PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDXPPASS EARNSAFGFQ GRLLHLSAGQ RLGVHLHTEA RARHAWQLTQ GATVLGLFRV
241 TPEIPAGLPS PRSE (SEQ ID NO:156)
```

FIG. 36GGG

P186
```
 81                     PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLXPASS EARNSAFGFQ GRLLHLSAGQ RLGVHLHTEA RARHAWQLTQ GATVLGLFRV
241 TPEIPAGLPS PRSE (SEQ ID NO:157)
```

P187
FIG. 36HHH
```
 81                      PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPXASS EARNSAFGFQ GRLLHLSAGQ RLGVHLHTEA RARHAWQLTQ GATVLGLFRV
241 TPEIPAGLPS PRSE (SEQ ID NO:158)
```

S189
FIG. 36III
```
 81                      PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPAXS EARNSAFGFQ GRLLHLSAGQ RLGVHLHTEA RARHAWQLTQ GATVLGLFRV
241 TPEIPAGLPS PRSE (SEQ ID NO:159)
```

S190
FIG. 36JJJ
```
 81                      PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASX EARNSAFGFQ GRLLHLSAGQ RLGVHLHTEA RARHAWQLTQ GATVLGLFRV
241 TPEIPAGLPS PRSE (SEQ ID NO:160)
```

E191
FIG. 36KKK
```
 81                      PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS XARNSAFGFQ GRLLHLSAGQ RLGVHLHTEA RARHAWQLTQ GATVLGLFRV
241 TPEIPAGLPS PRSE (SEQ ID NO:161)
```

R193
FIG. 36LLL
```
 81                      PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EAXNSAFGFQ GRLLHLSAGQ RLGVHLHTEA RARHAWQLTQ GATVLGLFRV
241 TPEIPAGLPS PRSE (SEQ ID NO:162)
```

FIG. 36MMM

N194
```
 81                      PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EAR{X}SAFGFQ GRLLHLSAGQ RLGVHLHTEA RARHAWQLTQ GATVLGLFRV
241 TPEIPAGLPS PRSE (SEQ ID NO:163)
```

FIG. 36NNN

S195
```
 81                      PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARN{X}AFGFQ GRLLHLSAGQ RLGVHLHTEA RARHAWQLTQ GATVLGLFRV
241 TPEIPAGLPS PRSE (SEQ ID NO:164)
```

FIG. 36OOO

F197
```
 81                      PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSA{X}GFQ GRLLHLSAGQ RLGVHLHTEA RARHAWQLTQ GATVLGLFRV
241 TPEIPAGLPS PRSE (SEQ ID NO:165)
```

FIG. 36PPP

Q210
```
 81                      PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAG{X} RLGVHLHTEA RARHAWQLTQ GATVLGLFRV
241 TPEIPAGLPS PRSE (SEQ ID NO:166)
```

FIG. 36QQQ

R211
```
 81                      PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ {X}LGVHLHTEA RARHAWQLTQ GATVLGLFRV
241 TPEIPAGLPS PRSE (SEQ ID NO:167)
```

FIG. 36RRR

L212
```
  81            PAGLLDLRQG MFAQLVAQNV LLIDGPLSWY SDPGLAGVSL
 121 TGGLSYKEDT KELVVAKAGV YYVFFQLELR RVVAGEGSGS VSLALHLQPL RSAAGAAALA
 181 LTVDLPPASS EARNSAFGFQ GRLLHLSAGQ RXGVHLHTEA RARHAWQLTQ GATVLGLFRV
 241 TPEIPAGLPS PRSE (SEQ ID NO:168)
```

FIG. 36SSS

G213
```
  81            PAGLLDLRQG MFAQLVAQNV LLIDGPLSWY SDPGLAGVSL
 121 TGGLSYKEDT KELVVAKAGV YYVFFQLELR RVVAGEGSGS VSLALHLQPL RSAAGAAALA
 181 LTVDLPPASS EARNSAFGFQ GRLLHLSAGQ RLXVHLHTEA RARHAWQLTQ GATVLGLFRV
 241 TPEIPAGLPS PRSE (SEQ ID NO:169)
```

FIG. 36TTT

V214
```
  81            PAGLLDLRQG MFAQLVAQNV LLIDGPLSWY SDPGLAGVSL
 121 TGGLSYKEDT KELVVAKAGV YYVFFQLELR RVVAGEGSGS VSLALHLQPL RSAAGAAALA
 181 LTVDLPPASS EARNSAFGFQ GRLLHLSAGQ RLGXHLHTEA RARHAWQLTQ GATVLGLFRV
 241 TPEIPAGLPS PRSE (SEQ ID NO:170)
```

FIG. 36UUU

H215
```
  81            PAGLLDLRQG MFAQLVAQNV LLIDGPLSWY SDPGLAGVSL
 121 TGGLSYKEDT KELVVAKAGV YYVFFQLELR RVVAGEGSGS VSLALHLQPL RSAAGAAALA
 181 LTVDLPPASS EARNSAFGFQ GRLLHLSAGQ RLGVXLHTEA RARHAWQLTQ GATVLGLFRV
 241 TPEIPAGLPS PRSE (SEQ ID NO:171)
```

FIG. 36VVV

L216
```
  81            PAGLLDLRQG MFAQLVAQNV LLIDGPLSWY SDPGLAGVSL
 121 TGGLSYKEDT KELVVAKAGV YYVFFQLELR RVVAGEGSGS VSLALHLQPL RSAAGAAALA
 181 LTVDLPPASS EARNSAFGFQ GRLLHLSAGQ RLGVHXHTEA RARHAWQLTQ GATVLGLFRV
 241 TPEIPAGLPS PRSE (SEQ ID NO:172)
```

FIG. 36WWW

H217
```
 81                       PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLXTEA RARHAWQLTQ GATVLGLFRV
241 TPEIPAGLPS PRSE (SEQ ID NO:173)
```

FIG. 36XXX

T218
```
 81                       PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHXEA RARHAWQLTQ GATVLGLFRV
241 TPEIPAGLPS PRSE (SEQ ID NO:174)
```

FIG. 36YYY

E219
```
 81                       PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTXA RARHAWQLTQ GATVLGLFRV
241 TPEIPAGLPS PRSE (SEQ ID NO:175)
```

FIG. 36ZZZ

R221
```
 81                       PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA XARHAWQLTQ GATVLGLFRV
241 TPEIPAGLPS PRSE (SEQ ID NO:176)
```

FIG. 36AAAA

R223
```
 81                       PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RAXHAWQLTQ GATVLGLFRV
241 TPEIPAGLPS PRSE (SEQ ID NO:177)
```

H224

FIG. 36BBBB

```
 81            PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARXAWQLTQ GATVLGLFRV
241 TPEIPAGLPS PRSE (SEQ ID NO:178)
```

W226

FIG. 36CCCC

```
 81            PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAXQLTQ GATVLGLFRV
241 TPEIPAGLPS PRSE (SEQ ID NO:179)
```

L228

FIG. 36DDDD

```
 81            PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQXTQ GATVLGLFRV
241 TPEIPAGLPS PRSE (SEQ ID NO:180)
```

T229

FIG. 36EEEE

```
 81            PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLXQ GATVLGLFRV
241 TPEIPAGLPS PRSE (SEQ ID NO:181)
```

Q230

FIG. 36FFFF

```
 81            PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTX GATVLGLFRV
241 TPEIPAGLPS PRSE (SEQ ID NO:182)
```

FIG. 36GGGG

G231
```
 81                       PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ XATVLGLFRV
241 TPEIPAGLPS PRSE (SEQ ID NO:183)
```

FIG. 36HHHH

T233
```
 81                       PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GAXVLGLFRV
241 TPEIPAGLPS PRSE (SEQ ID NO:184)
```

FIG. 36IIII

V234
```
 81                       PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATXLGLFRV
241 TPEIPAGLPS PRSE (SEQ ID NO:185)
```

FIG. 37

*Homo sapiens*
4-1BB
```
  1 mgnscyniva tlllvlnfer trslqdpcsn cpagtfcdnn rnqicspcpp nsfssaggqr
 61 tcdicrqckg vfrtrkecss tsnaecdctp gfhclgagcs mceqdckqgq eltkkgckdc
121 cfgtfndqkr gicrpwtncs ldgksvlvng tkerdvvcgp spadlspgas svtppapare
181 pghspqiisf flaltstall fllffltlrf svvkrgrkkl lyifkqpfmr pvqttqeedg
241 cscrfpeeee ggcel (SEQ ID NO:186)
```

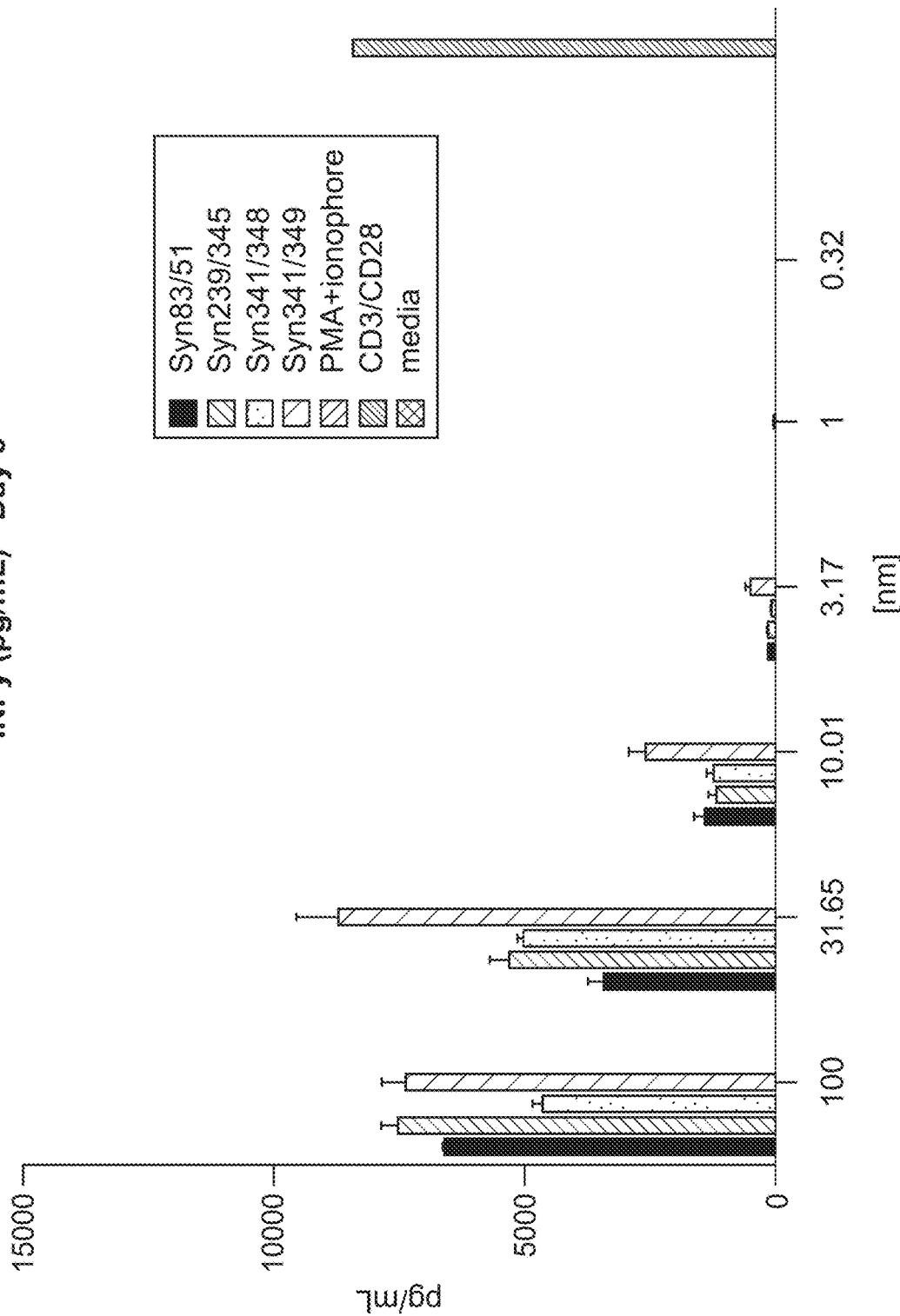

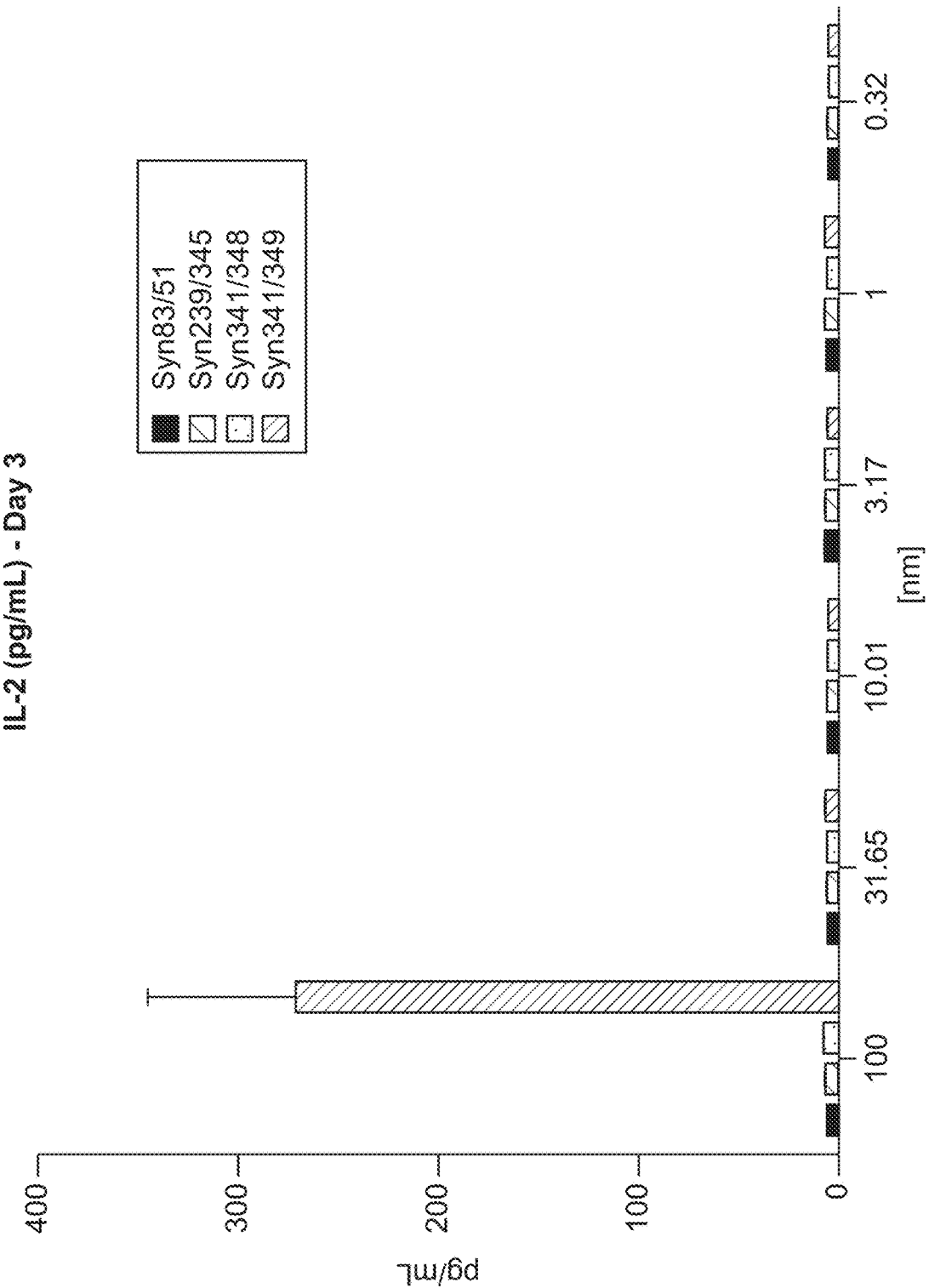

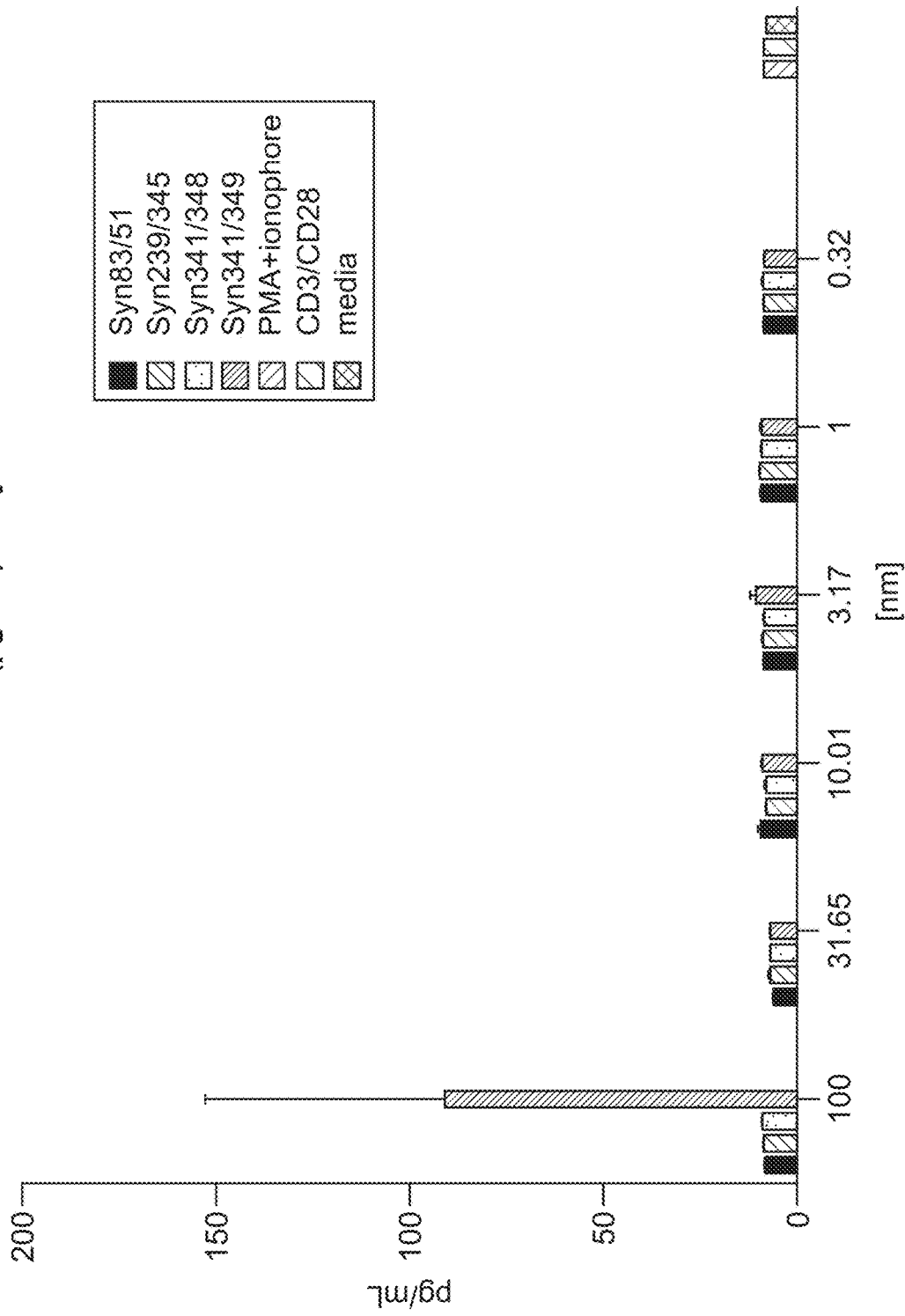

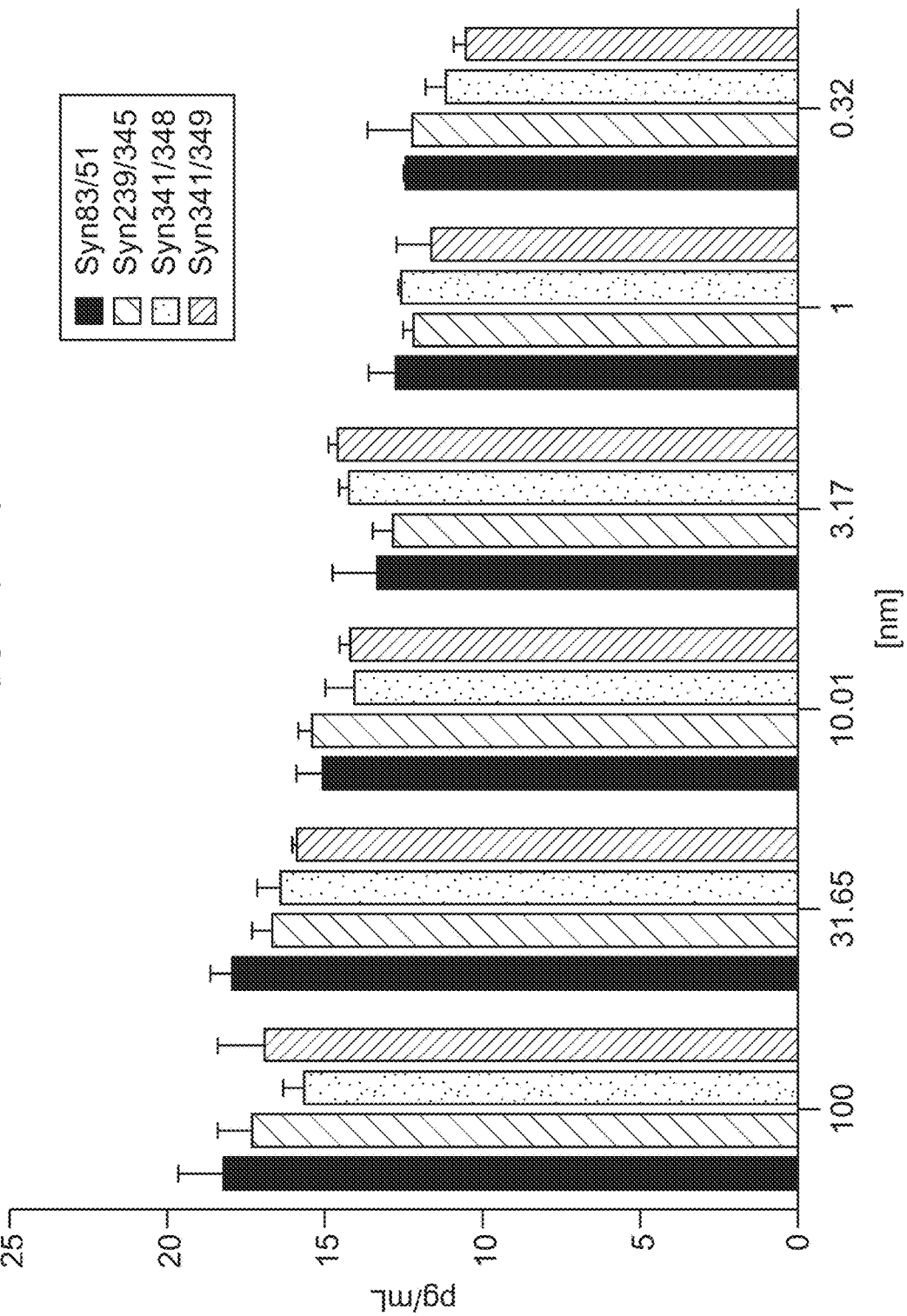

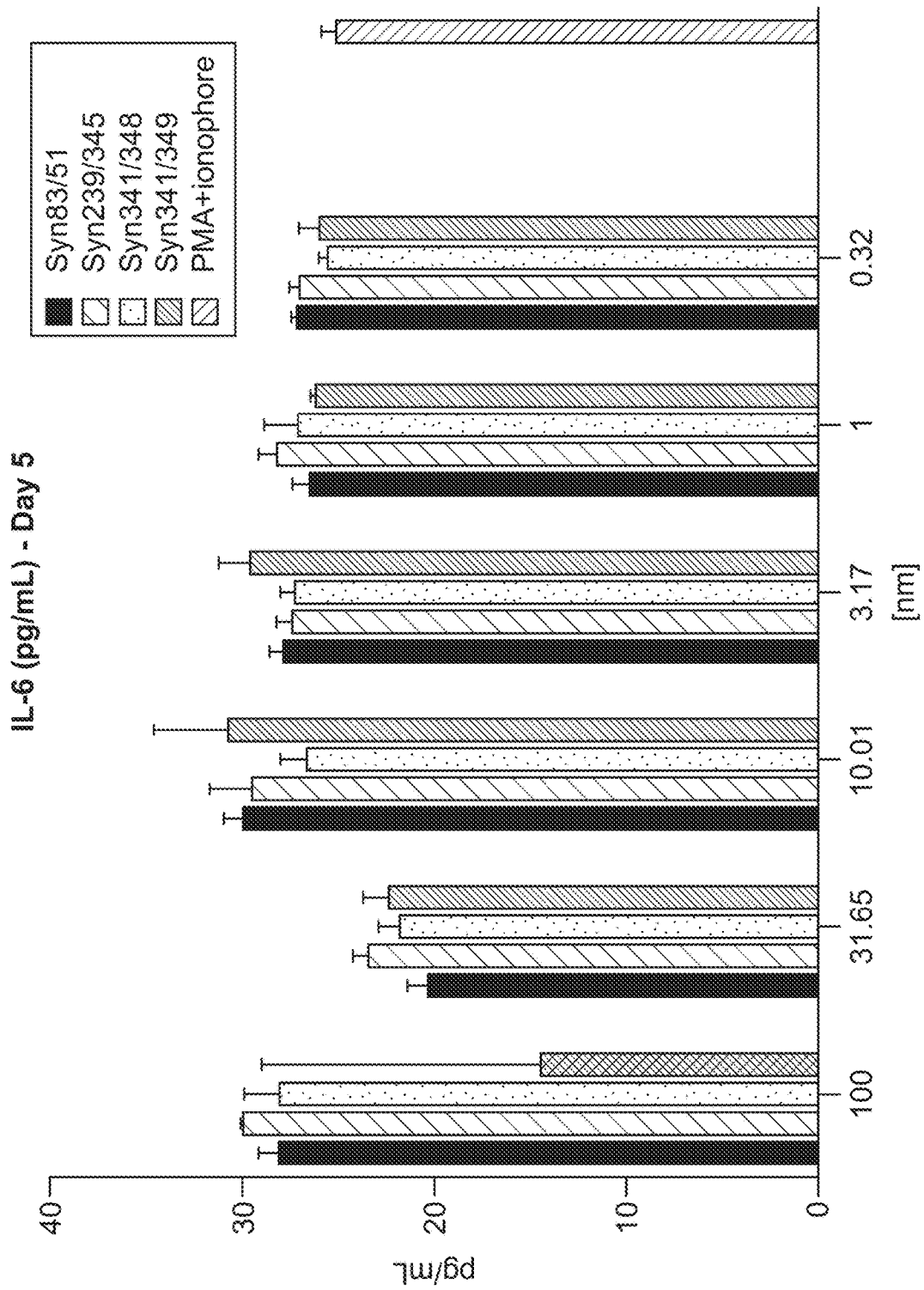

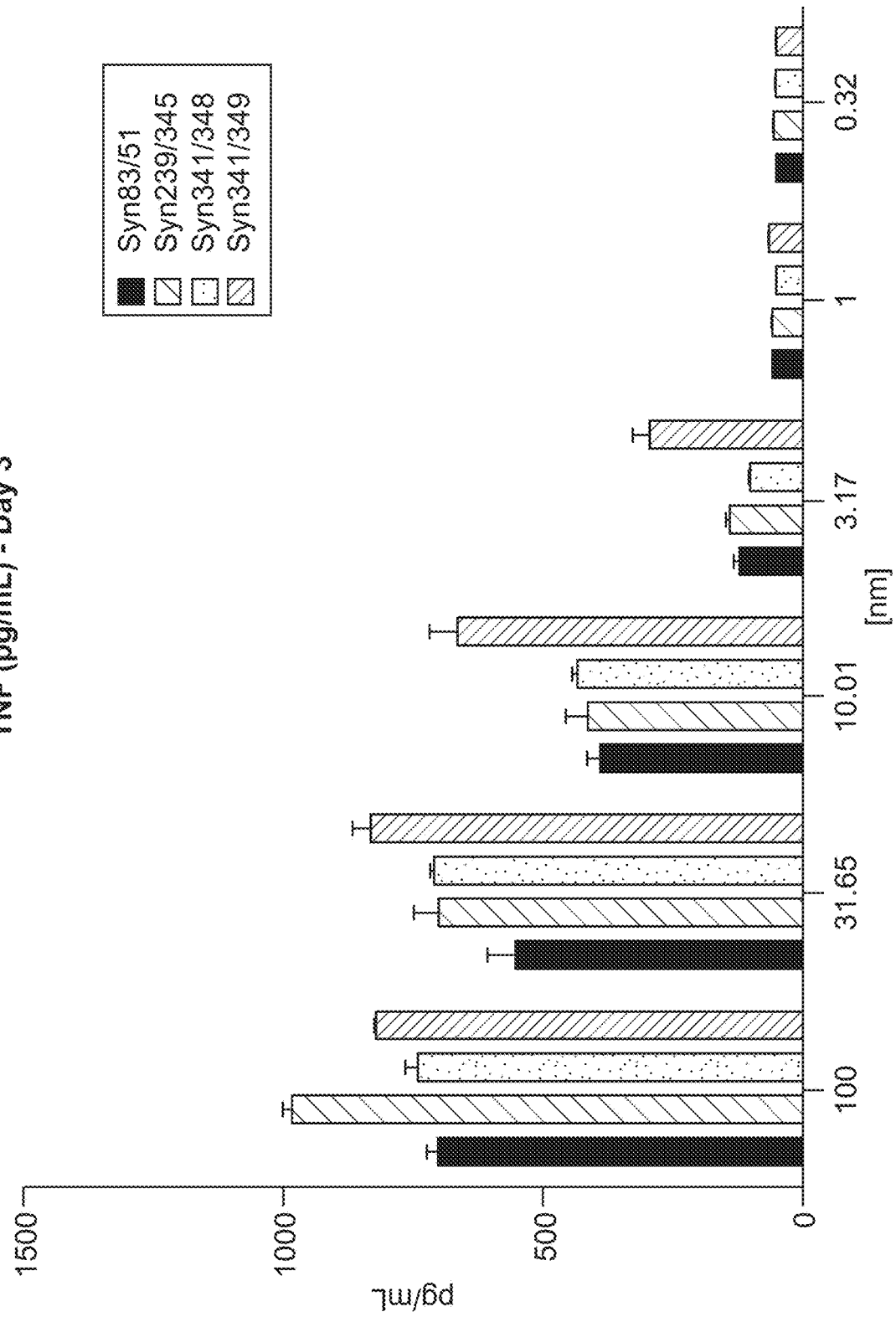

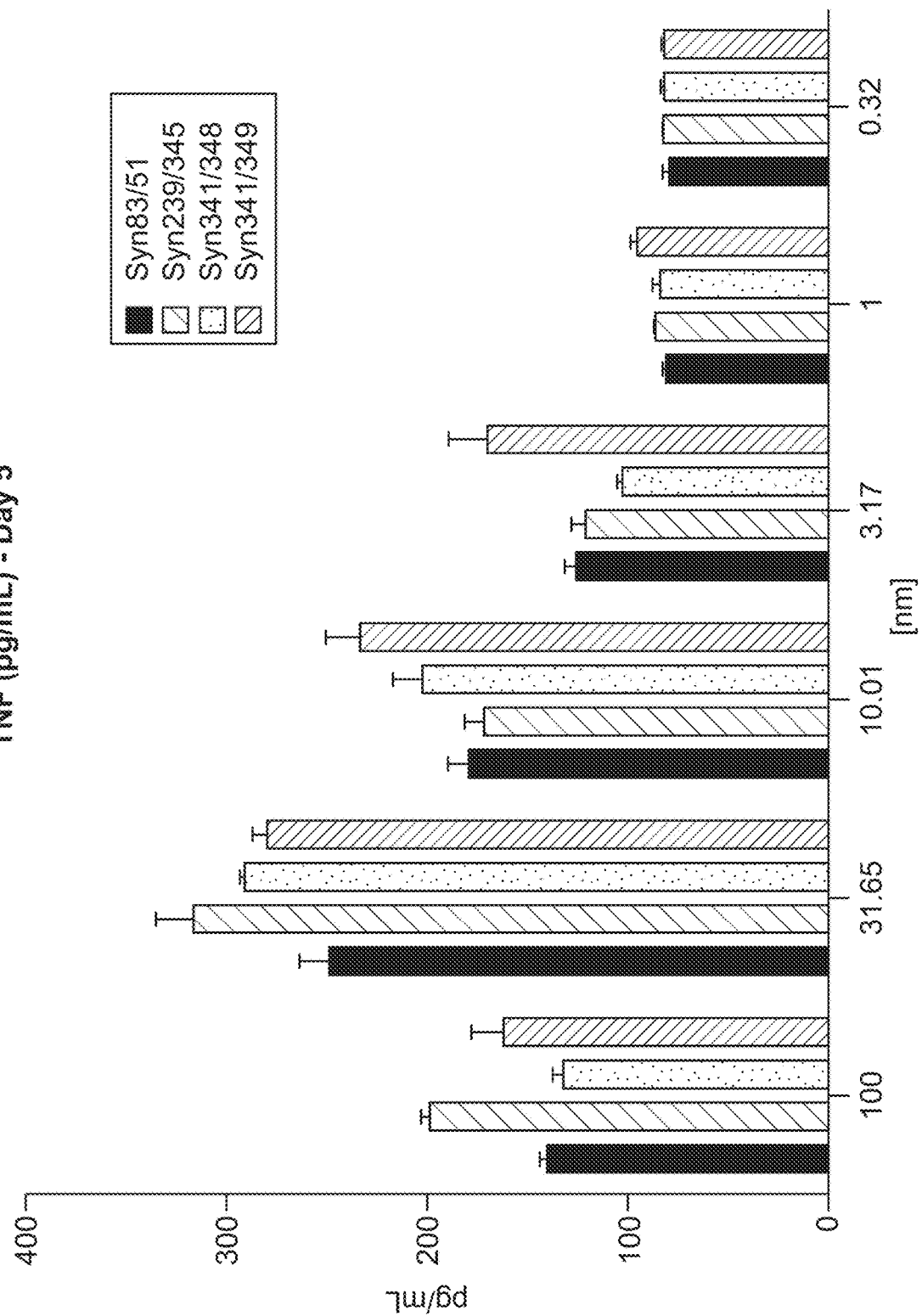

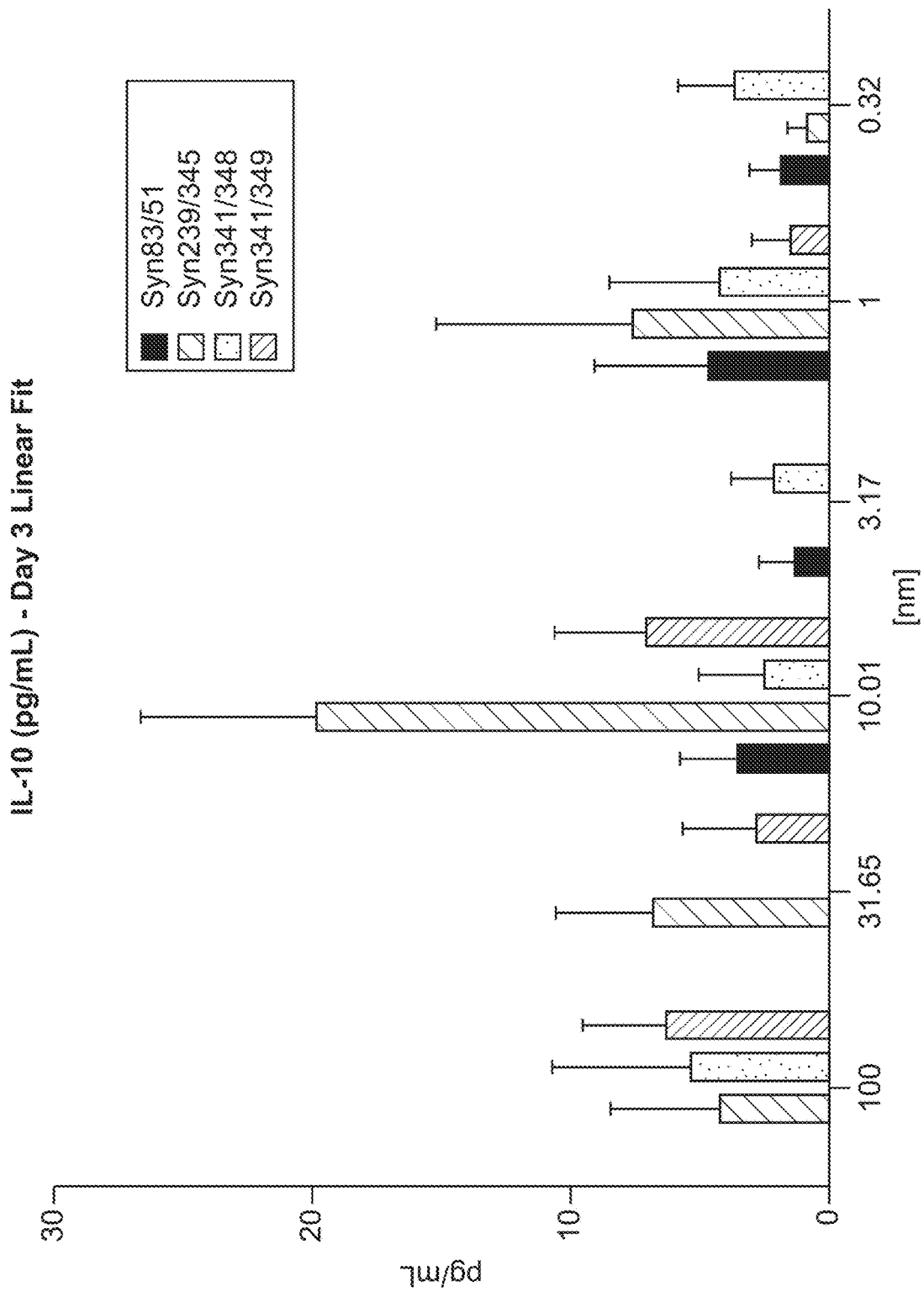

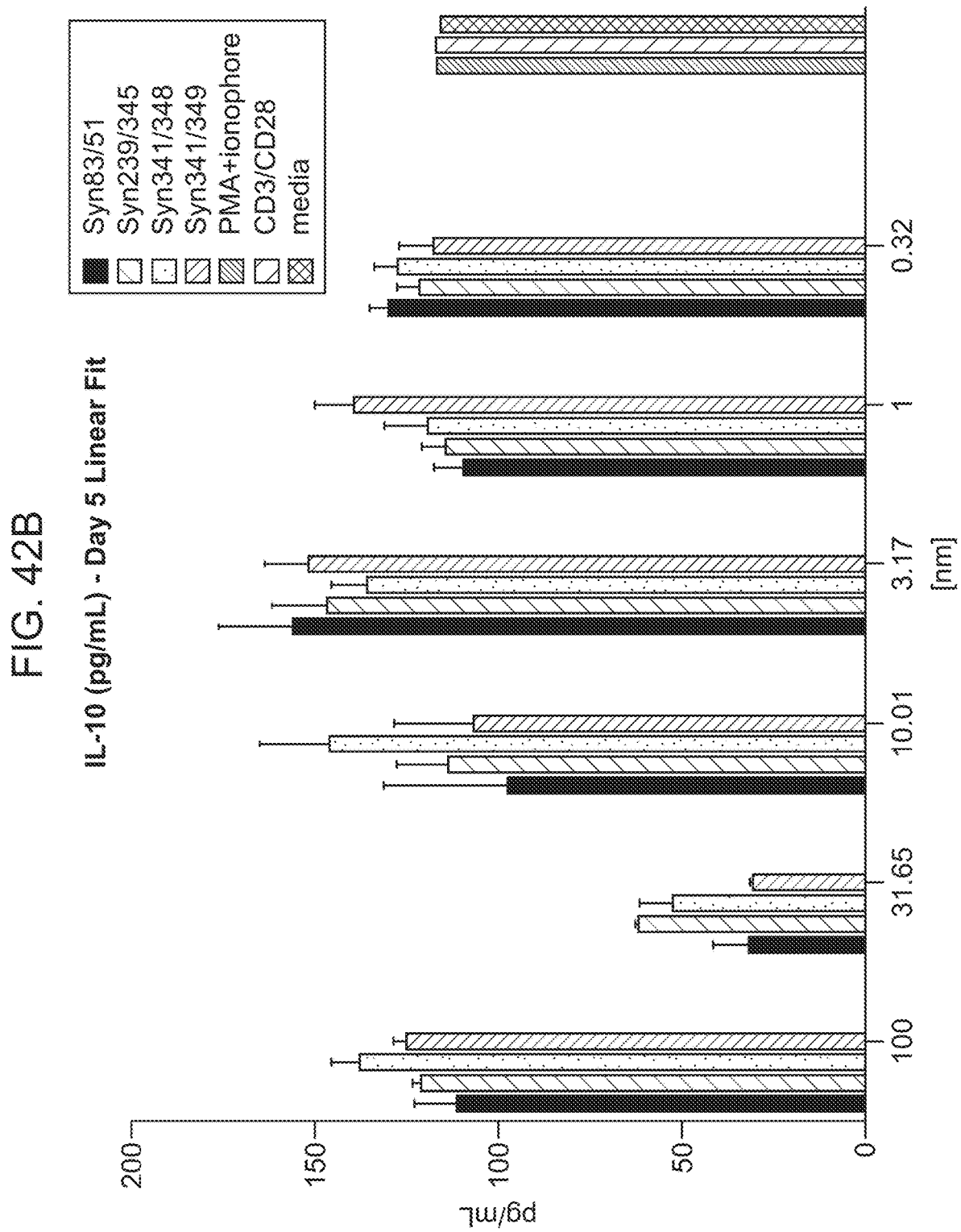

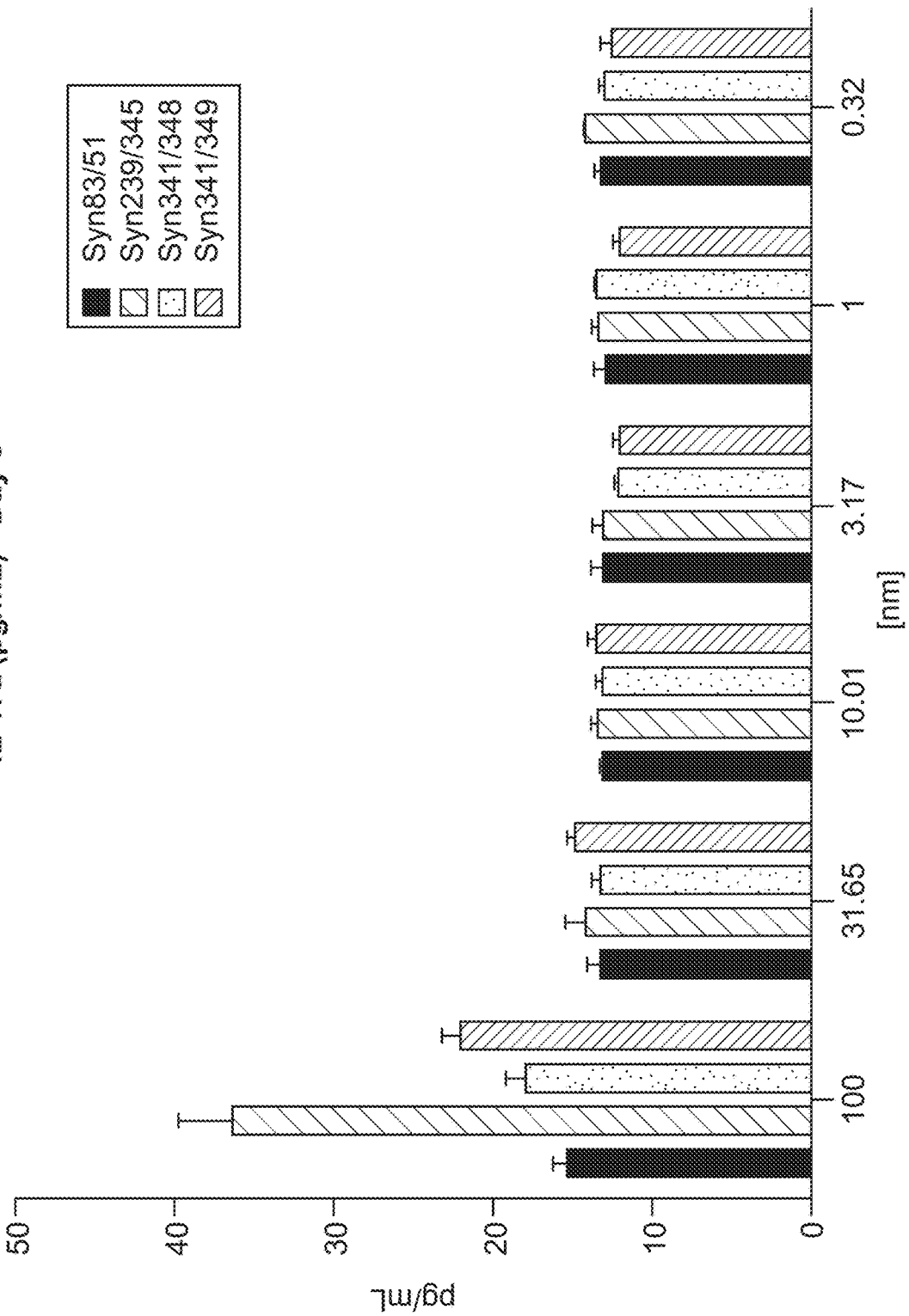

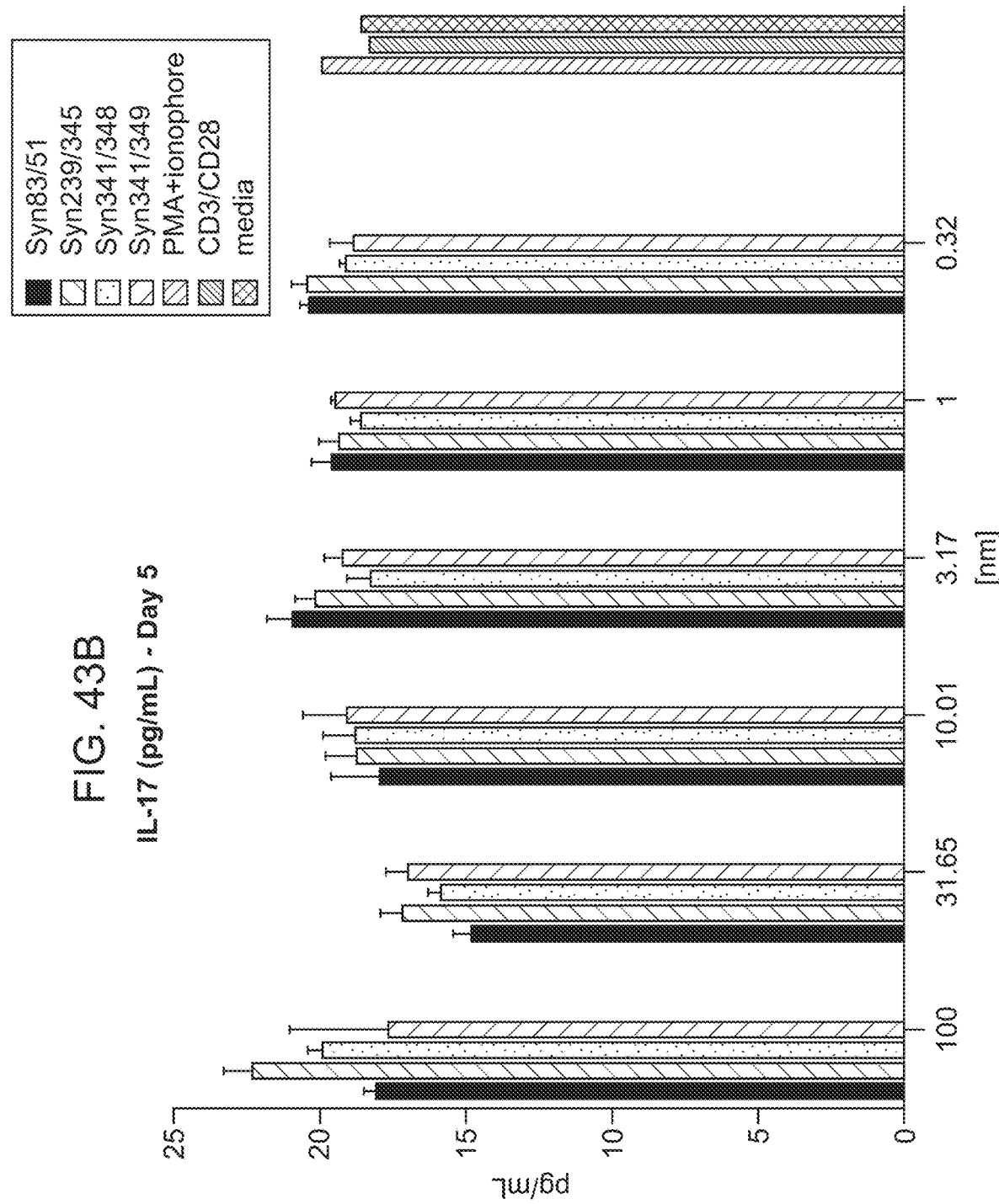

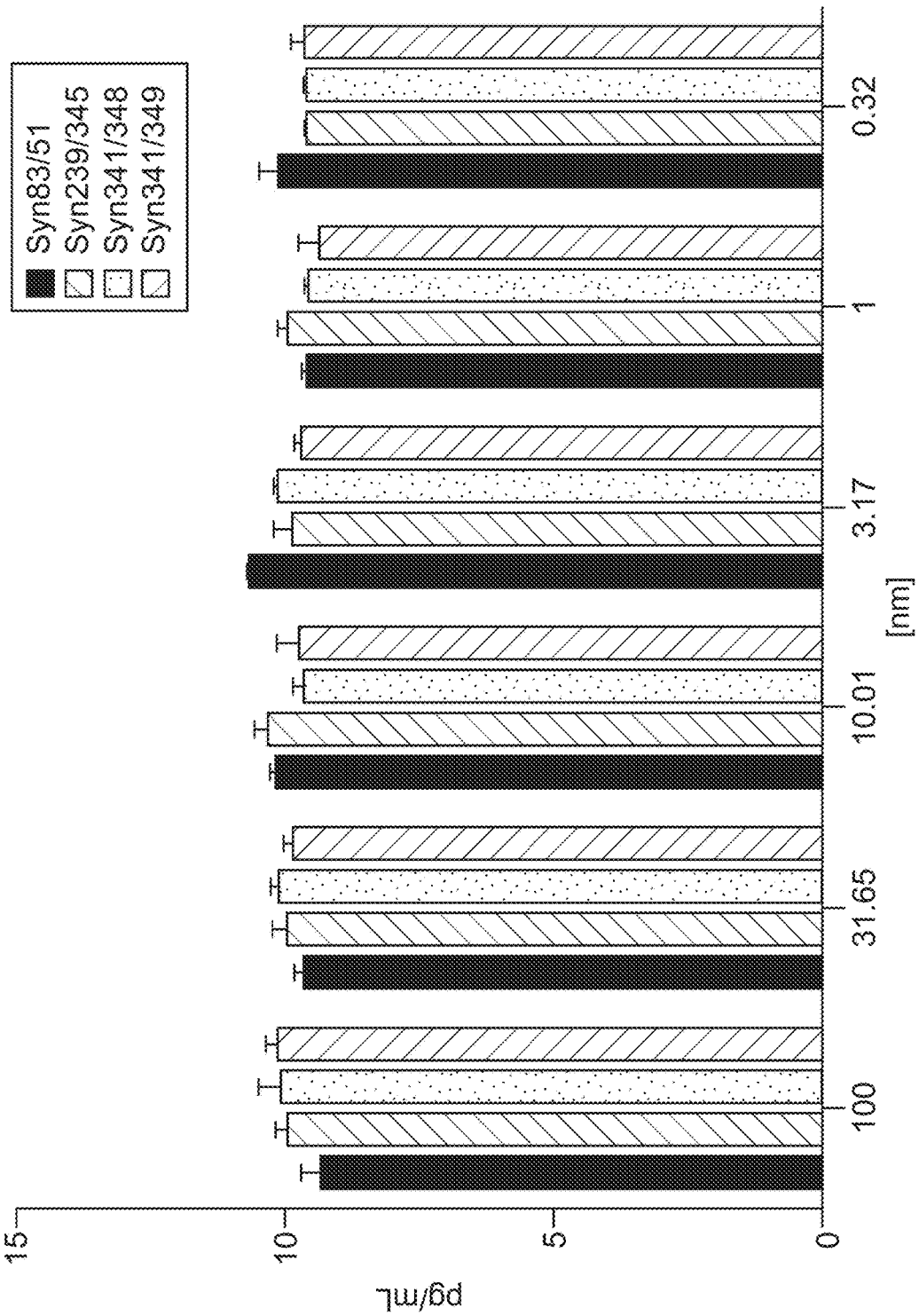

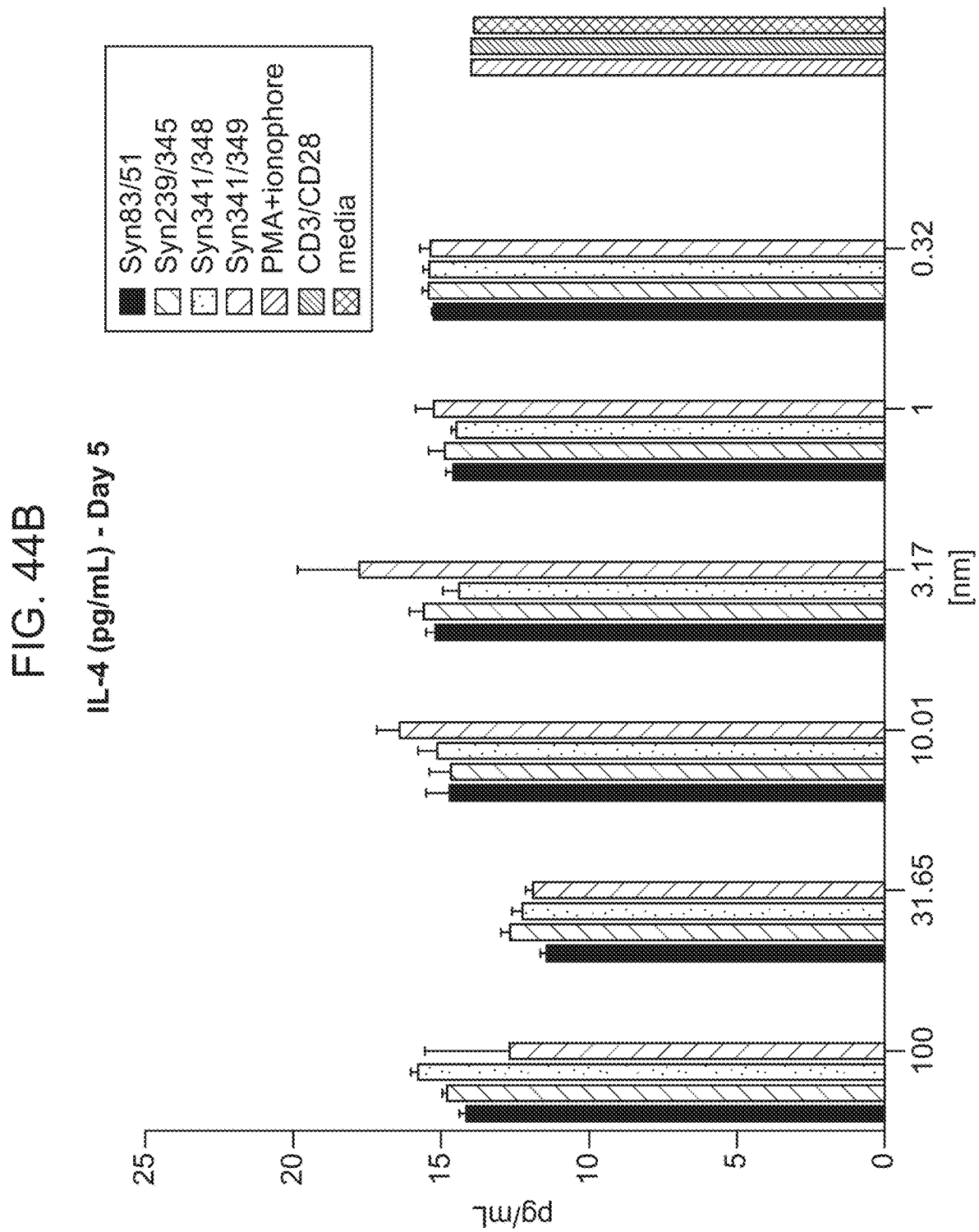

FIG. 47

| 4-1BBL variant | Expression level mg/L | Expression level mg/L | Fold over wild-type |
|---|---|---|---|
| M91A | 105.9 | 115.9 | 14 |
| F92A | 48.9 | 41.6 | 5.8 |
| Q94A | 13.8 | 23.1 | 2.3 |
| L95A | 81.8 | 63.3 | 9.2 |
| V96A | 16.2 | 24.4 | 2.6 |
| Q98A | 43.0 | 43.0 | 5.5 |
| N99A | 35.3 | 53.3 | 5.6 |
| V100A | 37.6 | 42.6 | 5.1 |
| L101A | 137.8 | 203.2 | 21.7 |
| L102A | 148.0 | 184.4 | 21.2 |
| I103A | 48.0 | 68.0 | 7.4 |
| D104A | 70.5 | 65.1 | 3.9 |
| G105A | 23.8 | 37.6 | 2.6 |
| P106A | 81.2 | 66.0 | 9.4 |
| L107A | 13.8 | 13.4 | 1.7 |
| S108A | 66.2 | 72.1 | 8.8 |
| W109A | 15.6 | 30.8 | 2.9 |
| Y110A | 107.0 | 110.1 | 13.8 |
| S111A | 104.0 | 109.0 | 13.6 |
| D112A | 28.0 | 32.1 | 3.8 |
| P113A | 60.1 | 60.4 | 7.7 |
| G114A | 94.8 | 81.7 | 3.9 |
| L115A | 23.0 | 26.4 | 3.1 |
| G117A | 4.4 | 12.5 | |
| V118A | 4.2 | 5.3 | |
| S119A | 4.6 | 5.6 | |
| L120A | 4.6 | 4.6 | |
| T121A | 4.9 | 6.3 | |
| G122A | 9.8 | 9.5 | |
| G123A | 2.5 | 10.4 | |
| L124A | 3.1 | 8.5 | |

FIG. 47 (Cont.)

| 4-1BBL variant | Expression level mg/L | Expression level mg/L | Fold over wild-type |
|---|---|---|---|
| S125A | 8.9 | 8.3 | |
| Y126A | 2.3 | 0.6 | |
| E128A | 6.1 | 14.6 | |
| D129A | 2.2 | 0.0 | |
| T130A | 1.9 | 2.6 | |
| K131A | 7.0 | 15.3 | |
| E132A | 2.3 | 6.8 | |
| F144A | 1.5 | 0.0 | |
| F145A | 8.2 | 6.3 | |
| Q146A | 5.7 | 10.5 | |
| L147A | 10.3 | 16.8 | |
| E148A | 5.7 | 4.4 | |
| L149A | 9.9 | 12.9 | |
| R150A | 10.3 | 4.7 | |
| R151A | 1.8 | 0.0 | |
| V152A | 2.9 | 6.7 | |
| V153A | 3.7 | 7.9 | |
| G155A | 6.9 | 13.1 | |
| E156A | 4.3 | 4.0 | |
| G157A | 12.3 | 18.7 | |
| S158A | 6.7 | 6.3 | |
| D184A | 3.6 | 5.0 | |
| L185A | 2.2 | 0.0 | |
| P186A | 4.3 | 2.2 | |
| P187A | 2.9 | 0.0 | |
| S189A | 3.8 | 6.1 | |
| S190A | 2.4 | 3.1 | |
| E191A | 1.8 | 4.1 | |
| R193A | 6.6 | 7.5 | |
| N194A | 4.3 | 0.1 | |
| S195A | 3.2 | 1.6 | |

FIG. 47 (Cont.)

| 4-1BBL variant | Expression level mg/L | Expression level mg/L | Fold over wild-type |
|---|---|---|---|
| F197A | 3.1 | 6.5 | |
| Q210A | 5.1 | 3.9 | |
| R211A | 1.6 | 3.5 | |
| L212A | 2.0 | 9.8 | |
| G213A | 5.0 | 2.9 | |
| V214A | 2.7 | 7.5 | |
| H215A | 3.3 | 2.4 | |
| L216A | 3.4 | 10.2 | |
| H217A | 8.6 | 3.2 | |
| T218A | 6.6 | 9.9 | |
| E219A | 2.8 | 5.2 | |
| R221A | 3.3 | 8.7 | |
| R223A | 6.2 | 9.7 | |
| H224A | 4.1 | 6.0 | |
| W226A | 1.9 | 0.0 | |
| L228A | 3.1 | 0.0 | |
| T229A | 6.0 | 7.8 | |
| Q230A | 2.7 | 4.7 | |
| G231A | 1.9 | 2.4 | |
| T233A | 1.8 | 0.0 | |
| V234A | 1.9 | 0.0 | |
| wt | 3.8 | 11.9 | |

FIG. 49
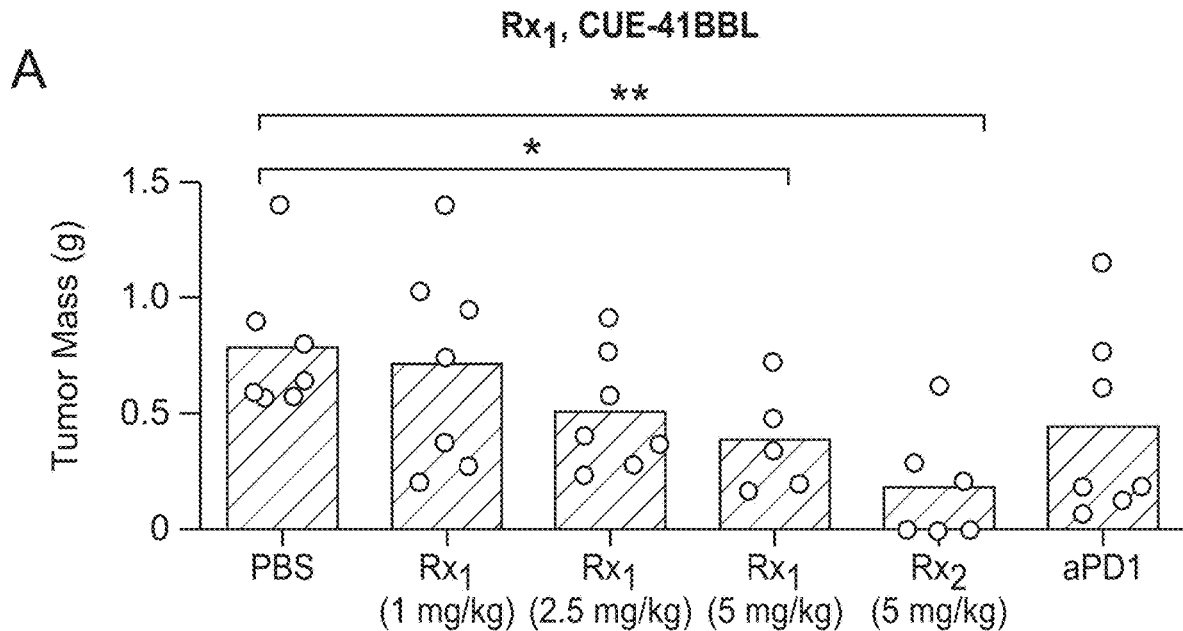
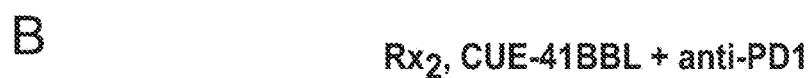

PD-L1  
*Mus musculus*  
NP_068693  
Amino acids 19-290

FIG. 50A

```
  1 mrifagiift acchllraft itapkdlyvv eygsnvtmec rfpvereldl lalvvyweke
 61 deqviqfvag eedlkpqhsn frgraslpkd qllkgnaalq itdvklqdag vycciisygg
121 adykritlkv napyrkinqr isvdpatseh elicqaegyp eaeviwtnsd hqpvsgkrsv
181 ttsrtegmll nvtsslrvna tandvfyctf wrsqpgqnht aeliipelpa thppqnrthw
241 vllgsillfl ivvstvllfl rkqvrmldve kcgvedtssk nrndtqfeet
```

(SEQ ID NO:187)

PD-L1  
*Homo sapiens*  
NP_054852  
Amino acids 19-290

FIG. 50B

```
  1 mrifavfifm tywhllnaft vtvpkdlyvv eygsnmtiec kfpvekqldl aalivyweme
 61 dkniiqfvhg eedlkvqhss yrqrarllkd qlslgnaalq itdvklqdag vyrcmisygg
121 adykritvkv napynkinqr ilvvdpvtse heltcqaegy pkaeviwtss dhqvlsgktt
181 ttnskreekl fnvtstlrin tttneifyct frrldpeenh taelvipelp lahppnerth
241 lvilgaillc lgvaltfifr lrkgrmmdvk kcgiqdtnsk kqsdthleet
```

(SEQ ID NO:188)

FIG. 51

CD80 (B7-1) Ectodomain

```
                                 vihvtk evkevatlsc ghnvsveela
qtriywqkek kmvltmmsgd mniwpeyknr tifditnnls ivilalrpsd egtyecvvlk
yekdafkreh laevtlsvka dfptpsisdf eiptsnirri icstsggfpe phlswlenge
elnainttvs qdpetelyav ssklfnmtt nhsfmcliky ghlrvnqtfn wnttkqehfp
dn
```
(SEQ ID NO:189)

FIG. 52

*Homo sapiens*
ICOS-L
GenBank NP_056074
Amino acids 19-302

```
  1 mrlgspgllf llfsslradt qekevramvg sdvelscacp egsrfdlndv yvywqtsesk
 61 tvvtyhipqn sslenvdsry rnralmspag mlrgdfslrl fnvtpqdeqk fhclvlsqsl
121 gfqevlsvev tlhvaanfsv pvvsaphsps qdeltftcts ingyprpnvy winktdnsll
181 dqalqndtvf lnmrglydvv svlriartps vnigccienv llqqnltvgs qtgndigerd
241 kitenpvstg eknaatwsil avlcllvvva vaigwvcrdr clqhsyagaw avspeteltg
301 hv
```
(SEQ ID NO:190)

FIG. 53

*Homo sapiens*
GenBank NP_003317
OX4L

```
  1 mervqpleen vgnaarprfe rnklllvasv iqglgllicf tyiclhfsal qvshrypriq
 61 sikvqfteyk kekgfiltsq kedeimkvqn nsviincdgf ylislkgyfs qevnislhyq
121 kdeeplfqlk kvrsvnslmv asltykdkvy lnvttdntsl ddfhvnggel ilihqnpgef
181 cvl
```
(SEQ ID NO:191)

FIG. 54

*Homo sapiens*
GenBank NP_079515
PD-L2
Amino acids 20-273

```
  1 mifllllmlsl elqlhqiaal ftvtvpkely iiehgsnvtl ecnfdtgshv nlgaitaslq
 61 kvendtsphr eratlleeql plgkasfhip qvqvrdegqy qciiiygvaw dykyltlkvk
121 asyrkinthi lkvpetdeve ltcqatgypl aevswpnvsv pantshsrtp eglyqvtsvl
181 rlkpppgrnf scvfwnthvr eltlasidlq sqmeprthpt wllhifipfc iiafifiatv
241 ialrkqlcqk lysskdttkr pvtttkrevn sai
```
(SEQ ID NO:192)

FIG. 55

Homo sapiens
GenBank NP_787058
CD86 (B7-2)
Amino acids 31-329

```
  1 mdpqctmgls nilfvmafll sqaaplkiqa yfnetadlpc qfansqnqsl selvvfwqdq
 61 enlvlnevyl gkekfdsvhs kymgrtsfds dswtlrlhnl qikdkglyqc iihhkkptgm
121 irihqmnsel svlanfsqpe ivpisniten vyinltcssi hgypepkkms vllrtknsti
181 eydgimqksq dnvtelydvs islsvsfpdv tsnmtifcil etdktrllss pfsieledpq
241 pppdhipwit avlptviicv mvfclilwkw kkkkrprnsy kcgtntmere eseqtkkrek
301 ihipersdea qrvfksskts scdksdtcf
```
(SEQ ID NO:193)

FIG. 56

Fas ligand (FasL)
Homo sapiens
GenBank NP_000630
Amino acids 1-281

```
  1 mqqpfnypyp qiywvdssas spwappgtvl pcptsvprrp gqrrpppppp ppplpppppp
 61 pplpplplpp lkkrgnhstg lcllvmffmv lvalvglglg mfqlfhlqke laelrestsq
121 mhtasslekq ighpspppek kelrkvahlt gksnsrsmpl ewedtygivl lsgvkykkgg
181 lvinetglyf vyskvyfrgq scnnlplshk vymrnskypq dlvmmegkmm sycttgqmwa
241 rssylgavfn ltsadhlyvn vselslvnfe esqtffglyk l
```
(SEQ ID NO:194)

1

METHODS FOR MODULATING AN IMMUNE RESPONSE

CROSS-REFERENCE

This application is a continuation of U.S. patent application Ser. No. 16/830,831, filed Mar. 26, 2020, which is a continuation of U.S. patent application Ser. No. 16/489,586, filed Aug. 28, 2019, which is a national stage filing under 35 U.S.C. § 371 of PCT/US2018/022492, filed Mar. 14, 2018, which claims the benefit of U.S. Provisional Patent Application No. 62/471,832, filed Mar. 15, 2017, and of U.S. Provisional Patent Application No. 62/521,009, filed Jun. 16, 2017, which applications are incorporated herein by reference in their entirety.

INCORPORATION-BY-REFERENCE OF MATERIAL ELECTRONICALLY SUBMITTED

A Sequence Listing is provided herewith as a Sequence Listing XML, "CUEB-108CON5_SEQ_LIST" created on Nov. 3, 2022 and having a size of 277,000 bytes. The contents of the Sequence Listing XML are incorporated by reference herein in their entirety.

INTRODUCTION

An adaptive immune response involves the engagement of the T cell receptor (TCR), present on the surface of a T cell, with a small peptide antigen non-covalently presented on the surface of an antigen presenting cell (APC) by a major histocompatibility complex (MHC; also referred to in humans as a human leukocyte antigen (HLA) complex). This engagement represents the immune system's targeting mechanism and is a requisite molecular interaction for T cell modulation (activation or inhibition) and effector function. Following epitope-specific cell targeting, the targeted T cells are activated through engagement of costimulatory proteins found on the APC with counterpart costimulatory proteins the T cells. Both signals—epitope/TCR binding and engagement of APC costimulatory proteins with T cell costimulatory proteins—are required to drive T cell specificity and activation or inhibition. The TCR is specific for a given epitope; however, the costimulatory protein not epitope specific and instead is generally expressed on all T cells or on large T cell subsets.

SUMMARY

The present disclosure provides methods of modulating an immune response in an individual. The present disclosure provides methods of treatment. The present disclosure provides methods comprising administering a multimeric polypeptide (synTac) and an immune checkpoint inhibitor to an individual. The present disclosure provides methods comprising administering a multimeric polypeptide (synTac) to an individual who is undergoing treatment with immune checkpoint inhibitor.

BRIEF DESCRIPTION OF THE DRAWINGS

FIG. 2A-2Q provide an amino acid sequence of wild-type human IL-2 (FIG. 2A); and amino acid sequences of variant IL-2 polypeptides (FIG. 2B-2Q).

FIG. 3A-3C provide amino acid sequences of IL-2 receptor alpha chain (FIG. 3A), beta chain (FIG. 3B), and gamma chain (FIG. 3C).

FIG. 4A-4C provide amino acid sequences of immunoglobulin Fc polypeptides.

FIG. 5A-5C provide amino acid sequences of human leukocyte antigen (HLA) Class I heavy chain polypeptides. Signal sequences are underlined.

FIG. 6 provides a multiple amino acid sequence alignment of beta-2 microglobulin (β2M) precursors (i.e., including the leader sequence) from *Homo sapiens* (NP_004039.1; SEQ ID NO:95), *Pan troglodytes* (NP_001009066.1; SEQ ID NO:195), *Macaca mulatta* (NP_001040602.1; SEQ ID NO:96), *Bos taurus* (NP_776318.1; SEQ ID NO:97) and *Mus musculus* (NP_033865.2; SEQ ID NO:98). Amino acids 1-20 are a signal peptide.

FIG. 7A depicts unpurified yields; FIG. 7B depicts purified product.

FIG. 8A-8B depict production of IL-2/synTacs of the present disclosure, in which the IL-2 polypeptide is present on the light chain (the polypeptide chain with the light chain (e.g., β2M) of an MHC Class I molecule) or on the heavy chain (the polypeptide chain with the heavy chain of an MHC Class I molecule).

FIG. 12 depicts IL-2/synTac binding to specific (lymphocytic choriomeningitis virus; LCMV) or non-specific (OT1; recognizing ovalbumin) CD8$^+$ T cells.

FIG. 14A-14F depict the percent phospho-signal transducer and activator of transcription 5 (pSTAT5)-positive cells following stimulation of CD8$^+$ antigen-specific (LCMV) or non-specific (BL6) cells with IL-2/synTacs of the present disclosure at various IL-2/synTac concentrations.

FIG. 15 depicts in vivo activity of an IL-2/synTac of the present disclosure. The left panel depicts the fold change in the number of antigen-specific CD8$^+$ T cells following administration of phosphate buffered saline (PBS), recombinant IL-2 (rIL-2), or an IL-2/synTac of the present disclosure. The right panel depicts antigen-specific and non-antigen-specific responses following administration of PBS, rIL-2, or an IL-2/synTac of the present disclosure.

FIG. 21 provides an amino acid sequence of a heavy chain of an IL-2/synTac of the present disclosure, with a leader peptide, where the IL-2/synTac heavy chain comprises an IgG1 Fc with an N297A substitution.

FIG. 22 provides an amino acid sequence of a heavy chain of an IL-2/synTac of the present disclosure, without a leader peptide, where the IL-2/synTac heavy chain comprises an IgG1 Fc with an N297A substitution.

FIG. 23A-23B provide a nucleotide sequence (FIG. 23A) encoding the IL-2/synTac heavy chain depicted in FIG. 21; and a key (FIG. 23B) to the sequence.

FIG. 24 provides an amino acid sequence of a heavy chain of an IL-2/synTac, with a leader peptide, where the IL-2/synTac heavy chain comprises an IgG1 Fc with L234A and L235A substitutions.

FIG. 25 provides an amino acid sequence of a heavy chain of an IL-2/synTac, without a leader peptide, where the IL-2/synTac heavy chain comprises an IgG1 Fc with L234A and L235A substitutions.

FIG. 26A-26B provide a nucleotide sequence (FIG. 26A) encoding the IL-2/synTac heavy chain depicted in FIG. 24; and a key (FIG. 26B) to the sequence.

FIG. 27 provides an amino acid sequence of a heavy chain of an IL-2/synTac, with a leader peptide, where the IL-2/synTac heavy chain comprises an IgG1 Fc with L234F, L235E, and P331S substitutions.

FIG. 28 provides an amino acid sequence of a heavy chain of an IL-2/synTac, without a leader peptide, where the IL-2/synTac heavy chain comprises an IgG1 Fc with L234F, L235E, and P331S substitutions.

FIG. 29A-29B provide a nucleotide sequence (FIG. 29A) encoding the IL-2/synTac heavy chain depicted in FIG. 27; and a key (FIG. 29B) to the sequence.

FIG. 30 provides an amino acid sequence of a light chain of an IL-2/synTac, with a leader peptide, where the IL-2/synTac light chain comprises a human papilloma virus (HPV) E7 epitope.

FIG. 31 provides an amino acid sequence of a light chain of an IL-2/synTac, without a leader peptide, where the IL-2/synTac light chain comprises an HPV E7 epitope.

FIG. 32 provides a nucleotide sequence encoding the IL-2/synTac light chain depicted in FIG. 30.

FIG. 33A-33D provide amino acid sequences of a wild-type human IgG1 Fc (FIG. 33A), an IgG1 Fc with L234F, L235E, and P331S substitutions (FIG. 33B), an IgG1 Fc with an N297A substitution (FIG. 33C), and an IgG1 Fc with L234A and L235A substitutions (FIG. 33D).

FIG. 34A-34C provide amino acid sequence of a β2-microglobulin (R12C) polypeptide (FIG. 34A), a variant IL-2 (H16A; F42A) polypeptide (FIG. 34B), and a Class I MHC-H chain A0201 (Y84A; A236C) (FIG. 34C).

FIG. 35 depicts synergistic effects of an IL-2/synTac and an anti-PD1 antibody on reducing tumor volume.

FIG. 36A-36IIII provide an amino acid sequence of a 4-1BBL (FIG. 36A) and examples of variant 4-1BBL polypeptides (FIG. 36B-36IIII).

FIG. 37 provides an amino acid sequence of 4-1BB.

FIG. 38A-38B depicts interferon-gamma (IFN-γ) secretion by target cells contacted with a synTac polypeptide for 3 days (FIG. 38A) or 5 days (FIG. 8B) according to an embodiment of the present disclosure.

FIG. 39A-39B depicts interleukin-2 (IL-2) secretion by target cells contacted with a synTac polypeptide for 3 days (FIG. 39A) or 5 days (FIG. 9B) according to an embodiment of the present disclosure.

FIG. 40A-40B depicts interleukin-6 (IL-6) secretion by target cells contacted with a synTac polypeptide for 3 days (FIG. 40A) or 5 days (FIG. 40B) according to an embodiment of the present disclosure.

FIG. 41A-41B depicts tumor necrosis factor-alpha (TNFα) secretion by target cells contacted with a synTac polypeptide for 3 days (FIG. 41A) or 5 days (FIG. 41B) according to an embodiment of the present disclosure.

FIG. 42A-42B depicts interleukin-10 (IL-10) secretion by target cells contacted with a synTac polypeptide for 3 days (FIG. 42A) or 5 days (FIG. 42B) according to an embodiment of the present disclosure.

FIG. 43A-43B depicts interleukin-17A (IL-17A) secretion by target cells contacted with a synTac polypeptide for 3 days (FIG. 43A) or 5 days (FIG. 43B) according to an embodiment of the present disclosure.

FIG. 44A-44B depicts interleukin-4 (IL-4) secretion by target cells contacted with a synTac polypeptide for 3 days (FIG. 44A) or 5 days (FIG. 44B) according to an embodiment of the present disclosure.

FIG. 47 depicts expression levels of various synTac polypeptides produced in CHO cells.

FIG. 49 depicts the effect of co-administration of various doses of a 4-1BBL/synTac and an anti-PD1 antibody on tumor mass and percent granzyme $B^+$ tumor infiltrating lymphocytes (TILs).

FIG. 50A-50B provide amino acid sequences of PD-L1 polypeptides.

FIG. 51 provides an amino acid sequence of a CD80 polypeptide.

FIG. 52 provides an amino acid sequence of an ICOS-L polypeptide.

FIG. 53 provides an amino acid sequence of an OX40L polypeptide.

FIG. 54 provides an amino acid sequence of a PD-L2 polypeptide.

FIG. 55 provides an amino acid sequence of a CD86 (B7-2) polypeptide.

FIG. 56 provides an amino acid sequence of a Fas ligand (FAS-L) polypeptide.

DEFINITIONS

Figure 1C:
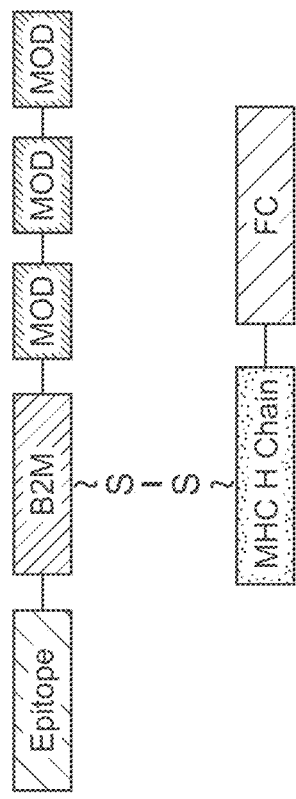
FIG. 1A-1D schematically depict various embodiments of a T-cell modulatory multimeric polypeptide. In these embodiments, disulfide bonds are formed between MHC (e.g., HLA) polypeptides present in separate polypeptides.
Figure 1D:
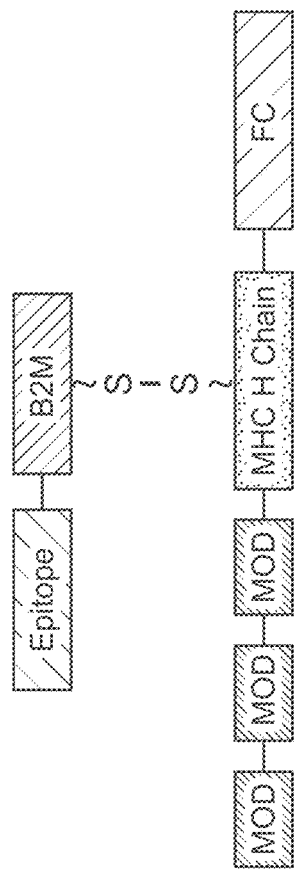
Figure 1A:
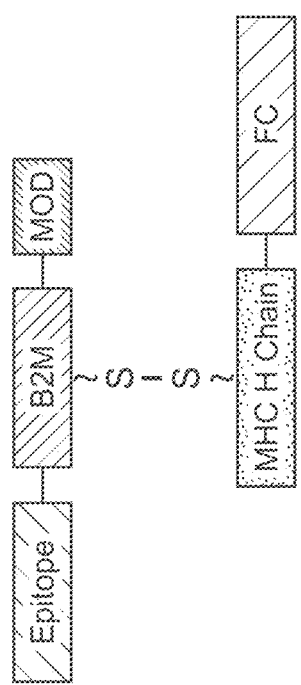
Figure 1B:
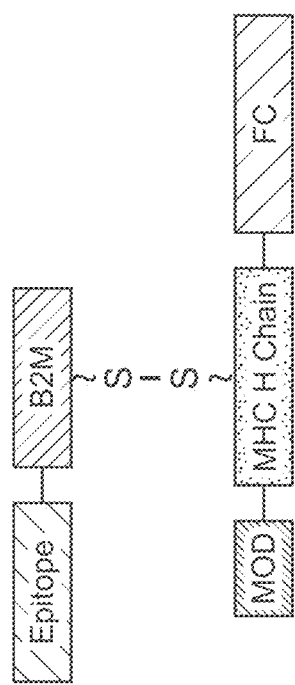

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various convenient methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/, ebi.ac.uk/Tools/msa/muscle/, mafft.cbrc.jp/alignment/software/. See, e.g., Altschul et al. (1990), J. Mol. Biol. 215:403-10.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

"Binding" as used herein (e.g. with reference to binding of a T-cell modulatory multimeric polypeptide to a polypeptide (e.g., a T-cell receptor) on a T cell) refers to a non-covalent interaction between. Binding interactions are generally characterized by a dissociation constant ($K_D$) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower $K_D$.

The term "immunological synapse" or "immune synapse" as used herein generally refers to the natural interface between two interacting immune cells of an adaptive immune response including, e.g., the interface between an antigen-presenting cell (APC) or target cell and an effector cell, e.g., a lymphocyte, an effector T cell, a natural killer cell, and the like. An immunological synapse between an APC and a T cell is generally initiated by the interaction of a T cell antigen receptor and major histocompatibility complex molecules, e.g., as described in Bromley et al., Annu Rev Immunol. 2001; 19:375-96; the disclosure of which is incorporated herein by reference in its entirety.

"T cell" includes all types of immune cells expressing CD3, including T-helper cells (CD4+ cells), cytotoxic T-cells (CD8+ cells), T-regulatory cells (Treg), and NK-T cells.

"Co-stimulatory polypeptide," (also referred to herein as an "immunomodulatory polypeptide") as the term is used herein, includes a polypeptide on an antigen presenting cell (APC) (e.g., a dendritic cell, a B cell, and the like) that specifically binds a cognate co-stimulatory polypeptide (also referred to herein as a "cognate co-immunomodulatory polypeptide") on a T cell, thereby providing a signal which, in addition to the primary signal provided by, for instance, binding of a TCR/CD3 complex with a major histocompatibility complex (MHC) polypeptide loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, Fas ligand (FasL), inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, LIGHT, NKG2C, B7-H3, and a ligand that specifically binds to CD83.

A "modulatory domain" ("MOD") of a T-cell modulatory multimeric polypeptide comprises a co-stimulatory polypeptide, e.g., an IL-2 polypeptide, such as a variant IL-2 polypeptide.

"Heterologous," as used herein, means a nucleotide or polypeptide that is not found in the native nucleic acid or protein, respectively.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system.

The terms "recombinant expression vector," or "DNA construct" are used interchangeably herein to refer to a DNA molecule comprising a vector and one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

The terms "antibodies" and "immunoglobulin" include antibodies or immunoglobulins of any isotype, fragments of antibodies that retain specific binding to antigen, including, but not limited to, Fab, Fv, scFv, and Fd fragments, chimeric antibodies, humanized antibodies, single-chain antibodies (scAb), single domain antibodies (dAb), single domain heavy chain antibodies, a single domain light chain antibodies, bi-specific antibodies, multi-specific antibodies, and fusion proteins comprising an antigen-binding (also referred to herein as antigen binding) portion of an antibody and a non-antibody protein. Also encompassed by the term are Fab', Fv, F(ab')$_2$, and or other antibody fragments that retain specific binding to antigen, and monoclonal antibodies. As used herein, a monoclonal antibody is an antibody produced by a group of identical cells, all of which were produced from a single cell by repetitive cellular replication. That is, the clone of cells only produces a single antibody species. While a monoclonal antibody can be produced using hybridoma production technology, other production methods known to those skilled in the art can also be used (e.g., antibodies derived from antibody phage display libraries).

An antibody can be monovalent or bivalent. An antibody can be an Ig monomer, which is a "Y-shaped" molecule that consists of four polypeptide chains: two heavy chains and two light chains connected by disulfide bonds.

The term "humanized antibody" as used herein refers to an antibody comprising portions of antibodies of different origin, wherein at least one portion comprises amino acid sequences of human origin. For example, a humanized antibody can comprise portions derived from an immunoglobulin of nonhuman origin with the requisite specificity, such as a mouse, and from immunoglobulin sequences of human origin (e.g., chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized antibody is an antibody containing one or more antibody chains comprising a CDR derived from an antibody of nonhuman origin and a framework region derived from a light and/or heavy chain of human origin (e.g., CDR-grafted antibodies with or without framework changes). Chimeric or CDR-grafted single chain antibodies are also encompassed by the term humanized immunoglobulin. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1. See also, Ladner et al., U.S. Pat. No. 4,946,778; Huston, U.S. Pat. No. 5,476,786; and Bird, R. E. et al., Science, 242: 423-426 (1988)), regarding single chain antibodies.

For example, humanized antibodies can be produced using synthetic and/or recombinant nucleic acids to prepare genes (e.g., cDNA) encoding the desired humanized chain. For example, nucleic acid (e.g., DNA) sequences coding for humanized variable regions can be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. For example, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993)).

"Antibody fragments" comprise a portion of an intact antibody, for example, the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 (1995)); domain antibodies (dAb; Holt et al. (2003) *Trends Biotechnol.* 21:484); single-chain antibody molecules; and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

"Fv" is the minimum antibody fragment that contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain ($CH_1$) of the heavy chain. Fab fragments differ from Fab' fragments by the addition of a few residues at the carboxyl terminus of the heavy chain $CH_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these classes can be further divided into subclasses (isotypes), e.g., IgG1, IgG2, IgG3, IgG4, IgA, and IgA2. The subclasses can be further divided into types, e.g., IgG2a and IgG2b.

"Single-chain Fv" or "sFv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFvs, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) *Proc. Natl. Acad. Sci. USA* 90:6444-6448.

As used herein, the term "affinity" refers to the equilibrium constant for the reversible binding of two agents (e.g., an antibody and an antigen) and is expressed as a dissociation constant ($K_D$). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1,000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. "Specific binding" refers to binding with an affinity of at least about $10^{-7}$ M or greater, e.g., $5 \times 10^{-7}$ M, $10^{-8}$ M, $5 \times 10^{-8}$ M, and greater. "Non-specific binding" refers to binding with an affinity of less than about $10^{-7}$ M, e.g., binding with an affinity of $10^{-6}$ M, $10^{-5}$ M, $10^{-4}$ M, etc.

As used herein, the term "CDR" or "complementarity determining region" is intended to mean the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991) (also referred to herein as Kabat 1991); by Chothia et al., J. Mol. Biol. 196:901-917 (1987) (also referred to herein as Chothia 1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues, which encompass the CDRs, as defined by each of the above cited references are set forth in the table below as a comparison. The CDRs listed in Table 2 were defined in accordance with Kabat 1991.

TABLE

CDR Definitions

|  | Kabat[1] | Chothia[2] | MacCallum[3] |
|---|---|---|---|
| $V_H$ CDR-1 | 31-35 | 26-32 | 30-35 |
| $V_H$ CDR-2 | 50-65 | 53-55 | 47-58 |
| $V_H$ CDR-3 | 95-102 | 96-101 | 93-101 |
| $V_L$ CDR-1 | 24-34 | 26-32 | 30-36 |
| $V_L$ CDR-2 | 50-56 | 50-52 | 46-55 |
| $V_L$ CDR-3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the terms "CDR-L1", "CDR-L2", and "CDR-L3" refer, respectively, to the first, second, and third CDRs in a light chain variable region. As used herein, the terms "CDR-H1", "CDR-H2", and "CDR-H3" refer, respectively, to the first, second, and third CDRs in a heavy chain variable region. As used herein, the terms "CDR-1", "CDR-2", and "CDR-3" refer, respectively, to the first, second and third CDRs of either chain's variable region.

As used herein, the term "framework" when used in reference to an antibody variable region is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term "framework region" is intended to mean each domain of the framework that is separated by the CDRs.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired. Mammals include, e.g., humans, non-human primates, rodents (e.g., rats; mice), lagomorphs (e.g., rabbits), ungulates (e.g., cows, sheep, pigs, horses, goats, and the like), etc.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a variant IL-2 polypeptide" includes a plurality of such polypeptides and reference to "the Class I HLA heavy chain polypeptide" includes reference to one or more Class I HLA heavy chain polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides treatment methods comprising administering to an individual in need thereof a T-cell modulatory multimeric polypeptide (a "synTac" multimeric polypeptide) and at least one additional therapeutic agent. In some cases, the at least one additional therapeutic agent is an immune checkpoint inhibitor. In some cases, the immune checkpoint inhibitor is an antibody specific for the immune checkpoint. The present disclosure provides methods comprising administering a multimeric polypeptide (synTac) and an immune checkpoint inhibitor to an individual. The present disclosure provides methods comprising administering a multimeric polypeptide (synTac) to an individual who is undergoing treatment with immune checkpoint inhibitor.

A "T-cell modulatory multimeric polypeptide" is also referred herein to as a "synTac polypeptide" or a "synTac multimeric polypeptide" or simply "synTac." A synTac polypeptide comprises a modulatory domain. In some cases, the modulatory domain comprises a wild-type amino acid sequence, e.g., an amino acid sequence found in a naturally-occurring modulatory polypeptide. In some cases, the modulatory domain is a variant modulatory domain, where the variant modulatory domain exhibits reduced binding affinity to an immunomodulatory polypeptide, compared to the affinity of a wild-type modulatory domain for the immunomodulatory polypeptide. A synTac polypeptide can modulate the activity of a target T-cell. A synTac polypeptide comprising a variant modulatory domain provides for enhanced target cell specificity.

In some cases, a treatment method of the present disclosure comprises administering to an individual in need thereof a synTac and an immune checkpoint inhibitor. In some cases, the synTac and the immune checkpoint inhibitor provide synergistic effects, compared to the effect(s) of the synTac when administered alone (in monotherapy) or the immune checkpoint inhibitor alone (in monotherapy).

The combination of a synTac and an immune checkpoint inhibitor is in some cases more effective than the additive effects of the synTac administered as monotherapy or the immune checkpoint inhibitor administered as monotherapy. For example, in some cases, a synergistic effect of a synTac and an immune checkpoint inhibitor permits the use of lower dosages of the synTac or the immune checkpoint inhibitor and/or less frequent administration of the synTac or the immune checkpoint inhibitor to an individual in need thereof. The ability to utilize lower dosages of therapeutic agents (a synTac or an immune checkpoint inhibitor) and/or to administer such agents less frequently can reduce toxicity or other adverse side effects that may be associated with the administration of the therapeutic agent in monotherapy, without reducing the efficacy of the therapeutic agent in a treatment. In addition, a synergistic effect of a synTac and an immune checkpoint inhibitor can result in enhanced clinical benefit, compared to the clinical benefit obtained with synTac monotherapy or immune checkpoint inhibitor monotherapy. Examples of clinical benefit include, e.g., reduced tumor mass in an individual; reduced number of cancer cells in an individual; increased survival time of the individual; increased remission time; and the like. Finally, a synergistic effect of a synTac and an immune checkpoint inhibitor can be reduced adverse or unwanted side effects associated with synTac monotherapy or immune checkpoint inhibitor monotherapy.

Immune Checkpoint Inhibitors

Exemplary immune checkpoint inhibitors include inhibitors that target immune checkpoint polypeptide such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, CD96, TIGIT, CD122, PD-1, PD-L1 and PD-L2. In some cases, the immune checkpoint polypeptide is a stimulatory checkpoint molecule selected from CD27, CD28, CD40, ICOS, OX40, GITR, CD122 and CD137. In some cases, the immune checkpoint polypeptide is an inhibitory checkpoint molecule selected from A2AR, B7-H3, B7-H4, BTLA, CTLA-4, IDO, KIR, LAG3, PD-1, TIM3, CD96, TIGIT and VISTA.

In some cases, the immune checkpoint inhibitor is an antibody specific for an immune checkpoint. In some cases, the anti-immune checkpoint antibody is a monoclonal antibody. In some cases, the anti-immune checkpoint antibody is humanized, or de-immunized such that the antibody does not substantially elicit an immune response in a human. In some cases, the anti-immune checkpoint antibody is a humanized monoclonal antibody. In some cases, the anti-immune checkpoint antibody is a de-immunized monoclonal antibody. In some cases, the anti-immune checkpoint antibody is a fully human monoclonal antibody. In some cases, the anti-immune checkpoint antibody inhibits binding of the immune checkpoint polypeptide to a ligand for the immune checkpoint polypeptide. In some cases, the anti-immune checkpoint antibody inhibits binding of the immune checkpoint polypeptide to a receptor for the immune checkpoint polypeptide.

Antibodies, e.g., monoclonal antibodies, that are specific for immune checkpoints and that function as immune checkpoint inhibitors, are known in the art. See, e.g., Wurz et al. (2016) *Ther. Adv. Med. Oncol.* 8:4; and Naidoo et al. (2015) *Ann. Oncol.* 26:2375.

Suitable anti-immune checkpoint antibodies include, but are not limited to, nivolumab (Bristol-Myers Squibb), pembrolizumab (Merck), pidilizumab (Curetech), AMP-224 (GlaxoSmithKline/Amplimmune), MPDL3280A (Roche), MDX-1105 (Medarex, Inc./Bristol Myer Squibb), MEDI-4736 (Medimmune/AstraZeneca), arelumab (Merck Serono), ipilimumab (YERVOY, (Bristol-Myers Squibb), tremelimumab (Pfizer), pidilizumab (CureTech, Ltd.), IMP321 (Immutep S.A.), MGA271 (Macrogenics), BMS-986016 (Bristol-Meyers Squibb), lirilumab (Bristol-Myers Squibb), urelumab (Bristol-Meyers Squibb), PF-05082566 (Pfizer), IPH2101 (Innate Pharma/Bristol-Myers Squibb), MEDI-6469 (MedImmune/AZ), CP-870,893 (Genentech), Mogamulizumab (Kyowa Hakko Kirin), Varlilumab (CellDex Therapeutics), Avelumab (EMD Serono), Galiximab (Biogen Idec), AMP-514 (Amplimmune/AZ), AUNP 12 (Aurigene and Pierre Fabre), Indoximod (NewLink Genetics), NLG-919 (NewLink Genetics), INCB024360 (Incyte); KN035; and combinations thereof.

Suitable anti-LAG3 antibodies include, e.g., BMS-986016 and LAG525. Suitable anti-GITR antibodies include, e.g., TRX518, MK-4166, INCAGN01876, and MK-1248. Suitable anti-OX40 antibodies include, e.g., MED10562, INCAGN01949, GSK2831781, GSK-3174998, MOXR-0916, PF-04518600, and LAG525. Suitable anti-VISTA antibodies are provided in, e.g., WO 2015/097536.

A suitable dosage of an anti-immune checkpoint antibody is from about 1 mg/kg to about 2400 mg/kg per day, such as from about 1 mg/kg to about 1200 mg/kg per day, including from about 50 mg/kg to about 1200 mg/kg per day. Other representative dosages of such agents include about 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, 2000 mg/kg, 2100 mg/kg, 2200 mg/kg, and 2300 mg/kg per day. The effective dose of the antibody may be administered as two, three, four, five, six or more sub-doses, administered separately at appropriate intervals throughout the day.

Anti-PD-1 Antibodies

In some cases, an immune checkpoint inhibitor is an anti-PD-1 antibody.

Suitable anti-PD-1 antibodies include, e.g., nivolumab, pembrolizumab (also known as MK-3475), pidilizumab, SHR-1210, PDR001, and AMP-224. In some cases, the anti-PD-1 monoclonal antibody is nivolumab, pembrolizumab or PDR001. Suitable anti-PD1 antibodies are described in U.S. Patent Publication No. 2017/0044259. For pidilizumab, see, e.g., Rosenblatt et al. (2011) *J. Immunother.* 34:409-18.

In some cases, the anti-PD1 antibody is pembrolizumab. The amino acid sequence of the heavy chain of pembrolizumab is:

```
                                            (SEQ ID NO: 51)
QVQLVQSGVEVKKPGASVKVSCKASGYTFTNYYMYWVRQAPGQGLEWMG

GINPSNGGTNFNEKFKNRVTLTTDSSTTTAYMELKSLQFDDTAVYYCAR

RDYRFDMGFDYWGQGTTVTVSSASTKGPSVFPLAPCSRSTSESTAALGC

LVKDYFPEPVTVSWNSGALTSGVHTFPAVLQSSGLYSLSSVVTVPSSSL

GTKTYTCNVDHKPSNTKVDKRVESKYGPPCPPCPAPEFLGGPSVFLFPP

KPKDTLMISRTPEVTCVVVDVSQEDPEVQFNWYVDGVEVHNAKTKPREE

QFNSTYRVVSVLTVLHQDWLNGKEYKCKVSNKGLPSSIEKTISKAKGQP

REPQVYTLPPSQEEMTKNQVSLTCLVKGFYPSDIAVEWESNGQPENNYK

TTPPVLDSDGSFFLYSRLTVDKSRWQEGNVFSCSVMHEALHNHYTQKSL

SLSLGK
```

The amino acid sequence of the heavy chain variable (VH) region is underlined.

The amino acid sequence of the light chain of pembrolizumab is:

```
                                            (SEQ ID NO: 52)
EIVLTQSPATLSLSPGERATLSCRASKGVSTSGYSYLHWYQQKPGQAPR

LLIYLASYLESGVPARFSGSGSGTDFTLTISSLEPEDFAVYYCQHSRDL

PLTFGGGTKVEIKRTVAAPSVFIFPPSDEQLKSGTASVVCLLNNFYPRE

AKVQWKVDNALQSGNSQESVTEQDSKDSTYSLSSTLTLSKADYEKHKVY

ACEVTHQGLSSPVTKSFNRGEC.
```

The amino acid sequence of the light chain variable (VL) region is underlined.

In some cases, the anti-PD-1 antibody comprises the VH and VL regions of pembrolizumab. In some cases, the anti-PD-1 antibody comprises heavy and light chain CDRs of pembrolizumab.

In some cases, the anti-PD-1 antibody is nivolumab (also known as MDX-1106 or BMS-936558; see, e.g., Topalian et al. (2012) N. Eng. J. Med. 366:2443-2454; and U.S. Pat. No. 8,008,449). The amino acid sequence of the heavy chain of nivolumab is:

```
                                            (SEQ ID NO: 53)
QVQLVESGGGVVQPGRSLRLDCKASGITFSNSGMHWVRQAPGKGLEWVA

VIWYDGSKRYYADSVKGRFTISRDNSKNTLFLQMNSLRAEDTAVYYCAT

NDDYWGQGTLVTVSSASTKGPSVFPLAPCSRSTSESTAALGCLVKDYFP

EPVTVSWNSGALTSGVHTFPAVLQSSGLYSLSSVVTVPSSSLGTKTYTC

NVDHKPSNTKVDKRVESKYGPPCPPCPAPEFLGGPSVFLFPPKPKDTLM

ISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK.
```

The amino acid sequence of the light chain of nivolumab is:

(SEQ ID NO: 54)
EIVLTQSPATLSLSPGERATLSCRASQSVSSYLAWYQQKPGQAPRLLIY

DASNRATGIPARFSGSGSGTDFTLTISSLEPEDFAVYYCQQSSNWPRTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.

In some cases, the anti-PD-1 antibody comprises heavy and light chain CDRs of nivolumab.

Anti-CTLA4 Antibodies

In some cases, the anti-CTLA-4 antibody is ipilimumab or tremelimumab. For tremelimumab, see, e.g., Ribas et al. (2013) *J. Clin. Oncol.* 31:616-22.

In some cases, the anti-CTLA-4 antibody is ipilimumab. The amino acid sequence of the heavy chain of ipilimumab is:

(SEQ ID NO: 55)
<u>QVQLVESGGGVVQPGRSLRLSCAASGFTFSSYTMHWVRQAPGKGLEWVT</u>

<u>FISYDGNNKYYADSVKGRFTISRDNSKNTLYLQMNSLRAEDTAIYYCAR</u>

<u>TGWLGPFDYWGQGTLVTVSSA</u>STKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKRVEPKSCDKTHTCPPCPAPELLGGPSVFLFP

PKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKS

LSLSPGK.

The amino acid sequence of the VH region is underlined.

The amino acid sequence of the light chain of ipilimumab is:

(SEQ ID NO: 56)
<u>EIVLTQSPGTLSLSPGERATLSCRASQSVGSSYLAWYQQKPGQAPRLLI</u>

<u>YGAFSRATGIPDRFSGSGSGTDFTLTISRLEPEDFAVYYCQQYGSSPWT</u>

<u>FGQGTKVEIK</u>RTVAAPSSLSSTLTLSKADYEKHKVYACEVTHQGLSSPV

TKSFNRGEC.

The amino acid sequence of the VL region is underlined.

In some cases, the anti-CTLA4 antibody comprises the VH and VL regions of ipilimumab. In some cases, the anti-CTLA4 antibody comprises heavy and light chain CDRs of ipilimumab.

Anti-PD-L1 Antibodies

In some cases, the immune checkpoint inhibitor is an anti-PD-L1 monoclonal antibody. In some cases, the anti-PD-L1 monoclonal antibody is BMS-935559, MEDI4736, MPDL3280A (also known as RG7446), KN035, or MSB0010718C. In some embodiments, the anti-PD-L1 monoclonal antibody is MPDL3280A (atezolizumab) or MEDI4736 (durvalumab). For durvalumab, see, e.g., WO 2011/066389. For atezolizumab, see, e.g., U.S. Pat. No. 8,217,149.

In some cases, the anti-PD-L1 antibody is atezolizumab. The amino acid sequence of the heavy chain of atezolizumab is:

(SEQ ID NO: 57)
EVQLVESGGGLVQPGGSLRLSCAASGFTFSDSWIHWVRQAPGKGLEWVA

WISPYGGSTYYADSVKGRFTISADTSKNTAYLQMNSLRAEDTAVYYCAR

RHWPGGFDYWGQGTLVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPRE

EQYASTYRVVSVLTVLHQDWLNGKEYKCKVSNKALPAPIEKTISKAKGQ

PREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKS

LSLSPGK.

The amino acid sequence of the light chain of atezolizumab is:

(SEQ ID NO: 58)
DIQMTQSPSSLSASVGDRVTITCRASQDVSTAVAWYQQKPGKAPKLLIY

SASFLYSGVPSRFSGSGSGTDFTLTISSLQPEDFATYYCQQYLYHPATF

GQGTKVEIKRTVAAPSVFIFPPSDEQLKSGTASVVCLLNNFYPREAKVQ

WKVDNALQSGNSQESVTEQDSKDSTSLSSTLTLSKADYEKHKVYACEVT

HQGLSSPVTKSFNRGEC.

In some cases, the anti-PD-L1 antibody comprises heavy and light chain CDRs of atezolizumab.

In some cases, the anti-PDL1 antibody is KN035, a fully humanized anti-PD-L1 single domain antibody fused to a human IgG1 Fc polypeptide. Zhang et al. (2017) *Cell Discov.* 3:17004; and WO 2017/020801. The single-domain antibody portion of KN035 can comprise the amino acid sequence:

(SEQ ID NO: 216)
QVQLQESGGGLVQPGGSLRLSCAAS<u>GKMSSRRC</u>MAWFRQAPGKERERVA

KLLTT<u>SGSTYLADSVKGRFTISONNAKSTVYLOMNSLKPEDTAMYYC</u><u>AA</u>

<u>DSFEDPTCTLVTSSGAFQY</u>WGQGTQVTVS, where the underlined amino acids are CDR1, CDR2, and CDR3.

T-Cell Modulatory Multimeric Polypeptides (synTacs)

Multimeric (e.g., heterodimeric, heterotrimeric) polypeptides suitable for use in a method of the present disclosure are described below. The multimeric polypeptides are T cell modulatory polypeptides, and are also referred to herein as "T-cell modulatory multimeric polypeptides," or "synTac" (for "immunological synapse for T cell activation").

A T-cell modulatory multimeric polypeptide comprises: a) a first polypeptide comprising, in order from N-terminus to C-terminus: i) an epitope; ii) a first major histocompatibility complex (MHC) polypeptide; and b) a second polypeptide comprising, in order from N-terminus to C-terminus: i) a second MHC polypeptide; and ii) optionally an immunoglobulin (Ig) Fc polypeptide or a non-Ig scaffold, where the multimeric polypeptide comprises one or more immunomodulatory ("MOD") domains, wherein the one or more immunomodulatory domain is: A) at the C-terminus of the first polypeptide; B) at the N-terminus of the second polypeptide; C) at the C-terminus of the second polypeptide; or D) at the C-terminus of the first polypeptide and at the N-terminus of the second polypeptide. In some cases, a T-cell multimeric polypeptide comprises: a) a first polypeptide comprising, in order from N-terminus to C-terminus: i) an epitope; ii) a first MHC polypeptide; and iii) an immunomodulatory domain; and b) a second polypeptide comprising, in order from N-terminus to C-terminus: i) a second MHC polypeptide; and ii) an Ig Fc polypeptide. In some cases, a T-cell multimeric polypeptide comprises: a) a first polypeptide comprising, in order from N-terminus to C-terminus: i) an epitope; and ii) a first MHC polypeptide; and b) a second polypeptide comprising, in order from N-terminus to C-terminus: i) an immunomodulatory domain; iii) a second MHC polypeptide; and ii) an Ig Fc polypeptide. In some cases, a T-cell multimeric polypeptide comprises: a) a first polypeptide comprising, in order from N-terminus to C-terminus: i) an epitope; and ii) a first MHC polypeptide; and b) a second polypeptide comprising, in order from N-terminus to C-terminus: i) a second MHC polypeptide; and ii) an Ig Fc polypeptide; and iii) an immunomodulatory ("MOD") domain. In some cases, a T-cell multimeric polypeptide comprises: a) a first polypeptide comprising, in order from N-terminus to C-terminus: i) an epitope; and ii) a first MHC polypeptide; and b) a second polypeptide comprising, in order from N-terminus to C-terminus: i) a second MHC polypeptide; and ii) an immunomodulatory domain. In some cases, a T-cell multimeric polypeptide comprises: a) a first polypeptide comprising, in order from N-terminus to C-terminus: i) an epitope; and ii) a first MHC polypeptide; and b) a second polypeptide comprising, in order from N-terminus to C-terminus: i) an immunomodulatory domain; and ii) a second MHC polypeptide. In some cases, a T-cell multimeric polypeptide comprises: a) a first polypeptide comprising, in order from N-terminus to C-terminus: i) an epitope; ii) a first MHC polypeptide; and iii) an immunomodulatory domain; and b) a second polypeptide comprising, in order from N-terminus to C-terminus: i) a second MHC polypeptide.

In some cases, a multimeric polypeptide comprises a non-Ig scaffold. For example, in some cases, the non-Ig scaffold is an XTEN polypeptide, a transferrin polypeptide, an Fc receptor polypeptide, an elastin-like polypeptide, a silk-like polypeptide, or a silk-elastin-like polypeptide.

In some cases, the first MHC polypeptide is a β2-microglobulin (β2M) polypeptide; and the second MHC polypeptide is an MHC class I heavy chain polypeptide. A suitable 32-M polypeptide comprises an amino acid sequence having at least 85%, at least 90%, at least 95%, at least 98%, at least 99%, or 100%, amino acid sequence identity to the amino acid sequence of a β2M polypeptide depicted in FIG. 6. In some cases, the MHC class I heavy chain polypeptide is an HLA-A, an HLA-B, or an HLA-C heavy chain. In some cases, the MHC class I heavy chain polypeptide comprises an amino acid sequence having at least 85%, at least 90%, at least 95%, at least 98%, at least 99%, or 100%, amino acid sequence identity to the amino acid sequence set forth in one of FIG. 5A-5C. In some cases, the first MHC polypeptide is an MHC Class II alpha chain polypeptide; and the second MHC polypeptide is an MHC class II beta chain polypeptide.

The epitope present in a multimeric polypeptide can be a T-cell epitope.

In some cases, a multimeric polypeptide comprises an Ig Fc polypeptide. In some cases, the Ig Fc polypeptide is an IgG1 Fc polypeptide, an IgG2 Fc polypeptide, an IgG3 Fc polypeptide, an IgG4 Fc polypeptide, an IgA Fc polypeptide, or an IgM Fc polypeptide. In some cases, the Ig Fc polypeptide comprises an amino acid sequence having at least 85%, at least 90%, at least 95%, at least 98%, at least 99%, or 100%, amino acid sequence identity to an amino acid sequence depicted in FIG. 4A-4C.

The first polypeptide and the second polypeptide of a multimeric polypeptide can be non-covalently associated. The first polypeptide and the second polypeptide of a multimeric polypeptide can be covalently linked. The first polypeptide and the second polypeptide of a multimeric polypeptide can be covalently linked, where the covalent linkage is via a disulfide bond. In some cases, the first MHC polypeptide or a linker between the epitope and the first MHC polypeptide comprises an amino acid substitution to provide a first Cys residue, and the second MHC polypeptide comprises an amino acid substitution to provide a second Cys residue, and wherein the disulfide linkage is between the first and the second Cys residues.

A multimeric polypeptide can include a linker between one or more of: the epitope and the first MHC polypeptide; two copies of the immunomodulatory ("MOD") polypeptide; the immunomodulatory polypeptide and the second MHC polypeptide; and the second MHC polypeptide and the Ig Fc polypeptide.

Immunomodulatory polypeptides suitable for inclusion in a T-cell multimeric polypeptide include, but are not limited to, a 4-1BBL polypeptide, a B7-1 polypeptide; a B7-2 polypeptide, an ICOS-L polypeptide, an OX-40L polypeptide, a CD80 polypeptide, a CD86 polypeptide, an IL-2 polypeptide, a PD-L1 polypeptide, a FasL polypeptide, and a PD-L2 polypeptide.

A multimeric polypeptide can include 2 or more immunomodulatory polypeptides. A multimeric polypeptide can include 2 immunomodulatory polypeptides. In some cases, the 2 immunomodulatory polypeptides are in tandem. A multimeric polypeptide can include 3 immunomodulatory polypeptides. In some cases, the 3 immunomodulatory polypeptides are in tandem.

A multimeric polypeptide can comprise a third polypeptide, where the third polypeptide comprises an immunomodulatory polypeptide comprising an amino acid sequence having at least 90%, amino acid sequence identity to the immunomodulatory polypeptide of the first polypeptide or the second polypeptide. In some cases, the third polypeptide is covalently linked to the first polypeptide.

Examples of suitable multimeric polypeptides are described in WO 2017/151940; WO 2017/201210; and PCT/US2017/067663. The disclosures of WO 2017/151940, WO 2017/201210, and PCT/US2017/067663 are incorporated by reference herein.

MHC Polypeptides

As noted above, a multimeric polypeptide of the present disclosure includes MHC polypeptides. For the purposes of the instant disclosure, the term "major histocompatibility complex (MHC) polypeptides" is meant to include MHC polypeptides of various species, including human MHC (also referred to as human leukocyte antigen (HLA)) polypeptides, rodent (e.g., mouse, rat, etc.) MHC polypeptides, and MHC polypeptides of other mammalian species (e.g., lagomorphs, non-human primates, canines, felines, ungulates (e.g., equines, bovines, ovines, caprines, etc.), and the like. The term "MHC polypeptide" is meant to include Class I MHC polypeptides (e.g., β-2 microglobulin and MHC class I heavy chain) and MHC Class II polypeptides (e.g., MHC Class II α polypeptide and MHC Class II β polypeptide).

As noted above, in some embodiments of a multimeric polypeptide of the present disclosure, the first and the second MHC polypeptides are Class I MHC polypeptides; e.g., in some cases, the first MHC polypeptide is an MHC Class I β2-microglobulin (β2M) polypeptide, and the second MHC polypeptide is an MHC Class I heavy chain (H chain). In other cases, the first and the second MHC polypeptides are Class II MHC polypeptides; e.g., in some cases, the first MHC polypeptide is an MHC Class II α-chain polypeptide, and the second MHC polypeptide is an MHC Class II β-chain polypeptide. In other cases, the first polypeptide is an MHC Class II β-chain polypeptide, and the second MHC polypeptide is an MHC Class II α-chain polypeptide.

In some cases, an MHC polypeptide of a multimeric polypeptide of the present disclosure is a human MHC polypeptide, where human MHC polypeptides are also referred to as "human leukocyte antigen" ("HLA") polypeptides. In some cases, an MHC polypeptide of a multimeric polypeptide of the present disclosure is a Class I HLA polypeptide, e.g., a β2-microglobulin polypeptide, or a Class I HLA heavy chain polypeptide. Class I HLA heavy chain polypeptides include HLA-A heavy chain polypeptides, HLA-B heavy chain polypeptides, HLA-C heavy chain polypeptides, HLA-E heavy chain polypeptides, HLA-F heavy chain polypeptides, and HLA-G heavy chain polypeptides. In some cases, an MHC polypeptide of a multimeric polypeptide of the present disclosure is a Class II HLA polypeptide, e.g., a Class II HLA α chain or a Class II HLA β chain. MHC Class II polypeptides include MCH Class II DP α and R polypeptides, DM α and β polypeptides, DOA α and β polypeptides, DOB α and β polypeptides, DQ α and β polypeptides, and DR α and β polypeptides.

In some cases, an MHC Class I heavy chain polypeptide of a multimeric polypeptide can comprise an amino acid sequence having at least 75%, at least 80%, at least 85%, at least 90%, at least 95%, at least 98%, at least 99%, or 100%, amino acid sequence identity to an amino acid sequence depicted in one of FIG. 5A-5C.

HLA-A

As an example, an MHC Class I heavy chain polypeptide of a multimeric polypeptide can comprise an amino acid sequence having at least 75%, at least 80%, at least 85%, at least 90%, at least 95%, at least 98%, at least 99%, or 100%, amino acid sequence identity to the following human HLA-A heavy chain amino acid sequence:

(SEQ ID NO: 59)
GSHSMRYFFTSVSRPGRGEPRFIAVGYVDDTQFVRFDSDAASQRMEPRA

PWIEQEGPEYWDGETRKVKAHSQTHRVDLGTLRGYYNQSEAGSHTVQRM

YGCDVGSDWRFLRGYHQYAYDGKDYIALKEDLRSWTAADMAAQTTKHKW

EAAHVAEQLRAYLEGTCVEWLRRYLENGKETLQRTDAPKTHMTHHAVSD

HEATLRCWALSFYPAEITLTWQRDGEDQTQDTELVETRPAGDGTFQKWA

AVVVPSGQEQRYTCHVQHEGLPKPLTLRWEP.

HLA-A (Y84A; A236C)

In some cases, the MHC Class I heavy chain polypeptide comprises Y84A and A236C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-A heavy chain (Y84A; A236C) amino acid sequence: GSHSMRYFFTSVSRP-GRGEPRFIAVGYVDDTQFVRFDSDAASQRMEPRAP-WIEQEGPEYWDGETRKVKAHSQTHRVDLGTLRGA̲Y-NQSEAGSHTVQRMYGCDVGSDWRFLRGYHQYAY-DGKDYIALKEDLRSWTAADMAAQTTKHKWEAAH-VAEQLRAYLEGTCVEWLRRY LENGKETLQRTDAPK-THMTHHAVSDHEATLRCWALSFYPAEITLTWQRD-GEDQTQDTELVETRPC̲GDGTFQKWAAVVVPSGQ-EQRYTCHVQHEGLPKPLTLRWEP (SEQ ID NO:50), where amino acid 84 is Ala and amino acid 236 is Cys. In some cases, the Cys-236 forms an interchain disulfide bond with Cys-12 of a variant β2M polypeptide that comprises an R12C substitution.

HLA-A (Y84C; A139C)

In some cases, the MHC Class I heavy chain polypeptide comprises Y84C and A139C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-A heavy chain (Y84C; A139C) amino acid sequence: GSHSMRYFFTSVSRPGRGEPR-FIAVGYVDDTQFVRFDSDAASQRMEPRAPWIEQEG-PEYWDGETRKVKAHSQTHRVDLGTLRGC̲YNQSEA-GSHTVQRMYGCDVGSDWRFLRGYHQYAY̲DGKD-YIALKEDLRSWTAADMC̲AQTTKHKWEAAHVAE-QLRAYLEGTCVEWLRRY̲LENGKETLQRTDAPKT-HMTHHAVSDHEATLRCWALSFYPAEITLTWQRD-GEDQTQDTE LVETRPAGDGTFQKWAAVVVPSGQE-QRYTCHVQHEGLPKPLTLRWEP (SEQ ID NO:196), where amino acid 84 is Cys and amino acid 139 is Cys. In some cases, Cys-84 forms an intrachain disulfide bond with Cys-139.

HLA-A A11 (HLA-A11)

As one non-limiting example, an MHC Class I heavy chain polypeptide of a multimeric polypeptide can comprise an amino acid sequence having at least 75%, at least 80%, at least 85%, at least 90%, at least 95%, at least 98%, at least 99%, or 100%, amino acid sequence identity to the following human HLA-A A11 (also referred to as "HLA-A11") heavy chain amino acid sequence:

(SEQ ID NO: 197)
GSHSMRYFYTSVSRPGRGEPRFIAVGYVDDTQFVRFDSDAASQRMEPRA

PWIEQEGPEYWDQETRNVKAQSQTDRVDLGTLRGYYNQSEDGSHTIQIM

YGCDVGPDGRFLRGYRQDAYDGKDYIALNEDLRSWTAADMAAQITKRKW

EAAHAAEQQRAYLEGTCVEWLRRYLENGKETLQRTDPPKTHMTHHPISD

HEATLRCWALGFYPAEITLTWQRDGEDQTQDTELVETRPAGDGTFQKWA

AVVVPSGEEQRYTCHVQHEGLPKPLTLRWE.

Such an MHC Class I heavy chain may be prominent in Asian populations, including populations of individuals of Asian descent.

HLA-A A11 (Y84A; A236C)

As one non-limiting example, in some cases, the MHC Class I heavy chain polypeptide is an HLA-A A11 allele that comprises Y84A and A236C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-A A11 heavy chain (Y84A; A236C) amino acid sequence: GSHSMRYFYTSVSR-PGRGEPRFIAVGYVDDTQFVRFDSDAASQRMEPRAP-WIEQEGPEY WDQETRNVKAQSQTDRVDLGTLRG AYNQSEDGSHTIQIMYGCDVGPDGRFLRGYRQD AYDGKDYIALNEDLRSWTAADMAAQITKRKWEAA-HAAEQQRAYLEGTCVEWLRRYL ENGKETLQRTDPP-KTHMTHHPISDHEATLRCWALGFYPAEITLTWQRD-GEDQTQDTEL VETRPCGDGTFQKWAAVVVPS-GEEQRYTCHVQHEGLPKPLTLRWE (SEQ ID NO:198), where amino acid 84 is Ala and amino acid 236 is Cys. In some cases, the Cys-236 forms an interchain disulfide bond with Cys-12 of a variant β2M polypeptide that comprises an R12C substitution.

HLA-B

As another example, an MHC Class I heavy chain polypeptide of a multimeric polypeptide can comprise an amino acid sequence having at least 75%, at least 80%, at least 85%, at least 90%, at least 95%, at least 98%, at least 99%, or 100%, amino acid sequence identity to the following human HLA-B heavy chain amino acid sequence:

(SEQ ID NO: 199)
GSHSMRYFYTSVSRPGRGEPRFISVGYVDDTQFVRFDSDAASPREEPRA

PWIEQEGPEYWDRNTQIYKAQAQTDRESLRNLRGYYNQSEAGSHTLQSM

YGCDVGPDGRLLRGHDQYAYDGKDYIALNEDLRSWTAADTAAQITQRKW

EAAREAEQRRAYLEGECVEWLRRYLENGKDKLERADPPKTHVTHHPISD

HEATLRCWALGFYPAEITLTWQRDGEDQTQDTELVETRPAGDRTFQKWA

AVVVPSGEEQRYTCHVQHEGLPKPLTLRWEP.

HLA-B (Y84A; A236C)

As one non-limiting example, in some cases, the MHC Class I heavy chain polypeptide is an HLA-B polypeptide that comprises Y84A and A236C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-B heavy chain (Y84A; A236C) amino acid sequence: GSHSMRYFYTSVS-RPGRGEPRFISVGYVDDTQFVRFDSDAASPREE-PRAPWIEQEGPEY WDRNTQIYKAQAQTDRESLRN-LRGAYNQSEAGSHTLQSMYGCDVGPDGRLLRG-HDQY AYDGKDYIALNEDLRSWTAADTAAQITQRK-WEAAREAEQRRAYLEGECVEWLRRYLE NGKDKL-ERADPPKTHVTHHPISDHEATLRCWALGFYPAEI-TLTWQRDGEDQTQDTELV ETRPCGDRTFQKWAAV-VVPSGEEQRYTCHVQHEGLPKPLTLRWEP (SEQ ID NO:200), where amino acid 84 is Ala and amino acid 236 is Cys. In some cases, the Cys-236 forms an interchain disulfide bond with Cys-12 of a variant β2M polypeptide that comprises an R12C substitution.

HLA-B (Y84C; A139C)

In some cases, the MHC Class I heavy chain polypeptide comprises Y84C and A139C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-B heavy chain (Y84C; A139C) amino acid sequence: GSHSMRYFYTSVSRP-GRGEPRFISVGYVDDTQFVRFDSDAASPREEPRAP-WIEQEGPEY WDRNTQIYKAQAQTDRESLRNLRG CYNQSEAGSHTLQSMYGCDVGPDGRLLRGHDQYA-YDGKDYIALNEDLRSWTAADTCAQITQRKWEAARE-AEQRRAYLEGECVEWLRRYLE NGKDKLERADPPK-THVTHHPISDHEATLRCWALGFYPAEITLTWQR-DGEDQTQDTELV ETRPAGDRTFQKWAAVVVPSGE-EQRYTCHVQHEGLPKPLTLRWEP (SEQ ID NO:201), where amino acid 84 is Cys and amino acid 139 is Cys. In some cases, Cys-84 forms an intrachain disulfide bond with Cys-139.

HLA-C

As another example, an MHC Class I heavy chain polypeptide of a multimeric polypeptide can comprise an amino acid sequence having at least 75%, at least 80%, at least 85%, at least 90%, at least 95%, at least 98%, at least 99%, or 100%, amino acid sequence identity to the following human HLA-C heavy chain amino acid sequence:

(SEQ ID NO: 202)
CSHSMRYFDTAVSRPGRGEPRFISVGYVDDTQFVRFDSDAASPRGEPRA

PWVEQEGPEYWDRETQNYKRQAQADRVSLRNLRGYYNQSEDGSHTLQRM

YGCDLGPDGRLLRGYDQSAYDGKDYIALNEDLRSWTAADTAAQITQRKL

EAARAAEQLRAYLEGTCVEWLRRYLENGKETLQRAEPPKTHVTHHPLSD

HEATLRCWALGFYPAEITLTWQRDGEDQTQDTELVETRPAGDGTFQKWA

AVVVPSGQEQRYTCHMQHEGLQEPLTLSWEP.

HLA-C (Y84A; A236C)

As one non-limiting example, in some cases, the MHC Class I heavy chain polypeptide is an HLA-C polypeptide that comprises Y84A and A236C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-C heavy chain (Y84A; A236C) amino acid sequence: CSHSMRYFD-TAVSRPGRGEPRFISVGYVDDTQFVRFDSDAASPR-GEPRAPWVEQEGPEY WDRETQNYKRQAQADRVS-LRNLRGAYNQSEDGSHTLQRMYGCDLGPDGRL-LRGYDQ SAYDGKDYIALNEDLRSWTAADTAAQI-TQRKLEAARAAEQLRAYLEGTCVEWLRRYLE NGK-ETLQRAEPPKTHVTHHPLSDHEATLRCWALGFY-PAEITLTWQRDGEDQTQDTELV ETRPCGDGTFQ-KWAAVVVPSGQEQRYTCHMQHEGLQEPLTLSWEP (SEQ ID NO:203), where amino acid 84 is Ala and amino acid 236 is Cys. In some cases, the Cys-236 forms an interchain disulfide bond with Cys-12 of a variant β2M polypeptide that comprises an R12C substitution.

HLA-C (Y84C; A139C)

In some cases, the MHC Class I heavy chain polypeptide comprises Y84C and A139C substitutions. For example, in some cases, the MHC Class I heavy chain polypeptide comprises an amino acid sequence having at least 75%, at least 80%, at least 85%, at least 90%, at least 95%, at least 98%, at least 99%, or 100%, amino acid sequence identity to the following human HLA-C heavy chain (Y84C; A139C)

amino acid sequence: CSHSMRYFDTAVSRPGR-
GEPRFISVGYVDDTQFVRFDSDAASPRGEPRAPW-
VEQEGPEY WDRETQNYKRQAQADRVSLRNLRG
CYNQSEDGSHTLQRMYGCDLGPDGRLLRGYDQ
SAYDGKDYIALNEDLRSWTAADTCAQITQRKLE-
AARAAEQLRAYLEGTCVEWLRRYLE NGKETLQRA-
EPPKTHVTHHPLSDHEATLRCWALGFYPAEITLT-
WQRDGEDQTQDTELV ETRPAGDGTFQKWAAVVV-
PSGQEQRYTCHMQHEGLQEPLTLSWEP (SEQ ID
NO:204), where amino acid 84 is Cys and amino acid 139
is Cys. In some cases, Cys-84 forms an intrachain disulfide
bond with Cys-139.

In some cases, an MHC Class I heavy chain polypeptide of a multimeric polypeptide can comprise an amino acid sequence having at least 75%, at least 80%, at least 85%, at least 90%, at least 95%, at least 98%, at least 99%, or 100%, amino acid sequence identity to an amino acid sequence depicted in one of FIG. 3A-3C.

As an example, an MHC Class I heavy chain polypeptide of a multimeric polypeptide can comprise an amino acid sequence having at least 75%, at least 80%, at least 85%, at least 90%, at least 95%, at least 98%, at least 99%, or 100%, amino acid sequence identity to amino acids 25-365 of the amino acid sequence of the human HLA-A heavy chain polypeptide depicted in FIG. 3A.

As another example, an MHC Class I heavy chain polypeptide of a multimeric polypeptide can comprise an amino acid sequence having at least 75%, at least 80%, at least 85%, at least 90%, at least 95%, at least 98%, at least 99%, or 100%, amino acid sequence identity to amino acids 25-362 of the amino acid sequence of the human HLA-B heavy chain polypeptide depicted in FIG. 3B.

As another example, an MHC Class I heavy chain polypeptide of a multimeric polypeptide can comprise an amino acid sequence having at least 75%, at least 80%, at least 85%, at least 90%, at least 95%, at least 98%, at least 99%, or 100%, amino acid sequence identity to amino acids 25-362 of the amino acid sequence of the human HLA-C heavy chain polypeptide depicted in FIG. 3C.

As another example, an MHC Class I heavy chain polypeptide of a multimeric polypeptide can comprise an amino acid sequence having at least 75%, at least 80%, at least 85%, at least 90%, at least 95%, at least 98%, at least 99%, or 100%, amino acid sequence identity to the following amino acid sequence:

```
                                          (SEQ ID NO: 60)
GPHSLRYFVTAVSRPGLGEPRFIAVGYVDDTQFVRFDSDADNPRFEPRA

PWMEQEGPEYWEEQTQRAKSDEQWFRVSLRTAQRYYNQSKGGSHTFQRM

FGCDVGSDWRLLRGYQQFAYDGRDYIALNEDLKTWTAADTAALITRRKW

EQAGDAEYYRAYLEGECVEWLRRYLELGNETLLRTDSPKAHVTYHPRSQ

VDVTLRCWALGFYPADITLTWQLNGEDLTQDMELVETRPAGDGTFQKWA

AVVVPLGKEQNYTCHVHHKGLPEPLTLRW.
```

A β2-microglobulin (β2M) polypeptide of a multimeric polypeptide can be a human β2M polypeptide, a non-human primate β2M polypeptide, a murine β2M polypeptide, and the like. In some instances, a β2M polypeptide comprises an amino acid sequence having at least 75%, at least 80%, at least 85%, at least 90%, at least 95%, at least 98%, at least 99%, or 100%, amino acid sequence identity to a β2M amino acid sequence depicted in FIG. 6. In some instances, a β2M polypeptide comprises an amino acid sequence having at least 75%, at least 80%, at least 85%, at least 90%, at least 95%, at least 98%, at least 99%, or 100%, amino acid sequence identity to amino acids 21 to 119 of a β2M amino acid sequence depicted in FIG. 6.

In some cases, an MHC polypeptide comprises a single amino acid substitution relative to a reference MHC polypeptide (where a reference MHC polypeptide can be a wild-type MHC polypeptide), where the single amino acid substitution substitutes an amino acid with a cysteine (Cys) residue. Such cysteine residues, when present in an MHC polypeptide of a first polypeptide of a multimeric polypeptide of the present disclosure, can form a disulfide bond with a cysteine residue present in a second polypeptide chain of a multimeric polypeptide of the present disclosure.

In some cases, a first MHC polypeptide in a first polypeptide of a multimeric polypeptide, and/or the second MHC polypeptide in the second polypeptide of a multimeric polypeptide, includes an amino acid substitution to substitute an amino acid with a cysteine, where the substituted cysteine in the first MHC polypeptide forms a disulfide bond with a cysteine in the second MHC polypeptide, where a cysteine in the first MHC polypeptide forms a disulfide bond with the substituted cysteine in the second MHC polypeptide, or where the substituted cysteine in the first MHC polypeptide forms a disulfide bond with the substituted cysteine in the second MHC polypeptide.

For example, in some cases, one of following pairs of residues in an HLA β2-microglobulin and an HLA Class I heavy chain is substituted with cysteines (where residue numbers are those of the mature polypeptide): 1) β2M residue 12, HLA Class I heavy chain residue 236; 2) β2M residue 12, HLA Class I heavy chain residue 237; 3) β2M residue 8, HLA Class I heavy chain residue 234; 4) β2M residue 10, HLA Class I heavy chain residue 235; 5) β2M residue 24, HLA Class I heavy chain residue 236; 6) β2M residue 28, HLA Class I heavy chain residue 232; 7) β2M residue 98, HLA Class I heavy chain residue 192; 8) β2M residue 99, HLA Class I heavy chain residue 234; 9) β2M residue 3, HLA Class I heavy chain residue 120; 10) β2M residue 31, HLA Class I heavy chain residue 96; 11) β2M residue 53, HLA Class I heavy chain residue 35; 12) β2M residue 60, HLA Class I heavy chain residue 96; 13) β2M residue 60, HLA Class I heavy chain residue 122; 14) β2M residue 63, HLA Class I heavy chain residue 27; 15) β2M residue Arg3, HLA Class I heavy chain residue Gly120; 16) β2M residue His31, HLA Class I heavy chain residue Gln96; 17) β2M residue Asp53, HLA Class I heavy chain residue Arg35; 18) β2M residue Trp60, HLA Class I heavy chain residue Gln96; 19) β2M residue Trp60, HLA Class I heavy chain residue Asp122; 20) β2M residue Tyr63, HLA Class I heavy chain residue Tyr27; 21) β2M residue Lys6, HLA Class I heavy chain residue Glu232; 22) β2M residue Gln8, HLA Class I heavy chain residue Arg234; 23) β2M residue Tyr10, HLA Class I heavy chain residue Pro235; 24) β2M residue Ser11, HLA Class I heavy chain residue Gln242; 25) β2M residue Asn24, HLA Class I heavy chain residue Ala236; 26) β2M residue Ser28, HLA Class I heavy chain residue Glu232; 27) β2M residue Asp98, HLA Class I heavy chain residue His192; and 28) β2M residue Met99, HLA Class I heavy chain residue Arg234. The amino acid numbering of the MHC/HLA Class I heavy chain is in reference to the mature MHC/HLA Class I heavy chain, without a signal peptide. For example, in the amino acid sequence depicted in FIG. 5A, which includes a signal peptide, Gly120 is Gly144; Gln96 is Gln120; etc. In some cases, the β2M polypeptide comprises an R12C substitution, and the HLA Class I heavy chain comprises an A236C substitution; in such cases, a disulfide bond forms between Cys-12 of the β2M polypeptide and Cys-236 of the HLA Class I heavy chain. For example, in some cases, residue 236 of the mature HLA-A amino acid sequence (i.e., residue 260 of the amino acid sequence depicted in FIG. 5A) is substituted with a Cys. In some cases, residue 236 of the mature HLA-B amino acid sequence (i.e., residue 260 of the amino acid sequence depicted in FIG. 5B) is substituted with a Cys. In some cases, residue 236 of the mature HLA-C amino acid sequence (i.e., residue 260 of the amino acid sequence depicted in FIG. 5C) is substituted with a Cys. In some cases, residue 32 (corresponding to Arg-12 of mature β2M) of an amino acid sequence depicted in FIG. 6 is substituted with a Cys.

In some cases, a β2M polypeptide comprises the amino acid sequence: IQRTPKIQVY S<u>R</u>HPAENGKS NFLNCYVSGF HPSDIEVDLLKNGERIEKVE HSDLSFSKDW SFYLLYYTEF TPTEKDEYAC RVNHVTLSQP KIVKWDRDM (SEQ ID NO:61). In some cases, a β2M polypeptide comprises the amino acid sequence: IQRTPKIQVY S <u>C</u>HPAENGKS NFLNCYVSGF HPSDIEVDLLKNGERIEKVE HSDLSFSKDW SFYLLYYTEF TPTEKDEYAC RVNHVTLSQP KIVKWDRDM (SEQ ID NO:48).

In some cases, an HLA Class I heavy chain polypeptide comprises the amino acid sequence:

```
                                          (SEQ ID NO: 59)
GSHSMRYFFTSVSRPGRGEPRFIAVGYVDDTQFVRFDSDAASQRMEPRA

PWIEQEGPEYWDGETRKVKAHSQTHRVDLGTLRGYYNQSEAGSHTVQRM

YGCDVGSDWRFLRGYHQYAYDGKDYIALKEDLRSWTAADMAAQTTKHKW

EAAHVAEQLRAYLEGTCVEWLRRYLENGKETLQRTDAPKTHMTHHAVSD

HEATLRCWALSFYPAEITLTWQRDGEDQTQDTELVETRPAGDGTFQKWA

AVVVPSGQEQRYTCHVQHEGLPKPLTLRWEP.
```

In some cases, an HLA Class I heavy chain polypeptide comprises the amino acid sequence:

```
                                          (SEQ ID NO: 62)
GSHSMRYFFTSVSRPGRGEPRFIAVGYVDDTQFVRFDSDAASQRMEPRA

PWIEQEGPEYWDGETRKVKAHSQTHRVDLGTLRGYYNQSEAGSHTVQRM

YGCDVGSDWRFLRGYHQYAYDGKDYIALKEDLRSWTAADMAAQTTKHKW

EAAHVAEQLRAYLEGTCVEWLRRYLENGKETLQRTDAPKTHMTHHAVSD

HEATLRCWALSFYPAEITLTWQRDGEDQTQDTELVETRPCGDGTFQKWA

AVVVPSGQEQRYTCHVQHEGLPKPLTLRWEP.
```

In some cases, an HLA Class I heavy chain polypeptide comprises the amino acid sequence:

```
                                          (SEQ ID NO: 50)
GSHSMRYFFTSVSRPGRGEPRHLAVGYVDDTQHVRFDSDAASQRMEPRA

PWIEQEGPEYWDGETRKVKAHSQTHRVDLGTLRGAYNQSEAGSHTVQRM

YGCDVGSDWRFLRGYHQYAYDGKDYIALKEDLRSWTAADMAAQTTKHKW

EAAHVAEQLRAYLEGTCVEWLRRYLENGKETLQRTDAPKTHMTHHAVSD

HEATLRCWALSFYPAEITLTWQRDGEDQTQDTELVETRPCGDGTFQKWA

AVVVPSGQEQRYTCHVQHEGLPKPLTLRWE.
```

In some cases, the β2M polypeptide comprises the following amino acid sequence:
IQRTPKIQVY S<u>C</u>HPAENGKS NFLNCYVSGF HPSDIEVDLLKNGERIEKVE HSDLSFSKDW SFYLLYYTEF TPTEKDEYAC RVNHVTLSQP KIVKWDRDM (SEQ ID NO:48); and the HLA ClassI heavy chain polypeptide of a multimeric polypeptide of the present disclosure comprises the following amino acid sequence:
GSHSMRYFFTSVSRPGRGEPRFIAVGYVDDTQF-VRFDSDAASQRMEPRAPWIEQ EGPEYWDGETRK-VKAHSQTHRVDLGTLRGYYNQSEAGSHTVQRMY-GCDVGSDWRFL RGYHQYAYDGKDYIALKEDLRSW-TAADMAAQTTKHKWEAAHVAEQLRAYLEGTCVE WLRRYLENGKETLQRTDAPKTHMTHHAVSDHEAT-LRCWALSFYPAEITLTWQRDGED QTQDTELVETRP<u>C</u>GDGTFQKWAAVVVPSGQEQRYTCHVQHEGLPKP-LTLRWEP (SEQ ID NO:62), where the Cys residues that are underlined and in bold form a disulfide bond with one another in the multimeric polypeptide.

In some cases, the β2M polypeptide comprises the amino acid sequence:

```
                                          (SEQ ID NO: 48)
IQRTPKIQVYSCHPAENGKSNFLNCYVSGFHPSDIEVDLLKNGERIEKV

EHSDLSFSKDWSFYLLYYTEFTPTEKDEYACRVNHVTLSQPKIVKWDRD

M.
```

Scaffold Polypeptides

A T-cell modulatory multimeric polypeptide comprises an Fc polypeptide, or another suitable scaffold polypeptide.

Suitable scaffold polypeptides include antibody-based scaffold polypeptides and non-antibody-based scaffolds. Non-antibody-based scaffolds include, e.g., albumin, an XTEN (extended recombinant) polypeptide, transferrin, an Fc receptor polypeptide, an elastin-like polypeptide (see, e.g., Hassouneh et al. (2012) *Methods Enzymol.* 502:215; e.g., a polypeptide comprising a pentapeptide repeat unit of (Val-Pro-Gly-X-Gly; SEQ ID NO:212), where X is any amino acid other than proline), an albumin-binding polypeptide, a silk-like polypeptide (see, e.g., Valluzzi et al. (2002) *Philos Trans R Soc Lond B Biol Sci.* 357:165), a silk-elastin-like polypeptide (SELP; see, e.g., Megeed et al. (2002) *Adv Drug Deliv Rev.* 54:1075), and the like. Suitable XTEN polypeptides include, e.g., those disclosed in WO 2009/023270, WO 2010/091122, WO 2007/103515, US 2010/0189682, and US 2009/0092582; see also Schellenberger et al. (2009) *Nat Biotechnol.* 27:1186). Suitable albumin polypeptides include, e.g., human serum albumin.

Suitable scaffold polypeptides will in some cases be a half-life extending polypeptides. Thus, in some cases, a suitable scaffold polypeptide increases the in vivo half-life (e.g., the serum half-life) of the multimeric polypeptide, compared to a control multimeric polypeptide lacking the scaffold polypeptide. For example, in some cases, a scaffold polypeptide increases the in vivo half-life (e.g., the serum half-life) of the multimeric polypeptide, compared to a control multimeric polypeptide lacking the scaffold polypeptide, by at least about 10%, at least about 15%, at least about 20%, at least about 25%, at least about 50%, at least about 2-fold, at least about 2.5-fold, at least about 5-fold, at least about 10-fold, at least about 25-fold, at least about 50-fold, at least about 100-fold, or more than 100-fold. As an example, in some cases, an Fc polypeptide increases the in vivo half-life (e.g., the serum half-life) of the multimeric polypeptide, compared to a control multimeric polypeptide lacking the Fc polypeptide, by at least about 10%, at least about 15%, at least about 20%, at least about 25%, at least about 50%, at least about 2-fold, at least about 2.5-fold, at least about 5-fold, at least about 10-fold, at least about 25-fold, at least about 50-fold, at least about 100-fold, or more than 100-fold.

Fc Polypeptides

In some cases, the first and/or the second polypeptide chain of a multimeric polypeptide comprises an Fc polypeptide. The Fc polypeptide of a multimeric polypeptide can be a human IgG1 Fc, a human IgG2 Fc, a human IgG3 Fc, a human IgG4 Fc, etc. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to an amino acid sequence of an Fc region depicted in FIGS. 4A-C. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG1 Fc polypeptide depicted in FIG. 4A. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG1 Fc polypeptide depicted in FIG. 4A; and comprises a substitution of N77; e.g., the Fc polypeptide comprises an N77A substitution. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgG2 Fc polypeptide depicted in FIG. 4A; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 99-325 of the human IgG2 Fc polypeptide depicted in FIG. 4A. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgG3 Fc polypeptide depicted in FIG. 4A; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 19-246 of the human IgG3 Fc polypeptide depicted in FIG. 4A. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgM Fc polypeptide depicted in FIG. 4B; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 1-276 to the human IgM Fc polypeptide depicted in FIG. 4B. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgA Fc polypeptide depicted in FIG. 4C; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 1-234 to the human IgA Fc polypeptide depicted in FIG. 4C.

In some cases, the Fc polypeptide present in a multimeric polypeptide comprises the amino acid sequence depicted in FIG. 33A (human IgG1 Fc). In some cases, the Fc polypeptide present in a multimeric polypeptide of the present disclosure comprises the amino acid sequence depicted in FIG. 33A (human IgG1 Fc), except for a substitution of N297 with an amino acid other than asparagine. In some cases, the Fc polypeptide present in a multimeric polypeptide of the present disclosure comprises the amino acid sequence depicted in FIG. 33C (human IgG1 Fc comprising an N297A substitution). In some cases, the Fc polypeptide present in a multimeric polypeptide of the present disclosure comprises the amino acid sequence depicted in FIG. 33A (human IgG1 Fc), except for a substitution of L234 with an amino acid other than leucine. In some cases, the Fc polypeptide present in a multimeric polypeptide of the present disclosure comprises the amino acid sequence depicted in FIG. 33A (human IgG1 Fc), except for a substitution of L235 with an amino acid other than leucine. In some cases, the Fc polypeptide present in a multimeric polypeptide of the present disclosure comprises the amino acid sequence depicted in FIG. 33D (human IgG1 Fc comprising an L234A substitution and an L235A substitution). In some cases, the Fc polypeptide present in a multimeric polypeptide of the present disclosure comprises the amino acid sequence depicted in FIG. 33A (human IgG1 Fc), except for a substitution of P331 with an amino acid other than proline; in some cases, the substitution is a P331S substitution. In some cases, the Fc polypeptide present in a multimeric polypeptide of the present disclosure comprises the amino acid sequence depicted in FIG. 33A (human IgG1 Fc), except for substitutions at L234 and L235 with amino acids other than leucine. In some cases, the Fc polypeptide present in a multimeric polypeptide of the present disclosure comprises the amino acid sequence depicted in FIG. 33A (human IgG1 Fc), except for substitutions at L234 and L235 with amino acids other than leucine, and a substitution of P331 with an amino acid other than proline. In some cases, the Fc polypeptide present in a multimeric polypeptide of the present disclosure comprises the amino acid sequence depicted in FIG. 33B (human IgG1 Fc comprising L234F, L235E, and P331S substitutions). In some cases, the Fc polypeptide present in a multimeric polypeptide is an IgG1 Fc polypeptide that comprises L234A and L235A substitutions.

Linkers

A multimeric polypeptide can include linker peptides interposed between, e.g., an epitope and an MHC polypeptide; between an MHC polypeptide and an immunomodulatory polypeptide; between an MHC polypeptide and an Ig Fc polypeptide; between a first immunomodulatory polypeptide and a second immunomodulatory polypeptide; or a between a second immunomodulatory polypeptide and a third immunomodulatory polypeptide.

For example, a multimeric polypeptide can include linker peptides interposed between, e.g., an epitope and an MHC polypeptide; between an MHC polypeptide and an immunomodulatory polypeptide; between an MHC polypeptide and an Ig Fc polypeptide; between a first variant IL-2 polypeptide and a second variant IL-2 polypeptide; or a between a second variant IL-2 polypeptide and a third variant IL-2 polypeptide. As another example, a multimeric polypeptide can include linker peptides interposed between, e.g., an epitope and an MHC polypeptide; between an MHC polypeptide and an immunomodulatory polypeptide; between an MHC polypeptide and an Ig Fc polypeptide; between a first variant 4-1BBL polypeptide and a second variant 4-1BBL polypeptide; or a between a second variant 4-1BBL polypeptide and a third variant 4-1BBL polypeptide.

Suitable linkers (also referred to as "spacers") can be readily selected and can be of any of a number of suitable lengths, such as from 1 amino acid to 25 amino acids, from 3 amino acids to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids. A suitable linker can be 1, 2, 3, 4, 5, 6, 7, 8, 9, 10, 11, 12, 13, 14, 15, 16, 17, 18, 19, 20, 21, 22, 23, 24, or 25 amino acids in length.

Exemplary linkers include glycine polymers $(G)_n$, glycine-serine polymers (including, for example, $(GS)_n$, $(GSGGS)_n$ (SEQ ID NO:210) and $(GGGS)_n$ (SEQ ID NO:211), where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see Scheraga, *Rev. Computational Chem.* 11173-142 (1992)).

Exemplary linkers can comprise amino acid sequences including, but not limited to, GGSG (SEQ ID NO:65), GGSGG (SEQ ID NO:66), GSGSG (SEQ ID NO:67), GSGGG (SEQ ID NO:68), GGGSG (SEQ ID NO:69), GSSSG (SEQ ID NO:70), and the like. Exemplary linkers can include, e.g., Gly(Ser$_4$)n, where n is 1, 2, 3, 4, 5, 6, 7, 8, 9, or 10. In some cases, a linker comprises the amino acid sequence (GSSSS)n (SEQ ID NO:71), where n is 4. In some cases, a linker comprises the amino acid sequence (GSSSS)n (SEQ ID NO:72), where n is 5. In some cases, a linker comprises the amino acid sequence (GGGGS)n (SEQ ID NO:205), where n is 1. In some cases, a linker comprises the amino acid sequence (GGGGS)n (SEQ ID NO:206), where n is 2. In some cases, a linker comprises the amino acid sequence (GGGGS)n (SEQ ID NO:207), where n is 3. In some cases, a linker comprises the amino acid sequence (GGGGS)n (SEQ ID NO:208), where n is 4. In some cases, a linker comprises the amino acid sequence (GGGGS)n (SEQ ID NO:209), where n is 5. In some cases, a linker comprises the amino acid sequence AAAGG (SEQ ID NO:73).

In some cases, a linker polypeptide, present in a first polypeptide of a multimeric polypeptide of the present disclosure, includes a cysteine residue that can form a disulfide bond with a cysteine residue present in a second polypeptide of a multimeric polypeptide of the present disclosure. In some cases, for example, a suitable linker comprises the amino acid sequence GCGASGG-GGSGGGGS (SEQ ID NO:74).

Epitopes

An epitope (a peptide presenting one or more epitopes) present in a multimeric polypeptide of the present disclosure can have a length of from about 4 amino acids to about 25 amino acids, e.g., the epitope can have a length of from 4 amino acids (aa) to 10 aa, from 10 aa to 15 aa, from 15 aa to 20 aa, or from 20 aa to 25 aa. For example, an epitope present in a multimeric polypeptide of the present disclosure can have a length of 4 amino acids (aa), 5 aa, 6 aa, 7, aa, 8 aa, 9 aa, 10 aa, 11 aa, 12 aa, 13 aa, 14 aa, 15 aa, 16 aa, 17 aa, 18 aa, 19 aa, 20 aa, 21 aa, 22 aa, 23 aa, 24 aa, or 25 aa. In some cases, an epitope present in a multimeric polypeptide of the present disclosure has a length of from 5 amino acids to 10 amino acids, e.g., 5 aa, 6 aa, 7 aa, 8 aa, 9 aa, or 10 aa.

An epitope present in a multimeric polypeptide of the present disclosure is specifically bound by a T-cell, i.e., the epitope is specifically bound by an epitope-specific T cell. An epitope-specific T cell binds an epitope having a reference amino acid sequence, but does not substantially bind an epitope that differs from the reference amino acid sequence. For example, an epitope-specific T cell binds an epitope having a reference amino acid sequence, and binds an epitope that differs from the reference amino acid sequence, if at all, with an affinity that is less than $10^{-6}$ M, less than $10^{-5}$ M, or less than $10^{-4}$ M. An epitope-specific T cell can bind an epitope for which it is specific with an affinity of at least $10^{-7}$ M, at least $10^{-8}$ M, at least $10^{-9}$ M, or at least $10^{-10}$ M.

Suitable epitopes include, but are not limited to, epitopes present in a cancer-associated antigen. Cancer-associated antigens include, but are not limited to, α-folate receptor; carbonic anhydrase IX (CAIX); CD19; CD20; CD22; CD30; CD33; CD44v7/8; carcinoembryonic antigen (CEA); epithelial glycoprotein-2 (EGP-2); epithelial glycoprotein-40 (EGP-40); folate binding protein (FBP); fetal acetylcholine receptor; ganglioside antigen GD2; Her2/neu; IL-13R-a2; kappa light chain; LeY; L1 cell adhesion molecule; melanoma-associated antigen (MAGE); MAGE-A1; mesothelin; MUC1; NKG2D ligands; oncofetal antigen (h5T4); prostate stem cell antigen (PSCA); prostate-specific membrane antigen (PSMA); tumor-associate glycoprotein-72 (TAG-72); and vascular endothelial growth factor receptor-2 (VEGF-R2). See, e.g., Vigneron et al. (2013) *Cancer Immunity* 13:15; and Vigneron (2015) *BioMed Res. Int'l* Article ID 948501. In some cases, the epitope is a human papilloma virus E7 antigen epitope; see, e.g., Ramos et al. (2013) *J. Immunother.* 36:66.

In some cases, the epitope is HPV16E7/82-90 (LLMGTL-GIV; SEQ ID NO:75). In some cases, the epitope is HPV16E7/86-93 (TLGIVCPI; SEQ ID NO:76). In some cases, the epitope is HPV16E7/11-20 (YMLDLQPETT; SEQ ID NO:77). In some cases, the epitope is HPV16E7/11-19 (YMLDLQPET; SEQ ID NO:78). See, e.g., Ressing et al. ((1995) *J. Immunol.* 154:5934) for additional suitable HPV epitopes.

Immunomodulatory Polypeptides

Suitable immunomodulatory polypeptides include, but are not limited to, an IL-2 polypeptide, a 4-1BBL polypeptide, a B7-1 polypeptide; a B7-2 polypeptide, an ICOS-L polypeptide, an OX-40L polypeptide, a CD80 polypeptide, a CD86 polypeptide, a PD-L1 polypeptide, a FasL polypeptide, and a PD-L2 polypeptide.

In some cases, the immunomodulatory polypeptide comprises an amino acid sequence having at least 80%, at least 85%, at least 90%, at least 95%, at least 98%, at least 99%, or 100%, amino acid sequence identity with the amino acid sequence of a PD-L1 polypeptide depicted in FIG. 50A or FIG. 50B.

In some cases, the immunomodulatory polypeptide comprises an amino acid sequence having at least 80%, at least 85%, at least 90%, at least 95%, at least 98%, at least 99%, or 100%, amino acid sequence identity with the amino acid sequence of a CD80 polypeptide depicted in FIG. 51.

In some cases, the immunomodulatory polypeptide comprises an amino acid sequence having at least 80%, at least 85%, at least 90%, at least 95%, at least 98%, at least 99%, or 100%, amino acid sequence identity with the amino acid sequence of an ICOS-L polypeptide depicted in FIG. 51.

In some cases, the immunomodulatory polypeptide comprises an amino acid sequence having at least 80%, at least 85%, at least 90%, at least 95%, at least 98%, at least 99%, or 100%, amino acid sequence identity with the amino acid sequence of an OX40L polypeptide depicted in FIG. 53.

In some cases, the immunomodulatory polypeptide comprises an amino acid sequence having at least 80%, at least 85%, at least 90%, at least 95%, at least 98%, at least 99%, or 100%, amino acid sequence identity with the amino acid sequence of a PD-L2 polypeptide depicted in FIG. 54.

In some cases, the immunomodulatory polypeptide comprises an amino acid sequence having at least 80%, at least 85%, at least 90%, at least 95%, at least 98%, at least 99%, or 100%, amino acid sequence identity with the amino acid sequence of a CD86 polypeptide depicted in FIG. 55.

In some cases, the immunomodulatory polypeptide comprises an amino acid sequence having at least 80%, at least 85%, at least 90%, at least 95%, at least 98%, at least 99%, or 100%, amino acid sequence identity with the amino acid sequence of a FAS-L polypeptide depicted in FIG. 56.

In some cases, the immunomodulatory polypeptide present in a synTac exhibits reduced binding affinity to a cognate co-immunomodulatory polypeptide expressed on the surface of a T cell, compared to the binding affinity of a wild-type immunomodulatory polypeptide for the same cognate co-immunomodulatory polypeptide. In some cases, where a synTac comprises a reduced-affinity immunomodulatory polypeptide, the synTac polypeptide exhibits reduced binding to a cognate co-immunomodulatory polypeptide expressed on the surface of a T cell. For example, in some cases, a synTac polypeptide that comprises a reduced-affinity immunomodulatory polypeptide binds a cognate co-immunomodulatory polypeptide with a binding affinity that is at least 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of a control synTac polypeptide comprising a wild-type immunomodulatory polypeptide for the same cognate co-immunomodulatory polypeptide.

Determining Binding Affinity

Binding affinity between an immunomodulatory polypeptide and its cognate co-immunomodulatory polypeptide can be determined by bio-layer interferometry (BLI) using purified immunomodulatory polypeptide and purified cognate co-immunomodulatory polypeptide. Binding affinity between a synTac of the present disclosure and its cognate co-immunomodulatory polypeptide can also be determined by BLI using purified synTac and the cognate co-immunomodulatory polypeptide. BLI methods are well known to those skilled in the art. See, e.g., Lad et al. (2015) *J. Biomol. Screen.* 20(4):498-507; and Shah and Duncan (2014) *J. Vis. Exp.* 18:e51383. The specific and relative binding affinities described in this disclosure between an immunomodulatory polypeptide and its cognate co-immunomodulatory polypeptide, or between a synTac and its cognate co-immunomodulatory polypeptide, can be determined using the following procedures.

To determine binding affinity between a synTac of the present disclosure and its cognate co-immunomodulatory polypeptide, a BLI assay can be carried out using an Octet RED 96 (Pal FortéBio) instrument, or a similar instrument, as follows. To determine binding affinity of a T-cell modulatory multimeric polypeptide (e.g., a synTac of the present disclosure; or a control T-cell modulatory multimeric polypeptide (where a control T-cell modulatory multimeric polypeptide comprises a wild-type immunomodulatory polypeptide)), the T-cell modulatory multimeric polypeptide is immobilized onto an insoluble support (a "biosensor"). The immobilized T-cell modulatory multimeric polypeptide is the "target." Immobilization can be effected by immobilizing a capture antibody onto the insoluble support, where the capture antibody immobilizes the T-cell modulatory multimeric polypeptide. For example, immobilization can be effected by immobilizing anti-Fc (e.g., anti-human IgG Fc) antibodies onto the insoluble support, where the immobilized anti-Fc antibodies bind to and immobilize the T-cell modulatory multimeric polypeptide (where the T-cell modulatory multimeric polypeptide comprises an IgFc polypeptide). A co-immunomodulatory polypeptide is applied, at several different concentrations, to the immobilized T-cell modulatory multimeric polypeptide, and the instrument's response recorded. Assays are conducted in a liquid medium comprising 25 mM HEPES pH 6.8, 5% poly(ethylene glycol) 6000, 50 mM KCl, 0.1% bovine serum albumin, and 0.02% Tween 20 nonionic detergent. Binding of the co-immunomodulatory polypeptide to the immobilized T-cell modulatory multimeric polypeptide is conducted at 30° C. As a positive control for binding affinity, an anti-MHC Class I monoclonal antibody can be used. For example, anti-HLA Class I monoclonal antibody W6/32 (American Type Culture Collection No. HB-95; Parham et al. (1979) *J. Immunol.* 123:342), which has a $K_D$ of 7 nM, can be used. A standard curve can be generated using serial dilutions of the anti-MHC Class I monoclonal antibody. The co-immunomodulatory polypeptide, or the anti-MHC Class I mAb, is the "analyte." BLI analyzes the interference pattern of white light reflected from two surfaces: i) from the immobilized polypeptide ("target"); and ii) an internal reference layer. A change in the number of molecules ("analyte"; e.g., co-immunomodulatory polypeptide; anti-HLA antibody) bound to the biosensor tip causes a shift in the interference pattern; this shift in interference pattern can be measured in real time. The two kinetic terms that describe the affinity of the target/analyte interaction are the association constant ($k_a$) and dissociation constant ($k_d$). The ratio of these two terms ($k_d/k_a$) gives rise to the affinity constant $K_D$.

As noted above, determining binding affinity between an immunomodulatory polypeptide (e.g., IL-2 or an IL-2 variant) and its cognate co-immunomodulatory polypeptide (e.g., IL-2R) also can be determined by BLI. The assay is similar to that described above for the synTac multimeric polypeptide. A BLI assay can be carried out using an Octet RED 96 (Pal FortéBio) instrument, or a similar instrument, as follows. A component immunomodulatory polypeptide of a synTac of the present disclosure (e.g., a variant IL-2 polypeptide of the present disclosure); and a control immunomodulatory polypeptide (where a control immunomodulatory polypeptide comprises a wild-type immunomodulatory polypeptide, e.g. wild-type IL-2)) are immobilized onto an insoluble support (a "biosensor"). The immunomodulatory polypeptide is the "target." Immobilization can be effected by immobilizing a capture antibody onto the insoluble support, where the capture antibody immobilizes the immunomodulatory polypeptide. For example, if the target is fused to an immuno-affinity tag (e.g. FLAG, human IgG Fc) immobilization can be effected by immobilizing with the appropriate antibody to the immuno-affinity tag (e.g. anti-human IgG Fc) onto the insoluble support, where the immobilized antibodies bind to and immobilize the immunomodulatory polypeptide (where the immunomodulatory polypeptide comprises an IgFc polypeptide). A co-immunomodulatory polypeptide (or polypeptides) is applied, at several different concentrations, to the immobilized immunomodulatory polypeptide, and the instrument's response recorded. Alternatively, a co-immunomodulatory polypeptide (or polypeptides) is immobilized to the biosensor (e.g., for the IL-2 receptor heterotrimer, as a monomeric subunit, heterodimeric subcomplex, or the complete heterotrimer) and the immunomodulatory polypeptide is applied, at several different concentrations, to the immobilized coimmunomodulatory polypeptide(s), and the instrument's response is recorded. Assays are conducted in a liquid medium comprising 25 mM HEPES pH 6.8, 5% poly(ethylene glycol) 6000, 50 mM KCl, 0.1% bovine serum albumin, and 0.02% Tween 20 nonionic detergent. Binding of the co-immunomodulatory polypeptide to the immobilized immunomodulatory polypeptide is conducted at 30° C. As a positive control for binding affinity, an anti-MHC Class I monoclonal antibody can be used. For example, anti-HLA Class I monoclonal antibody W6/32 (American Type Culture Collection No. HB-95; Parham et al. (1979) *J. Immunol.* 123:342), which has a $K_D$ of 7 nM, can be used. A standard curve can be generated using serial dilutions of the anti-MHC Class I monoclonal antibody. The co-immunomodulatory polypeptide, or the anti-MHC Class I mAb, is the "analyte." BLI analyzes the interference pattern of white light reflected from two surfaces: i) from the immobilized polypeptide ("target"); and ii) an internal reference layer. A change in the number of molecules ("analyte"; e.g., co-immunomodulatory polypeptide; anti-HLA antibody) bound to the biosensor tip causes a shift in the interference pattern; this shift in interference pattern can be measured in real time. The two kinetic terms that describe the affinity of the target/analyte interaction are the association constant ($k_a$) and dissociation constant ($k_d$). The ratio of these two terms ($k_d/k_a$) gives rise to the affinity constant $K_D$. Determining the binding affinity of both a wild-type immunomodulatory polypeptide (e.g., IL-2) for its receptor (e.g., IL-2R) and a variant immunomodulatory polypeptide (e.g., an IL-2 variant as disclosed herein) for its cognate co-immunomodulatory polypeptide (e.g., its receptor) (e.g., IL-2R) thus allows one to determine the relative binding affinity of the variant co-immunomodulatory polypeptide, as compared to the wild-type co-immunomodulatory polypeptide, for the cognate co-immunomodulatory polypeptide. That is, one can determine whether the binding affinity of a variant immunomodulatory polypeptide for its receptor (its cognate co-immunomodulatory polypeptide) is reduced as compared to the binding affinity of the wild-type immunomodulatory polypeptide for the same cognate co-immunomodulatory polypeptide, and, if so, what is the percentage reduction from the binding affinity of the wild-type co-immunomodulatory polypeptide.

The BLI assay is carried out in a multi-well plate. To run the assay, the plate layout is defined, the assay steps are defined, and biosensors are assigned in Octet Data Acquisition software. The biosensor assembly is hydrated. The hydrated biosensor assembly and the assay plate are equilibrated for 10 minutes on the Octet instrument. Once the data are acquired, the acquired data are loaded into the Octet Data Analysis software. The data are processed in the Processing window by specifying method for reference subtraction, y-axis alignment, inter-step correction, and Savitzky-Golay filtering. Data are analyzed in the Analysis window by specifying steps to analyze (Association and Dissociation), selecting curve fit model (1:1), fitting method (global), and window of interest (in seconds). The quality of fit is evaluated. $K_D$ values for each data trace (analyte concentration) can be averaged if within a 3-fold range. $K_D$ error values should be within one order of magnitude of the affinity constant values; $R^2$ values should be above 0.95. See, e.g., Abdiche et al. (2008) *J. Anal. Biochem.* 377:209.

In some cases, the ratio of: i) the binding affinity of a control T-cell modulatory multimeric polypeptide (where the control comprises a wild-type immunomodulatory polypeptide, e.g., wild-type IL-2) to a cognate co-immunomodulatory polypeptide (e.g., IL-2R) to ii) the binding affinity of a T-cell modulatory multimeric polypeptide of the present disclosure comprising a variant of the wild-type immunomodulatory polypeptide (e.g., variant IL-2) to the cognate co-immunomodulatory polypeptide (e.g., IL-2R), when measured by BLI (as described above), is at least 1.5:1, at least 2:1, at least 5:1, at least 10:1, at least 15:1, at least 20:1, at least 25:1, at least 50:1, at least 100:1, at least 500:1, at least $10^2$:1, at least $5 \times 10^2$:1, at least $10^3$:1, at least $5 \times 10^3$:1, at least $10^4$:1, at least $10^5$:1, or at least $10^6$:1. In some cases, the ratio of: i) the binding affinity of a control T-cell modulatory multimeric polypeptide (where the control comprises a wild-type immunomodulatory polypeptide) to a cognate co-immunomodulatory polypeptide to ii) the binding affinity of a T-cell modulatory multimeric polypeptide of the present disclosure comprising a variant of the wild-type immunomodulatory polypeptide to the cognate co-immunomodulatory polypeptide, when measured by BLI, is in a range of from 1.5:1 to $10^6$:1, e.g., from 1.5:1 to 10:1, from 10:1 to 50:1, from 50:1 to $10^2$:1, from $10^2$:1 to $10^1$:1, from $10^3$:1 to $10^4$:1, from $10^4$:1 to $10^5$:1, or from $10^5$:1 to $10^6$:1.

In some cases, the ratio of: i) the binding affinity of a control immunomodulatory polypeptide (where the control comprises a wild-type immunomodulatory polypeptide, e.g., wild-type IL-2) to a cognate co-immunomodulatory polypeptide (e.g., IL-2R) to ii) the binding affinity of a immunomodulatory polypeptide of the present disclosure comprising a variant of the wild-type immunomodulatory polypeptide (e.g., variant IL-2) to the cognate co-immunomodulatory polypeptide (e.g., IL-2R), when measured by BLI (as described above), is at least 1.5:1, at least 2:1, at least 5:1, at least 10:1, at least 15:1, at least 20:1, at least 25:1, at least 50:1, at least 100:1, at least 500:1, at least $10^2$:1, at least $5 \times 10^2$:1, at least $10^3$:1, at least $5 \times 10^3$:1, at least $10^4$:1, at least $10^5$:1, or at least $10^6$:1. In some cases, the ratio of: i) the binding affinity of a control immunomodulatory polypeptide (where the control comprises a wild-type immunomodulatory polypeptide) to a cognate co-immunomodulatory polypeptide to ii) the binding affinity of a immunomodulatory polypeptide of the present disclosure comprising a variant of the wild-type immunomodulatory polypeptide to the cognate co-immunomodulatory polypeptide, when measured by BLI, is in a range of from 1.5:1 to $10^6$:1, e.g., from 1.5:1 to 10:1, from 10:1 to 50:1, from 50:1 to $10^2$:1, from $10^2$:1 to $10^3$:1, from $10^3$:1 to $10^4$:1, from $10^4$:1 to $10^5$:1, or from $10^5$:1 to $10^6$:1.

IL-2/synTac

In some cases, a multimeric polypeptide comprises a wild-type (naturally-occurring) IL-2 as the modulatory domain. In some cases, a multimeric polypeptide comprises a variant IL-2 polypeptide as the modulatory domain.

A T-cell modulatory multimeric polypeptide that comprises an IL-2 polypeptide as the modulatory ("MOD") domain is also referred to as an "IL-2/synTac," "an IL-2/synTac polypeptide" or an "IL-2/multimeric polypeptide."

In some cases, an IL-2/synTac polypeptide comprises a wild-type IL-2 polypeptide. In some cases, a synTac polypeptide comprises a single copy of a wild-type IL-2 polypeptide. In some cases, a synTac polypeptide comprises two copies of a wild-type IL-2 polypeptide. In some cases, a synTac polypeptide comprises three copies of a wild-type IL-2 polypeptide. In some cases, the wild-type IL-2 polypeptide comprises an amino acid sequence having at least 90%, at least 95%, at least 98%, or at least 99%, amino acid sequence identity to the amino acid sequence depicted in FIG. 2A. A wild-type amino acid sequence of a human IL2 polypeptide can be as follows: APTSSSTKKT QLQL EHLLLD LQMILNGINN YKNPKLTRML TFKF YMPKKA TELKHLQCLEEELKPLEEVL NLAQSK- NFHL RPRDLISNIN VIVLELKGSE TTFMCEYADE TATIVEFLNRWITFCQSIIS TLT (SEQ ID NO:1).

In some cases, a synTac polypeptide comprises a variant IL-2 polypeptide. A variant IL-2 polypeptide present in a multimeric polypeptide exhibits reduced binding affinity to an IL2R, compared to the binding affinity of wild-type IL-2 to the IL2R. A multimeric polypeptide that comprises a variant IL-2 polypeptide also exhibits reduced binding affinity for an IL2R, compared to a control multimeric polypeptide comprising a wild-type IL-2 for IL2R (e.g., an IL2R comprising alpha, beta, and gamma polypeptides comprising the amino acid sequences (mature form) depicted in FIG. 3A-3C).

In some cases, an IL-2/synTac polypeptide exhibits reduced binding affinity to IL2R, compared to the binding affinity of an IL2 polypeptide comprising the amino acid sequence depicted in FIG. 2A for IL2R. For example, in some cases, an IL-2/synTac polypeptide binds IL2R with a binding affinity that is less than the binding affinity of a control synTac polypeptide comprising an IL2 polypeptide comprising the amino acid sequence depicted in FIG. 2A for an IL2R comprising alpha, beta, and gamma polypeptides comprising the amino acid sequences (mature form) depicted in FIG. 3A-3C. For example, in some cases, an IL-2/synTac polypeptide binds IL2R with a binding affinity that is at least 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of a control synTac polypeptide comprising an IL-2 polypeptide comprising the amino acid sequence depicted in FIG. 2A for IL2R (e.g., an IL2R comprising alpha, beta, and gamma polypeptides comprising the amino acid sequences (mature form) depicted in FIG. 3A-3C).

In some cases, an IL-2/synTac polypeptide has a binding affinity for IL2R that is from 100 nm to about 100 μM. In some cases, an IL-2/synTac polypeptide has a binding affinity for IL2R that is from about 100 nM to 500 nM. For example, in some cases, an IL-2/synTac polypeptide has a binding affinity for IL2R (e.g., an IL2R comprising alpha, beta, and gamma polypeptides comprising the amino acid sequences (mature form) depicted in FIG. 3A-3C) that is from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, or from about 450 nM to about 500 nM. In some cases, an IL-2/synTac polypeptide has a binding affinity for IL2R (e.g., an IL2R comprising alpha, beta, and gamma polypeptides comprising the amino acid sequences (mature form) depicted in FIG. 3A-3C) that is from about 500 nM to 1 M. For example, in some cases, an IL-2/synTac polypeptide has a binding affinity for IL2R (e.g., an IL2R comprising alpha, beta, and gamma polypeptides comprising the amino acid sequences (mature form) depicted in FIG. 3A-3C) that is from about 500 nM to about 600 nM, from about 600 nM to about 700 nM, from about 700 nM to about 800 nM, from about 800 nM to about 900 nM, or from about 900 nM to about 1 μM. In some cases, an IL-2/synTac polypeptide has a binding affinity for IL2R (e.g., an IL2R comprising alpha, beta, and gamma polypeptides comprising the amino acid sequences (mature form) depicted in FIG. 3A-3C) that is from about 1 μM to 10 μM. For example, in some cases, an IL-2/synTac polypeptide has a binding affinity for IL2R (e.g., an IL2R comprising alpha, beta, and gamma polypeptides comprising the amino acid sequences (mature form) depicted in FIG. 3A-3C) that is from about 1 μM to 2 μM, from about 2 μM to about 3 μM, from about 3 μM to about 4 μM, from about 4 μM to about 5 μM, from about 5 μM to about 6 μM, from about 6 μM to about 7 μM, from about 7 μM to about 8 μM, from about 8 μM to about 9 μM, or from about 9 μM to about 10 μM. In some cases, an IL-2/synTac polypeptide has a binding affinity for IL2R (e.g., an IL2R comprising alpha, beta, and gamma polypeptides comprising the amino acid sequences (mature form) depicted in FIG. 3A-3C) that is from about 10 μM to 100 μM. For example, in some cases, an IL-2/synTac polypeptide has a binding affinity for IL2R (e.g., an IL2R comprising alpha, beta, and gamma polypeptides comprising the amino acid sequences (mature form) depicted in FIG. 3A-3C) that is from about 10 μM to about 20 μM, from about 20 μM to about 30 μM, from about 30 μM to about 40 μM, from about 40 μM to about 50 μM, from about 50 μM to about 60 μM, from about 60 μM to about 70 μM, from about 70 μM to about 80 μM, from about 80 μM to about 90 μM, or from about 90 μM to about 100 μM.

A variant IL2 polypeptide present in an IL-2/synTac polypeptide can have a single amino acid substitution relative to a wild-type IL2 polypeptide (e.g., a IL2 polypeptide comprising the amino acid sequence depicted in FIG. 2A or as set forth in SEQ ID NO:1). In some cases, a variant IL2 polypeptide present in an IL-2/synTac polypeptide has from 2 to 10 amino acid substitutions relative to a wild-type IL2 polypeptide (e.g., a IL2 polypeptide comprising the amino acid sequence depicted in FIG. 2A or as set forth in SEQ ID NO:1). In some cases, a variant IL2 polypeptide present in a synTac polypeptide of the present disclosure has 2 amino acid substitutions relative to a wild-type IL2 polypeptide (e.g., a IL2 polypeptide comprising the amino acid sequence depicted in FIG. 2A or as set forth in SEQ ID NO:1). In some cases, a variant IL2 polypeptide present in a synTac polypeptide of the present disclosure has 3 amino acid substitutions relative to a wild-type IL2 polypeptide (e.g., a IL2 polypeptide comprising the amino acid sequence depicted in FIG. 2A or as set forth in SEQ ID NO:1). In some cases, a variant IL2 polypeptide present in a synTac polypeptide of the present disclosure has 4 amino acid substitutions relative to a wild-type IL2 polypeptide (e.g., a IL2 polypeptide comprising the amino acid sequence depicted in FIG. 2A or as set forth in SEQ ID NO:1). In some cases, a variant IL2 polypeptide present in a synTac polypeptide of the present disclosure has 5 amino acid substitutions relative to a wild-type IL2 polypeptide (e.g., a IL2 polypeptide comprising the amino acid sequence depicted in FIG. 2A or as set forth in SEQ ID NO:1). In some cases, a variant IL2 polypeptide present in a synTac polypeptide of the present disclosure has 6 amino acid substitutions relative to a wild-type IL2 polypeptide (e.g., a IL2 polypeptide comprising the amino acid sequence depicted in FIG. 2A or as set forth in SEQ ID NO:1). In some cases, a variant IL2 polypeptide present in a synTac polypeptide of the present disclosure has 7 amino acid substitutions relative to a wild-type IL2 polypeptide (e.g., a IL2 polypeptide comprising the amino acid sequence depicted in FIG. 2A or as set forth in SEQ ID NO:1). In some cases, a variant IL2 polypeptide present in a synTac polypeptide of the present disclosure has 8 amino acid substitutions relative to a wild-type IL2 polypeptide (e.g., a IL2 polypeptide comprising the amino acid sequence depicted in FIG. 2A or as set forth in SEQ ID NO:1). In some cases, a variant IL2 polypeptide present in a synTac polypeptide of the present disclosure has 9 amino acid substitutions relative to a wild-type IL2 polypeptide (e.g., a IL2 polypeptide comprising the amino acid sequence depicted in FIG. 2A or as set forth in SEQ ID NO:1). In some cases, a variant IL2 polypeptide present in a synTac polypeptide of the present disclosure has 10 amino acid substitutions relative to a wild-type IL2 polypeptide (e.g., a IL2 polypeptide comprising the amino acid sequence depicted in FIG. 2A or as set forth in SEQ ID NO:1).

In some cases, a multimeric polypeptide of the present disclosure comprises a first polypeptide and a second polypeptide, where the first polypeptide comprises, in order from amino terminus (N-terminus) to carboxyl terminus (C-terminus): a) an epitope (e.g., a T-cell epitope); b) a first major histocompatibility complex (MHC) polypeptide and c) an immunomodulatory polypeptide (e.g., a variant IL2 polypeptide of the present disclosure); and where the second polypeptide comprises, in order from N-terminus to C-terminus: a) a second MHC polypeptide; and b) an immunoglobulin (Ig) Fc polypeptide. In other cases, a multimeric polypeptide of the present disclosure comprises a first polypeptide and a second polypeptide, where the first polypeptide comprises, in order from N-terminus to C-terminus: a) an epitope (e.g., a T-cell epitope); and b) a first MHC polypeptide; and where the second polypeptide comprises, in order from N-terminus to C-terminus: a) an immunomodulatory polypeptide (e.g., a variant IL2 polypeptide of the present disclosure); b) a second MHC polypeptide; and c) an Ig Fc polypeptide. In some instances, the first and the second MHC polypeptides are Class I MHC polypeptides; e.g., in some cases, the first MHC polypeptide is an MHC Class I β2-microglobulin (B2M or β2M) polypeptide, and the second MHC polypeptide is an MHC Class I heavy chain (H chain); or the first MHC polypeptide is an MHC Class I H chain, and the second MHC polypeptide is an MHC Class I β2M polypeptide). In other cases, the first and the second MHC polypeptides are Class II MHC polypeptides; e.g., in some cases, the first MHC polypeptide is an MHC Class II α-chain polypeptide, and the second MHC polypeptide is an MHC Class II f-chain polypeptide. In other cases, the first polypeptide is an MHC Class II β-chain polypeptide, and the second MHC polypeptide is an MHC Class II α-chain polypeptide. In some cases, the multimeric polypeptide includes two or more immunomodulatory polypeptides, where at least one of the immunomodulatory polypeptides is a variant IL2 immunomodulatory polypeptide of the present disclosure. Where a multimeric polypeptide of the present disclosure includes two or more immunomodulatory polypeptides, in some cases, the two or more immunomodulatory polypeptides are present in the same polypeptide chain, and may be in tandem. Where a multimeric polypeptide of the present disclosure includes two or more immunomodulatory polypeptides, in some cases, the two or more immunomodulatory polypeptides are present in separate polypeptides. In some cases, a multimeric polypeptide of the present disclosure is a heterodimer. In some cases, a multimeric polypeptide of the present disclosure is a trimeric polypeptide.

In some cases, a multimeric polypeptide comprises: a) a first polypeptide comprising, in order from N-terminus to C-terminus: i) an epitope; and ii) a first MHC polypeptide; and b) a second polypeptide comprising, in order from N-terminus to C-terminus: i) a second MHC polypeptide; and ii) an Ig Fc polypeptide; and iii) an immunomodulatory domain (e.g., a variant IL2 polypeptide of the present disclosure). In some cases, a multimeric polypeptide of the present disclosure comprises: a) a first polypeptide comprising, in order from N-terminus to C-terminus: i) an epitope; and ii) a first MHC polypeptide; and b) a second polypeptide comprising, in order from N-terminus to C-terminus: i) a second MHC polypeptide; and ii) an immunomodulatory domain (e.g., a variant IL2 polypeptide of the present disclosure). In some cases, a multimeric polypeptide of the present disclosure comprises: a) a first polypeptide comprising, in order from N-terminus to C-terminus: i) an epitope; and ii) a first MHC polypeptide; and b) a second polypeptide comprising, in order from N-terminus to C-terminus: i) an immunomodulatory domain (e.g., a variant IL2 polypeptide of the present disclosure); and ii) a second MHC polypeptide. In some cases, a multimeric polypeptide of the present disclosure comprises: a) a first polypeptide comprising, in order from N-terminus to C-terminus: i) an epitope; ii) a first MHC polypeptide; and iii) an immunomodulatory domain (e.g., a variant IL2 polypeptide of the present disclosure); and b) a second polypeptide comprising, in order from N-terminus to C-terminus: i) a second MHC polypeptide. In some cases, where a multimeric polypeptide of the present disclosure comprises a non-Ig scaffold, the non-Ig scaffold is an XTEN peptide, a transferrin polypeptide, an Fc receptor polypeptide, an elastin-like polypeptide, a silk-like polypeptide, or a silk-elastin-like polypeptide.

In some cases, a multimeric polypeptide of the present disclosure is monovalent. In some cases, a multimeric polypeptide of the present disclosure is multivalent. In some cases, a multivalent multimeric polypeptide of the present disclosure comprises an immunoglobulin Fc polypeptide on one of the first or the second polypeptide. For example, depending on the Fc polypeptide present in a multimeric polypeptide of the present disclosure, the multimeric polypeptide can be a homodimer, where two molecules of the multimeric polypeptide are present in the homodimer, where the two molecules of the multimeric polypeptide can be disulfide linked to one another, e.g., via the Fc polypeptide present in the two molecules. As another example, a multimeric polypeptide of the present disclosure can comprise three, four, or five molecules of the multimeric polypeptide, where the molecules of the multimeric polypeptide can be disulfide linked to one another, e.g., via the Fc polypeptide present in the molecules.

In some cases, a multimeric polypeptide comprises: a) a first polypeptide comprising, in order from N-terminus to C-terminus: i) an epitope; ii) a β2M polypeptide; and iii) a variant IL2 polypeptide of the present disclosure; and b) a second polypeptide comprising, in order from N-terminus to C-terminus: i) a Class I MHC heavy chain; and ii) an Fc polypeptide. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a variant IL2 polypeptide of the present disclosure; ii) a Class I MHC heavy chain; and iii) an Fc polypeptide. In some cases, a multimeric polypeptide of the present disclosure comprises: a) a first polypeptide comprising, in order from N-terminus to C-terminus: i) an epitope; ii) a β2M polypeptide; iii) a first variant IL2 polypeptide of the present disclosure; iv) a second variant IL2 polypeptide of the present disclosure; and v) a third variant IL2 polypeptide of the present disclosure; and b) a second polypeptide comprising, in order from N-terminus to C-terminus: i) a Class I MHC heavy chain; and ii) an Fc polypeptide. In some cases, the first, second, and third variant IL2 polypeptides have the same amino acid sequence. In some cases, the first, second, and third variant IL2 polypeptides differ from one another in amino acid sequence. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a first variant IL2 polypeptide of the present disclosure; ii) a second variant IL2 polypeptide of the present disclosure; and iii) a third variant IL2 polypeptide of the present disclosure; iv) a Class I MHC heavy chain; and v) an Fc polypeptide. In some cases, the first, second, and third variant IL2 polypeptides have the same amino acid sequence. In some cases, the first, second, and third variant IL2 polypeptides differ from one another in amino acid sequence.

F42 Substitution

In some cases, a variant IL-2 polypeptide present in a multimeric polypeptide comprises an amino acid sequence having at least 90%, at least 95%, at least 98%, or at least 99%, amino acid sequence identity to the amino acid sequence depicted in FIG. 2B, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2B, where amino acid 42 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2B, where amino acid 42 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2B, where amino acid 42 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2B, where amino acid 42 is Val. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2B, where amino acid 42 is Leu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2B, where amino acid 42 is Ile. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and 02M, the IL-2 polypeptide(s) is/are on the polypeptide chain comprising the β2M polypeptide. In some cases, the variant IL-2 polypeptide, or the synTac comprising same, has a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about M, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant IL-2 polypeptide present in a multimeric polypeptide of the present disclosure has a length of 133 amino acids.

Y45 Substitution

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 45 is an amino acid other than a tyrosine, e.g., where amino acid 45 is Gly, Ala, Val, Leu, Ile, Pro, Phe, Trp, Ser, Thr, Cys, Met, Asn, Gln, Lys, Arg, His, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 45 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 45 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 45 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 45 is Val. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 45 is Leu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2F, where amino acid 45 is Ile. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and 02M, the IL-2 polypeptide(s) is/are on the polypeptide chain comprising the β2M polypeptide. In some cases, the variant IL-2 polypeptide, or the synTac comprising same, has a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about M, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, the variant IL-2 polypeptide present in a multimeric polypeptide of the present disclosure has a length of 133 amino acids.

Q126 Substitution

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2G, where amino acid 126 is an amino acid other than a glutamine, e.g., where amino acid 126 is Gly, Ala, Val, Leu, Ile, Pro, Phe, Tyr, Trp, Ser, Thr, Cys, Met, Asn, Lys, Arg, His, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2G, where amino acid 126 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2G, where amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2G, where amino acid 126 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2G, where amino acid 126 is Val. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2G, where amino acid 126 is Leu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2G, where amino acid 126 is Ile. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and 02M, the IL-2 polypeptide(s) is/are on the polypeptide chain comprising the β2M polypeptide. In some cases, the variant IL-2 polypeptide, or a synTac comprising same, has a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about M, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, the variant IL-2 polypeptide present in a multimeric polypeptide of the present disclosure has a length of 133 amino acids.

F42 and H16 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; and where amino acid 16 is an amino acid other than a histidine, e.g., where amino acid 16 is Gly, Ala, Val, Leu, Ile, Pro, Phe, Tyr, Trp, Ser, Thr, Cys, Met, Asn, Gln, Lys, Arg, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 42 is Ala, Gly, Val, Leu, or Ile; and where amino acid 16 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 42 is Ala and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 42 is Ala and amino acid 16 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 42 is Val and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 42 is Leu, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2H, where amino acid 42 is Ile and amino acid 16 is Ala. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and 02M, the IL-2 polypeptide(s) is/are on the polypeptide chain comprising the β2M polypeptide. In some cases, a multimeric polypeptide of the present disclosure comprises 2 copies of the IL-2 variant comprising F42A and H16A substitutions, where the multimeric polypeptide comprises HLA Class I heavy chain and β2M polypeptides, and where the 2 copies of IL-2 (F42A, H16A) are on the polypeptide chain comprising the HLA Class I heavy chain. In some cases, the variant IL-2 polypeptide, or a synTac comprising same, has a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 M to about 10 µM, from about 10 µM to about 15 µM, from about 15 µM to about 20 µM, from about 20 µM to about 25 µM, from about 25 µM to about 50 µM, from about 50 µM to about 75 M, or from about 75 µM to about 100 µM. In some cases, the variant IL-2 polypeptide present in a multimeric polypeptide of the present disclosure has a length of 133 amino acids. In some cases, the variant IL-2 polypeptide comprises the amino acid sequence depicted in FIG. 34B (comprising H16A and F42A substitutions).

F42 and D20 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; and where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala, Gly, Val, Leu, or Ile; and where amino acid 20 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala, Gly, Val, Leu, or Ile; and where amino acid 20 is Asn, Gln, Lys, Arg, or His. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Val and amino acid 20 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Leu, and amino acid 20 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ile and amino acid 20 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is Asn. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is Gln. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is Lys. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is Arg. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala and amino acid 20 is His. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or a synTac comprising same, has a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 μM, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant IL-2 polypeptide present in a multimeric polypeptide of the present disclosure has a length of 133 amino acids.

F42, D20, and E15 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; and where amino acid 15 is an amino acid other than a glutamic acid, e.g., where amino acid 15 is Gly, Ala, Val, Leu, Ile, Pro, Phe, Tyr, Trp, Ser, Thr, Cys, Met, Asn, Gln, Lys, Arg, His, or Asp. In some cases, a variant IL-2 polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, Gly, Val, Leu, or Ile; where amino acid 20 is Ala, Gly, Val, Leu, or Ile; and where amino acid 15 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, Gly, Val, Leu, or Ile; where amino acid 20 is Asn, Gln, Lys, Arg, or His; and where amino acid 15 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, amino acid 20 is Ala, and amino acid 15 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, amino acid 20 is Gly, and amino acid 15 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is Val, amino acid 20 is Ala, and amino acid 15 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is Leu, amino acid 20 is Ala, and amino acid 15 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ile, amino acid 20 is Ala, and amino acid 15 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, amino acid 20 is Asn, and amino acid 15 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala, amino acid 20 is Gln, and amino acid 15 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, amino acid 20 is Lys, and amino acid 15 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2J, where amino acid 42 is Ala, amino acid 20 is Arg, and amino acid 15 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2I, where amino acid 42 is Ala, amino acid 20 is His, and amino acid 15 is Ala. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, the variant IL-2 polypeptide, or a synTac comprising same, has a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 M, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, the variant IL-2 polypeptide present in a multimeric polypeptide of the present disclosure has a length of 133 amino acids.

F42, D20, and H16 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; and where amino acid 16 is an amino acid other than a histidine, e.g., where amino acid 16 is Gly, Ala, Val, Leu, Ile, Pro, Phe, Tyr, Trp, Ser, Thr, Cys, Met, Asn, Gln, Lys, Arg, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, Gly, Val, Leu, or Ile; where amino acid 20 is Ala, Gly, Val, Leu, or Ile; and where amino acid 16 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, Gly, Val, Leu, or Ile; where amino acid 20 is Asn, Gln, Lys, Arg, or His; and where amino acid 16 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is Gly, and amino acid 16 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Val, amino acid 20 is Ala, and amino acid 16 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Leu, amino acid 20 is Ala, and amino acid 16 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ile, amino acid 20 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is Asn, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is Gln, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is Lys, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is Arg, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2K, where amino acid 42 is Ala, amino acid 20 is His, and amino acid 16 is Ala. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or a synTac comprising same, has a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, the variant IL-2 polypeptide present in a multimeric polypeptide of the present disclosure has a length of 133 amino acids.

F42, D20, and Q126 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; and where amino acid 126 is an amino acid other than a glutamine, e.g., where amino acid 126 is Gly, Ala, Val, Leu, Ile, Pro, Phe, Tyr, Trp, Ser, Thr, Cys, Met, Asn, Lys, Arg, His, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, Gly, Val, Leu, or Ile; where amino acid 20 is Ala, Gly, Val, Leu, or Ile; and where amino acid 126 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, Gly, Val, Leu, or Ile; where amino acid 20 is Asn, Gln, Lys, Arg, or His; and where amino acid 126 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is Ala, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is Gly, and amino acid 126 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Val, amino acid 20 is Ala, and amino acid 126 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Leu, amino acid 20 is Ala, and amino acid 126 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ile, amino acid 20 is Ala, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is Asn, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is Gln, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is Lys, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is Arg, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2L, where amino acid 42 is Ala, amino acid 20 is His, and amino acid 126 is Ala. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or a synTac comprising same, has a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, the variant IL-2 polypeptide present in a multimeric polypeptide of the present disclosure has a length of 133 amino acids.

F42, D20, and Y45 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; and where amino acid 45 is an amino acid other than a tyrosine, e.g., where amino acid 45 is Gly, Ala, Val, Leu, Ile, Pro, Phe, Trp, Ser, Thr, Cys, Met, Asn, Gln, Lys, Arg, His, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, Gly, Val, Leu, or Ile; where amino acid 20 is Ala, Gly, Val, Leu, or Ile; and where amino acid 45 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, Gly, Val, Leu, or Ile; where amino acid 20 is Asn, Gln, Lys, Arg, or His; and where amino acid 45 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is Ala, and amino acid 45 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is Gly, and amino acid 45 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Val, amino acid 20 is Ala, and amino acid 45 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Leu, amino acid 20 is Ala, and amino acid 45 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ile, amino acid 20 is Ala, and amino acid 45 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is Asn, and amino acid 45 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is Gln, and amino acid 45 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is Lys, and amino acid 45 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is Arg, and amino acid 45 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2M, where amino acid 42 is Ala, amino acid 20 is His, and amino acid 45 is Ala. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or a synTac comprising same, has a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, the variant IL-2 polypeptide present in a multimeric polypeptide of the present disclosure has a length of 133 amino acids.

F4, D20, Y45, and H16 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; where amino acid 45 is an amino acid other than a tyrosine, e.g., where amino acid 45 is Gly, Ala, Val, Leu, Ile, Pro, Phe, Trp, Ser, Thr, Cys, Met, Asn, Gln, Lys, Arg, His, Asp, or Glu; and where amino acid 16 is an amino acid other than a histidine, e.g., where amino acid 16 is Gly, Ala, Val, Leu, Ile, Pro, Phe, Tyr, Trp, Ser, Thr, Cys, Met, Asn, Gln, Lys, Arg, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, Gly, Val, Leu, or Ile; where amino acid 20 is Ala, Gly, Val, Leu, or Ile; where amino acid 45 is Ala, Gly, Val, Leu, or Ile; and where amino acid 16 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, Gly, Val, Leu, or Ile; where amino acid 20 is Asn, Gln, Lys, Arg, or His; where amino acid 45 is Ala, Gly, Val, Leu, or Ile; and where amino acid 16 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is Ala, amino acid 45 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is Gly, amino acid 45 is Gly, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Val, amino acid 20 is Ala, amino acid 45 is Gly, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Leu, amino acid 20 is Ala, amino acid 45 is Gly, and amino acid 16 is Val. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ile, amino acid 20 is Ala, amino acid 45 is Ala, and amino acid 16 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is Asn, amino acid 45 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is Gln, amino acid 45 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is Lys, amino acid 45 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is Arg, amino acid 45 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2N, where amino acid 42 is Ala, amino acid 20 is His, amino acid 45 is Ala, and amino acid 16 is Ala. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or a synTac comprising same, has a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, the variant IL-2 polypeptide present in a multimeric polypeptide of the present disclosure has a length of 133 amino acids.

F42, D20, Y45, and Q126 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; where amino acid 45 is an amino acid other than a tyrosine, e.g., where amino acid 45 is Gly, Ala, Val, Leu, Ile, Pro, Phe, Trp, Ser, Thr, Cys, Met, Asn, Gln, Lys, Arg, His, Asp, or Glu; and where amino acid 126 is an amino acid other than a glutamine, e.g., where amino acid 126 is Gly, Ala, Val, Leu, Ile, Pro, Phe, Tyr, Trp, Ser, Thr, Cys, Met, Asn, Lys, Arg, His, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, Gly, Val, Leu, or Ile; where amino acid 20 is Ala, Gly, Val, Leu, or Ile; where amino acid 45 is Ala, Gly, Val, Leu, or Ile; and where amino acid 126 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, Gly, Val, Leu, or Ile; where amino acid 20 is Asn, Gln, Lys, Arg, or His; where amino acid 45 is Ala, Gly, Val, Leu, or Ile; and where amino acid 126 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is Ala, amino acid 45 is Ala, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is Gly, amino acid 45 is Gly, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Val, amino acid 20 is Ala, amino acid 45 is Gly, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Leu, amino acid 20 is Ala, amino acid 45 is Gly, and amino acid 126 is Val. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ile, amino acid 20 is Ala, amino acid 45 is Ala, and amino acid 126 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is Asn, amino acid 45 is Ala, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is Gln, amino acid 45 is Ala, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is Lys, amino acid 45 is Ala, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is Arg, amino acid 45 is Ala, and amino acid 126 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2O, where amino acid 42 is Ala, amino acid 20 is His, amino acid 45 is Ala, and amino acid 126 is Ala. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or a synTac comprising same, has a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, the variant IL-2 polypeptide present in a multimeric polypeptide of the present disclosure has a length of 133 amino acids.

F42, D20, Y45, H16, and Q126 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 20 is an amino acid other than an aspartic acid, e.g., where amino acid 20 is Gly, Ala, Val, Leu, Ile, Pro, Phe, Tyr, Trp, Ser, Thr, Cys, Met, Asn, Gln, Lys, Arg, His, or Glu; where amino acid 45 is an amino acid other than a tyrosine, e.g., where amino acid 45 is Gly, Ala, Val, Leu, Ile, Pro, Phe, Trp, Ser, Thr, Cys, Met, Asn, Gln, Lys, Arg, His, Asp, or Glu; where amino acid 126 is an amino acid other than a glutamine, e.g., where amino acid 126 is Gly, Ala, Val, Leu, Ile, Pro, Phe, Tyr, Trp, Ser, Thr, Cys, Met, Asn, Lys, Arg, His, Asp, or Glu; and where amino acid 16 is an amino acid other than a histidine, e.g., where amino acid 16 is Gly, Ala, Val, Leu, Ile, Pro, Phe, Tyr, Trp, Ser, Thr, Cys, Met, Asn, Gln, Lys, Arg, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, Gly, Val, Leu, or Ile; where amino acid 20 is Ala, Gly, Val, Leu, or Ile; where amino acid 45 is Ala, Gly, Val, Leu, or Ile; where amino acid 126 is Ala, Gly, Val, Leu, or Ile; and where amino acid 16 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is Ala, amino acid 45 is Ala, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is Gly, amino acid 45 is Gly, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Val, amino acid 20 is Ala, amino acid 45 is Gly, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Leu, amino acid 20 is Ala, amino acid 45 is Gly, amino acid 126 is Val, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ile, amino acid 20 is Ala, amino acid 45 is Ala, amino acid 126 is Gly, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is Asn, amino acid 45 is Ala, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is Gln, amino acid 45 is Ala, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is Lys, amino acid 45 is Ala, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is Arg, amino acid 45 is Ala, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2P, where amino acid 42 is Ala, amino acid 20 is His, amino acid 45 is Ala, amino acid 126 is Ala, and amino acid 16 is Ala. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or a synTac comprising same, has a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM. In some cases, the variant IL-2 polypeptide present in a multimeric polypeptide of the present disclosure has a length of 133 amino acids.

F42, Q126, and H16 Substitutions

In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is an amino acid other than a phenylalanine, e.g., where amino acid 42 is Gly, Ala, Val, Leu, Ile, Pro, Tyr, Trp, Ser, Thr, Cys, Met, Asn, Gln, Lys, Arg, His, Asp, or Glu; where amino acid 126 is an amino acid other than a glutamine, e.g., where amino acid 126 is Gly, Ala, Val, Leu, Ile, Pro, Phe, Tyr, Trp, Ser, Thr, Cys, Met, Asn, Lys, Arg, His, Asp, or Glu; and where amino acid 16 is an amino acid other than a histidine, e.g., where amino acid 16 is Gly, Ala, Val, Leu, Ile, Pro, Phe, Tyr, Trp, Ser, Thr, Cys, Met, Asn, Gln, Lys, Arg, Asp, or Glu. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, Gly, Val, Leu, or Ile; where amino acid 126 is Ala, Gly, Val, Leu, or Ile; and where amino acid 16 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is an amino acid other than a phenylalanine, e.g., where amino acid 42 is Ala, Gly, Val, Leu, or Ile; where amino acid 126 is Asn, Gln, Lys, Arg, or His; and where amino acid 16 is Ala, Gly, Val, Leu, or Ile. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is Gly, and amino acid 16 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Val, amino acid 126 is Ala, and amino acid 16 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Leu, amino acid 126 is Ala, and amino acid 16 is Gly. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ile, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is Asn, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is Ala, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is Lys, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is Arg, and amino acid 16 is Ala. In some cases, a variant IL-2 polypeptide present in a multimeric polypeptide of the present disclosure comprises an amino acid sequence having at least 90%, at least 95%, at least 98%, or at least 99%, amino acid sequence identity to the amino acid sequence depicted in FIG. 2Q, where amino acid 42 is Ala, amino acid 126 is His, and amino acid 16 is Ala. In some cases, a single copy of the variant IL-2 polypeptide is present in a multimeric polypeptide of the present disclosure. In some cases, a multimeric polypeptide of the present disclosure comprises two copies of the variant IL-2 polypeptide, e.g., where the two copies are in tandem with no linker between the two copies, or are in tandem and separated by a linker peptide. In some cases, a multimeric polypeptide of the present disclosure comprises three copies of the variant IL-2 polypeptide, e.g., where the three copies are in tandem with no linker between the three copies, or are in tandem and separated by a linker peptide. In some cases, where an IL-2/synTac of the present disclosure comprises HLA Class I heavy chain and β2M, the IL-2 polypeptide(s) is/are on the polypeptide chain comprising the HLA Class I heavy chain. In some cases, where an IL-2/synTac of the present disclosure comprises HLA Class I heavy chain and β2M, the IL-2 polypeptide(s) is/are on the polypeptide chain comprising the β2M polypeptide. In some cases, the variant IL-2 polypeptide, or a synTac comprising the variant IL-2 polypeptide, has a binding affinity for IL2R that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, to about 1 μM to about 5 μM, from about 5 μM to about 10 M, from about 10 μM to about 15 μM, from about 15 μM to about 20 μM, from about 20 μM to about 25 μM, from about 25 μM to about 50 μM, from about 50 μM to about 75 μM, or from about 75 μM to about 100 μM. In some cases, the variant IL-2 polypeptide has a length of 133 amino acids.

4-1BBL

In some cases, a synTac suitable for use in a method of the present disclosure comprises a 4-1BBL polypeptide as the immunomodulatory domain(s). Suitable 4-1BBL immunomodulatory domains include a wild-type 4-1BBL immunomodulatory domain, and a variant 4-1BBL immunomodulatory domain.

A wild-type human 4-1BBL amino acid sequence is provided in FIG. 36A. The tumor necrosis factor (TNF) homology domain (THD) of human 4-1BBL comprises amino acids 81-254, amino acids 80-254, or amino acids 80-246 of the amino acid sequence depicted in FIG. 36A. Thus, a wild-type amino acid sequence of the THD of human 4-1BBL can be, e.g., one of SEQ ID NOs:213-215, as follows:

```
                                            (SEQ ID NO: 213)
PAGLLDLRQG MFAQLVAQNV LLIDGPLSWY SDPGLAGVSL

TGGLSYKEDT KELVVAKAGV YYVFFQLELR RVVAGEGSGS

VSLALHLQPL RSAAGAAALA LTVDLPPASS EARNSAFGFQ

GRLLHLSAGQ RLGVHLHTEA RARHAWQLTQ GATVLGLFRV

TPEIPAGLPS PRSE.

(SEQ ID NO: 214)
D PAGLLDLRQG MFAQLVAQNV LLIDGPLSWY SDPGLAGVSL

TGGLSYKEDT KELVVAKAGV YYVFFQLELR RVVAGEGSGS

VSLALHLQPL RSAAGAAALA LTVDLPPASS EARNSAFGFQ

GRLLHLSAGQ RLGVHLHTEA RARHAWQLTQ GATVLGLFRV

TPEIPAGLPS PRSE.

(SEQ ID NO: 215)
D PAGLLDLRQG MFAQLVAQNV LLIDGPLSWY SDPGLAGVSL

TGGLSYKEDT KELVVAKAGV YYVFFQLELR RVVAGEGSGS

VSLALHLQPL RSAAGAAALA LTVDLPPASS EARNSAFGFQ

GRLLHLSAGQ RLGVHLHTEA RARHAWQLTQ GATVLGLFRV

TPEIPA.
```

Wild-type 4-1BBL binds to 4-1BB (CD137). An amino acid sequences of 4-1BB is provided in FIG. 37. A variant 4-1BBL polypeptide of the present disclosure binds to 4-1BB with reduced affinity compared to binding of wild-type 4-1BBL to 4-1BB.

Variant 4-1BBL polypeptides include those having an amino acid sequence that has at least 80%, at least 85%, at least 90%, at least 95%, or at least 99% amino acid sequence identity to a corresponding wild-type 4-1BBL polypeptide, and include variant 4-1BBL polypeptides that differ by 1, 2, 3, 4, 5, 6, 7, 8, 9, 10, 11, 12, 13, 14, or 15 amino acids, or more than 15 amino acids, relative to a corresponding wild-type 4-1BBL polypeptide. In some cases, a variant 4-1BBL polypeptide differs in amino acid sequence from a wild-type 4-1BBL polypeptide by only a single amino acid. In some cases, a variant 4-1BBL polypeptide differs in amino acid sequence from a wild-type 4-1BBL polypeptide by no more than 2 amino acids. In some cases, a variant 4-1BBL polypeptide differs in amino acid sequence from a wild-type 4-1BBL polypeptide by no more than 3 amino acids. In some cases, a variant 4-1BBL polypeptide differs in amino acid sequence from a wild-type 4-1BBL polypeptide by no more than 4 amino acids. In some cases, a variant 4-1BBL polypeptide differs in amino acid sequence from a wild-type 4-1BBL polypeptide by no more than 5 amino acids.

In some cases, the variant 4-1BBL polypeptide present in a multimeric polypeptide of the present disclosure exhibits reduced binding affinity to 4-1BB, compared to the binding affinity of a 4-1BBL polypeptide comprising the amino acid sequence depicted in FIG. 36A for 4-1BB. For example, in some cases, the variant 4-1BBL polypeptide present in a multimeric polypeptide of the present disclosure binds 4-1BB with a binding affinity that is less than the binding affinity of a 4-1BBL polypeptide comprising the amino acid sequence depicted in FIG. 36A for a 4-1BB polypeptide comprising the amino acid sequence depicted in FIG. 37. For example, in some cases, the variant 4-1BBL polypeptide present in a multimeric polypeptide of the present disclosure binds 4-1BB with a binding affinity that is at least 10% less, at least 15% less, at least 20% less, at least 25% less, at least 30% less, at least 35% less, at least 40% less, at least 45% less, at least 50% less, at least 55% less, at least 60% less, at least 65% less, at least 70% less, at least 75% less, at least 80% less, at least 85% less, at least 90% less, at least 95% less, or more than 95% less, than the binding affinity of a 4-1BBL polypeptide comprising the amino acid sequence depicted in FIG. 36A for 4-1BB (e.g., a 4-1BB polypeptide comprising the amino acid sequence depicted in FIG. 37).

In some cases, the variant 4-1BBL polypeptide present in a multimeric polypeptide of the present disclosure exhibits reduced binding affinity to 4-1BB, compared to the binding affinity of a 4-1BBL polypeptide comprising the amino acid sequence depicted in SEQ ID NO:213 for 4-1BB. For example, in some cases, the variant 4-1BBL polypeptide present in a multimeric polypeptide of the present disclosure binds 4-1BB with a binding affinity that is less than the binding affinity of a 4-1BBL polypeptide comprising the amino acid sequence depicted in SEQ ID NO:213 for a 4-1BB polypeptide comprising the amino acid sequence depicted in one of FIG. 37A-37C. For example, in some cases, the variant 4-1BBL polypeptide present in a multimeric polypeptide of the present disclosure binds 4-1BB with a binding affinity that is at least 10% less, at least 15% less, at least 20% less, at least 25% less, at least 30% less, at least 35% less, at least 40% less, at least 45% less, at least 50% less, at least 55% less, at least 60% less, at least 65% less, at least 70% less, at least 75% less, at least 80% less, at least 85% less, at least 90% less, at least 95% less, or more than 95% less, than the binding affinity of a 4-1BBL polypeptide comprising the amino acid sequence depicted in SEQ ID NO:213 for 4-1BB (e.g., a 4-1BB polypeptide comprising the amino acid sequence depicted in FIG. 37).

In some cases, a variant 4-1BBL polypeptide present in a multimeric polypeptide of the present disclosure has a binding affinity to 4-1BB that is from 100 nM to 100 µM. As another example, in some cases, a variant 4-1BBL polypeptide present in a multimeric polypeptide of the present disclosure has a binding affinity for 4-1BB (e.g., a 4-1BB polypeptide comprising the amino acid sequence depicted in FIG. 37) that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 M to about 15 µM, from about 15 µM to about 20 µM, from about 20 µM to about 25 µM, from about 25 µM to about 50 µM, from about 50 µM to about 75 µM, or from about 75 µM to about 100 µM.

In some cases, a variant 4-1BBL polypeptide present in a multimeric polypeptide of the present disclosure exhibits increased production in a mammalian host cell, compared to the production in the same mammalian host cell of a control multimeric polypeptide comprising a wild-type 4-1BBL polypeptide (e.g., a 4-1BBL polypeptide comprising the amino acid sequence depicted in FIG. 36A or as set forth in SEQ ID NO:213). For example, in some cases, a variant 4-1BBL polypeptide present in a multimeric polypeptide, when expressed in a mammalian host cell, is produced in an amount that is from 25% higher to about 50% higher, from about 50% higher to about 75% higher, from about 75% higher to about 2-fold higher, from about 2-fold higher to about 5-fold higher, from about 5-fold higher to about 10-fold higher, from about 10-fold higher to about 20-fold higher, from about 20-fold higher to about 30-fold higher, from about 30-fold higher to about 40-fold higher, from about 40-fold higher to about 50-fold higher, from about 50-fold higher to about 75-fold higher, from about 75-fold higher to about 100-fold higher, or more than 100-fold higher, than the amount of a control multimeric polypeptide comprising a wild-type 4-1BBL polypeptide (e.g., a 4-1BBL polypeptide comprising the amino acid sequence depicted in FIG. 36A or as set forth in SEQ ID NO:213) produced in the same mammalian host cell.

In some cases, a variant 4-1BBL polypeptide present in a multimeric polypeptide is produced in a mammalian host cell in an amount of from about 50 mg/L to about 75 mg/L, from about 75 mg/L to about 100 mg/L, from about 100 mg/L to about 150 mg/L, from about 150 mg/L to about 200 mg/L, from about 200 mg/L to about 250 mg/L, from about 250 mg/L to about 500 mg/L, or more than 500 mg/L. In some cases, a variant 4-1BBL polypeptide present in a multimeric polypeptide is produced in a mammalian host cell in an amount of from about 10 mg/L to about 15 mg/L, from about 15 mg/L to about 20 mg/L, from about 20 mg/L to about 25 mg/L, from about 25 mg/L to about 30 mg/L, from about 35 mg/L to about 40 mg/L, from about 40 mg/L to about 45 mg/L, or from about 45 mg/L to about 50 mg/L.

A variant 4-1BBL polypeptide present in a multimeric polypeptide can have a single amino acid substitution relative to a wild-type 4-1BBL polypeptide (e.g., a 4-1BBL polypeptide comprising the amino acid sequence depicted in FIG. 36A or as set forth in SEQ ID NO:213). In some cases, a variant 4-1BBL polypeptide present in a multimeric polypeptide of the present disclosure has from 2 to 10 amino acid substitutions relative to a wild-type 4-1BBL polypeptide (e.g., a 4-1BBL polypeptide comprising the amino acid sequence depicted in FIG. 36A or as set forth in SEQ ID NO:213). In some cases, a variant 4-1BBL polypeptide present in a multimeric polypeptide of the present disclosure has 2 amino acid substitutions relative to a wild-type 4-1BBL polypeptide (e.g., a 4-1BBL polypeptide comprising the amino acid sequence depicted in FIG. 36A or as set forth in SEQ ID NO:213). In some cases, a variant 4-1BBL polypeptide present in a multimeric polypeptide of the present disclosure has 3 amino acid substitutions relative to a wild-type 4-1BBL polypeptide (e.g., a 4-1BBL polypeptide comprising the amino acid sequence depicted in FIG. 36A or as set forth in SEQ ID NO:213). In some cases, a variant 4-1BBL polypeptide present in a multimeric polypeptide of the present disclosure has 4 amino acid substitutions relative to a wild-type 4-1BBL polypeptide (e.g., a 4-1BBL polypeptide comprising the amino acid sequence depicted in FIG. 36A or as set forth in SEQ ID NO:213). In some cases, a variant 4-1BBL polypeptide present in a multimeric polypeptide of the present disclosure has 5 amino acid substitutions relative to a wild-type 4-1BBL polypeptide (e.g., a 4-1BBL polypeptide comprising the amino acid sequence depicted in FIG. 36A or as set forth in SEQ ID NO:213). In some cases, a variant 4-1BBL polypeptide present in a multimeric polypeptide of the present disclosure has 6 amino acid substitutions relative to a wild-type 4-1BBL polypeptide (e.g., a 4-1BBL polypeptide comprising the amino acid sequence depicted in FIG. 36A or as set forth in SEQ ID NO:213). In some cases, a variant 4-1BBL polypeptide of the present disclosure has 7 amino acid substitutions relative to a wild-type 4-1BBL polypeptide (e.g., a 4-1BBL polypeptide comprising the amino acid sequence depicted in FIG. 36A or as set forth in SEQ ID NO:213). In some cases, a variant 4-1BBL polypeptide present in a multimeric polypeptide of the present disclosure has 8 amino acid substitutions relative to a wild-type 4-1BBL polypeptide (e.g., a 4-1BBL polypeptide comprising the amino acid sequence depicted in FIG. 36A or as set forth in SEQ ID NO:213). In some cases, a variant 4-1BBL polypeptide present in a multimeric polypeptide of the present disclosure has 9 amino acid substitutions relative to a wild-type 4-1BBL polypeptide (e.g., a 4-1BBL polypeptide comprising the amino acid sequence depicted in FIG. 36A or as set forth in SEQ ID NO:213). In some cases, a variant 4-1BBL polypeptide present in a multimeric polypeptide of the present disclosure has 10 amino acid substitutions relative to a wild-type 4-1BBL polypeptide (e.g., a 4-1BBL polypeptide comprising the amino acid sequence depicted in FIG. 36A or as set forth in SEQ ID NO:213).

In some cases, a variant 4-1BBL polypeptide present in a multimeric polypeptide of the present disclosure has from 11 to 50 amino acid substitutions relative to a wild-type 4-1BBL polypeptide (e.g., a 4-1BBL polypeptide comprising the amino acid sequence depicted in FIG. 36A or as set forth in SEQ ID NO:213). For example, in some cases, a variant 4-1BBL polypeptide present in a multimeric polypeptide of the present disclosure has from 11 to 15, from 15 to 20, from 20 to 25, from 25 to 30, from 30 to 35, from 35 to 40, from 40 to 45, or from 45 to 50, amino acid substitutions relative to a wild-type 4-1BBL polypeptide (e.g., a 4-1BBL polypeptide comprising the amino acid sequence depicted in FIG. 36A or as set forth in SEQ ID NO:213).

Suitable variant 4-1BBL polypeptides that can be included in a multimeric polypeptide of the present disclosure include those described above.

4-1BBL with K127 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at K48. In some cases, a variant 4-1BBL polypeptide present in a multimeric polypeptide of the present disclosure comprises the amino acid sequence set forth in SEQ ID NO:214, with an amino acid substitution at K48. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at K48. In some cases, a variant 4-1BBL polypeptide present in a multimeric polypeptide of the present disclosure comprises the amino acid sequence set forth in SEQ ID NO:215, with an amino acid substitution at K48.

K127+M91 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at M91, where amino acid 91 is Gly, Ala, Val, Leu, Ile, Pro, Phe, Tyr, Trp, Ser, Thr, Cys, Asn, Gln, Lys, Arg, His, Asp, or Glu. In some cases, amino acid 127 is Ala; and amino acid 91 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 11 is other than methionine, e.g., where amino acid 11 is Gly, Ala, Val, Leu, Ile, Pro, Phe, Tyr, Trp, Ser, Thr, Cys, Asn, Gln, Lys, Arg, His, Asp, or Glu. In some cases, amino acid 47 is Ala; and amino acid 11 is Ala.

K127+F92 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at F92, where amino acid 92 is Gly, Ala, Val, Leu, Ile, Pro, Tyr, Trp, Ser, Thr, Cys, Met, Asn, Gln, Lys, Arg, His, Asp, or Glu. In some cases, amino acid 127 is Ala; and amino acid 92 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 12 is other than phenylalanine, e.g., where amino acid 12 is Gly, Ala, Val, Leu, Ile, Pro, Tyr, Trp, Ser, Thr, Cys, Met, Asn, Gln, Lys, Arg, His, Asp, or Glu. In some cases, amino acid 47 is Ala; and amino acid 12 is Ala.

K127+Q94 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at Q94, where amino acid 94 is Gly, Ala, Val, Leu, Ile, Pro, Phe, Tyr, Trp, Ser, Thr, Cys, Met, Asn, Lys, Arg, His, Asp, or Glu. In some cases, amino acid 127 is Ala; and amino acid 94 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 14 is other than glutamine, e.g., where amino acid 14 is Gly, Ala, Val, Leu, Ile, Pro, Phe, Tyr, Trp, Ser, Thr, Cys, Met, Asn, Lys, Arg, His, Asp, or Glu. In some cases, amino acid 47 is Ala; and amino acid 14 is Ala.

K127+L95 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at L95, where amino acid 95 is Gly, Ala, Val, Ile, Pro, Phe, Tyr, Trp, Ser, Thr, Cys, Met, Asn, Gln, Lys, Arg, His, Asp, or Glu. In some cases, amino acid 127 is Ala; and amino acid 95 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 15 is other than leucine, e.g., where amino acid 15 is Gly, Ala, Val, Ile, Pro, Phe, Tyr, Trp, Ser, Thr, Cys, Met, Asn, Gln, Lys, Arg, His, Asp, or Glu. In some cases, amino acid 47 is Ala; and amino acid 15 is Ala.

K127+V96 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at V96, where amino acid 96 is Gly, Ala, Leu, Ile, Pro, Phe, Tyr, Trp, Ser, Thr, Cys, Met, Asn, Gln, Lys, Arg, His, Asp, or Glu. In some cases, amino acid 127 is Ala; and amino acid 96 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 16 is other than a valine, e.g., where amino acid 16 is Gly, Ala, Leu, Ile, Pro, Phe, Tyr, Trp, Ser, Thr, Cys, Met, Asn, Gln, Lys, Arg, His, Asp, or Glu. In some cases, amino acid 47 is Ala; and amino acid 16 is Ala.

K127+Q98 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at Q98, where amino acid 98 is Gly, Ala, Val, Leu, Ile, Pro, Phe, Tyr, Trp, Ser, Thr, Cys, Met, Asn, Lys, Arg, His, Asp, or Glu. In some cases, amino acid 127 is Ala; and amino acid 98 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 18 is other than glutamine, e.g., where amino acid 18 is Gly, Ala, Val, Leu, Ile, Pro, Phe, Tyr, Trp, Ser, Thr, Cys, Met, Asn, Lys, Arg, His, Asp, or Glu. In some cases, amino acid 47 is Ala; and amino acid 18 is Ala.

K127+N99 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at N99, where amino acid 99 is Gly, Ala, Val, Leu, Ile, Pro, Phe, Tyr, Trp, Ser, Thr, Cys, Met, Gln, Lys, Arg, His, Asp, or Glu. In some cases, amino acid 127 is Ala; and amino acid 99 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 19 is other than an asparagine, e.g., where amino acid 19 is Gly, Ala, Val, Leu, Ile, Pro, Phe, Tyr, Trp, Ser, Thr, Cys, Met, Gln, Lys, Arg, His, Asp, or Glu. In some cases, amino acid 47 is Ala; and amino acid 19 is Ala.

K127+V100 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at V100, where amino acid 100 is Gly, Ala, Leu, Ile, Pro, Phe, Tyr, Trp, Ser, Thr, Cys, Met, Asn, Gln, Lys, Arg, His, Asp, or Glu. In some cases, amino acid 127 is Ala; and amino acid 100 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 20 is other than a valine, e.g., where amino acid 20 is Gly, Ala, Leu, Ile, Pro, Phe, Tyr, Trp, Ser, Thr, Cys, Met, Asn, Gln, Lys, Arg, His, Asp, or Glu. In some cases, amino acid 47 is Ala; and amino acid 20 is Ala.

K127+L101 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at L101, where amino acid 101 is Gly, Ala, Val, Ile, Pro, Phe, Tyr, Trp, Ser, Thr, Cys, Met, Asn, Gln, Lys, Arg, His, Asp, or Glu. In some cases, amino acid 127 is Ala; and amino acid 101 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 21 is other than leucine, e.g., where amino acid 21 is Gly, Ala, Val, Ile, Pro, Phe, Tyr, Trp, Ser, Thr, Cys, Met, Asn, Gln, Lys, Arg, His, Asp, or Glu. In some cases, amino acid 47 is Ala; and amino acid 21 is Ala.

K127+L102 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at L102, where amino acid 102 is Gly, Ala, Val, Ile, Pro, Phe, Tyr, Trp, Ser, Thr, Cys, Met, Asn, Gln, Lys, Arg, His, Asp, or Glu. In some cases, amino acid 127 is Ala; and amino acid 102 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 22 is other than leucine, e.g., where amino acid 22 is Gly, Ala, Val, Ile, Pro, Phe, Tyr, Trp, Ser, Thr, Cys, Met, Asn, Gln, Lys, Arg, His, Asp, or Glu. In some cases, amino acid 47 is Ala; and amino acid 22 is Ala.

K127+I103 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at 1103, where amino acid 103 is Gly, Ala, Val, Leu, Pro, Phe, Tyr, Trp, Ser, Thr, Cys, Met, Asn, Gln, Lys, Arg, His, Asp, or Glu. In some cases, amino acid 127 is Ala; and amino acid 103 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 23 is other than isoleucine, e.g., where amino acid 23 is Gly, Ala, Val, Leu, Pro, Phe, Tyr, Trp, Ser, Thr, Cys, Met, Asn, Gln, Lys, Arg, His, Asp, or Glu. In some cases, amino acid 47 is Ala; and amino acid 23 is Ala.

K127+D104 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at D104, where amino acid 104 is Gly, Ala, Val, Leu, Ile, Pro, Phe, Tyr, Trp, Ser, Thr, Cys, Met, Asn, Gln, Lys, Arg, His, or Glu. In some cases, amino acid 127 is Ala; and amino acid 104 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 24 is other than aspartic acid, e.g., where amino acid 24 is Gly, Ala, Val, Leu, Ile, Pro, Phe, Tyr, Trp, Ser, Thr, Cys, Met, Asn, Gln, Lys, Arg, His, or Glu. In some cases, amino acid 47 is Ala; and amino acid 24 is Ala.

K127+G105 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at G105, where amino acid 105 is Ala, Val, Leu, Ile, Pro, Phe, Tyr, Trp, Ser, Thr, Cys, Met, Asn, Gln, Lys, Arg, His, Asp, or Glu. In some cases, amino acid 127 is Ala; and amino acid 105 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 25 is other than glycine, e.g., where amino acid 25 is Ala, Val, Leu, Ile, Pro, Phe, Tyr, Trp, Ser, Thr, Cys, Met, Asn, Gln, Lys, Arg, His, Asp, or Glu. In some cases, amino acid 47 is Ala; and amino acid 25 is Ala.

K127+P106 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at P106, where amino acid 106 is Gly, Ala, Val, Leu, Ile, Phe, Tyr, Trp, Ser, Thr, Cys, Met, Asn, Gln, Lys, Arg, His, Asp, or Glu. In some cases, amino acid 127 is Ala; and amino acid 106 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 26 is other than proline, e.g., where amino acid 26 is Gly, Ala, Val, Leu, Ile, Phe, Tyr, Trp, Ser, Thr, Cys, Met, Asn, Gln, Lys, Arg, His, Asp, or Glu. In some cases, amino acid 47 is Ala; and amino acid 26 is Ala.

K127+L107 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at L107, where amino acid 107 is Gly, Ala, Val, Ile, Pro, Phe, Tyr, Trp, Ser, Thr, Cys, Met, Asn, Gln, Lys, Arg, His, Asp, or Glu. In some cases, amino acid 127 is Ala; and amino acid 107 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 27 is other than leucine, e.g., where amino acid 27 is Gly, Ala, Val, Ile, Pro, Phe, Tyr, Trp, Ser, Thr, Cys, Met, Asn, Gln, Lys, Arg, His, Asp, or Glu. In some cases, amino acid 47 is Ala; and amino acid 27 is Ala.

K127+S108 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at S108, where amino acid 108 is Gly, Ala, Val, Leu, Ile, Pro, Phe, Tyr, Trp, Thr, Cys, Met, Asn, Gln, Lys, Arg, His, Asp, or Glu. In some cases, amino acid 127 is Ala; and amino acid 108 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 28 is other than serine, e.g., where amino acid 28 is Gly, Ala, Val, Leu, Ile, Pro, Phe, Tyr, Trp, Thr, Cys, Met, Asn, Gln, Lys, Arg, His, Asp, or Glu. In some cases, amino acid 47 is Ala; and amino acid 28 is Ala.

K127+W109 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at W109, where amino acid 109 is Gly, Ala, Val, Leu, Ile, Pro, Phe, Tyr, Ser, Thr, Cys, Met, Asn, Gln, Lys, Arg, His, Asp, or Glu. In some cases, amino acid 127 is Ala; and amino acid 109 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 29 is other than tryptophan, e.g., where amino acid 29 is Gly, Ala, Val, Leu, Ile, Pro, Phe, Tyr, Ser, Thr, Cys, Met, Asn, Gln, Lys, Arg, His, Asp, or Glu. In some cases, amino acid 47 is Ala; and amino acid 29 is Ala.

K127+Y110 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at Y110, where amino acid 110 is Gly, Ala, Val, Leu, Ile, Pro, Phe, Trp, Ser, Thr, Cys, Met, Asn, Gln, Lys, Arg, His, Asp, or Glu. In some cases, amino acid 127 is Ala; and amino acid 110 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 30 is other than tyrosine, e.g., where amino acid 30 is Gly, Ala, Val, Leu, Ile, Pro, Phe, Trp, Ser, Thr, Cys, Met, Asn, Gln, Lys, Arg, His, Asp, or Glu. In some cases, amino acid 47 is Ala; and amino acid 30 is Ala.

K127+S111 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at S111, where amino acid 111 is Gly, Ala, Val, Leu, Ile, Pro, Phe, Tyr, Trp, Thr, Cys, Met, Asn, Gln, Lys, Arg, His, Asp, or Glu. In some cases, amino acid 127 is Ala; and amino acid 111 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 31 is other than serine, e.g., where amino acid 31 is Gly, Ala, Val, Leu, Ile, Pro, Phe, Tyr, Trp, Thr, Cys, Met, Asn, Gln, Lys, Arg, His, Asp, or Glu. In some cases, amino acid 47 is Ala; and amino acid 31 is Ala.

K127+D112 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at D112, where amino acid 112 is Gly, Ala, Val, Leu, Ile, Pro, Phe, Tyr, Trp, Ser, Thr, Cys, Met, Asn, Gln, Lys, Arg, His, or Glu. In some cases, amino acid 127 is Ala; and amino acid 112 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 32 is other than aspartic acid, e.g., where amino acid 32 is Gly, Ala, Val, Leu, Ile, Pro, Phe, Tyr, Trp, Ser, Thr, Cys, Met, Asn, Gln, Lys, Arg, His, or Glu. In some cases, amino acid 47 is Ala; and amino acid 32 is Ala.

K127+P113 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at P113, where amino acid 113 is Gly, Ala, Val, Leu, Ile, Phe, Tyr, Trp, Ser, Thr, Cys, Met, Asn, Gln, Lys, Arg, His, Asp, or Glu. In some cases, amino acid 127 is Ala; and amino acid 113 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 33 is other than proline, e.g., where amino acid 33 is Gly, Ala, Val, Leu, Ile, Phe, Tyr, Trp, Ser, Thr, Cys, Met, Asn, Gln, Lys, Arg, His, Asp, or Glu. In some cases, amino acid 47 is Ala; and amino acid 33 is Ala.

K127+G114 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at G114, where amino acid 114 is Ala, Val, Leu, Ile, Pro, Phe, Tyr, Trp, Ser, Thr, Cys, Met, Asn, Gln, Lys, Arg, His, Asp, or Glu. In some cases, amino acid 127 is Ala; and amino acid 114 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 34 is other than glycine, e.g., where amino acid 34 is Ala, Val, Leu, Ile, Pro, Phe, Tyr, Trp, Ser, Thr, Cys, Met, Asn, Gln, Lys, Arg, His, Asp, or Glu. In some cases, amino acid 47 is Ala; and amino acid 34 is Ala.

K127+L115 Substitutions

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36B, where: i) amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; and ii) an amino acid substitution at L115, where amino acid 115 is Gly, Ala, Val, Ile, Pro, Phe, Tyr, Trp, Ser, Thr, Cys, Met, Asn, Gln, Lys, Arg, His, Asp, or Glu. In some cases, amino acid 127 is Ala; and amino acid 115 is Ala. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where: i) amino acid 47 is an amino acid other than a lysine, e.g., where amino acid 47 is Gly, Ala, Val, Leu, Ile, Pro, Phe, Tyr, Trp, Ser, Thr, Cys, Met, Asn, Gln, Arg, His, Asp, or Glu; and ii) amino acid 35 is other than leucine, e.g., where amino acid 35 is Gly, Ala, Val, Ile, Pro, Phe, Tyr, Trp, Ser, Thr, Cys, Met, Asn, Gln, Lys, Arg, His, Asp, or Glu. In some cases, amino acid 47 is Ala; and amino acid 35 is Ala.

4-1BBL with Q227 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36D where amino acid 227 (indicated by an "x") is an amino acid other than a glutamine, e.g., where amino acid 227 is Gly, Ala, Val, Leu, Ile, Pro, Phe, Tyr, Trp, Ser, Thr, Cys, Met, Asn, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 147 is other than glutamine, e.g., where amino acid 147 is Gly, Ala, Val, Leu, Ile, Pro, Phe, Tyr, Trp, Ser, Thr, Cys, Met, Asn, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at Q148. In some cases, a variant 4-1BBL polypeptide present in a multimeric polypeptide of the present disclosure comprises the amino acid sequence set forth in SEQ ID NO:214, with an amino acid substitution at Q148. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at Q148. In some cases, a variant 4-1BBL polypeptide present in a multimeric polypeptide of the present disclosure comprises the amino acid sequence set forth in SEQ ID NO:215, with an amino acid substitution at Q148.

4-1BBL with M91 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36E, where amino acid 91 (indicated by an "x") is an amino acid other than a methionine, e.g., where amino acid 91 is Gly, Ala, Val, Leu, Ile, Pro, Phe, Tyr, Trp, Ser, Thr, Cys, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 11 is other than a methionine, e.g., where amino acid 11 is Gly, Ala, Val, Leu, Ile, Pro, Phe, Tyr, Trp, Ser, Thr, Cys, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at M12. In some cases, a variant 4-1BBL polypeptide present in a multimeric polypeptide of the present disclosure comprises the amino acid sequence set forth in SEQ ID NO:214, with an amino acid substitution at M12. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at M12. In some cases, a variant 4-1BBL polypeptide present in a multimeric polypeptide of the present disclosure comprises the amino acid sequence set forth in SEQ ID NO:215, with an amino acid substitution at M12.

4-1BBL with F92 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36F, where amino acid 92 (indicated by an "x") is an amino acid other than a phenylalanine, e.g., where amino acid 92 is Gly, Ala, Val, Leu, Ile, Pro, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 12 is other than a phenylalanine, e.g., where amino acid 12 is Gly, Ala, Val, Leu, Ile, Pro, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at F13. In some cases, a variant 4-1BBL polypeptide present in a multimeric polypeptide of the present disclosure comprises the amino acid sequence set forth in SEQ ID NO:214, with an amino acid substitution at F13. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at F13. In some cases, a variant 4-1BBL polypeptide present in a multimeric polypeptide of the present disclosure comprises the amino acid sequence set forth in SEQ ID NO:215, with an amino acid substitution at F13.

4-1BBL with Q94 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36G, where amino acid 94 (indicated by an "x") is an amino acid other than a glutamine, e.g., where amino acid 94 is Gly, Ala, Val, Leu, Ile, Pro, Phe, Tyr, Trp, Ser, Thr, Cys, Met, Asn, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 14 is other than a glutamine, e.g., where amino acid 14 is Gly, Ala, Val, Leu, Ile, Pro, Phe, Tyr, Trp, Ser, Thr, Cys, Met, Asn, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at Q15. In some cases, a variant 4-1BBL polypeptide present in a multimeric polypeptide of the present disclosure comprises the amino acid sequence set forth in SEQ ID NO:214, with an amino acid substitution at Q15. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at Q15. In some cases, a variant 4-1BBL polypeptide present in a multimeric polypeptide of the present disclosure comprises the amino acid sequence set forth in SEQ ID NO:215, with an amino acid substitution at Q15.

4-1BBL with L95 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36H, where amino acid 95 (indicated by an "x") is an amino acid other than a leucine, e.g., where amino acid 95 is Gly, Ala, Val, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 15 is other than a leucine, e.g., where amino acid 15 is Gly, Ala, Val, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at L16. In some cases, a variant 4-1BBL polypeptide present in a multimeric polypeptide of the present disclosure comprises the amino acid sequence set forth in SEQ ID NO:214, with an amino acid substitution at L16. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at L16. In some cases, a variant 4-1BBL polypeptide present in a multimeric polypeptide of the present disclosure comprises the amino acid sequence set forth in SEQ ID NO:215, with an amino acid substitution at L16.

4-1BBL with V96 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36I, where amino acid 96 (indicated by an "x") is an amino acid other than a valine, e.g., where amino acid 96 is Gly, Ala, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 16 is other than a valine, e.g., where amino acid 16 is Gly, Ala, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at V17. In some cases, a variant 4-1BBL polypeptide present in a multimeric polypeptide of the present disclosure comprises the amino acid sequence set forth in SEQ ID NO:214, with an amino acid substitution at V17. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at V17. In some cases, a variant 4-1BBL polypeptide present in a multimeric polypeptide of the present disclosure comprises the amino acid sequence set forth in SEQ ID NO:215, with an amino acid substitution at V17.

4-1BBL with Q98 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36J, where amino acid 98 (indicated by an "x") is an amino acid other than a glutamine, e.g., where amino acid 98 is Gly, Ala, Val, Leu, Ile, Pro, Phe, Tyr, Trp, Ser, Thr, Cys, Met, Asn, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 18 is other than a glutamine, e.g., where amino acid 18 is Gly, Ala, Val, Leu, Ile, Pro, Phe, Tyr, Trp, Ser, Thr, Cys, Met, Asn, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at Q19. In some cases, a variant 4-1BBL polypeptide present in a multimeric polypeptide of the present disclosure comprises the amino acid sequence set forth in SEQ ID NO:214, with an amino acid substitution at Q19. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at Q19. In some cases, a variant 4-1BBL polypeptide present in a multimeric polypeptide of the present disclosure comprises the amino acid sequence set forth in SEQ ID NO:215, with an amino acid substitution at Q19.

4-1BBL with N99 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36K, where amino acid 99 (indicated by an "x") is an amino acid other than an asparagine, e.g., where amino acid 99 is Gly, Ala, Val, Leu, Ile, Pro, Phe, Tyr, Trp, Ser, Thr, Cys, Met, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 19 is other than an asparagine, e.g., where amino acid 19 is Gly, Ala, Val, Leu, Ile, Pro, Phe, Tyr, Trp, Ser, Thr, Cys, Met, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at N20. In some cases, a variant 4-1BBL polypeptide present in a multimeric polypeptide of the present disclosure comprises the amino acid sequence set forth in SEQ ID NO:214, with an amino acid substitution at N20. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at N20. In some cases, a variant 4-1BBL polypeptide present in a multimeric polypeptide of the present disclosure comprises the amino acid sequence set forth in SEQ ID NO:215, with an amino acid substitution at N20.

4-1BBL with V100 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36L, where amino acid 100 (indicated by an "x") is an amino acid other than a valine, e.g., where amino acid 100 is Gly, Ala, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 20 is other than a valine, e.g., where amino acid 20 is Gly, Ala, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at V21. In some cases, a variant 4-1BBL polypeptide present in a multimeric polypeptide of the present disclosure comprises the amino acid sequence set forth in SEQ ID NO:214, with an amino acid substitution at V21. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at V21. In some cases, a variant 4-1BBL polypeptide present in a multimeric polypeptide of the present disclosure comprises the amino acid sequence set forth in SEQ ID NO:215, with an amino acid substitution at V21.

4-1BBL with L101 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36M, where amino acid 101 (indicated by an "x") is an amino acid other than a leucine, e.g., where amino acid 101 is Gly, Ala, Val, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 21 is other than a leucine, e.g., where amino acid 21 is Gly, Ala, Val, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at L22. In some cases, a variant 4-1BBL polypeptide present in a multimeric polypeptide of the present disclosure comprises the amino acid sequence set forth in SEQ ID NO:214, with an amino acid substitution at L22. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at L22. In some cases, a variant 4-1BBL polypeptide present in a multimeric polypeptide of the present disclosure comprises the amino acid sequence set forth in SEQ ID NO:215, with an amino acid substitution at L22.

4-1BBL with L102 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36N, where amino acid 102 (indicated by an "x") is an amino acid other than a leucine, e.g., where amino acid 102 is Gly, Ala, Val, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 22 is other than a leucine, e.g., where amino acid 22 is Gly, Ala, Val, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at L23. In some cases, a variant 4-1BBL polypeptide present in a multimeric polypeptide of the present disclosure comprises the amino acid sequence set forth in SEQ ID NO:214, with an amino acid substitution at L23. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at L23. In some cases, a variant 4-1BBL polypeptide present in a multimeric polypeptide of the present disclosure comprises the amino acid sequence set forth in SEQ ID NO:215, with an amino acid substitution at L23.

4-1BBL with I103 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36O, where amino acid 103 (indicated by an "x") is an amino acid other than an isoleucine, e.g., where amino acid 103 is Gly, Ala, Val, Leu, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 23 is other than an isoleucine, e.g., where amino acid 23 is Gly, Ala, Val, Leu, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at 124. In some cases, a variant 4-1BBL polypeptide present in a multimeric polypeptide of the present disclosure comprises the amino acid sequence set forth in SEQ ID NO:214, with an amino acid substitution at 124. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at 124. In some cases, a variant 4-1BBL polypeptide present in a multimeric polypeptide of the present disclosure comprises the amino acid sequence set forth in SEQ ID NO:215, with an amino acid substitution at 124.

4-1BBL with D104 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36P, where amino acid 104 (indicated by an "x") is an amino acid other than an aspartic acid, e.g., where amino acid 104 is Gly, Ala, Val, Leu, Ile, Pro, Phe, Tyr, Trp, Ser, Thr, Cys, Met, Asn, Gln, Lys, Arg, His, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 24 is other than an aspartic acid, e.g., where amino acid 24 is Gly, Ala, Val, Leu, Ile, Pro, Phe, Tyr, Trp, Ser, Thr, Cys, Met, Asn, Gln, Lys, Arg, His, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at D25. In some cases, a variant 4-1BBL polypeptide present in a multimeric polypeptide of the present disclosure comprises the amino acid sequence set forth in SEQ ID NO:214, with an amino acid substitution at D25. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at D25. In some cases, a variant 4-1BBL polypeptide present in a multimeric polypeptide of the present disclosure comprises the amino acid sequence set forth in SEQ ID NO:215, with an amino acid substitution at D25.

4-1BBL with G105 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36Q, where amino acid 105 (indicated by an "x") is an amino acid other than a glycine, e.g., where amino acid 105 is Ala, Val, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 25 is other than a glycine, e.g., where amino acid 25 is Ala, Val, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at G26. In some cases, a variant 4-1BBL polypeptide present in a multimeric polypeptide of the present disclosure comprises the amino acid sequence set forth in SEQ ID NO:214, with an amino acid substitution at G26. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at G26. In some cases, a variant 4-1BBL polypeptide present in a multimeric polypeptide of the present disclosure comprises the amino acid sequence set forth in SEQ ID NO:215, with an amino acid substitution at G26.

4-1BBL with P106 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36R, where amino acid 106 (indicated by an "x") is an amino acid other than a proline, e.g., where amino acid 106 is Gly, Ala, Val, Leu, Ile, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 26 is other than a proline, e.g., where amino acid 26 is Gly, Ala, Val, Leu, Ile, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at P27. In some cases, a variant 4-1BBL polypeptide present in a multimeric polypeptide of the present disclosure comprises the amino acid sequence set forth in SEQ ID NO:214, with an amino acid substitution at P27. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at P27. In some cases, a variant 4-1BBL polypeptide present in a multimeric polypeptide of the present disclosure comprises the amino acid sequence set forth in SEQ ID NO:215, with an amino acid substitution at P27.

4-1BBL with L107 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36S, where amino acid 107 (indicated by an "x") is an amino acid other than a leucine, e.g., where amino acid 107 is Gly, Ala, Val, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 27 is other than a leucine, e.g., where amino acid 27 is Gly, Ala, Val, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at L28. In some cases, a variant 4-1BBL polypeptide present in a multimeric polypeptide of the present disclosure comprises the amino acid sequence set forth in SEQ ID NO:214, with an amino acid substitution at L28. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at L28. In some cases, a variant 4-1BBL polypeptide present in a multimeric polypeptide of the present disclosure comprises the amino acid sequence set forth in SEQ ID NO:215, with an amino acid substitution at L28.

4-1BBL with S108 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36T, where amino acid 108 (indicated by an "x") is an amino acid other than a serine, e.g., where amino acid 108 is Gly, Ala, Val, Leu, Ile, Pro, Phe, Tyr, Trp, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 28 is other than a serine, e.g., where amino acid 28 is Gly, Ala, Val, Leu, Ile, Pro, Phe, Tyr, Trp, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at S29. In some cases, a variant 4-1BBL polypeptide present in a multimeric polypeptide of the present disclosure comprises the amino acid sequence set forth in SEQ ID NO:214, with an amino acid substitution at S29. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at S29. In some cases, a variant 4-1BBL polypeptide present in a multimeric polypeptide of the present disclosure comprises the amino acid sequence set forth in SEQ ID NO:215, with an amino acid substitution at S29.

4-1BBL with W109 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36U, where amino acid 109 (indicated by an "x") is an amino acid other than a tryptophan, e.g., where amino acid 109 is Gly, Ala, Val, Leu, Ile, Pro, Phe, Tyr, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 29 is other than a tryptophan, e.g., where amino acid 29 is Gly, Ala, Val, Leu, Ile, Pro, Phe, Tyr, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at W30. In some cases, a variant 4-1BBL polypeptide present in a multimeric polypeptide of the present disclosure comprises the amino acid sequence set forth in SEQ ID NO:214, with an amino acid substitution at W30. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at W30. In some cases, a variant 4-1BBL polypeptide present in a multimeric polypeptide of the present disclosure comprises the amino acid sequence set forth in SEQ ID NO:215, with an amino acid substitution at W30.

4-1BBL with Y110 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36V, where amino acid 110 (indicated by an "x") is an amino acid other than a tyrosine, e.g., where amino acid 110 is Gly, Ala, Val, Leu, Ile, Pro, Phe, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 30 is other than a tyrosine, e.g., where amino acid 30 is Gly, Ala, Val, Leu, Ile, Pro, Phe, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at Y31. In some cases, a variant 4-1BBL polypeptide present in a multimeric polypeptide of the present disclosure comprises the amino acid sequence set forth in SEQ ID NO:214, with an amino acid substitution at Y31. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at Y31. In some cases, a variant 4-1BBL polypeptide present in a multimeric polypeptide of the present disclosure comprises the amino acid sequence set forth in SEQ ID NO:215, with an amino acid substitution at Y31.

4-1BBL with S111 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36W, where amino acid 111 (indicated by an "x") is an amino acid other than a serine, e.g., where amino acid 111 is Gly, Ala, Val, Leu, Ile, Pro, Phe, Tyr, Trp, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 31 is other than a serine, e.g., where amino acid 31 is Gly, Ala, Val, Leu, Ile, Pro, Phe, Tyr, Trp, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at S32. In some cases, a variant 4-1BBL polypeptide present in a multimeric polypeptide of the present disclosure comprises the amino acid sequence set forth in SEQ ID NO:214, with an amino acid substitution at S32. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at S32. In some cases, a variant 4-1BBL polypeptide present in a multimeric polypeptide of the present disclosure comprises the amino acid sequence set forth in SEQ ID NO:215, with an amino acid substitution at S32.

4-1BBL with D112 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36X, where amino acid 112 (indicated by an "x") is an amino acid other than an aspartic acid, e.g., where amino acid 112 is Gly, Ala, Val, Leu, Ile, Pro, Phe, Tyr, Trp, Ser, Thr, Cys, Met, Asn, Gln, Lys, Arg, His, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 32 is other than an aspartic acid, e.g., where amino acid 32 is Gly, Ala, Val, Leu, Ile, Pro, Phe, Tyr, Trp, Ser, Thr, Cys, Met, Asn, Gln, Lys, Arg, His, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at D33. In some cases, a variant 4-1BBL polypeptide present in a multimeric polypeptide of the present disclosure comprises the amino acid sequence set forth in SEQ ID NO:214, with an amino acid substitution at D33. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at D33. In some cases, a variant 4-1BBL polypeptide present in a multimeric polypeptide of the present disclosure comprises the amino acid sequence set forth in SEQ ID NO:215, with an amino acid substitution at D33.

4-1BBL with P113 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36Y, where amino acid 113 (indicated by an "x") is an amino acid other than a proline, e.g., where amino acid 113 is Gly, Ala, Val, Leu, Ile, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 33 is other than a proline, e.g., where amino acid 33 is Gly, Ala, Val, Leu, Ile, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at P34. In some cases, a variant 4-1BBL polypeptide present in a multimeric polypeptide of the present disclosure comprises the amino acid sequence set forth in SEQ ID NO:214, with an amino acid substitution at P34. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at P34. In some cases, a variant 4-1BBL polypeptide present in a multimeric polypeptide of the present disclosure comprises the amino acid sequence set forth in SEQ ID NO:215, with an amino acid substitution at P34.

4-1BBL with G114 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36Z, where amino acid 114 (indicated by an "x") is an amino acid other than a glycine, e.g., where amino acid 114 is Ala, Val, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 34 is other than a glycine, e.g., where amino acid 34 is Ala, Val, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at G35. In some cases, a variant 4-1BBL polypeptide present in a multimeric polypeptide of the present disclosure comprises the amino acid sequence set forth in SEQ ID NO:214, with an amino acid substitution at G35. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at G35. In some cases, a variant 4-1BBL polypeptide present in a multimeric polypeptide of the present disclosure comprises the amino acid sequence set forth in SEQ ID NO:215, with an amino acid substitution at G35.

4-1BBL with L115 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36AA, where amino acid 115 (indicated by an "x") is an amino acid other than a leucine, e.g., where amino acid 115 is Gly, Ala, Val, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 35 is other than a leucine, e.g., where amino acid 35 is Gly, Ala, Val, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at L36. In some cases, a variant 4-1BBL polypeptide present in a multimeric polypeptide of the present disclosure comprises the amino acid sequence set forth in SEQ ID NO:214, with an amino acid substitution at L36. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at L36. In some cases, a variant 4-1BBL polypeptide present in a multimeric polypeptide of the present disclosure comprises the amino acid sequence set forth in SEQ ID NO:215, with an amino acid substitution at L36.

4-1BBL with G117 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36BB, where amino acid 117 (indicated by an "x") is an amino acid other than a glycine, e.g., where amino acid 117 is Ala, Val, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 37 is other than a glycine, e.g., where amino acid 37 is Ala, Val, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at G38. In some cases, a variant 4-1BBL polypeptide present in a multimeric polypeptide of the present disclosure comprises the amino acid sequence set forth in SEQ ID NO:214, with an amino acid substitution at G38. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at G38. In some cases, a variant 4-1BBL polypeptide present in a multimeric polypeptide of the present disclosure comprises the amino acid sequence set forth in SEQ ID NO:215, with an amino acid substitution at G38.

4-1BBL with V118 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36CC, where amino acid 118 (indicated by an "x") is an amino acid other than a valine, e.g., where amino acid 118 is Gly, Ala, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 38 is other than a valine, e.g., where amino acid 38 is Gly, Ala, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at V39. In some cases, a variant 4-1BBL polypeptide present in a multimeric polypeptide of the present disclosure comprises the amino acid sequence set forth in SEQ ID NO:214, with an amino acid substitution at V39. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at V39. In some cases, a variant 4-1BBL polypeptide present in a multimeric polypeptide of the present disclosure comprises the amino acid sequence set forth in SEQ ID NO:215, with an amino acid substitution at V39.

4-1BBL with S119 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36DD, where amino acid 119 (indicated by an "x") is an amino acid other than a serine, e.g., where amino acid 119 is Gly, Ala, Val, Leu, Ile, Pro, Phe, Tyr, Trp, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 39 is other than a serine, e.g., where amino acid 39 is Gly, Ala, Val, Leu, Ile, Pro, Phe, Tyr, Trp, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at S40. In some cases, a variant 4-1BBL polypeptide present in a multimeric polypeptide of the present disclosure comprises the amino acid sequence set forth in SEQ ID NO:214, with an amino acid substitution at S40. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at S40. In some cases, a variant 4-1BBL polypeptide present in a multimeric polypeptide of the present disclosure comprises the amino acid sequence set forth in SEQ ID NO:215, with an amino acid substitution at S40.

4-1BBL with L120 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36EE, where amino acid 120 (indicated by an "x") is an amino acid other than a leucine, e.g., where amino acid 120 is Gly, Ala, Val, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 40 is other than a leucine, e.g., where amino acid 40 is Gly, Ala, Val, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at L41. In some cases, a variant 4-1BBL polypeptide present in a multimeric polypeptide of the present disclosure comprises the amino acid sequence set forth in SEQ ID NO:214, with an amino acid substitution at L41. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at L41. In some cases, a variant 4-1BBL polypeptide present in a multimeric polypeptide of the present disclosure comprises the amino acid sequence set forth in SEQ ID NO:215, with an amino acid substitution at L41.

4-1BBL with T121 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36FF, where amino acid 121 (indicated by an "x") is an amino acid other than a threonine, e.g., where amino acid 121 is Gly, Ala, Val, Leu, Ile, Pro, Phe, Tyr, Trp, Ser, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 41 is other than a threonine, e.g., where amino acid 41 is Gly, Ala, Val, Leu, Ile, Pro, Phe, Tyr, Trp, Ser, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at T42. In some cases, a variant 4-1BBL polypeptide present in a multimeric polypeptide of the present disclosure comprises the amino acid sequence set forth in SEQ ID NO:214, with an amino acid substitution at T42. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at T42. In some cases, a variant 4-1BBL polypeptide present in a multimeric polypeptide of the present disclosure comprises the amino acid sequence set forth in SEQ ID NO:215, with an amino acid substitution at T42.

4-1BBL with G122 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36GG, where amino acid 122 (indicated by an "x") is an amino acid other than a glycine, e.g., where amino acid 122 is Ala, Val, Leu, Ile, Pro, Phe, Tyr, Trp, Ser, Thr, Cys, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 42 is other than a glycine, e.g., where amino acid 42 is Ala, Val, Leu, Ile, Pro, Phe, Tyr, Trp, Ser, Thr, Cys, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at G43. In some cases, a variant 4-1BBL polypeptide present in a multimeric polypeptide of the present disclosure comprises the amino acid sequence set forth in SEQ ID NO:214, with an amino acid substitution at G43. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at G43. In some cases, a variant 4-1BBL polypeptide present in a multimeric polypeptide of the present disclosure comprises the amino acid sequence set forth in SEQ ID NO:215, with an amino acid substitution at G43.

4-1BBL with G123 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36HH, where amino acid 123 (indicated by an "x") is an amino acid other than a glycine, e.g., where amino acid 123 is Ala, Val, Leu, Ile, Pro, Phe, Tyr, Trp, Ser, Thr, Cys, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 43 is other than a glycine, e.g., where amino acid 43 is Ala, Val, Leu, Ile, Pro, Phe, Tyr, Trp, Ser, Thr, Cys, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at G44. In some cases, a variant 4-1BBL polypeptide present in a multimeric polypeptide of the present disclosure comprises the amino acid sequence set forth in SEQ ID NO:214, with an amino acid substitution at G44. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at G44. In some cases, a variant 4-1BBL polypeptide present in a multimeric polypeptide of the present disclosure comprises the amino acid sequence set forth in SEQ ID NO:215, with an amino acid substitution at G44.

4-1BBL with L124 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36II, where amino acid 124 (indicated by an "x") is an amino acid other than a leucine, e.g., where amino acid 124 is Gly, Ala, Val, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 44 is other than a leucine, e.g., where amino acid 44 is Gly, Ala, Val, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at L45. In some cases, a variant 4-1BBL polypeptide present in a multimeric polypeptide of the present disclosure comprises the amino acid sequence set forth in SEQ ID NO:214, with an amino acid substitution at L45. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at L45. In some cases, a variant 4-1BBL polypeptide present in a multimeric polypeptide of the present disclosure comprises the amino acid sequence set forth in SEQ ID NO:215, with an amino acid substitution at L45.

4-1BBL with S125 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36JJ, where amino acid 125 (indicated by an "x") is an amino acid other than a serine, e.g., where amino acid 125 is Gly, Ala, Val, Leu, Ile, Pro, Phe, Tyr, Trp, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 45 is other than a serine, e.g., where amino acid 45 is Gly, Ala, Val, Leu, Ile, Pro, Phe, Tyr, Trp, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at S46. In some cases, a variant 4-1BBL polypeptide present in a multimeric polypeptide of the present disclosure comprises the amino acid sequence set forth in SEQ ID NO:214, with an amino acid substitution at S46. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at S46. In some cases, a variant 4-1BBL polypeptide present in a multimeric polypeptide of the present disclosure comprises the amino acid sequence set forth in SEQ ID NO:215, with an amino acid substitution at S46.

4-1BBL with Y126 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36KK, where amino acid 126 (indicated by an "x") is an amino acid other than a tyrosine, e.g., where amino acid 126 is Gly, Ala, Val, Leu, Ile, Pro, Phe, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 46 is other than a tyrosine, e.g., where amino acid 46 is Gly, Ala, Val, Leu, Ile, Pro, Phe, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at Y47. In some cases, a variant 4-1BBL polypeptide present in a multimeric polypeptide of the present disclosure comprises the amino acid sequence set forth in SEQ ID NO:214, with an amino acid substitution at Y47. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at Y47. In some cases, a variant 4-1BBL polypeptide present in a multimeric polypeptide of the present disclosure comprises the amino acid sequence set forth in SEQ ID NO:215, with an amino acid substitution at Y47.

4-1BBL with E128 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36LL, where amino acid 128 (indicated by an "x") is an amino acid other than a glutamic acid, e.g., where amino acid 128 is Gly, Ala, Val, Leu, Ile, Pro, Phe, Tyr, Trp, Ser, Thr, Cys, Met, Asn, Gln, Lys, Arg, His, or Asp. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 48 is other than a glutamic acid, e.g., where amino acid 48 is Gly, Ala, Val, Leu, Ile, Pro, Phe, Tyr, Trp, Ser, Thr, Cys, Met, Asn, Gln, Lys, Arg, His, or Asp.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at E49. In some cases, a variant 4-1BBL polypeptide present in a multimeric polypeptide of the present disclosure comprises the amino acid sequence set forth in SEQ ID NO:214, with an amino acid substitution at E49. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at E49. In some cases, a variant 4-1BBL polypeptide present in a multimeric polypeptide of the present disclosure comprises the amino acid sequence set forth in SEQ ID NO:215, with an amino acid substitution at E49.

4-1BBL with D129 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36MM, where amino acid 129 (indicated by an "x") is an amino acid other than an aspartic acid, e.g., where amino acid 129 is Gly, Ala, Val, Leu, Ile, Pro, Phe, Tyr, Trp, Ser, Thr, Cys, Met, Asn, Gln, Lys, Arg, His, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 49 is other than an aspartic acid, e.g., where amino acid 49 is Gly, Ala, Val, Leu, Ile, Pro, Phe, Tyr, Trp, Ser, Thr, Cys, Met, Asn, Gln, Lys, Arg, His, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at D50. In some cases, a variant 4-1BBL polypeptide present in a multimeric polypeptide of the present disclosure comprises the amino acid sequence set forth in SEQ ID NO:214, with an amino acid substitution at D50. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at D50. In some cases, a variant 4-1BBL polypeptide present in a multimeric polypeptide of the present disclosure comprises the amino acid sequence set forth in SEQ ID NO:215, with an amino acid substitution at D50.

4-1BBL with T130 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36NN, where amino acid 130 (indicated by an "x") is an amino acid other than a threonine, e.g., where amino acid 130 is Gly, Ala, Val, Leu, Ile, Pro, Phe, Tyr, Trp, Ser, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 50 is other than a threonine, e.g., where amino acid 50 is Gly, Ala, Val, Leu, Ile, Pro, Phe, Tyr, Trp, Ser, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at T51. In some cases, a variant 4-1BBL polypeptide present in a multimeric polypeptide of the present disclosure comprises the amino acid sequence set forth in SEQ ID NO:214, with an amino acid substitution at T51. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at T51. In some cases, a variant 4-1BBL polypeptide present in a multimeric polypeptide of the present disclosure comprises the amino acid sequence set forth in SEQ ID NO:215, with an amino acid substitution at T51.

4-1BBL with K131 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36OO, where amino acid 131 (indicated by an "x") is an amino acid other than a lysine, e.g., where amino acid 131 is Gly, Ala, Val, Leu, Ile, Pro, Phe, Tyr, Trp, Ser, Thr, Cys, Met, Asn, Gln, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 51 is other than a lysine, e.g., where amino acid 51 is Gly, Ala, Val, Leu, Ile, Pro, Phe, Tyr, Trp, Ser, Thr, Cys, Met, Asn, Gln, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at K52. In some cases, a variant 4-1BBL polypeptide present in a multimeric polypeptide of the present disclosure comprises the amino acid sequence set forth in SEQ ID NO:214, with an amino acid substitution at K52. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at K52. In some cases, a variant 4-1BBL polypeptide present in a multimeric polypeptide of the present disclosure comprises the amino acid sequence set forth in SEQ ID NO:215, with an amino acid substitution at K52.

4-1BBL with E132 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36PP, where amino acid 132 (indicated by an "x") is an amino acid other than a glutamic acid, e.g., where amino acid 132 is Gly, Ala, Val, Leu, Ile, Pro, Phe, Tyr, Trp, Ser, Thr, Cys, Met, Asn, Gln, Lys, Arg, His, or Asp. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 52 is other than a glutamic acid, e.g., where amino acid 52 is Gly, Ala, Val, Leu, Ile, Pro, Phe, Tyr, Trp, Ser, Thr, Cys, Met, Asn, Gln, Lys, Arg, His, or Asp.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at E53. In some cases, a variant 4-1BBL polypeptide present in a multimeric polypeptide of the present disclosure comprises the amino acid sequence set forth in SEQ ID NO:214, with an amino acid substitution at E53. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at E53. In some cases, a variant 4-1BBL polypeptide present in a multimeric polypeptide of the present disclosure comprises the amino acid sequence set forth in SEQ ID NO:215, with an amino acid substitution at E53.

4-1BBL with F144 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36QQ, where amino acid 144 (indicated by an "x") is an amino acid other than a phenylalanine, e.g., where amino acid 144 is Gly, Ala, Val, Leu, Ile, Pro, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 64 is other than a phenylalanine, e.g., where amino acid 64 is Gly, Ala, Val, Leu, Ile, Pro, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at F65. In some cases, a variant 4-1BBL polypeptide present in a multimeric polypeptide of the present disclosure comprises the amino acid sequence set forth in SEQ ID NO:214, with an amino acid substitution at F65. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at F65. In some cases, a variant 4-1BBL polypeptide present in a multimeric polypeptide of the present disclosure comprises the amino acid sequence set forth in SEQ ID NO:215, with an amino acid substitution at F65.

4-1BBL with F145 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36RR, where amino acid 145 (indicated by an "x") is an amino acid other than a phenylalanine, e.g., where amino acid 145 is Gly, Ala, Val, Leu, Ile, Pro, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 65 is other than a phenylalanine, e.g., where amino acid 65 is Gly, Ala, Val, Leu, Ile, Pro, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at F66. In some cases, a variant 4-1BBL polypeptide present in a multimeric polypeptide of the present disclosure comprises the amino acid sequence set forth in SEQ ID NO:214, with an amino acid substitution at F66. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at F66. In some cases, a variant 4-1BBL polypeptide present in a multimeric polypeptide of the present disclosure comprises the amino acid sequence set forth in SEQ ID NO:215, with an amino acid substitution at F66.

4-1BBL with Q146 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36SS, where amino acid 146 (indicated by an "x") is an amino acid other than a glutamine, e.g., where amino acid 146 is Gly, Ala, Val, Leu, Ile, Pro, Phe, Tyr, Trp, Ser, Thr, Cys, Met, Asn, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 66 is other than a glutamine, e.g., where amino acid 66 is Gly, Ala, Val, Leu, Ile, Pro, Phe, Tyr, Trp, Ser, Thr, Cys, Met, Asn, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at Q67. In some cases, a variant 4-1BBL polypeptide present in a multimeric polypeptide of the present disclosure comprises the amino acid sequence set forth in SEQ ID NO:214, with an amino acid substitution at Q67. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at Q67. In some cases, a variant 4-1BBL polypeptide present in a multimeric polypeptide of the present disclosure comprises the amino acid sequence set forth in SEQ ID NO:215, with an amino acid substitution at Q67.

4-1BBL with L147 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36TT, where amino acid 147 (indicated by an "x") is an amino acid other than a leucine, e.g., where amino acid 147 is Gly, Ala, Val, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 67 is other than a leucine, e.g., where amino acid 67 is Gly, Ala, Val, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at L68. In some cases, a variant 4-1BBL polypeptide present in a multimeric polypeptide of the present disclosure comprises the amino acid sequence set forth in SEQ ID NO:214, with an amino acid substitution at L68. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at L68. In some cases, a variant 4-1BBL polypeptide present in a multimeric polypeptide of the present disclosure comprises the amino acid sequence set forth in SEQ ID NO:215, with an amino acid substitution at L68.

4-1BBL with E148 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36UU, where amino acid 148 (indicated by an "x") is an amino acid other than a glutamic acid, e.g., where amino acid 148 is Gly, Ala, Val, Leu, Ile, Pro, Phe, Tyr, Trp, Ser, Thr, Cys, Met, Asn, Gln, Lys, Arg, His, or Asp. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 68 is other than a glutamic acid, e.g., where amino acid 68 is Gly, Ala, Val, Leu, Ile, Pro, Phe, Tyr, Trp, Ser, Thr, Cys, Met, Asn, Gln, Lys, Arg, His, or Asp.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at E69. In some cases, a variant 4-1BBL polypeptide present in a multimeric polypeptide of the present disclosure comprises the amino acid sequence set forth in SEQ ID NO:214, with an amino acid substitution at E69. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at E69. In some cases, a variant 4-1BBL polypeptide present in a multimeric polypeptide of the present disclosure comprises the amino acid sequence set forth in SEQ ID NO:215, with an amino acid substitution at E69.

4-1BBL with L149 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36VV, where amino acid 149 (indicated by an "x") is an amino acid other than a leucine, e.g., where amino acid 149 is Gly, Ala, Val, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 69 is other than a leucine, e.g., where amino acid 69 is Gly, Ala, Val, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at L70. In some cases, a variant 4-1BBL polypeptide present in a multimeric polypeptide of the present disclosure comprises the amino acid sequence set forth in SEQ ID NO:214, with an amino acid substitution at L70. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at L70. In some cases, a variant 4-1BBL polypeptide present in a multimeric polypeptide of the present disclosure comprises the amino acid sequence set forth in SEQ ID NO:215, with an amino acid substitution at L70.

4-1BBL with R150 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36WW, where amino acid 150 (indicated by an "x") is an amino acid other than an arginine, e.g., where amino acid 150 is Gly, Ala, Val, Leu, Ile, Pro, Phe, Tyr, Trp, Ser, Thr, Cys, Met, Asn, Gln, Lys, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 70 is other than an arginine, e.g., where amino acid 70 is Gly, Ala, Val, Leu, Ile, Pro, Phe, Tyr, Trp, Ser, Thr, Cys, Met, Asn, Gln, Lys, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at R71. In some cases, a variant 4-1BBL polypeptide present in a multimeric polypeptide of the present disclosure comprises the amino acid sequence set forth in SEQ ID NO:214, with an amino acid substitution at R71. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at R71. In some cases, a variant 4-1BBL polypeptide present in a multimeric polypeptide of the present disclosure comprises the amino acid sequence set forth in SEQ ID NO:215, with an amino acid substitution at R71.

4-1BBL with R1S1 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36XX, where amino acid 151 (indicated by an "x") is an amino acid other than an arginine, e.g., where amino acid 151 is Gly, Ala, Val, Leu, Ile, Pro, Phe, Tyr, Trp, Ser, Thr, Cys, Met, Asn, Gln, Lys, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 71 is other than an arginine, e.g., where amino acid 71 is Gly, Ala, Val, Leu, Ile, Pro, Phe, Tyr, Trp, Ser, Thr, Cys, Met, Asn, Gln, Lys, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at R72. In some cases, a variant 4-1BBL polypeptide present in a multimeric polypeptide of the present disclosure comprises the amino acid sequence set forth in SEQ ID NO:214, with an amino acid substitution at R72. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at R72. In some cases, a variant 4-1BBL polypeptide present in a multimeric polypeptide of the present disclosure comprises the amino acid sequence set forth in SEQ ID NO:215, with an amino acid substitution at R72.

4-1BBL with V152 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36YY, where amino acid 152 (indicated by an "x") is an amino acid other than a valine, e.g., where amino acid 152 is Gly, Ala, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 72 is other than a valine, e.g., where amino acid 72 is Gly, Ala, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at V73. In some cases, a variant 4-1BBL polypeptide present in a multimeric polypeptide of the present disclosure comprises the amino acid sequence set forth in SEQ ID NO:214, with an amino acid substitution at V73. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at V73. In some cases, a variant 4-1BBL polypeptide present in a multimeric polypeptide of the present disclosure comprises the amino acid sequence set forth in SEQ ID NO:215, with an amino acid substitution at V73.

4-1BBL with V153 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36ZZ, where amino acid 153 (indicated by an "x") is an amino acid other than a valine, e.g., where amino acid 153 is Gly, Ala, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 73 is other than a valine, e.g., where amino acid 73 is Gly, Ala, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at V74. In some cases, a variant 4-1BBL polypeptide present in a multimeric polypeptide of the present disclosure comprises the amino acid sequence set forth in SEQ ID NO:214, with an amino acid substitution at V74. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at V74. In some cases, a variant 4-1BBL polypeptide present in a multimeric polypeptide of the present disclosure comprises the amino acid sequence set forth in SEQ ID NO:215, with an amino acid substitution at V74.

4-1BBL with G155 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36AAA, where amino acid 155 (indicated by an "x") is an amino acid other than a glycine, e.g., where amino acid 155 is Ala, Val, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 75 is other than a glycine, e.g., where amino acid 75 is Ala, Val, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at G76. In some cases, a variant 4-1BBL polypeptide present in a multimeric polypeptide of the present disclosure comprises the amino acid sequence set forth in SEQ ID NO:214, with an amino acid substitution at G76. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at G76. In some cases, a variant 4-1BBL polypeptide present in a multimeric polypeptide of the present disclosure comprises the amino acid sequence set forth in SEQ ID NO:215, with an amino acid substitution at G76.

4-1BBL with E156 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36BBB, where amino acid 156 (indicated by an "x") is an amino acid other than a glutamic acid, e.g., where amino acid 156 is Gly, Ala, Val, Leu, Ile, Pro, Phe, Tyr, Trp, Ser, Thr, Cys, Met, Asn, Gln, Lys, Arg, His, or Asp. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 76 is other than a glutamic acid, e.g., where amino acid 76 is Gly, Ala, Val, Leu, Ile, Pro, Phe, Tyr, Trp, Ser, Thr, Cys, Met, Asn, Gln, Lys, Arg, His, or Asp.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at E77. In some cases, a variant 4-1BBL polypeptide present in a multimeric polypeptide of the present disclosure comprises the amino acid sequence set forth in SEQ ID NO:214, with an amino acid substitution at E77. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at E77. In some cases, a variant 4-1BBL polypeptide present in a multimeric polypeptide of the present disclosure comprises the amino acid sequence set forth in SEQ ID NO:215, with an amino acid substitution at E77.

4-1BBL with G157 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36CCC, where amino acid 157 (indicated by an "x") is an amino acid other than a glycine, e.g., where amino acid 157 is Ala, Val, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 77 is other than a glycine, e.g., where amino acid 77 is Ala, Val, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at G78. In some cases, a variant 4-1BBL polypeptide present in a multimeric polypeptide of the present disclosure comprises the amino acid sequence set forth in SEQ ID NO:214, with an amino acid substitution at G78. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at G78. In some cases, a variant 4-1BBL polypeptide present in a multimeric polypeptide of the present disclosure comprises the amino acid sequence set forth in SEQ ID NO:215, with an amino acid substitution at G78.

4-1BBL with S158 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36DDD, where amino acid 158 (indicated by an "x") is an amino acid other than a serine, e.g., where amino acid 158 is Gly, Ala, Val, Leu, Ile, Pro, Phe, Tyr, Trp, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 78 is other than a serine, e.g., where amino acid 78 is Gly, Ala, Val, Leu, Ile, Pro, Phe, Tyr, Trp, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at S79. In some cases, a variant 4-1BBL polypeptide present in a multimeric polypeptide of the present disclosure comprises the amino acid sequence set forth in SEQ ID NO:214, with an amino acid substitution at S79. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at S79. In some cases, a variant 4-1BBL polypeptide present in a multimeric polypeptide of the present disclosure comprises the amino acid sequence set forth in SEQ ID NO:215, with an amino acid substitution at S79.

4-1BBL with D184 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36EEE, where amino acid 184 (indicated by an "x") is an amino acid other than an aspartic acid, e.g., where amino acid 184 is Gly, Ala, Val, Leu, Ile, Pro, Phe, Tyr, Trp, Ser, Thr, Cys, Met, Asn, Gln, Lys, Arg, His, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 104 is other than an aspartic acid, e.g., where amino acid 104 is Gly, Ala, Val, Leu, Ile, Pro, Phe, Tyr, Trp, Ser, Thr, Cys, Met, Asn, Gln, Lys, Arg, His, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at D105. In some cases, a variant 4-1BBL polypeptide present in a multimeric polypeptide of the present disclosure comprises the amino acid sequence set forth in SEQ ID NO:214, with an amino acid substitution at D105. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at D105. In some cases, a variant 4-1BBL polypeptide present in a multimeric polypeptide of the present disclosure comprises the amino acid sequence set forth in SEQ ID NO:215, with an amino acid substitution at D105.

4-1BBL with L185 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36FFF, where amino acid 185 (indicated by an "x") is an amino acid other than a leucine, e.g., where amino acid 185 is Gly, Ala, Val, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 105 is other than a leucine, e.g., where amino acid 105 is Gly, Ala, Val, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at L106. In some cases, a variant 4-1BBL polypeptide present in a multimeric polypeptide of the present disclosure comprises the amino acid sequence set forth in SEQ ID NO:214, with an amino acid substitution at L106. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at L106. In some cases, a variant 4-1BBL polypeptide present in a multimeric polypeptide of the present disclosure comprises the amino acid sequence set forth in SEQ ID NO:215, with an amino acid substitution at L106.

4-1BBL with P186 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36GGG, where amino acid 186 (indicated by an "x") is an amino acid other than a proline, e.g., where amino acid 186 is Gly, Ala, Val, Leu, Ile, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 106 is other than a proline, e.g., where amino acid 106 is Gly, Ala, Val, Leu, Ile, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at P107. In some cases, a variant 4-1BBL polypeptide present in a multimeric polypeptide of the present disclosure comprises the amino acid sequence set forth in SEQ ID NO:214, with an amino acid substitution at P107. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at P107. In some cases, a variant 4-1BBL polypeptide present in a multimeric polypeptide of the present disclosure comprises the amino acid sequence set forth in SEQ ID NO:215, with an amino acid substitution at P107.

4-1BBL with P187 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36HHH, where amino acid 187 (indicated by an "x") is an amino acid other than a proline, e.g., where amino acid 187 is Gly, Ala, Val, Leu, Ile, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 107 is other than a proline, e.g., where amino acid 107 is Gly, Ala, Val, Leu, Ile, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at P108. In some cases, a variant 4-1BBL polypeptide present in a multimeric polypeptide of the present disclosure comprises the amino acid sequence set forth in SEQ ID NO:214, with an amino acid substitution at P108. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at P108. In some cases, a variant 4-1BBL polypeptide present in a multimeric polypeptide of the present disclosure comprises the amino acid sequence set forth in SEQ ID NO:215, with an amino acid substitution at P108.

4-1BBL with S189 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36III, where amino acid 189 (indicated by an "x") is an amino acid other than a serine, e.g., where amino acid 189 is Gly, Ala, Val, Leu, Ile, Pro, Phe, Tyr, Trp, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 109 is other than a serine, e.g., where amino acid 109 is Gly, Ala, Val, Leu, Ile, Pro, Phe, Tyr, Trp, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at S110. In some cases, a variant 4-1BBL polypeptide present in a multimeric polypeptide of the present disclosure comprises the amino acid sequence set forth in SEQ ID NO:214, with an amino acid substitution at S110. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at S110. In some cases, a variant 4-1BBL polypeptide present in a multimeric polypeptide of the present disclosure comprises the amino acid sequence set forth in SEQ ID NO:215, with an amino acid substitution at S110.

4-1BBL with S190 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36JJJ, where amino acid 190 (indicated by an "x") is an amino acid other than a serine, e.g., where amino acid 190 is Gly, Ala, Val, Leu, Ile, Pro, Phe, Tyr, Trp, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 110 is other than a serine, e.g., where amino acid 110 is Gly, Ala, Val, Leu, Ile, Pro, Phe, Tyr, Trp, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at S111. In some cases, a variant 4-1BBL polypeptide present in a multimeric polypeptide of the present disclosure comprises the amino acid sequence set forth in SEQ ID NO:214, with an amino acid substitution at S111. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at S111. In some cases, a variant 4-1BBL polypeptide present in a multimeric polypeptide of the present disclosure comprises the amino acid sequence set forth in SEQ ID NO:215, with an amino acid substitution at S111.

4-1BBL with E191 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36KKK, where amino acid 191 (indicated by an "x") is an amino acid other than a glutamic acid, e.g., where amino acid 191 is Gly, Ala, Val, Leu, Ile, Pro, Phe, Tyr, Trp, Ser, Thr, Cys, Met, Asn, Gln, Lys, Arg, His, or Asp. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 111 is other than a glutamic acid, e.g., where amino acid 111 is Gly, Ala, Val, Leu, Ile, Pro, Phe, Tyr, Trp, Ser, Thr, Cys, Met, Asn, Gln, Lys, Arg, His, or Asp.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214, with an amino acid substitution at E112. In some cases, a variant 4-1BBL polypeptide present in a multimeric polypeptide of the present disclosure comprises the amino acid sequence set forth in SEQ ID NO:214, with an amino acid substitution at E112. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at E112. In some cases, a variant 4-1BBL polypeptide present in a multimeric polypeptide of the present disclosure comprises the amino acid sequence set forth in SEQ ID NO:215, with an amino acid substitution at E112.

4-1BBL with R193 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36LLL, where amino acid 193 (indicated by an "x") is an amino acid other than an arginine, e.g., where amino acid 193 is Gly, Ala, Val, Leu, Ile, Pro, Phe, Tyr, Trp, Ser, Thr, Cys, Met, Asn, Gln, Lys, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 113 is other than arginine, e.g., where amino acid 113 is Gly, Ala, Val, Leu, Ile, Pro, Phe, Tyr, Trp, Ser, Thr, Cys, Met, Asn, Gln, Lys, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at R114. In some cases, a variant 4-1BBL polypeptide present in a multimeric polypeptide of the present disclosure comprises the amino acid sequence set forth in SEQ ID NO:214 with an amino acid substitution at R114. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at R114. In some cases, a variant 4-1BBL polypeptide present in a multimeric polypeptide of the present disclosure comprises the amino acid sequence set forth in SEQ ID NO:215, with an amino acid substitution at R114.

4-1BBL with N194 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36MMM, where amino acid 194 (indicated by an "x") is an amino acid other than a asparagine, e.g., where amino acid 194 is Gly, Ala, Val, Leu, Ile, Pro, Phe, Tyr, Trp, Ser, Thr, Cys, Met, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 114 is other than a asparagine, e.g., where amino acid 114 is Gly, Ala, Val, Leu, Ile, Pro, Phe, Tyr, Trp, Ser, Thr, Cys, Met, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at N115. In some cases, a variant 4-1BBL polypeptide present in a multimeric polypeptide of the present disclosure comprises the amino acid sequence set forth in SEQ ID NO:214 with an amino acid substitution at N115. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at N115. In some cases, a variant 4-1BBL polypeptide present in a multimeric polypeptide of the present disclosure comprises the amino acid sequence set forth in SEQ ID NO:215, with an amino acid substitution at N115.

4-1BBL with S195 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36NNN, where amino acid 195 (indicated by an "x") is an amino acid other than a serine, e.g., where amino acid 195 is Gly, Ala, Val, Leu, Ile, Pro, Phe, Tyr, Trp, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 115 is other than a serine, e.g., where amino acid 115 is Gly, Ala, Val, Leu, Ile, Pro, Phe, Tyr, Trp, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at S116. In some cases, a variant 4-1BBL polypeptide present in a multimeric polypeptide of the present disclosure comprises the amino acid sequence set forth in SEQ ID NO:214 with an amino acid substitution at S116. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at S116. In some cases, a variant 4-1BBL polypeptide present in a multimeric polypeptide of the present disclosure comprises the amino acid sequence set forth in SEQ ID NO:215, with an amino acid substitution at S116.

4-1BBL with F197 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36OOO, where amino acid 197 (indicated by an "x") is an amino acid other than a phenylalanine, e.g., where amino acid 197 is Gly, Ala, Val, Leu, Ile, Pro, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 117 is other than a phenylalanine, e.g., where amino acid 117 is Gly, Ala, Val, Leu, Ile, Pro, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at F118. In some cases, a variant 4-1BBL polypeptide present in a multimeric polypeptide of the present disclosure comprises the amino acid sequence set forth in SEQ ID NO:214 with an amino acid substitution at F118. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at F118. In some cases, a variant 4-1BBL polypeptide present in a multimeric polypeptide of the present disclosure comprises the amino acid sequence set forth in SEQ ID NO:215, with an amino acid substitution at F118.

4-1BBL with Q210 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36PPP, where amino acid 210 (indicated by an "x") is an amino acid other than a glutamine, e.g., where amino acid 210 is Gly, Ala, Val, Leu, Ile, Pro, Phe, Tyr, Trp, Ser, Thr, Cys, Met, Asn, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 130 is other than a glutamine, e.g., where amino acid 130 is Gly, Ala, Val, Leu, Ile, Pro, Phe, Tyr, Trp, Ser, Thr, Cys, Met, Asn, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at Q131. In some cases, a variant 4-1BBL polypeptide present in a multimeric polypeptide of the present disclosure comprises the amino acid sequence set forth in SEQ ID NO:214 with an amino acid substitution at Q131. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at Q131. In some cases, a variant 4-1BBL polypeptide present in a multimeric polypeptide of the present disclosure comprises the amino acid sequence set forth in SEQ ID NO:215, with an amino acid substitution at Q131.

4-1BBL with R211 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36QQQ, where amino acid 211 (indicated by an "x") is an amino acid other than an arginine, e.g., where amino acid 211 is Gly, Ala, Val, Leu, Ile, Pro, Phe, Tyr, Trp, Ser, Thr, Cys, Met, Asn, Gln, Lys, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 131 is other than an arginine, e.g., where amino acid 131 is Gly, Ala, Val, Leu, Ile, Pro, Phe, Tyr, Trp, Ser, Thr, Cys, Met, Asn, Gln, Lys, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at R132. In some cases, a variant 4-1BBL polypeptide present in a multimeric polypeptide of the present disclosure comprises the amino acid sequence set forth in SEQ ID NO:214 with an amino acid substitution at R132. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at R132. In some cases, a variant 4-1BBL polypeptide present in a multimeric polypeptide of the present disclosure comprises the amino acid sequence set forth in SEQ ID NO:215, with an amino acid substitution at R132.

4-1BBL with L212 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36RRR, where amino acid 212 (indicated by an "x") is an amino acid other than a leucine, e.g., where amino acid 212 is Gly, Ala, Val, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 132 is other than a leucine, e.g., where amino acid 132 is Gly, Ala, Val, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at L133. In some cases, a variant 4-1BBL polypeptide present in a multimeric polypeptide of the present disclosure comprises the amino acid sequence set forth in SEQ ID NO:214 with an amino acid substitution at L133. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at L133. In some cases, a variant 4-1BBL polypeptide present in a multimeric polypeptide of the present disclosure comprises the amino acid sequence set forth in SEQ ID NO:215, with an amino acid substitution at L133.

4-1BBL with G213 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36SSS, where amino acid 213 (indicated by an "x") is an amino acid other than a glycine, e.g., where amino acid 213 is Ala, Val, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 133 is other than a glycine, e.g., where amino acid 133 is Ala, Val, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at G134. In some cases, a variant 4-1BBL polypeptide present in a multimeric polypeptide of the present disclosure comprises the amino acid sequence set forth in SEQ ID NO:214 with an amino acid substitution at G134. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at G134. In some cases, a variant 4-1BBL polypeptide present in a multimeric polypeptide of the present disclosure comprises the amino acid sequence set forth in SEQ ID NO:215, with an amino acid substitution at G134.

4-1BBL with V214 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36TTT, where amino acid 214 (indicated by an "x") is an amino acid other than a valine, e.g., where amino acid 214 is Gly, Ala, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 134 is other than a valine, e.g., where amino acid 134 is Gly, Ala, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at V135. In some cases, a variant 4-1BBL polypeptide present in a multimeric polypeptide of the present disclosure comprises the amino acid sequence set forth in SEQ ID NO:214 with an amino acid substitution at V135. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at V135. In some cases, a variant 4-1BBL polypeptide present in a multimeric polypeptide of the present disclosure comprises the amino acid sequence set forth in SEQ ID NO:215, with an amino acid substitution at V135.

4-1BBL with H215 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36UUU, where amino acid 215 (indicated by an "x") is an amino acid other than a histidine, e.g., where amino acid 215 is Gly, Ala, Val, Leu, Ile, Pro, Phe, Tyr, Trp, Ser, Thr, Cys, Met, Asn, Gln, Lys, Arg, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 135 is other than a histidine, e.g., where amino acid 135 is Gly, Ala, Val, Leu, Ile, Pro, Phe, Tyr, Trp, Ser, Thr, Cys, Met, Asn, Gln, Lys, Arg, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at H136. In some cases, a variant 4-1BBL polypeptide present in a multimeric polypeptide of the present disclosure comprises the amino acid sequence set forth in SEQ ID NO:214 with an amino acid substitution at H136. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at H136. In some cases, a variant 4-1BBL polypeptide present in a multimeric polypeptide of the present disclosure comprises the amino acid sequence set forth in SEQ ID NO:215, with an amino acid substitution at H136.

4-1BBL with L216 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36VVV, where amino acid 216 (indicated by an "x") is an amino acid other than a leucine, e.g., where amino acid 216 is Gly, Ala, Val, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 136 is other than a leucine, e.g., where amino acid 136 is Gly, Ala, Val, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at L137. In some cases, a variant 4-1BBL polypeptide present in a multimeric polypeptide of the present disclosure comprises the amino acid sequence set forth in SEQ ID NO:214 with an amino acid substitution at L137. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at L137. In some cases, a variant 4-1BBL polypeptide present in a multimeric polypeptide of the present disclosure comprises the amino acid sequence set forth in SEQ ID NO:215, with an amino acid substitution at L137.

4-1BBL with H217 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36WWW, where amino acid 217 (indicated by an "x") is an amino acid other than a histidine, e.g., where amino acid 217 is Gly, Ala, Val, Leu, Ile, Pro, Phe, Tyr, Trp, Ser, Thr, Cys, Met, Asn, Gln, Lys, Arg, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 137 is other than a histidine, e.g., where amino acid 137 is Gly, Ala, Val, Leu, Ile, Pro, Phe, Tyr, Trp, Ser, Thr, Cys, Met, Asn, Gln, Lys, Arg, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at H138. In some cases, a variant 4-1BBL polypeptide present in a multimeric polypeptide of the present disclosure comprises the amino acid sequence set forth in SEQ ID NO:214 with an amino acid substitution at H138. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at H138. In some cases, a variant 4-1BBL polypeptide present in a multimeric polypeptide of the present disclosure comprises the amino acid sequence set forth in SEQ ID NO:215, with an amino acid substitution at H138.

4-1BBL with T218 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36XXX, where amino acid 218 (indicated by an "x") is an amino acid other than a threonine, e.g., where amino acid 218 is Gly, Ala, Val, Leu, Ile, Pro, Phe, Tyr, Trp, Ser, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 138 is other than a threonine, e.g., where amino acid 138 is Gly, Ala, Val, Leu, Ile, Pro, Phe, Tyr, Trp, Ser, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at T139. In some cases, a variant 4-1BBL polypeptide present in a multimeric polypeptide of the present disclosure comprises the amino acid sequence set forth in SEQ ID NO:214 with an amino acid substitution at T139. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at T139. In some cases, a variant 4-1BBL polypeptide present in a multimeric polypeptide of the present disclosure comprises the amino acid sequence set forth in SEQ ID NO:215, with an amino acid substitution at T139.

4-1BBL with E219 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36YYY, where amino acid 219 (indicated by an "x") is an amino acid other than a glutamic acid, e.g., where amino acid 219 is Gly, Ala, Val, Leu, Ile, Pro, Phe, Tyr, Trp, Ser, Thr, Cys, Met, Asn, Gln, Lys, Arg, His, or Asp. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 139 is other than a glutamic acid, e.g., where amino acid 139 is Gly, Ala, Val, Leu, Ile, Pro, Phe, Tyr, Trp, Ser, Thr, Cys, Met, Asn, Gln, Lys, Arg, His, or Asp.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at E140. In some cases, a variant 4-1BBL polypeptide present in a multimeric polypeptide of the present disclosure comprises the amino acid sequence set forth in SEQ ID NO:214 with an amino acid substitution at E140. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at E140. In some cases, a variant 4-1BBL polypeptide present in a multimeric polypeptide of the present disclosure comprises the amino acid sequence set forth in SEQ ID NO:215, with an amino acid substitution at E140.

4-1BBL with R221 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36ZZZ, where amino acid 221 (indicated by an "x") is an amino acid other than an arginine, e.g., where amino acid 221 is Gly, Ala, Val, Leu, Ile, Pro, Phe, Tyr, Trp, Ser, Thr, Cys, Met, Asn, Gln, Lys, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 141 is other than an arginine, e.g., where amino acid 141 is Gly, Ala, Val, Leu, Ile, Pro, Phe, Tyr, Trp, Ser, Thr, Cys, Met, Asn, Gln, Lys, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at R142. In some cases, a variant 4-1BBL polypeptide present in a multimeric polypeptide of the present disclosure comprises the amino acid sequence set forth in SEQ ID NO:214 with an amino acid substitution at R142. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at R142. In some cases, a variant 4-1BBL polypeptide present in a multimeric polypeptide of the present disclosure comprises the amino acid sequence set forth in SEQ ID NO:215, with an amino acid substitution at R142.

4-1BBL with R223 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36AAAA, where amino acid 223 (indicated by an "x") is an amino acid other than an arginine, e.g., where amino acid 223 is Gly, Ala, Val, Leu, Ile, Pro, Phe, Tyr, Trp, Ser, Thr, Cys, Met, Asn, Gln, Lys, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 143 is other than an arginine, e.g., where amino acid 143 is Gly, Ala, Val, Leu, Ile, Pro, Phe, Tyr, Trp, Ser, Thr, Cys, Met, Asn, Gln, Lys, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at R144. In some cases, a variant 4-1BBL polypeptide present in a multimeric polypeptide of the present disclosure comprises the amino acid sequence set forth in SEQ ID NO:214 with an amino acid substitution at R144. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at R144. In some cases, a variant 4-1BBL polypeptide present in a multimeric polypeptide of the present disclosure comprises the amino acid sequence set forth in SEQ ID NO:215, with an amino acid substitution at R144.

4-1BBL with H224 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36BBBB, where amino acid 224 (indicated by an "x") is an amino acid other than a histidine, e.g., where amino acid 224 is Gly, Ala, Val, Leu, Ile, Pro, Phe, Tyr, Trp, Ser, Thr, Cys, Met, Asn, Gln, Lys, Arg, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 144 is other than a histidine, e.g., where amino acid 144 is Gly, Ala, Val, Leu, Ile, Pro, Phe, Tyr, Trp, Ser, Thr, Cys, Met, Asn, Gln, Lys, Arg, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at H145. In some cases, a variant 4-1BBL polypeptide present in a multimeric polypeptide of the present disclosure comprises the amino acid sequence set forth in SEQ ID NO:214 with an amino acid substitution at H145. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at H145. In some cases, a variant 4-1BBL polypeptide present in a multimeric polypeptide of the present disclosure comprises the amino acid sequence set forth in SEQ ID NO:215, with an amino acid substitution at H145.

4-1BBL with W226 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36CCCC, where amino acid 226 (indicated by an "x") is an amino acid other than a tryptophan, e.g., where amino acid 226 is Gly, Ala, Val, Leu, Ile, Pro, Phe, Tyr, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 146 is other than a tryptophan, e.g., where amino acid 146 is Gly, Ala, Val, Leu, Ile, Pro, Phe, Tyr, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at W147. In some cases, a variant 4-1BBL polypeptide present in a multimeric polypeptide of the present disclosure comprises the amino acid sequence set forth in SEQ ID NO:214 with an amino acid substitution at W147. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at W147. In some cases, a variant 4-1BBL polypeptide present in a multimeric polypeptide of the present disclosure comprises the amino acid sequence set forth in SEQ ID NO:215, with an amino acid substitution at W147.

4-1BBL with L228 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36DDDD, where amino acid 228 (indicated by an "x") is an amino acid other than a leucine, e.g., where amino acid 228 is Gly, Ala, Val, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 148 is other than a leucine, e.g., where amino acid 148 is Gly, Ala, Val, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at L149. In some cases, a variant 4-1BBL polypeptide present in a multimeric polypeptide of the present disclosure comprises the amino acid sequence set forth in SEQ ID NO:214 with an amino acid substitution at L149. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at L149. In some cases, a variant 4-1BBL polypeptide present in a multimeric polypeptide of the present disclosure comprises the amino acid sequence set forth in SEQ ID NO:215, with an amino acid substitution at L149.

4-1BBL with T229 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36EEEE, where amino acid 229 (indicated by an "x") is an amino acid other than a threonine, e.g., where amino acid 229 is Gly, Ala, Val, Leu, Ile, Pro, Phe, Tyr, Trp, Ser, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 149 is other than a threonine, e.g., where amino acid 149 is Gly, Ala, Val, Leu, Ile, Pro, Phe, Tyr, Trp, Ser, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at T150. In some cases, a variant 4-1BBL polypeptide present in a multimeric polypeptide of the present disclosure comprises the amino acid sequence set forth in SEQ ID NO:214 with an amino acid substitution at T150. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at T150. In some cases, a variant 4-1BBL polypeptide present in a multimeric polypeptide of the present disclosure comprises the amino acid sequence set forth in SEQ ID NO:215, with an amino acid substitution at T150.

4-1BBL with Q230 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36FFFF, where amino acid 230 (indicated by an "x") is an amino acid other than a glutamine, e.g., where amino acid 230 is Gly, Ala, Val, Leu, Ile, Pro, Phe, Tyr, Trp, Ser, Thr, Cys, Met, Asn, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 150 is other than a glutamine, e.g., where amino acid 150 is Gly, Ala, Val, Leu, Ile, Pro, Phe, Tyr, Trp, Ser, Thr, Cys, Met, Asn, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at Q151. In some cases, a variant 4-1BBL polypeptide present in a multimeric polypeptide of the present disclosure comprises the amino acid sequence set forth in SEQ ID NO:214 with an amino acid substitution at Q151. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at Q151. In some cases, a variant 4-1BBL polypeptide present in a multimeric polypeptide of the present disclosure comprises the amino acid sequence set forth in SEQ ID NO:215, with an amino acid substitution at Q151.

4-1BBL with G231 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36GGGG, where amino acid 231 (indicated by an "x") is an amino acid other than a glycine, e.g., where amino acid 231 is Ala, Val, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 151 is other than a glycine, e.g., where amino acid 151 is Ala, Val, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at G152. In some cases, a variant 4-1BBL polypeptide present in a multimeric polypeptide of the present disclosure comprises the amino acid sequence set forth in SEQ ID NO:214 with an amino acid substitution at G152. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at G152. In some cases, a variant 4-1BBL polypeptide present in a multimeric polypeptide of the present disclosure comprises the amino acid sequence set forth in SEQ ID NO:215, with an amino acid substitution at G152.

4-1BBL with T233 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36HHHH, where amino acid 233 (indicated by an "x") is an amino acid other than a threonine, e.g., where amino acid 233 is Gly, Ala, Val, Leu, Ile, Pro, Phe, Tyr, Trp, Ser, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 153 is other than a threonine, e.g., where amino acid 153 is Gly, Ala, Val, Leu, Ile, Pro, Phe, Tyr, Trp, Ser, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at T154. In some cases, a variant 4-1BBL polypeptide present in a multimeric polypeptide of the present disclosure comprises the amino acid sequence set forth in SEQ ID NO:214 with an amino acid substitution at T154. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at T154. In some cases, a variant 4-1BBL polypeptide present in a multimeric polypeptide of the present disclosure comprises the amino acid sequence set forth in SEQ ID NO:215, with an amino acid substitution at T154.

4-1BBL with V234 Substitution

In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence depicted in FIG. 36IIII, where amino acid 234 (indicated by an "x") is an amino acid other than a valine, e.g., where amino acid 234 is Gly, Ala, Leu, Ile, Pro, Phe, Tyr, Trp, Ser, Thr, Cys, Met, Asn, Gln, Lys, Arg, His, Asp, or Glu. In some cases, the variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:213, where amino acid 154 is other than a valine, e.g., where amino acid 154 is Gly, Ala, Leu, Ile, Pro, Phe, Tyr, Trp, Ser, Thr, Cys, Met, Asn, Gln, Lys, Arg, His, Asp, or Glu.

In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:214 with an amino acid substitution at V155. In some cases, a variant 4-1BBL polypeptide present in a multimeric polypeptide of the present disclosure comprises the amino acid sequence set forth in SEQ ID NO:214 with an amino acid substitution at V155. In some cases, a variant 4-1BBL polypeptide present in a multimeric polypeptide of the present disclosure comprises an amino acid sequence having at least 90%, at least 95%, at least 98%, or at least 99%, amino acid sequence identity to the amino acid sequence set forth in SEQ ID NO:215, with an amino acid substitution at V155. In some cases, a variant 4-1BBL polypeptide present in a multimeric polypeptide of the present disclosure comprises the amino acid sequence set forth in SEQ ID NO:215, with an amino acid substitution at V155.

Exemplary Multimeric Polypeptides Comprising 4-1BBL Immunomodulatory Polypeptide Exemplary multimeric polypeptides that are suitable for use in a method of the present disclosure are described below.

K127

In some cases, a multimeric polypeptide of the present disclosure comprises: a) a first polypeptide comprising, in order from N-terminus to C-terminus: i) an epitope; ii) a β2M polypeptide; and iii) a variant 4-1BBL polypeptide comprising an amino acid sequence having at least 90%, at least 95%, at least 98%, or at least 99%, amino acid sequence identity to the amino acid sequence depicted in FIG. 36B, where amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; or a variant 4-1BBL polypeptide of the present disclosure comprising an amino acid sequence having at least 90%, at least 95%, at least 98%, or at least 99%, amino acid sequence identity to the amino acid sequence set forth in SEQ ID NO:213, with an amino acid substitution at K47, e.g., where amino acid 47 is Gly, Ala, Val, Leu, Ile, Pro, Phe, Tyr, Trp, Ser, Thr, Cys, Met, Asn, Gln, Arg, His, Asp, or Glu; and b) a second polypeptide comprising, in order from N-terminus to C-terminus: i) a Class I MHC heavy chain; and ii) an Fc polypeptide. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a variant 4-1BBL polypeptide comprising an amino acid sequence having at least 90%, at least 95%, at least 98%, or at least 99%, amino acid sequence identity to the amino acid sequence depicted in FIG. 36B, where amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; or a variant 4-1BBL polypeptide of the present disclosure comprising an amino acid sequence having at least 90%, at least 95%, at least 98%, or at least 99%, amino acid sequence identity to the amino acid sequence set forth in SEQ ID NO:213, with an amino acid substitution at K47, e.g., where amino acid 47 is Gly, Ala, Val, Leu, Ile, Pro, Phe, Tyr, Trp, Ser, Thr, Cys, Met, Asn, Gln, Arg, His, Asp, or Glu; ii) a Class I MHC heavy chain; and iii) an Fc polypeptide. In some cases, a multimeric polypeptide of the present disclosure comprises: a) a first polypeptide comprising, in order from N-terminus to C-terminus: i) an epitope; ii) a β2M polypeptide; iii) a first variant 4-1BBL polypeptide of the present disclosure; iv) a second variant 4-1BBL polypeptide of the present disclosure; and v) a third variant 4-1BBL polypeptide of the present disclosure; and b) a second polypeptide comprising, in order from N-terminus to C-terminus: i) a Class I MHC heavy chain; and ii) an Fc polypeptide. In some cases, each of the first, second, and third variant 4-1BBL polypeptides comprises an amino acid sequence having at least 90%, at least 95%, at least 98%, or at least 99%, amino acid sequence identity to the amino acid sequence depicted in FIG. 36B, where amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; e.g., each of the first, second, and third variant 4-1BBL polypeptides comprises an amino acid sequence having at least 90%, at least 95%, at least 98%, or at least 99%, amino acid sequence identity to the amino acid sequence set forth in SEQ ID NO:213, with an amino acid substitution at K47, e.g., where amino acid 47 is Gly, Ala, Val, Leu, Ile, Pro, Phe, Tyr, Trp, Ser, Thr, Cys, Met, Asn, Gln, Arg, His, Asp, or Glu. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a first variant 4-1BBL polypeptide of the present disclosure; ii) a second variant 4-1BBL polypeptide of the present disclosure; and iii) a third variant 4-1BBL polypeptide of the present disclosure; iv) a Class I MHC heavy chain; and v) an Fc polypeptide. In some cases, each of the first, second, and third variant 4-1BBL polypeptides comprises an amino acid sequence having at least 90%, at least 95%, at least 98%, or at least 99%, amino acid sequence identity to the amino acid sequence depicted in FIG. 36B, where amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; e.g., each of the first, second, and third variant 4-1BBL polypeptides comprises an amino acid sequence having at least 90%, at least 95%, at least 98%, or at least 99%, amino acid sequence identity to the amino acid sequence set forth in SEQ ID NO:213, with an amino acid substitution at K47, e.g., where amino acid 47 is Gly, Ala, Val, Leu, Ile, Pro, Phe, Tyr, Trp, Ser, Thr, Cys, Met, Asn, Gln, Arg, His, Asp, or Glu. In some cases, the variant 4-1BBL polypeptide comprises a K127 substitution and an M91 substitution (based on the numbering depicted in FIG. 36A). In some cases, the variant 4-1BBL polypeptide comprises a K127 substitution and an F92 substitution (based on the numbering depicted in FIG. 36A). In some cases, the variant 4-1BBL polypeptide comprises a K127 substitution and a Q94 substitution (based on the numbering depicted in FIG. 36A). In some cases, the variant 4-1BBL polypeptide comprises a K127 substitution and an L95 substitution (based on the numbering depicted in FIG. 36A). In some cases, the variant 4-1BBL polypeptide comprises a K127 substitution and a V96 substitution (based on the numbering depicted in FIG. 36A). In some cases, the variant 4-1BBL polypeptide comprises a K127 substitution and a Q98 substitution (based on the numbering depicted in FIG. 36A). In some cases, the variant 4-1BBL polypeptide comprises a K127 substitution and an N99 substitution (based on the numbering depicted in FIG. 36A). In some cases, the variant 4-1BBL polypeptide comprises a K127 substitution and a V100 substitution (based on the numbering depicted in FIG. 36A). In some cases, the variant 4-1BBL polypeptide comprises a K127 substitution and an L101 substitution (based on the numbering depicted in FIG. 36A). In some cases, the variant 4-1BBL polypeptide comprises a K127 substitution and an L102 substitution (based on the numbering depicted in FIG. 36A). In some cases, the variant 4-1BBL polypeptide comprises a K127 substitution and an 1103 substitution (based on the numbering depicted in FIG. 36A). In some cases, the variant 4-1BBL polypeptide comprises a K127 substitution and a D104 substitution (based on the numbering depicted in FIG. 36A). In some cases, the variant 4-1BBL polypeptide comprises a K127 substitution and a G105 substitution (based on the numbering depicted in FIG. 36A). In some cases, the variant 4-1BBL polypeptide comprises a K127 substitution and a P106 substitution (based on the numbering depicted in FIG. 36A). In some cases, the variant 4-1BBL polypeptide comprises a K127 substitution and an L107 substitution (based on the numbering depicted in FIG. 36A). In some cases, the variant 4-1BBL polypeptide comprises a K127 substitution and an S108 substitution (based on the numbering depicted in FIG. 36A). In some cases, the variant 4-1BBL polypeptide comprises a K127 substitution and a W109 substitution (based on the numbering depicted in FIG. 36A). In some cases, the variant 4-1BBL polypeptide comprises a K127 substitution and a Y110 substitution (based on the numbering depicted in FIG. 36A). In some cases, the variant 4-1BBL polypeptide comprises a K127 substitution and an S111 substitution (based on the numbering depicted in FIG. 36A). In some cases, the variant 4-1BBL polypeptide comprises a K127 substitution and a D112 substitution (based on the numbering depicted in FIG. 36A). In some cases, the variant 4-1BBL polypeptide comprises a K127 substitution and a P113 substitution (based on the numbering depicted in FIG. 36A). In some cases, the variant 4-1BBL polypeptide comprises a K127 substitution and a G114 substitution (based on the numbering depicted in FIG. 36A). In some cases, the variant 4-1BBL polypeptide comprises a K127 substitution and an L115 substitution (based on the numbering depicted in FIG. 36A).

In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a first variant 4-1BBL polypeptide of the present disclosure; ii) a linker; iii) a second variant 4-1BBL polypeptide of the present disclosure; iv) a linker; v) a third variant 4-1BBL polypeptide of the present disclosure; vi) a Class I MHC heavy chain; and vii) an Fc polypeptide. In some cases, each of the first, second, and third variant 4-1BBL polypeptides comprises an amino acid sequence having at least 90%, at least 95%, at least 98%, or at least 99%, amino acid sequence identity to the amino acid sequence depicted in FIG. 36B, where amino acid 127 (indicated by an "x") is an amino acid other than a lysine, e.g., where amino acid 127 is Gly, Ala, Val, Leu, Ile, Pro, Phe, Tyr, Trp, Ser, Thr, Cys, Met, Asn, Gln, Arg, His, Asp, or Glu; e.g., each of the first, second, and third variant 4-1BBL polypeptides comprises an amino acid sequence having at least 90%, at least 95%, at least 98%, or at least 99%, amino acid sequence identity to the amino acid sequence set forth in SEQ ID NO:213, with an amino acid substitution at K47, e.g., where amino acid 47 is Gly, Ala, Val, Leu, Ile, Pro, Phe, Tyr, Trp, Ser, Thr, Cys, Met, Asn, Gln, Arg, His, Asp, or Glu. In some cases, the linker comprises a (GSSSS)n (SEQ ID NO:131) sequence, where n is 1, 2, 3, 4, or 5. In some cases, n is 4. In some cases, n is 5. In some cases, the variant 4-1BBL polypeptide comprises a K127 substitution and an M91 substitution (based on the numbering depicted in FIG. 36A). In some cases, the variant 4-1BBL polypeptide comprises a K127 substitution and an F92 substitution (based on the numbering depicted in FIG. 36A). In some cases, the variant 4-1BBL polypeptide comprises a K127 substitution and a Q94 substitution (based on the numbering depicted in FIG. 36A). In some cases, the variant 4-1BBL polypeptide comprises a K127 substitution and an L95 substitution (based on the numbering depicted in FIG. 36A). In some cases, the variant 4-1BBL polypeptide comprises a K127 substitution and a V96 substitution (based on the numbering depicted in FIG. 36A). In some cases, the variant 4-1BBL polypeptide comprises a K127 substitution and a Q98 substitution (based on the numbering depicted in FIG. 36A). In some cases, the variant 4-1BBL polypeptide comprises a K127 substitution and an N99 substitution (based on the numbering depicted in FIG. 36A). In some cases, the variant 4-1BBL polypeptide comprises a K127 substitution and a V100 substitution (based on the numbering depicted in FIG. 36A). In some cases, the variant 4-1BBL polypeptide comprises a K127 substitution and an L101 substitution (based on the numbering depicted in FIG. 36A). In some cases, the variant 4-1BBL polypeptide comprises a K127 substitution and an L102 substitution (based on the numbering depicted in FIG. 36A). In some cases, the variant 4-1BBL polypeptide comprises a K127 substitution and an 1103 substitution (based on the numbering depicted in FIG. 36A). In some cases, the variant 4-1BBL polypeptide comprises a K127 substitution and a D104 substitution (based on the numbering depicted in FIG. 36A). In some cases, the variant 4-1BBL polypeptide comprises a K127 substitution and a G105 substitution (based on the numbering depicted in FIG. 36A). In some cases, the variant 4-1BBL polypeptide comprises a K127 substitution and a P106 substitution (based on the numbering depicted in FIG. 36A). In some cases, the variant 4-1BBL polypeptide comprises a K127 substitution and an L107 substitution (based on the numbering depicted in FIG. 36A). In some cases, the variant 4-1BBL polypeptide comprises a K127 substitution and an S108 substitution (based on the numbering depicted in FIG. 36A). In some cases, the variant 4-1BBL polypeptide comprises a K127 substitution and a W109 substitution (based on the numbering depicted in FIG. 36A). In some cases, the variant 4-1BBL polypeptide comprises a K127 substitution and a Y110 substitution (based on the numbering depicted in FIG. 36A). In some cases, the variant 4-1BBL polypeptide comprises a K127 substitution and an S111 substitution (based on the numbering depicted in FIG. 36A). In some cases, the variant 4-1BBL polypeptide comprises a K127 substitution and a D112 substitution (based on the numbering depicted in FIG. 36A). In some cases, the variant 4-1BBL polypeptide comprises a K127 substitution and a P113 substitution (based on the numbering depicted in FIG. 36A). In some cases, the variant 4-1BBL polypeptide comprises a K127 substitution and a G114 substitution (based on the numbering depicted in FIG. 36A). In some cases, the variant 4-1BBL polypeptide comprises a K127 substitution and an L115 substitution (based on the numbering depicted in FIG. 36A).

Q227

In some cases, a multimeric polypeptide of the present disclosure comprises: a) a first polypeptide comprising, in order from N-terminus to C-terminus: i) an epitope; ii) a β2M polypeptide; and iii) a variant 4-1BBL polypeptide comprising an amino acid sequence having at least 90%, at least 95%, at least 98%, or at least 99%, amino acid sequence identity to the amino acid sequence depicted in FIG. 36D, where amino acid 227 (indicated by an "x") is an amino acid other than a glutamine, e.g., where amino acid 227 is Gly, Ala, Val, Leu, Ile, Pro, Phe, Tyr, Trp, Ser, Thr, Cys, Met, Asn, Lys, Arg, His, Asp, or Glu; or a variant 4-1BBL polypeptide of the present disclosure comprising an amino acid sequence having at least 90%, at least 95%, at least 98%, or at least 99%, amino acid sequence identity to the amino acid sequence set forth in SEQ ID NO:213, with an amino acid substitution at Q147, e.g., where amino acid 147 is Gly, Ala, Val, Leu, Ile, Pro, Phe, Tyr, Trp, Ser, Thr, Cys, Met, Asn, Lys, Arg, His, Asp, or Glu; and b) a second polypeptide comprising, in order from N-terminus to C-terminus: i) a Class I MHC heavy chain; and ii) an Fc polypeptide. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a variant 4-1BBL polypeptide comprising an amino acid sequence having at least 90%, at least 95%, at least 98%, or at least 99%, amino acid sequence identity to the amino acid sequence depicted in FIG. 36D, where amino acid 227 (indicated by an "x") is an amino acid other than a glutamine, e.g., where amino acid 227 is Gly, Ala, Val, Leu, Ile, Pro, Phe, Tyr, Trp, Ser, Thr, Cys, Met, Asn, Lys, Arg, His, Asp, or Glu; or a variant 4-1BBL polypeptide of the present disclosure comprising an amino acid sequence having at least 90%, at least 95%, at least 98%, or at least 99%, amino acid sequence identity to the amino acid sequence set forth in SEQ ID NO:213, with an amino acid substitution at Q147, e.g., where amino acid 147 is Gly, Ala, Val, Leu, Ile, Pro, Phe, Tyr, Trp, Ser, Thr, Cys, Met, Asn, Lys, Arg, His, Asp, or Glu; ii) a Class I MHC heavy chain; and iii) an Fc polypeptide. In some cases, a multimeric polypeptide of the present disclosure comprises: a) a first polypeptide comprising, in order from N-terminus to C-terminus: i) an epitope; ii) a β2M polypeptide; iii) a first variant 4-1BBL polypeptide of the present disclosure; iv) a second variant 4-1BBL polypeptide of the present disclosure; and v) a third variant 4-1BBL polypeptide of the present disclosure; and b) a second polypeptide comprising, in order from N-terminus to C-terminus: i) a Class I MHC heavy chain; and ii) an Fc polypeptide. In some cases, each of the first, second, and third variant 4-1BBL polypeptides comprises an amino acid sequence having at least 90%, at least 95%, at least 98%, or at least 99%, amino acid sequence identity to the amino acid sequence depicted in FIG. 36D, where amino acid 227 (indicated by an "x") is an amino acid other than a glutamine, e.g., where amino acid 227 is Gly, Ala, Val, Leu, Ile, Pro, Phe, Tyr, Trp, Ser, Thr, Cys, Met, Asn, Lys, Arg, His, Asp, or Glu; or each of the first, second, and third variant 4-1BBL polypeptides comprises an amino acid sequence having at least 90%, at least 95%, at least 98%, or at least 99%, amino acid sequence identity to the amino acid sequence set forth in SEQ ID NO:213, with an amino acid substitution at Q147, e.g., where amino acid 147 is Gly, Ala, Val, Leu, Ile, Pro, Phe, Tyr, Trp, Ser, Thr, Cys, Met, Asn, Lys, Arg, His, Asp, or Glu. In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a first variant 4-1BBL polypeptide of the present disclosure; ii) a second variant 4-1BBL polypeptide of the present disclosure; and iii) a third variant 4-1BBL polypeptide of the present disclosure; iv) a Class I MHC heavy chain; and v) an Fc polypeptide. In some cases, each of the first, second, and third variant 4-1BBL polypeptides comprises an amino acid sequence having at least 90%, at least 95%, at least 98%, or at least 99%, amino acid sequence identity to the amino acid sequence depicted in FIG. 36D, where amino acid 227 (indicated by an "x") is an amino acid other than a glutamine, e.g., where amino acid 227 is Gly, Ala, Val, Leu, Ile, Pro, Phe, Tyr, Trp, Ser, Thr, Cys, Met, Asn, Lys, Arg, His, Asp, or Glu; or each of the first, second, and third variant 4-1BBL polypeptides comprises an amino acid sequence having at least 90%, at least 95%, at least 98%, or at least 99%, amino acid sequence identity to the amino acid sequence set forth in SEQ ID NO:213, with an amino acid substitution at Q147, e.g., where amino acid 147 is Gly, Ala, Val, Leu, Ile, Pro, Phe, Tyr, Trp, Ser, Thr, Cys, Met, Asn, Lys, Arg, His, Asp, or Glu.

In some cases, a multimeric polypeptide of the present disclosure comprises: a) a first polypeptide comprising, in order from N-terminus to C-terminus: i) an epitope; and ii) a β2M polypeptide; and b) a second polypeptide comprising, in order from N-terminus to C-terminus: i) a first variant 4-1BBL polypeptide of the present disclosure; ii) a linker; iii) a second variant 4-1BBL polypeptide of the present disclosure; iv) a linker; v) a third variant 4-1BBL polypeptide of the present disclosure; vi) a Class I MHC heavy chain; and vii) an Fc polypeptide. In some cases, each of the first, second, and third variant 4-1BBL polypeptides comprises an amino acid sequence having at least 90%, at least 95%, at least 98%, or at least 99%, amino acid sequence identity to the amino acid sequence depicted in FIG. 36D, where amino acid 227 (indicated by an "x") is an amino acid other than a glutamine, e.g., where amino acid 227 is Gly, Ala, Val, Leu, Ile, Pro, Phe, Tyr, Trp, Ser, Thr, Cys, Met, Asn, Lys, Arg, His, Asp, or Glu; or each of the first, second, and third variant 4-1BBL polypeptides comprises an amino acid sequence having at least 90%, at least 95%, at least 98%, or at least 99%, amino acid sequence identity to the amino acid sequence set forth in SEQ ID NO:213, with an amino acid substitution at Q147, e.g., where amino acid 147 is Gly, Ala, Val, Leu, Ile, Pro, Phe, Tyr, Trp, Ser, Thr, Cys, Met, Asn, Lys, Arg, His, Asp, or Glu. In some cases, the linker comprises a (GSSSS)n (SEQ ID NO:131) sequence, where n is 1, 2, 3, 4, or 5. In some cases, the linker comprises a (GSSSS)n (SEQ ID NO:131) sequence, where n is 4. In some cases, the linker comprises a (GSSSS)n (SEQ ID NO:131) sequence, where n is 5. In some cases, the linker comprises a (GGGGS)n sequence, where n is 1, 2, 3, 4, 5, 6, 7, 8, 9, or 10. In some cases, the linker comprises a (GGGGS)n sequence, where n is 2. In some cases, the linker comprises a (GGGGS)n sequence, where n is 3. In some cases, the linker comprises a (GGGGS)n sequence, where n is 4. In some cases, the linker comprises a (GGGGS)n sequence, where n is 5.

Multiple Immunomodulatory Domains

As noted above, in some cases, a multimeric polypeptide comprises two or more immunomodulatory polypeptides. In some cases, at least one of the two or more immunomodulatory polypeptide is a variant immunomodulatory polypeptide. For example, in the case of an IL-2/synTac, in some cases, at least one of the two or more immunomodulatory polypeptide is a variant IL-2 polypeptide. As another example, in the case of a 4-1BBL/synTac, in some cases, at least one of the two or more immunomodulatory polypeptide is a variant 4-1BBL polypeptide.

In some cases, a multimeric polypeptide comprises two or more copies of a variant IL-2 polypeptide of the present disclosure. In some cases, the two or more variant IL-2 polypeptides are on the same polypeptide chain of a multimeric polypeptide. In some cases, the two or more variant IL-2 polypeptides are on separate polypeptide chains of a multimeric polypeptide.

In some cases, a multimeric polypeptide comprises a first immunomodulatory polypeptide, and at least a second immunomodulatory polypeptide, where the first immunomodulatory polypeptide is a variant IL-2 polypeptide of the present disclosure, and the second immunomodulatory polypeptide is not an IL-2 polypeptide. For example, in some cases, the second immunomodulatory polypeptide is a member of the tumor necrosis factor (TNF) superfamily; e.g., a FasL polypeptide, a 4-1BBL polypeptide, a CD40 polypeptide, an OX40L polypeptide, a CD30L polypeptide, a CD70 polypeptide, etc. In some cases, the second immunomodulatory polypeptide of a multimeric polypeptide is a T-cell co-stimulatory polypeptide and is a member of the immunoglobulin (Ig) superfamily; e.g., a CD7 polypeptide, a CD86 polypeptide, an ICAM polypeptide, etc. In some cases, the second immunomodulatory polypeptide is 4-1BBL, OX40L, ICOS-L, ICAM, PD-L1, CD86, FasL, and PD-L2. Suitable immunomodulatory polypeptides of a multimeric polypeptide of the present disclosure include, e.g., CD7, CD30L, CD40, CD70, CD83, HLA-G, MICA, MICB, HVEM, lymphotoxin beta receptor, 3/TR6, ILT3, ILT4, or HVEM.

Further T cell modulatory domains (MODs) that can be included in a multimeric polypeptide of the present disclosure include naturally occurring or synthetic human gene products (protein), affinity reagents (e.g., an antibody, antibody fragment, single chain Fvs, aptamers, nanobody) targeting a human gene product, including, but not limited to all secreted proteins arising from classical and non-classical (e.g., FGF2, IL1, S100A4) secretion mechanisms, and ecto-domains of all cell surface proteins anchored by naturally occurring genetically encoded protein segments (single or multiple membrane spans) or post-translational modifications such as GPI linkages). Any naturally occurring or synthetic affinity reagent (e.g., antibody, antibody fragment, single chain Fvs, aptamer, nanobody, lectin, etc) targeting a cell surface glycan or other post-translational modification (e.g., sulfation). Examples include, but are not limited to, members of the TNF/TNFR family (OX40L, ICOSL, FASL, LTA, LTB TRAIL, CD153, TNFSF9, RANKL, TWEAK, TNFSF13, TNFSF13b, TNFSF14, TNFSF15, TNFSF18, CD40LG, CD70) or affinity reagents directed at the TNF/TNFR family members; members of the Immunoglobulin superfamily (VISTA, PD1, PD-L1, PD-L2, B71, B72, CTLA4, CD28, TIM3, CD4, CD8, CD19, T cell receptor chains, ICOS, ICOS ligand, HHLA2, butyrophilins, BTLA, B7-H3, B7-H4, CD3, CD79a, CD79b, IgSF CAMS (including CD2, CD58, CD48, CD150, CD229, CD244, ICAM-1), Leukocyte immunoglobulin like receptors (LILR), killer cell immunoglobulin like receptors (KIR)), lectin superfamily members, selectins, cytokines/chemokine and cytokine/chemokine receptors, growth factors and growth factor receptors), adhesion molecules (integrins, fibronectins, cadherins), or ecto-domains of multi-span integral membrane protein, or affinity reagents directed at the Immunoglobulin superfamily and listed gene products. In addition, active homologs/orthologs of these gene products, including but not limited to, viral sequences (e.g., CMV, EBV), bacterial sequences, fungal sequences, eukaryotic pathogens (e.g., *Schistosoma, Plasmodium, Babesia, Eimeria, Theileria,* *Toxoplasma, Entamoeba, Leishmania,* and *Trypanosoma*), and mammalian-derived coding regions. In addition, a MOD may comprise a small molecules drug targeting a human gene product.

Additional Polypeptides

A polypeptide chain of a multimeric polypeptide can include one or more polypeptides in addition to those described above. Suitable additional polypeptides include epitope tags and affinity domains. The one or more additional polypeptide can be included at the N-terminus of a polypeptide chain of a multimeric polypeptide, at the C-terminus of a polypeptide chain of a multimeric polypeptide, or internally within a polypeptide chain of a multimeric polypeptide.

Epitope Tag

Suitable epitope tags include, but are not limited to, hemagglutinin (HA; e.g., YPYDVPDYA (SEQ ID NO:79); FLAG (e.g., DYKDDDDK (SEQ ID NO:80); c-myc (e.g., EQKLISEEDL; SEQ ID NO:81), and the like.

Affinity Domain

Affinity domains include peptide sequences that can interact with a binding partner, e.g., such as one immobilized on a solid support, useful for identification or purification. DNA sequences encoding multiple consecutive single amino acids, such as histidine, when fused to the expressed protein, may be used for one-step purification of the recombinant protein by high affinity binding to a resin column, such as nickel sepharose. Exemplary affinity domains include His5 (HHHHH) (SEQ ID NO:82), HisX6 (HHHHHH) (SEQ ID NO:83), C-myc (EQKLISEEDL) (SEQ ID NO:81), Flag (DYKDDDDK) (SEQ ID NO:80), StrepTag (WSHPQFEK) (SEQ ID NO:84), hemagglutinin, e.g., HA Tag (YPYDVPDYA) (SEQ ID NO:79), glutathione-S-transferase (GST), thioredoxin, cellulose binding domain, RYIRS (SEQ ID NO:85), Phe-His-His-Thr (SEQ ID NO:86), chitin binding domain, S-peptide, T7 peptide, SH2 domain, C-end RNA tag, WEAAAREACCRECCARA (SEQ ID NO:87), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin D9K, calbindin D28K, and calretinin, inteins, biotin, streptavidin, MyoD, Id, leucine zipper sequences, and maltose binding protein.

Examples of IL-2/Multimeric Polypeptides

The following are non-limiting embodiments of an IL-2/synTac multimeric polypeptide suitable for use in a treatment method of the present disclosure.

In some cases, an IL-2/synTac multimeric polypeptide comprises: a) a first polypeptide comprising, in order from N-terminus to C-terminus: i) an epitope; ii) a β2-microglobulin (β2M) polypeptide comprising the amino acid sequence depicted in FIG. 34A; and b) a second polypeptide comprising, in order from N-terminus to C-terminus: i) a variant IL-2 polypeptide of the present disclosure; ii) a major histocompatibility complex (MHC) heavy chain polypeptide comprising the amino acid sequence depicted in FIG. 34C; and iii) an IgG1 Fc polypeptide comprising one or more amino acid substitutions selected from N297A, L234A, L235A, L234F, L235E, and P331S. In some cases, the variant IL-2 polypeptide comprises an H16A and an F42A substitution. In some cases, the IgG1 Fc polypeptide comprises an N297A substitution. In some cases, the IgG1 Fc polypeptide comprises an L234A substitution and an L235A substitution. In some cases, the IgG1 Fc polypeptide comprises an L234F substitution and an L235E substitution. In some cases, the IgG1 Fc polypeptide comprises an L234F substitution, an L235E substitution, and a P331S substitution. In some cases, the second polypeptide comprises two copies of the variant IL-2 polypeptide. In some cases, the first polypeptide comprises a peptide linker between the epitope and the β2M polypeptide. In some cases, the second polypeptide comprises a peptide linker between one or more of: a) a first copy of the variant IL-2 polypeptide and a second copy of the variant IL-2 polypeptide; b) the variant IL-2 polypeptide and the MHC heavy chain polypeptide; and c) between the MHC heavy chain polypeptide and the IgG1 Fc polypeptide. In some cases, the peptide linker is selected from (GGGGS)$_3$ (SEQ ID NO:207), (GGGGS)$_4$ (SEQ ID NO:208), and AAAGG (SEQ ID NO:73). In some cases, the IgG1 Fc polypeptide comprises the amino acid sequence depicted in FIG. 33B. In some cases, the IgG1 Fc polypeptide comprises the amino acid sequence depicted in FIG. 33C. In some cases, the IgG1 Fc polypeptide comprises the amino acid sequence depicted in FIG. 33D.

In some cases, a multimeric polypeptide comprises: a) a first polypeptide comprising, in order from N-terminus to C-terminus: i) an epitope; ii) a β2-microglobulin polypeptide comprising the amino acid sequence depicted in FIG. 34A; and b) a second polypeptide comprising, in order from N-terminus to C-terminus: i) a variant IL-2 polypeptide comprising the amino acid sequence depicted in FIG. 34B; ii) a major histocompatibility complex (MHC) heavy chain polypeptide comprising the amino acid sequence depicted in FIG. 34C; and iii) an IgG1 Fc polypeptide comprising one or more amino acid substitutions selected from N297A, L234A, L235A, L234F, L235E, and P331S. In some cases, the IgG1 Fc polypeptide comprises an N297A substitution. In some cases, the IgG1 Fc polypeptide comprises an L234A substitution and an L235A substitution. In some cases, the IgG1 Fc polypeptide comprises an L234F substitution and an L235E substitution. In some cases, the IgG1 Fc polypeptide comprises an L234F substitution, an L235E substitution, and a P331S substitution. In some cases, the IgG1 Fc polypeptide comprises the amino acid sequence depicted in FIG. 33B. In some cases, the IgG1 Fc polypeptide comprises the amino acid sequence depicted in FIG. 33C. In some cases, the IgG1 Fc polypeptide comprises the amino acid sequence depicted in FIG. 33D. In some cases, the second polypeptide comprises two copies of the variant IL-2 polypeptide. In some cases, the first polypeptide comprises a peptide linker between the epitope and the β2M polypeptide. In some cases, the second polypeptide comprises a peptide linker between one or more of: a) a first copy of the variant IL-2 polypeptide and a second copy of the variant IL-2 polypeptide; b) the variant IL-2 polypeptide and the MHC heavy chain polypeptide; and c) between the MHC heavy chain polypeptide and the IgG1 Fc polypeptide. In some cases, the peptide linker is selected from (GGGGS)$_3$ (SEQ ID NO:207), (GGGGS)$_4$ (SEQ ID NO:208), and AAAGG (SEQ ID NO:73).

In some cases, multimeric polypeptide comprises: a) a first polypeptide comprising, in order from N-terminus to C-terminus: i) an epitope comprising the amino acid sequence YMLDLQPETT (SEQ ID NO:77); ii) a β2-microglobulin polypeptide comprising the amino acid sequence depicted in FIG. 34A; and b) a second polypeptide comprising, in order from N-terminus to C-terminus: i) a variant IL-2 polypeptide comprising the amino acid sequence depicted in FIG. 34B; ii) a major histocompatibility complex (MHC) heavy chain polypeptide comprising the amino acid sequence depicted in FIG. 34C; and iii) an IgG1 Fc polypeptide comprising the amino acid sequence depicted in FIG. 33A, 33B, 33C, or 33D. In some cases, the IgG1 Fc polypeptide comprises the amino acid sequence depicted in FIG. 33B. In some cases, the IgG1 Fc polypeptide comprises the amino acid sequence depicted in FIG. 33C. In some cases, the IgG1 Fc polypeptide comprises the amino acid sequence depicted in FIG. 33D. In some cases, the second polypeptide comprises two copies of the variant IL-2 polypeptide. In some cases, the first polypeptide comprises a peptide linker between the epitope and the β2M polypeptide. In some cases, the second polypeptide comprises a peptide linker between one or more of: a) a first copy of the variant IL-2 polypeptide and a second copy of the variant IL-2 polypeptide; b) the variant IL-2 polypeptide and the MHC heavy chain polypeptide; and c) between the MHC heavy chain polypeptide and the IgG1 Fc polypeptide. In some cases, the peptide linker is selected from (GGGGS)$_3$ (SEQ ID NO:207), (GGGGS)$_4$ (SEQ ID NO:208), and AAAGG (SEQ ID NO:73). In some cases, the IgG1 Fc polypeptide comprises the amino acid sequence depicted in FIG. 33B. In some cases, the IgG1 Fc polypeptide comprises the amino acid sequence depicted in FIG. 33C. In some cases, the IgG1 Fc polypeptide comprises the amino acid sequence depicted in FIG. 33D.

In some cases, a multimeric polypeptide comprises: a) a first polypeptide comprising the amino acid sequence depicted in FIG. 31; and b) a second polypeptide comprising the amino acid sequence depicted in FIG. 22.

In some cases, a multimeric polypeptide comprises: a) a first polypeptide comprising the amino acid sequence depicted in FIG. 31; and b) a second polypeptide comprising the amino acid sequence depicted in FIG. 25.

In some cases, a multimeric polypeptide comprises: a) a first polypeptide comprising the amino acid sequence depicted in FIG. 31; and ab) a second polypeptide comprising the amino acid sequence depicted in FIG. 28.

Formulations, Doses, and Routes of Administration

In carrying out a treatment method of the present disclosure, a synTac can be formulated in a composition comprising a pharmaceutically acceptable excipient, and an immune checkpoint inhibitor can be formulated in a composition comprising a pharmaceutically acceptable excipient. For simplicity, the term "active agent" is used below to refer to a synTac or an immune checkpoint inhibitor. In general, the synTac and the immune checkpoint inhibitor are present in separate compositions.

The composition may comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", 19$^{th}$ Ed. (1995), or latest edition, Mack Publishing Co; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

A pharmaceutical composition can comprise a synTac or an immune checkpoint inhibitor, and a pharmaceutically acceptable excipient. In some cases, a pharmaceutical composition will be suitable for administration to a subject, e.g., will be sterile. For example, in some cases, a pharmaceutical composition will be suitable for administration to a human subject, e.g., where the composition is sterile and is free of detectable pyrogens and/or other toxins.

The compositions may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate, hydrochloride, sulfate salts, solvates (e.g., mixed ionic salts, water, organics), hydrates (e.g., water), and the like.

For example, compositions may include aqueous solution, powder form, granules, tablets, pills, suppositories, capsules, suspensions, sprays, and the like. The composition may be formulated according to the various routes of administration described below.

Where an active agent (a synTac or an immune checkpoint inhibitor) is administered as an injectable (e.g. subcutaneously, intraperitoneally, intramuscularly, and/or intravenously) directly into a tissue, a formulation can be provided as a ready-to-use dosage form, or as non-aqueous form (e.g. a reconstitutable storage-stable powder) or aqueous form, such as liquid composed of pharmaceutically acceptable carriers and excipients. The formulations may also be provided so as to enhance serum half-life of an active agent following administration. For example, the protein may be provided in a liposome formulation, prepared as a colloid, or other conventional techniques for extending serum half-life. A variety of methods are available for preparing liposomes, as described in, e.g., Szoka et al. 1980 Ann. Rev. Biophys. Bioeng. 9:467, U.S. Pat. Nos. 4,235,871, 4,501,728 and 4,837,028. The preparations may also be provided in controlled release or slow-release forms.

Other examples of formulations suitable for parenteral administration include isotonic sterile injection solutions, anti-oxidants, bacteriostats, and solutes that render the formulation isotonic with the blood of the intended recipient, suspending agents, solubilizers, thickening agents, stabilizers, and preservatives. For example, a subject pharmaceutical composition can be present in a container, e.g., a sterile container, such as a syringe. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

The concentration of an active agent (a synTac or an immune checkpoint inhibitor) in a formulation can vary widely (e.g., from less than about 0.1%, usually at or at least about 2% to as much as 20% to 50% or more by weight) and will usually be selected primarily based on fluid volumes, viscosities, and patient-based factors in accordance with the particular mode of administration selected and the patient's needs.

The present disclosure provides a container comprising an active agent (a synTac or an immune checkpoint inhibitor), e.g., a container comprising a liquid composition comprising an active agent. The container can be, e.g., a syringe, an ampoule, and the like. In some cases, the container is sterile. In some cases, both the container and the composition are sterile.

The present disclosure provides compositions, including pharmaceutical compositions, comprising an active agent (a synTac or an immune checkpoint inhibitor). A composition can comprise: a) an active agent (a synTac or an immune checkpoint inhibitor); and b) an excipient, as described above. In some cases, the excipient is a pharmaceutically acceptable excipient.

Compositions Comprising a Nucleic Acid or a Recombinant Expression Vector

In some cases, a synTac is administered as a multimeric polypeptide per se. In other instances, one or more nucleic acids comprising nucleotide sequences encoding a synTac are administered, instead of administering a synTac as a multimeric polypeptide per se. The nucleic acid(s) can be present in a pharmaceutical composition. A pharmaceutical composition can comprise one or more recombinant expression vectors comprising the one or more nucleic acids. A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

A pharmaceutical formulation can include a nucleic acid or recombinant expression vector of the present disclosure in an amount of from about 0.001% to about 90% (w/w). In the description of formulations, below, "nucleic acid or recombinant expression vector" will be understood to include a nucleic acid or recombinant expression vector comprising nucleotide sequences encoding a synTac.

A nucleic acid or recombinant expression vector can be admixed, encapsulated, conjugated or otherwise associated with other compounds or mixtures of compounds; such compounds can include, e.g., liposomes or receptor-targeted molecules. A nucleic acid or recombinant expression vector can be combined in a formulation with one or more components that assist in uptake, distribution and/or absorption.

A nucleic acid or recombinant expression vector composition can be formulated into any of many possible dosage forms such as, but not limited to, tablets, capsules, gel capsules, liquid syrups, soft gels, suppositories, and enemas. A nucleic acid or recombinant expression vector composition can also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

A formulation comprising a nucleic acid or recombinant expression vector can be a liposomal formulation. As used herein, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that can interact with negatively charged DNA molecules to form a stable complex. Liposomes that are pH sensitive or negatively charged are believed to entrap DNA rather than complex with it. Both cationic and noncationic liposomes can be used to deliver a subject nucleic acid or recombinant expression vector.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein by reference in its entirety.

The formulations and compositions of the present disclosure may also include surfactants. The use of surfactants in drug products, formulations and in emulsions is well known in the art. Surfactants and their uses are further described in U.S. Pat. No. 6,287,860.

In one embodiment, various penetration enhancers are included, to effect the efficient delivery of nucleic acids. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein by reference in its entirety.

Compositions and formulations for oral administration include powders or granules, microparticulates, nanoparticulates, suspensions or solutions in water or non-aqueous media, capsules, gel capsules, sachets, tablets, or minitablets. Thickeners, flavoring agents, diluents, emulsifiers, dispersing aids or binders may be desirable. Suitable oral formulations include those in which a subject antisense nucleic acid is administered in conjunction with one or more penetration enhancers surfactants and chelators. Suitable surfactants include, but are not limited to, fatty acids and/or esters or salts thereof, bile acids and/or salts thereof. Suitable bile acids/salts and fatty acids and their uses are further described in U.S. Pat. No. 6,287,860. Also suitable are combinations of penetration enhancers, for example, fatty acids/salts in combination with bile acids/salts. An exemplary suitable combination is the sodium salt of lauric acid, capric acid, and UDCA. Further penetration enhancers include, but are not limited to, polyoxyethylene-9-lauryl ether, and polyoxyethylene-20-cetyl ether. Suitable penetration enhancers also include propylene glycol, dimethylsulfoxide, triethanoiamine, N,N-dimethylacetamide, N,N-dimethylformamide, 2-pyrrolidone and derivatives thereof, tetrahydrofurfuryl alcohol, and AZONE™.

Treatment Methods

The present disclosure provides a treatment method, comprising administering a synTac and an immune checkpoint inhibitor. In some cases, the method comprises administering to an individual in need thereof: a) a first composition comprising a synTac; and b) a second composition comprising an immune checkpoint inhibitor. In some cases, a treatment method of the present disclosure comprises administering to an individual in need thereof: a) a first composition comprising one or more recombinant expression vectors comprising nucleotide sequences encoding a synTac; and b) a second composition comprising an immune checkpoint inhibitor. In some cases, a treatment method of the present disclosure comprises administering to an individual in need thereof: a) a first composition comprising one or more mRNA molecules comprising nucleotide sequences encoding a multimeric polypeptide; and b) a second composition comprising an immune checkpoint inhibitor. In some cases, the immune checkpoint inhibitor is an antibody specific for an immune checkpoint polypeptide.

Thus, for example, a treatment method of the present disclosure can comprise co-administration of a synTac (e.g., a 4-1BBL synTac, IL-2 synTac, etc., as described above) and an antibody specific for an immune checkpoint. By "co-administration" is meant that both a synTac (e.g., a 4-1BBL synTac, IL-2 synTac, etc., as described above) and an antibody specific for an immune checkpoint are administered to an individual, although not necessarily at the same time, in order to achieve a therapeutic effect that is the result of having administered both the synTac and the immune checkpoint inhibitor. The administration of the synTac (e.g., a 4-1BBL synTac, IL-2 synTac, etc.) and the antibody specific for an immune checkpoint can be substantially simultaneous, e.g., the synTac (e.g., a 4-1BBL synTac, IL-2 synTac, etc.) can be administered to an individual within about 1 minute to about 24 hours (e.g., within about 1 minute, within about 5 minutes, within about 15 minutes, within about 30 minutes, within about 1 hour, within about 4 hours, within about 8 hours, within about 12 hours, or within about 24 hours) of administration of the antibody specific for an immune checkpoint. In some cases, a synTac (e.g., a 4-1BBL synTac, IL-2 synTac, etc.) is administered to an individual who is undergoing treatment with an antibody specific for an immune checkpoint. The administration of the synTac (e.g., a 4-1BBL synTac, IL-2 synTac, etc.) and the antibody specific for an immune checkpoint can occur at different times and/or at different frequencies.

Thus, for example, a treatment method of the present disclosure can comprise co-administration of a 4-1BBL synTac and an antibody specific for an immune checkpoint. By "co-administration" is meant that both a 4-1BBL synTac and an antibody specific for an immune checkpoint are administered to an individual, although not necessarily at the same time, in order to achieve a therapeutic effect that is the result of having administered both the synTac and the immune checkpoint inhibitor. The administration of the 4-1BBL synTac and the antibody specific for an immune checkpoint can be substantially simultaneous, e.g., the 4-1BBL synTac can be administered to an individual within about 1 minute to about 24 hours (e.g., within about 1 minute, within about 5 minutes, within about 15 minutes, within about 30 minutes, within about 1 hour, within about 4 hours, within about 8 hours, within about 12 hours, or within about 24 hours) of administration of the antibody specific for an immune checkpoint. In some cases, a 4-1BBL synTac is administered to an individual who is undergoing treatment with an antibody specific for an immune checkpoint. The administration of the 4-1BBL synTac and the antibody specific for an immune checkpoint can occur at different times and/or at different frequencies.

As another example, a treatment method of the present disclosure can comprise co-administration of a synTac (e.g., an IL-2 synTac, as described above) and an antibody specific for an immune checkpoint. By "co-administration" is meant that both an IL-2 synTac and an antibody specific for an immune checkpoint are administered to an individual, although not necessarily at the same time, in order to achieve a therapeutic effect that is the result of having administered both the synTac and the immune checkpoint inhibitor. The administration of the IL-2 synTac and the antibody specific for an immune checkpoint can be substantially simultaneous, e.g., the IL-2 synTac can be administered to an individual within about 1 minute to about 24 hours (e.g., within about 1 minute, within about 5 minutes, within about 15 minutes, within about 30 minutes, within about 1 hour, within about 4 hours, within about 8 hours, within about 12 hours, or within about 24 hours) of administration of the antibody specific for an immune checkpoint. In some cases, an IL-2 synTac is administered to an individual who is undergoing treatment with an antibody specific for an immune checkpoint. The administration of the IL-2 synTac and the antibody specific for an immune checkpoint can occur at different times and/or at different frequencies.

The present disclosure provides a treatment method, comprising administering a synTac and an immune checkpoint inhibitor. A treatment method of the present disclosure can modulate an activity of a target T cell. In some cases, e.g., where the target T cell is a CD8 T cell, the multimeric polypeptide comprises Class I MHC polypeptides (e.g., β2-microglobulin and Class I MHC heavy chain). In some cases, e.g., where the target T cell is a CD4$^+$ T cell, the multimeric polypeptide comprises Class II MHC polypeptides (e.g., Class II MHC α chain; Class II MHC β chain).

Where a multimeric polypeptide includes an immunomodulatory polypeptide that is an activating polypeptide, a method of the present disclosure activates the epitope-specific T cell. In some instances, the epitope-specific T cell is a T cell that is specific for an epitope present on a cancer cell, and contacting the epitope-specific T cell with the multimeric polypeptide increases cytotoxic activity of the T cell toward the cancer cell. In some instances, the epitope-specific T cell is a T cell that is specific for an epitope present on a cancer cell, and a method of the present disclosure increases the number of the epitope-specific T cells.

In some instances, the epitope-specific T cell is a T cell that is specific for an epitope present on a virus-infected cell, and a method of the present disclosure increases cytotoxic activity of the T cell toward the virus-infected cell. In some instances, the epitope-specific T cell is a T cell that is specific for an epitope present on a virus-infected cell, and a method of the present disclosure increases the number of the epitope-specific T cells.

Where a multimeric polypeptide of the present disclosure includes an immunomodulatory polypeptide that is an inhibiting polypeptide, a method of the present disclosure inhibits the epitope-specific T cell. In some instances, the epitope-specific T cell is a self-reactive T cell that is specific for an epitope present in a self antigen, and a method of the present disclosure reduces the number of the self-reactive T cells.

In some cases, the immunomodulatory polypeptide is an activating polypeptide, and the multimeric polypeptide activates the epitope-specific T cell. In some cases, the epitope is a cancer-associated epitope, and the multimeric polypeptide increases the activity of a T cell specific for the cancer-associate epitope.

In some cases, a treatment method of the present disclosure treats a cancer in an individual having the cancerl. Thus, the present disclosure provides a method of treating cancer in an individual, the method comprising administering to the individual: a) a multimeric polypeptide of the present disclosure, or one or more nucleic acids (e.g., expression vectors; mRNA; etc.) comprising nucleotide sequences encoding the multimeric polypeptide, where the multimeric polypeptide comprises a T-cell epitope that is a cancer epitope, and where the multimeric polypeptide comprises a stimulatory immunomodulatory polypeptide; and b) an immune checkpoint inhibitor. In some cases, "effective amounts" of a multimeric polypeptide and an immune checkpoint inhibitor are amounts that, when administered in one or more doses to an individual in need thereof, reduce the number of cancer cells in the individual. For example, in some cases, "effective amounts" of a multimeric polypeptide and an immune checkpoint inhibitor are amounts that, when administered in one or more doses to an individual in need thereof, reduce the number of cancer cells in the individual by at least 10%, at least 15%, at least 20%, at least 25%, at least 30%, at least 40%, at least 50%, at least 60%, at least 70%, at least 80%, at least 90%, or at least 95%, compared to the number of cancer cells in the individual before administration of the multimeric polypeptide and the immune checkpoint inhibitor, or in the absence of administration with the multimeric polypeptide and the immune checkpoint inhibitor. In some cases, "effective amounts" of a multimeric polypeptide and an immune checkpoint inhibitor are amounts that, when administered in one or more doses to an individual in need thereof, reduce the number of cancer cells in the individual to undetectable levels. In some cases, "effective amounts" of a multimeric polypeptide and an immune checkpoint inhibitor are amounts that, when administered in one or more doses to an individual in need thereof, reduce the tumor mass in the individual. For example, in some cases, "effective amounts" of a multimeric polypeptide and an immune checkpoint inhibitor are amounts that, when administered in one or more doses to an individual in need thereof, reduce the tumor mass in the individual by at least 10%, at least 15%, at least 20%, at least 25%, at least 30%, at least 40%, at least 50%, at least 60%, at least 70%, at least 80%, at least 90%, or at least 95%, compared to the tumor mass in the individual before administration of the multimeric polypeptide and the immune checkpoint inhibitor, or in the absence of administration with the multimeric polypeptide and the immune checkpoint inhibitor. In some cases, "effective amounts" of a multimeric polypeptide and an immune checkpoint inhibitor are amounts that, when administered in one or more doses to an individual in need thereof, increase survival time of the individual. For example, in some cases, "effective amounts" of a multimeric polypeptide and an immune checkpoint inhibitor are amounts that, when administered in one or more doses to an individual in need thereof, increase survival time of the individual by at least 1 month, at least 2 months, at least 3 months, from 3 months to 6 months, from 6 months to 1 year, from 1 year to 2 years, from 2 years to 5 years, from 5 years to 10 years, or more than 10 years, compared to the expected survival time of the individual in the absence of administration with the multimeric polypeptide and the immune checkpoint inhibitor.

In some instances, the epitope-specific T cell is a T cell that is specific for an epitope present on a virus-infected cell, and a method of the present disclosure increases cytotoxic activity of the T cell toward the virus-infected cell. In some instances, the epitope-specific T cell is a T cell that is specific for an epitope present on a virus-infected cell, and a method of the present disclosure increases the number of the epitope-specific T cells.

As noted above, in some cases, in carrying out a subject treatment method, a multimeric polypeptide is administered to an individual in need thereof, as the polypeptide per se. In other instances, in carrying out a subject treatment method, one or more nucleic acids comprising nucleotide sequences encoding a multimeric polypeptide is/are administering to an individual in need thereof. Thus, in other instances, one or more nucleic acids encoding a synTac is/are administered to an individual in need thereof.

Dosages—synTac

A suitable dosage of a synTac can be determined by an attending physician or other qualified medical personnel, based on various clinical factors. As is well known in the medical arts, dosages for any one patient depend upon many factors, including the patient's size, body surface area, age, the particular polypeptide or nucleic acid to be administered, sex of the patient, time, and route of administration, general health, and other drugs being administered concurrently. A multimeric polypeptide (synTac) may be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 g to 10 mg per kilogram of body weight per minute. A multimeric polypeptide can be administered in an amount of from about 1 mg/kg body weight to 50 mg/kg body weight, e.g., from about 1 mg/kg body weight to about 5 mg/kg body weight, from about 5 mg/kg body weight to about 10 mg/kg body weight, from about 10 mg/kg body weight to about 15 mg/kg body weight, from about 15 mg/kg body weight to about 20 mg/kg body weight, from about 20 mg/kg body weight to about 25 mg/kg body weight, from about 25 mg/kg body weight to about 30 mg/kg body weight, from about 30 mg/kg body weight to about 35 mg/kg body weight, from about 35 mg/kg body weight to about 40 mg/kg body weight, or from about 40 mg/kg body weight to about 50 mg/kg body weight.

In some cases, a suitable dose of a multimeric polypeptide is from 0.01 µg to 100 g per kg of body weight, from 0.1 µg to 10 g per kg of body weight, from 1 µg to 1 g per kg of body weight, from 10 µg to 100 mg per kg of body weight, from 100 µg to 10 mg per kg of body weight, or from 100 µg to 1 mg per kg of body weight. Persons of ordinary skill in the art can easily estimate repetition rates for dosing based on measured residence times and concentrations of the administered agent in bodily fluids or tissues. Following successful treatment, it may be desirable to have the patient undergo maintenance therapy to prevent the recurrence of the disease state, wherein a multimeric polypeptide is administered in maintenance doses, ranging from 0.01 µg to 100 g per kg of body weight, from 0.1 µg to 10 g per kg of body weight, from 1 g to 1 g per kg of body weight, from 10 µg to 100 mg per kg of body weight, from 100 µg to 10 mg per kg of body weight, or from 100 µg to 1 mg per kg of body weight.

Those of skill will readily appreciate that dose levels can vary as a function of the specific multimeric polypeptide, the severity of the symptoms and the susceptibility of the subject to side effects. Preferred dosages for a given compound are readily determinable by those of skill in the art by a variety of means.

In some embodiments, multiple doses of a multimeric polypeptide (or a nucleic acid or a recombinant expression vector encoding same) are administered. The frequency of administration of a multimeric polypeptide can vary depending on any of a variety of factors, e.g., severity of the symptoms, etc. For example, in some embodiments, a multimeric polypeptide is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of a multimeric polypeptide, e.g., the period of time over which a multimeric polypeptide is administered, can vary, depending on any of a variety of factors, e.g., patient response, etc. For example, a multimeric polypeptide can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

A suitable dosage of a synTac can be determined by an attending physician or other qualified medical personnel, based on various clinical factors. As is well known in the medical arts, dosages for any one patient depend upon many factors, including the patient's size, body surface area, age, the particular polypeptide or nucleic acid to be administered, sex of the patient, time, and route of administration, general health, and other drugs being administered concurrently. A multimeric polypeptide (synTac) may be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 g to 10 mg per kilogram of body weight per minute. A multimeric polypeptide can be administered in an amount of from about 1 mg/kg body weight to 50 mg/kg body weight, e.g., from about 1 mg/kg body weight to about 5 mg/kg body weight, from about 5 mg/kg body weight to about 10 mg/kg body weight, from about 10 mg/kg body weight to about 15 mg/kg body weight, from about 15 mg/kg body weight to about 20 mg/kg body weight, from about 20 mg/kg body weight to about 25 mg/kg body weight, from about 25 mg/kg body weight to about 30 mg/kg body weight, from about 30 mg/kg body weight to about 35 mg/kg body weight, from about 35 mg/kg body weight to about 40 mg/kg body weight, or from about 40 mg/kg body weight to about 50 mg/kg body weight.

In some cases, a suitable dose of a multimeric polypeptide is from 0.01 µg to 100 g per kg of body weight, from 0.1 µg to 10 g per kg of body weight, from 1 µg to 1 g per kg of body weight, from 10 µg to 100 mg per kg of body weight, from 100 µg to 10 mg per kg of body weight, or from 100 µg to 1 mg per kg of body weight. Persons of ordinary skill in the art can easily estimate repetition rates for dosing based on measured residence times and concentrations of the administered agent in bodily fluids or tissues. Following successful treatment, it may be desirable to have the patient undergo maintenance therapy to prevent the recurrence of the disease state, wherein a multimeric polypeptide is administered in maintenance doses, ranging from 0.01 µg to 100 g per kg of body weight, from 0.1 µg to 10 g per kg of body weight, from 1 g to 1 g per kg of body weight, from 10 µg to 100 mg per kg of body weight, from 100 µg to 10 mg per kg of body weight, or from 100 µg to 1 mg per kg of body weight.

Those of skill will readily appreciate that dose levels can vary as a function of the specific multimeric polypeptide, the severity of the symptoms and the susceptibility of the subject to side effects. Preferred dosages for a given compound are readily determinable by those of skill in the art by a variety of means.

In some embodiments, multiple doses of a multimeric polypeptide (or a nucleic acid or a recombinant expression vector encoding same) are administered. The frequency of administration of a multimeric polypeptide can vary depending on any of a variety of factors, e.g., severity of the symptoms, etc. For example, in some embodiments, a multimeric polypeptide is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of a multimeric polypeptide, e.g., the period of time over which a multimeric polypeptide is administered, can vary, depending on any of a variety of factors, e.g., patient response, etc. For example, a multimeric polypeptide can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Dosages—Immune Checkpoint Inhibitor

A suitable dosage of an immune checkpoint inhibitor can be determined by an attending physician or other qualified medical personnel, based on various clinical factors. As is well known in the medical arts, dosages for any one patient depend upon many factors, including the patient's size, body surface area, age, the particular polypeptide or nucleic acid to be administered, sex of the patient, time, and route of administration, general health, and other drugs being administered concurrently. An immune checkpoint inhibitor may be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 μg to 10 mg per kilogram of body weight per minute. An immune checkpoint inhibitor can be administered in an amount of from about 1 mg/kg body weight to 50 mg/kg body weight, e.g., from about 1 mg/kg body weight to about 5 mg/kg body weight, from about 5 mg/kg body weight to about 10 mg/kg body weight, from about 10 mg/kg body weight to about 15 mg/kg body weight, from about 15 mg/kg body weight to about 20 mg/kg body weight, from about 20 mg/kg body weight to about 25 mg/kg body weight, from about 25 mg/kg body weight to about 30 mg/kg body weight, from about 30 mg/kg body weight to about 35 mg/kg body weight, from about 35 mg/kg body weight to about 40 mg/kg body weight, or from about 40 mg/kg body weight to about 50 mg/kg body weight.

In some cases, a suitable dose of an immune checkpoint inhibitor is from 0.01 μg to 100 g per kg of body weight, from 0.1 μg to 10 g per kg of body weight, from 1 μg to 1 g per kg of body weight, from 10 μg to 100 mg per kg of body weight, from 100 μg to 10 mg per kg of body weight, or from 100 μg to 1 mg per kg of body weight. Persons of ordinary skill in the art can easily estimate repetition rates for dosing based on measured residence times and concentrations of the administered agent in bodily fluids or tissues. Following successful treatment, it may be desirable to have the patient undergo maintenance therapy to prevent the recurrence of the disease state, wherein an immune checkpoint inhibitor is administered in maintenance doses, ranging from 0.01 μg to 100 g per kg of body weight, from 0.1 μg to 10 g per kg of body weight, from 1 μg to 1 g per kg of body weight, from 10 μg to 100 mg per kg of body weight, from 100 g to 10 mg per kg of body weight, or from 100 μg to 1 mg per kg of body weight.

Those of skill will readily appreciate that dose levels can vary as a function of the specific immune checkpoint inhibitor, the severity of the symptoms and the susceptibility of the subject to side effects. Preferred dosages for a given compound are readily determinable by those of skill in the art by a variety of means.

In some embodiments, multiple doses of an immune checkpoint inhibitor are administered. The frequency of administration an immune checkpoint inhibitor can vary depending on any of a variety of factors, e.g., severity of the symptoms, etc. For example, in some embodiments, a multimeric polypeptide is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of an immune checkpoint inhibitor, e.g., the period of time over which an immune checkpoint inhibitor is administered, can vary, depending on any of a variety of factors, e.g., patient response, etc. For example, an immune checkpoint inhibitor can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

The following are non-limiting examples.

Pembrolizumab can be administered to an individual in need thereof in an amount of 2 mg/kg every 3 weeks. Pembrolizumab can be administered to an individual in need thereof in an amount of 200 mg every 3 weeks. In some cases, a method of the present disclosure provides for a reduced amount of an anti-PD1 that needs to be administered to achieve clinical benefit. For example, in some cases, the amount of pembrolizumab that needs to be administered to achieve clinical benefit can be reduced by from 10% to 50%, or more than 50%, compared to the amount of pembrolizumab that needs to be administered to achieve clinical benefit in the absence of treatment with a synTac.

Nivolumab can be administered to an individual in need thereof in an amount of 3 mg/kg every 2 weeks. Nivolumab can be administered to an individual in need thereof in an amount of 240 mg every 2 weeks. In some cases, a method of the present disclosure provides for a reduced amount of an anti-PD1 that needs to be administered to achieve clinical benefit. For example, in some cases, the amount of nivolumab that needs to be administered to achieve clinical benefit can be reduced by from 10% to 50%, or more than 50%, compared to the amount of nivolumab that needs to be administered to achieve clinical benefit in the absence of treatment with a synTac.

Atezolizumab can be administered to an individual in need thereof in an amount of 1200 mg every 3 weeks. In some cases, a method of the present disclosure provides for a reduced amount of an anti-PD1 that needs to be administered to achieve clinical benefit. For example, in some cases, the amount of atezolizumab that needs to be administered to achieve clinical benefit can be reduced by from 10% to 50%, or more than 50%, compared to the amount of atezolizumab that needs to be administered to achieve clinical benefit in the absence of treatment with a synTac.

Ipilimumab can be administered to an individual in need thereof in an amount of 3 mg/kg every 3 weeks. Ipilimumab can be administered to an individual in need thereof in an amount of 10 mg/kg every 3 weeks. Ipilimumab can be administered to an individual in need thereof in an amount of 10 mg/kg every 12 weeks. In some cases, a method of the present disclosure provides for a reduced amount of an anti-PD1 that needs to be administered to achieve clinical benefit. For example, in some cases, the amount of ipilimumab that needs to be administered to achieve clinical benefit can be reduced by from 10% to 50%, or more than 50%, compared to the amount of ipilimumab that needs to be administered to achieve clinical benefit in the absence of treatment with a synTac.

Routes of Administration

An active agent (a multimeric polypeptide; an immune checkpoint inhibitor) is administered to an individual using any available method and route suitable for drug delivery, including in vivo and ex vivo methods, as well as systemic and localized routes of administration. In some cases, a synTac is administered by a first route of administration; and an immune checkpoint inhibitor is administered by a second route of administration that is different from the first route of administration. In some cases, a synTac and an immune checkpoint inhibitor are administered by the same routes of administration.

Conventional and pharmaceutically acceptable routes of administration include intratumoral, peritumoral, intramuscular, intratracheal, intracranial, subcutaneous, intradermal, topical application, intravenous, intraarterial, rectal, nasal, oral, and other enteral and parenteral routes of administration. Routes of administration may be combined, if desired, or adjusted depending upon the multimeric polypeptide, the immune checkpoint inhibitor and/or the desired effect.

In some cases, a multimeric polypeptide is administered intravenously; and an immune checkpoint inhibitor intravenously. In some cases, a multimeric polypeptide is administered intramuscularly; and an immune checkpoint inhibitor intramuscularly. In some cases, a multimeric polypeptide is administered locally; and an immune checkpoint inhibitor locally. In some cases, a multimeric polypeptide is administered intratumorally; and an immune checkpoint inhibitor intratumorally. In some cases, a multimeric polypeptide is administered peritumorally; and an immune checkpoint inhibitor peritumorally. In some cases, a multimeric polypeptide is administered intracranially; and an immune checkpoint inhibitor intracranially. In some cases, a multimeric polypeptide is administered subcutaneously; and an immune checkpoint inhibitor subcutaneously.

In some cases, a multimeric polypeptide is administered intravenously; and an immune checkpoint inhibitor peritumorally. In some cases, a multimeric polypeptide is administered intramuscularly; and an immune checkpoint inhibitor intravenously. In some cases, a multimeric polypeptide is administered systemically; and an immune checkpoint inhibitor locally. In some cases, a multimeric polypeptide is administered intratumorally; and an immune checkpoint inhibitor intravenously. In some cases, a multimeric polypeptide is administered systemically; and an immune checkpoint inhibitor peritumorally. In some cases, a multimeric polypeptide is administered intravenously; and an immune checkpoint inhibitor intracranially. In some cases, a multimeric polypeptide is administered subcutaneously; and an immune checkpoint inhibitor intravenously.

A multimeric polypeptide and an immune checkpoint inhibitor can be administered to a host using any available conventional methods and routes suitable for delivery of conventional drugs, including systemic or localized routes. In general, routes of administration contemplated for use in a method of the present disclosure include, but are not necessarily limited to, enteral, parenteral, and inhalational routes.

Parenteral routes of administration other than inhalation administration include, but are not necessarily limited to, topical, transdermal, subcutaneous, intramuscular, intraorbital, intracapsular, intraspinal, intrasternal, intratumoral, peritumoral, and intravenous routes, i.e., any route of administration other than through the alimentary canal. Parenteral administration can be carried to effect systemic or local delivery of an active agent (a synTac or an immune checkpoint inhibitor). Where systemic delivery is desired, administration can involve intravenous delivery.

Subjects Suitable for Treatment

Subjects suitable for treatment with a method of the present disclosure include individuals who have cancer, including individuals who have been diagnosed as having cancer, individuals who have been treated for cancer but who failed to respond to the treatment, and individuals who have been treated for cancer and who initially responded but subsequently became refractory to the treatment. Subjects suitable for treatment with a method of the present disclosure include individuals who have an infection (e.g., an infection with a pathogen such as a bacterium, a virus, a protozoan, etc.), including individuals who have been diagnosed as having an infection, and individuals who have been treated for an infection but who failed to respond to the treatment. Subjects suitable for treatment with a method of the present disclosure include individuals who have bacterial infection, including individuals who have been diagnosed as having a bacterial infection, and individuals who have been treated for a bacterial infection but who failed to respond to the treatment. Subjects suitable for treatment with a method of the present disclosure include individuals who have a viral infection, including individuals who have been diagnosed as having a viral infection, and individuals who have been treated for a viral infection but who failed to respond to the treatment. Subjects suitable for treatment with a method of the present disclosure include individuals who have an autoimmune disease, including individuals who have been diagnosed as having an autoimmune disease, and individuals who have been treated for a autoimmune disease but who failed to respond to the treatment.

In some cases, a method of the present disclosure comprises administering a synTac to an individual who is undergoing treatment with an immune checkpoint inhibitor. In some cases, a method of the present disclosure comprises administering a synTac to an individual who is undergoing treatment with an anti-PD1 antibody. For example, in some cases, a method of the present disclosure comprises administering a synTac to an individual who is undergoing treatment with pembrolizumab. As another example, in some cases, a method of the present disclosure comprises administering a synTac to an individual who is undergoing treatment with nivolumab. In some cases, a method of the present disclosure comprises administering a synTac to an individual who is undergoing treatment with an anti-PD-L1 antibody. For example, in some cases, a method of the present disclosure comprises administering a synTac to an individual who is undergoing treatment with atezolizumab. In some cases, a method of the present disclosure comprises administering a synTac to an individual who is undergoing treatment with an anti-CTLA4 antibody. For example, in some cases, a method of the present disclosure comprises administering a synTac to an individual who is undergoing treatment with ipilimumab. As another example, in some cases, a method of the present disclosure comprises administering a synTac to an individual who is undergoing treatment with tremelimumab.

In some cases, e.g., where the epitope is an HPV epitope, a subject suitable for treatment with a method of the present disclosure is an individual who has been diagnosed as having an HPV-associated cancer or an HPV-attributable cancer. HPV-associated and HPV-attributable cancers include, e.g., head and neck cancer; cervical cancer; and genitoanal cancer.

Methods of Selectively Delivering a Costimulatory Polypeptide Together with an Immune Checkpoint Inhibitor to an Individual The present disclosure thus provides a method of delivering a costimulatory polypeptide such as IL-2, or a reduced-affinity variant of a naturally occurring costimulatory polypeptide such as an IL-2 variant disclosed herein, to a selected T cell or a selected T cell population, e.g., in a manner such that a TCR specific for a given epitope is targeted, together with co-administration of a checkpoint inhibitor so as to provide the patient with the therapeutic effect of both the selective delivery of the costimulatory polypeptide and the checkpoint inhibitor. The present disclosure provides a method of delivering a costimulatory polypeptide such as IL-2, or a reduced-affinity variant of a naturally occurring costimulatory polypeptide such as an IL-2 variant disclosed herein, selectively to a target T cell bearing a TCR specific for the epitope present in a multimeric polypeptide of the present disclosure, together with co-administration of a checkpoint inhibitor so as to provide the patient with the therapeutic effect of both the selective delivery of the costimulatory polypeptide and the checkpoint inhibitor. The method comprises contacting a population of T cells with a multimeric polypeptide of the present disclosure. The population of T cells can be a mixed population that comprises: i) the target T cell; and ii) non-target T cells that are not specific for the epitope (e.g., T cells that are specific for an epitope(s) other than the epitope to which the epitope-specific T cell binds). The epitope-specific T cell is specific for the epitope-presenting peptide present in the multimeric polypeptide, and binds to the peptide HLA complex or peptide MHC complex provided by the multimeric polypeptide. Contacting the population of T cells with the multimeric polypeptide delivers the costimulatory polypeptide (e.g., IL-2 or a reduced-affinity variant of IL-2) present in the multimeric polypeptide selectively to the T cell(s) that are specific for the epitope present in the multimeric polypeptide. The checkpoint inhibitor is co-administered with the multimeric polypeptide (either together or at different times before and/or after administration of the multimeric polypeptide) so as to provide the patient with the therapeutic effect of both the selective delivery of the costimulatory polypeptide and the checkpoint inhibitor.

Thus, the present disclosure provides a method of delivering to a patient (i) a checkpoint inhibitor as described above and (ii) a costimulatory polypeptide such as IL-2, or a reduced-affinity variant of a naturally occurring costimulatory polypeptide such as an IL-2 variant disclosed herein, or a combination of both, selectively to a target T cell, the method comprising contacting a mixed population of T cells with a multimeric polypeptide of the present disclosure. The mixed population of T cells comprises the target T cell and non-target T cells. The target T cell is specific for the epitope present within the multimeric polypeptide. Contacting the mixed population of T cells with a multimeric polypeptide of the present disclosure delivers the costimulatory polypeptide(s) present within the multimeric polypeptide to the target T cell. The co-administration of the checkpoint inhibitor with the multimeric polypeptide (either together or at different times before and/or after administration of the multimeric polypeptide) thus provides the patient with the therapeutic effect of both the selective delivery of the costimulatory polypeptide and the checkpoint inhibitor.

For example, a multimeric polypeptide of the present disclosure is contacted with a population of T cells comprising: i) a target T cell(s) that is specific for the epitope present in the multimeric polypeptide; and ii) a non-target T cell(s), e.g., a T cell(s) that is specific for a second epitope(s) that is not the epitope present in the multimeric polypeptide. Contacting the population results in selective delivery of the costimulatory polypeptide(s) (e.g., naturally-occurring costimulatory polypeptide (e.g., naturally occurring IL-2) or reduced-affinity variant of a naturally occurring costimulatory polypeptide (e.g., an IL-2 variant disclosed herein)), which is present in the multimeric polypeptide, to the target T cell. Thus, e.g., less than 50%, less than 40%, less than 30%, less than 25%, less than 20%, less than 15%, less than 10%, less than 5%, or less than 4%, 3%, 2% or 1%, of the non-target T cells bind the multimeric polypeptide and, as a result, the costimulatory polypeptide (e.g., IL-2 or IL-2 variant) present in the multimeric polypeptides is substantially not delivered to the non-target T cells. The co-administration of the checkpoint inhibitor with the multimeric polypeptide (either together or at different times before and/or after administration of the multimeric polypeptide) thus provides the patient with the therapeutic effect of both the selective delivery of the costimulatory polypeptide and the checkpoint inhibitor.

In some cases, the population of T cells is in vitro. In some cases, the population of T cells is in vitro, and a biological response (e.g., T cell activation and/or expansion and/or phenotypic differentiation) of the target T cell population to the multimeric polypeptide of the present disclosure is elicited in the context of an in vitro culture. For example, a mixed population of T cells can be obtained from an individual, and can be contacted with the multimeric polypeptide in vitro. Such contacting can comprise single or multiple exposures of the population of T cells to a defined dose(s) and/or exposure schedule(s). In some cases, said contacting results in selectively binding/activating and/or expanding target T cells within the population of T cells, and results in generation of a population of activated and/or expanded target T cells. As an example, a mixed population of T cells can be peripheral blood mononuclear cells (PBMC). For example, PBMC from a patient can be obtained by standard blood drawing and PBMC enrichment techniques before being exposed to 0.1-1000 nM of a multimeric polypeptide of the present disclosure under standard lymphocyte culture conditions. At time points before, during, and after exposure of the mixed T cell population at a defined dose and schedule, the abundance of target T cells in the in vitro culture can be monitored by specific peptide-MHC multimers and/or phenotypic markers and/or functional activity (e.g. cytokine ELISpot assays). In some cases, upon achieving an optimal abundance and/or phenotype of antigen specific cells in vitro, all or a portion of the population of activated and/or expanded target T cells is administered to the individual (the individual from whom the mixed population of T cells was obtained), which individual already has received administration of a checkpoint inhibitor prior to the administration of the target T cells and/or will receive administration of a checkpoint inhibitor after the administration of target T cells.

In some cases, the population of T cells is in vitro. For example, a mixed population of T cells is obtained from an individual, and is contacted with a multimeric polypeptide of the present disclosure in vitro. Such contacting, which can comprise single or multiple exposures of the T cells to a defined dose(s) and/or exposure schedule(s) in the context of in vitro cell culture, can be used to determine whether the mixed population of T cells includes T cells that are specific for the epitope presented by the multimeric polypeptide. The presence of T cells that are specific for the epitope of the multimeric polypeptide can be determined by assaying a sample comprising a mixed population of T cells, which population of T cells comprises T cells that are not specific for the epitope (non-target T cells) and may comprise T cells that are specific for the epitope (target T cells). Known assays can be used to detect activation and/or proliferation of the target T cells, thereby providing an ex vivo assay that can determine whether a particular multimeric polypeptide (synTac) possesses an epitope that binds to T cells present in the individual and thus whether the multimeric polypeptide has potential use as a therapeutic composition for that individual. Suitable known assays for detection of activation and/or proliferation of target T cells include, e.g., flow cytometric characterization of T cell phenotype and/or antigen specificity and/or proliferation. Such an assay to detect the presence of epitope-specific T cells, e.g., a companion diagnostic, can further include additional assays (e.g. effector cytokine ELISpot assays) and/or appropriate controls (e.g. antigen-specific and antigen-nonspecific multimeric peptide-HLA staining reagents) to determine whether the multimeric polypeptide is selectively binding/activating and/or expanding the target T cell. Thus, for example, the present disclosure provides a method of detecting, in a mixed population of T cells obtained from an individual, the presence of a target T cell that binds an epitope of interest, the method comprising: a) contacting in vitro the mixed population of T cells with a multimeric polypeptide of the present disclosure, wherein the multimeric polypeptide comprises the epitope of interest; and b) detecting activation and/or proliferation of T cells in response to said contacting, wherein activated and/or proliferated T cells indicates the presence of the target T cell. Alternatively, and/or in addition, if activation and/or expansion (proliferation) of the desired T cell population is obtained using the multimeric polypeptide, then all or a portion of the population of T cells comprising the activated/expanded T cells can be administered back to the individual (who has received administration of a checkpoint inhibitor before administration of the T cells and/or will receive administration of a checkpoint inhibitor after administration of the T cells) as a therapy.

In some instances, the population of T cells is in vivo in an individual. In such instances, a method of the present disclosure for selectively delivering a costimulatory polypeptide (e.g., IL-2 or a reduced-affinity IL-2) to an epitope-specific T cell comprises administering the multimeric polypeptide to the individual.

The epitope-specific T cell to which a costimulatory polypeptide (e.g., IL-2 or a reduced-affinity IL-2) is being selectively delivered is also referred to herein as a "target T cell." In some cases, the target T cell is a regulatory T cell (Treg). In some cases, the Treg inhibits or suppresses activity of an autoreactive T cell.

In some cases, the target T cell is a cytotoxic T cell. For example, the target T cell can be a cytotoxic T cell specific for a cancer epitope (e.g., an epitope presented by a cancer cell).

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure designated Aspects 1-122, Aspects A-Z, Aspects AA-ZZ, and Aspects AAA-BBB, are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A variant IL-2 polypeptide comprising an amino acid sequence having at least 85% amino acid sequence identity to set forth in SEQ ID NO:1, wherein the variant IL-2 polypeptide has one or more amino acid substitutions relative to set forth in SEQ ID NO:1, and wherein the variant IL-2 polypeptide exhibits reduced binding affinity to an IL-2 receptor (IL2R) comprising alpha, beta, and gamma polypeptides having amino acid sequences depicted in FIG. 3A-3C, compared to the binding affinity of the IL-2 amino acid sequence set forth in one of SEQ ID NO:1 for the IL2R.

Aspect 2. The variant IL2 polypeptide of aspect 1, wherein the variant comprises a substitution of one or more of E15, H16, D20, F42, Y45, and Q126.

Aspect 3. The variant IL2 polypeptide of aspect 1 or aspect 2, wherein the variant immunomodulatory polypeptide exhibits from less than 10% to less than 50% of the binding affinity exhibited by the IL2 amino acid sequence set forth in SEQ ID NO:1 for the IL2R.

Aspect 4. The variant IL2 polypeptide of any one of aspects 1-3, wherein the variant comprises substitutions of F42 with Ala, Gly, Val, Ile, or Leu.

Aspect 5. The variant IL2 polypeptide of any one of aspects 1-3, wherein the variant comprises substitutions of F42 and D20.

Aspect 6. The variant IL2 polypeptide of any one of aspects 1-3, wherein the variant comprises substitutions of F42 and H16.

Aspect 7. The variant IL2 polypeptide of any one of aspects 1-3, wherein the variant comprises substitutions of F42, D20, and Y45; or wherein the variant comprises substitutions of F42, H16, and Q126.

Aspect 8. A multimeric polypeptide comprising:
a) a first polypeptide comprising, in order from N-terminus to C-terminus:
  i) an epitope;
  ii) a first major histocompatibility complex (MHC) polypeptide; and
b) a second polypeptide comprising, in order from N-terminus to C-terminus:
  i) a second MHC polypeptide; and
  ii) optionally an immunoglobulin (Ig) Fc polypeptide or a non-Ig scaffold,
wherein the multimeric polypeptide comprises one or more immunomodulatory domains, wherein the one or more immunomodulatory domain is:
  A) at the C-terminus of the first polypeptide;
  B) at the N-terminus of the second polypeptide;
  C) at the C-terminus of the second polypeptide; or
  D) at the C-terminus of the first polypeptide and at the N-terminus of the second polypeptide, wherein at least one of the one or more immunomodulatory domains is a variant IL2 polypeptide of any one of aspects 1-7, and wherein the multimeric polypeptide exhibits reduced binding affinity to an IL-2 receptor (IL2R) comprising alpha, beta, and gamma polypeptides having amino acid sequences depicted in FIG. 3A-3C, compared to the binding affinity of a control multimeric polypeptide comprising the IL2 amino acid sequence set forth in SEQ ID NO:1 for the IL2R polypeptide.

Aspect 9. The multimeric polypeptide of aspect 8, wherein:

a) the first polypeptide comprises, in order from N-terminus to C-terminus:
i) the epitope;
ii) the first MHC polypeptide; and
iii) the variant IL2 polypeptide; and b) the second polypeptide comprises, in order from N-terminus to C-terminus:
i) the second MHC polypeptide; and
ii) the Ig Fc polypeptide.

Aspect 10. The multimeric polypeptide of aspect 8, wherein:

a) the first polypeptide comprises, in order from N-terminus to C-terminus:
i) the epitope; and
ii) the first MHC polypeptide; and b) the second polypeptide comprises, in order from N-terminus to C-terminus:
i) the variant IL2 polypeptide;
ii) the second MHC polypeptide; and
iii) the Ig Fc polypeptide.

Aspect 11. The multimeric polypeptide of aspect 8, wherein:

a) the first polypeptide comprises, in order from N-terminus to C-terminus:
i) the epitope; and
ii) the first MHC polypeptide; and b) the second polypeptide comprises, in order from N-terminus to C-terminus:
i) the second MHC polypeptide; and
ii) the variant IL2 polypeptide.

Aspect 12. The multimeric polypeptide of aspect 8, wherein:

a) the first polypeptide comprises, in order from N-terminus to C-terminus:
i) the epitope; and
ii) the first MHC polypeptide; and b) second polypeptide comprising, in order from N-terminus to C-terminus:
i) the variant IL2 polypeptide; and
ii) the second MHC polypeptide.

Aspect 13. The multimeric polypeptide of aspect 8, wherein:

a) the first polypeptide comprises, in order from N-terminus to C-terminus:
i) the epitope;
ii) the first MHC polypeptide; and
iii) the variant IL2 polypeptide; and b) the second polypeptide comprises the second MHC polypeptide.

Aspect 14. The multimeric polypeptide of aspect 8, wherein the non-Ig scaffold is an XTEN polypeptide, a transferrin polypeptide, an elastin-like polypeptide, a silk-like polypeptide, or a silk-elastin-like polypeptide.

Aspect 15. The multimeric polypeptide of any one of aspects 8-14, wherein the first MHC polypeptide is a β2-microglobulin polypeptide; and wherein the second MHC polypeptide is an MHC class I heavy chain polypeptide.

Aspect 16. The multimeric polypeptide of aspect 15, wherein the β2-microglobulin polypeptide comprises an amino acid sequence having at least 85% amino acid sequence identity to one of the amino acid sequences set forth in FIG. 6.

Aspect 17. The multimeric polypeptide of aspect 15, wherein the MHC class I heavy chain polypeptide is an HLA-A, an HLA-B, or an HLA-C heavy chain.

Aspect 18. The multimeric polypeptide of aspect 15, wherein the MHC class I heavy chain polypeptide comprises an amino acid sequence having at least 85% amino acid sequence identity to the amino acid sequence set forth in one of FIG. 5A-5C.

Aspect 19. The multimeric polypeptide of any one of aspects 8-14, wherein the first MHC polypeptide is an MHC Class II alpha chain polypeptide; and wherein the second MHC polypeptide is an MHC class II beta chain polypeptide.

Aspect 20. The multimeric polypeptide of any one of aspects 8-19, wherein the epitope is a T-cell epitope.

Aspect 21. The multimeric polypeptide of any one of aspects 8-13 and 15-20, wherein multimeric polypeptide comprises an Fc polypeptide, and wherein the Ig Fc polypeptide is an IgG1 Fc polypeptide, an IgG2 Fc polypeptide, an IgG3 Fc polypeptide, an IgG4 Fc polypeptide, an IgA Fc polypeptide, or an IgM Fc polypeptide.

Aspect 22. The multimeric polypeptide of aspect 21, wherein the Ig Fc polypeptide comprises an amino acid sequence having at least 85% amino acid sequence identity to an amino acid sequence depicted in FIG. 4A-4C.

Aspect 23. The multimeric polypeptide of any one of aspects 8-22, wherein the first polypeptide and the second polypeptide are non-covalently associated.

Aspect 24. The multimeric polypeptide of any one of aspects 8-22, wherein the first polypeptide and the second polypeptide are covalently linked to one another.

Aspect 25. The multimeric polypeptide of aspect 24, wherein the covalent linkage is via a disulfide bond.

Aspect 26. The multimeric polypeptide of aspect 25, wherein the first MHC polypeptide or a linker between the epitope and the first MHC polypeptide comprises an amino acid substitution to provide a first Cys residue, and the second MHC polypeptide comprises an amino acid substitution to provide a second Cys residue, and wherein the disulfide linkage is between the first and the second Cys residues.

Aspect 27. The multimeric polypeptide of any one of aspects 8-26, comprising a linker interposed between the epitope and the first MHC polypeptide.

Aspect 28. The multimeric polypeptide of any one of aspects 8-26, comprising a linker interposed between the MHC polypeptide and the immunomodulatory polypeptide.

Aspect 29. The multimeric polypeptide of any one of aspects 8-28, comprising 2 variant IL2 polypeptides.

Aspect 30. The multimeric polypeptide of any one of aspects 8-28, comprising 3 variant IL2 polypeptides.

Aspect 31. The multimeric polypeptide of aspect 29 or aspect 30, wherein the 2 or 3 variant IL2 polypeptides are in tandem, and wherein the multimeric polypeptide comprises a linker between the variant IL2 polypeptides.

Aspect 32. The multimeric polypeptide of any one of aspects 8-28, wherein the variant IL2 comprises a substitution of one or more of E15, H16, D20, F42, Y45, and Q126.

Aspect 33. The multimeric polypeptide of any one of aspects 8-28, wherein the variant IL2 comprises a substitution of F42 with Ala, Gly, Val, Ile, or Leu.

Aspect 34. The multimeric polypeptide of aspect 33, wherein the variant IL2 comprises substitutions of F42 and D20.

Aspect 35. The multimeric polypeptide of aspect 33, wherein the variant IL2 comprises substitutions of F42 and H16.

Aspect 36. The multimeric polypeptide of aspect 33, wherein the variant IL2 comprises substitutions of F42, D20, and Y45; or wherein the variant IL-2 comprising substitutions of F42, H16, and Q126.

Aspect 37. A nucleic acid comprising a nucleotide sequence encoding a recombinant polypeptide,
  i) wherein the recombinant polypeptide comprises, in order from N-terminus to C-terminus:
    a) an epitope;
    b) a first major histocompatibility complex (MHC) polypeptide;
    c) an immunomodulatory polypeptide;
    d) a proteolytically cleavable linker or a ribosome skipping signal;
    e) a second MHC polypeptide; and
    f) an immunoglobulin (Ig) Fc polypeptide;
  wherein the immunomodulatory polypeptide is a variant immunomodulatory polypeptide of any one of aspects 1-7; or
  ii) wherein the recombinant polypeptide comprises, in order from N-terminus to C-terminus:
    a) an epitope;
    b) a first MHC polypeptide;
    c) a proteolytically cleavable linker or a ribosome skipping signal;
    d) an immunomodulatory polypeptide
    e) a second MHC polypeptide; and
    f) an Ig Fc polypeptide,
  wherein the immunomodulatory polypeptide is a variant immunomodulatory polypeptide of any one of aspects 1-7.

Aspect 38. The nucleic acid of aspect 37, wherein the first MHC polypeptide is a β2-microglobulin polypeptide; and wherein the second MHC polypeptide is an MHC class I heavy chain polypeptide.

Aspect 39. The nucleic acid of aspect 38, wherein the β2-microglobulin polypeptide comprises an amino acid sequence having at least 85% amino acid sequence identity to one of the amino acid sequences set forth in FIG. 6.

Aspect 40. The nucleic acid of aspect 38, wherein the MHC class I heavy chain polypeptide is an HLA-A, HLA-B, or HLA-C heavy chain.

Aspect 41. The nucleic acid of aspect 40, wherein the MHC class I heavy chain polypeptide comprises an amino acid sequence having at least 85% amino acid sequence identity to the amino acid sequence set forth in any one of FIG. 5A-5C.

Aspect 42. The nucleic acid of aspect 37, wherein the first MHC polypeptide is an MHC Class II alpha chain polypeptide; and wherein the second MHC polypeptide is an MHC class II beta chain polypeptide.

Aspect 43. The nucleic acid of any one of aspects 37-43, wherein the epitope is a T-cell epitope.

Aspect 44. The nucleic acid of any one of aspects 37-43, wherein the Ig Fc polypeptide is an IgG1 Fc polypeptide, an IgG2 Fc polypeptide, an IgG3 Fc polypeptide, an IgG4 Fc polypeptide, an IgA Fc polypeptide, or an IgM Fc polypeptide.

Aspect 45. The nucleic acid of aspect 44, wherein the Ig Fc polypeptide comprises an amino acid sequence having at least 85% amino acid sequence identity to an amino acid sequence depicted in FIGS. 4A-4C.

Aspect 46. The nucleic acid of any one of aspects 37-45, wherein the variant IL2 immunomodulatory polypeptide comprises a substitution of one or more of E15, H16, D20, F42, Y45, and Q126.

Aspect 47. The nucleic acid of any one of aspects 37-46, wherein the multimeric polypeptide comprises a second immunomodulatory polypeptide selected from a CD7, CD30L, CD40, CD70, CD83, HLA-G, MICA, MICB, HVEM, lymphotoxin beta receptor, 3/TR6, ILT3, ILT4, and HVEM.

Aspect 48. The nucleic acid of any one of aspects 37-47, wherein the proteolytically cleavable linker or ribosome skipping signal comprises an amino acid sequence selected from:
  a)

(SEQ ID NO: 88)
                    LEVLFQGP;

b)

(SEQ ID NO: 90)
                    ENLYTQS;

c) a furin cleavage site;
  d)

(SEQ ID NO: 89)
                    LVPR;

e)

(SEQ ID NO: 91)
          GSGATNFSLLKQAGDVEENPGP;

f)

(SEQ ID NO: 92)
          GSGEGRGSLLTCGDVEENPGP;

g)

(SEQ ID NO: 93)
          GSGQCTNYALLKLAGDVESNPGP;

and
  h)

(SEQ ID NO: 94)
          GSGVKQTLNFDLLKLAGDVESNPGP.

Aspect 49. The nucleic acid of aspect 31, wherein the recombinant polypeptide comprises, in order from N-terminus to C-terminus:
  a) a first leader peptide;
  b) the epitope;
  c) the first MHC polypeptide;
  d) the immunomodulatory polypeptide;
  e) the proteolytically cleavable linker or ribosome skipping signal;
  f) a second leader peptide;
  g) the second MHC polypeptide; and
  h) the immunoglobulin (Ig) Fc polypeptide.

Aspect 50. The nucleic acid of aspect 49, wherein the first leader peptide and the second leader peptide is a β2-M leader peptide.

Aspect 51. The nucleic acid of any one of aspects 37-50, wherein the nucleotide sequence is operably linked to a transcriptional control element.

Aspect 52. The nucleic acid of aspect 51, wherein the transcriptional control element is a promoter that is functional in a eukaryotic cell.

Aspect 53. The nucleic acid of any one of aspects 37-52, wherein the first MHC polypeptide or a linker between the epitope and the first MHC polypeptide comprises an amino acid substitution to provide a first Cys residue, and the second MHC polypeptide comprises an amino acid substitution to provide a second Cys residue, and wherein the first and the second Cys residues provide for a disulfide linkage between the first MHC polypeptide and the second MHC polypeptide.

Aspect 54. A recombinant expression vector comprising the nucleic acid of any one of aspects 37-52.

Aspect 55. The recombinant expression vector of aspect 54, wherein the vector is a viral vector or a non-viral vector.

Aspect 56. A host cell genetically modified with the recombinant expression vector of aspect 48-55.

Aspect 57. The host cell of aspect 56, wherein the host cell is in vitro.

Aspect 58. The host cell of aspect 57, wherein the host cell is genetically modified such that the cell does not produce an endogenous MHC β2-microglobulin polypeptide.

Aspect 59. A composition comprising:
  a) a first nucleic acid comprising a nucleotide sequence encoding a first polypeptide comprising, in order from N-terminus to C-terminus:
    i) an epitope;
    ii) a first MHC polypeptide; and
    iii) an immunomodulatory domain,
  wherein the immunomodulatory domain is a variant IL2 polypeptide of any one of aspects 1-7; and
  b) a first nucleic acid comprising a nucleotide sequence encoding a second polypeptide comprising, in order from N-terminus to C-terminus:
    i) a second MHC polypeptide; and
    ii) an Ig Fc polypeptide.

Aspect 60. A composition comprising:
  a) a first nucleic acid comprising a nucleotide sequence encoding a first polypeptide comprising, in order from N-terminus to C-terminus:
    i) an epitope; and
    ii) a first MHC polypeptide; and
  b) a first nucleic acid comprising a nucleotide sequence encoding a second polypeptide comprising, in order from N-terminus to C-terminus:
    i) an immunomodulatory domain, wherein the immunomodulatory domain is a variant IL2 polypeptide of any one of aspects 1-7;
    ii) a second MHC polypeptide; and
    iii) an Ig Fc polypeptide.

Aspect 61. The composition of aspect 59 or aspect 60, wherein the first and/or the second nucleic acid is present in a recombinant expression vector.

Aspect 62. A host cell genetically modified with the composition of any one of aspects 59-61.

Aspect 63. A method of producing the multimeric polypeptide of any one of aspects 8-36, the method comprising:
  a) culturing the host cell of any one of aspects 56-58 and 62 in vitro in a culture medium under conditions such that the host cell synthesizes the multimeric polypeptide; and
  b) isolating the multimeric polypeptide from the host cell and/or from the culture medium.

Aspect 64. The method of aspect 63, wherein the second polypeptide comprises an affinity tag, and wherein said isolating comprises contacting the multimeric polypeptide produced by the cell with a binding partner for the affinity tag, wherein the binding partner is immobilized, thereby immobilizing the multimeric polypeptide.

Aspect 65. The method of aspect 64, comprising eluting the immobilized multimeric polypeptide.

Aspect 66. A method of selectively activating an epitope-specific T cell, the method comprising contacting the T cell with the multimeric polypeptide of any one of aspects 8-36, wherein said contacting selectively activates the epitope-specific T cell.

Aspect 67. The method of aspect 66, wherein said contacting is in vitro.

Aspect 68. The method of aspect 66, wherein said contacting is in vivo.

Aspect 69. The method of aspect 66, wherein the epitope is a cancer-associated epitope, and wherein said administering selectively increases the activity of a T cell specific for the cancer-associate epitope.

Aspect 70. A method of treating cancer in an individual, the method comprising administering to the individual an effective amount of:
  a) the multimeric polypeptide of any one of aspects 8-36; or
  b) one or more recombinant expression vectors comprising nucleotide sequences encoding the multimeric polypeptide of any one of aspects 8-36; or
  c) one or more mRNAs comprising nucleotide sequences encoding the multimeric polypeptide of any one of aspects 8-36,
wherein the epitope is a cancer-associated epitope, and wherein said administering effective to selectively activate a cancer epitope-specific T cell in an individual.

Aspect 71. The method of aspect 70, wherein said administering is subcutaneous.

Aspect 72. The method of aspect 70, wherein said administering is intravenous.

Aspect 73. The method of aspect 70, wherein said administering is peritumoral.

Aspect 74. The method of aspect 70, wherein said administering is systemic.

Aspect 75. The method of aspect 70, wherein said administering is distal to a treatment site.

Aspect 76. The method of aspect 70, wherein said administering is local.

Aspect 77. The method of aspect 70, wherein said administering is at or near a treatment site.

Aspect 78. A composition comprising:
  a) the multimeric polypeptide of any one of aspects 8-36; and
  b) a pharmaceutically acceptable excipient.

Aspect 79. A composition comprising:
  a) the nucleic acid of any one of aspects 37-53 or the recombinant expression vector of aspect 54 or 55; and
  b) a pharmaceutically acceptable excipient.

Aspect 80. A multimeric polypeptide comprising:
  a) a first polypeptide comprising, in order from N-terminus to C-terminus:
    i) an epitope;
    ii) a β2-microglobulin (β2M) polypeptide comprising the amino acid sequence depicted in FIG. 34A; and
  b) a second polypeptide comprising, in order from N-terminus to C-terminus:

i) a variant IL-2 polypeptide of any one of aspects 1-7;
ii) a major histocompatibility complex (MHC) heavy chain polypeptide comprising the amino acid sequence depicted in FIG. 34C; and
iii) an IgG1 Fc polypeptide comprising one or more amino acid substitutions selected from N297A, L234A, L235A, L234F, L235E, and P331S (N77A, L14A, L15A, L14F, L15E, and P111S, respectively, based on the amino acid numbering depicted in FIG. 33A).

Aspect 81. The multimeric polypeptide of aspect 80, wherein the IgG1 Fc polypeptide comprises an N297A substitution (N77A based on the amino acid numbering depicted in FIG. 33A).

Aspect 82. The multimeric polypeptide of aspect 80, wherein the IgG1 Fc polypeptide comprises an L234A substitution and an L235A substitution (L14A and L15A based on the amino acid numbering depicted in FIG. 33A).

Aspect 83. The multimeric polypeptide of aspect 80, wherein the IgG1 Fc polypeptide comprises an L234F substitution and an L235E substitution (L14F and L15E based on the amino acid numbering depicted in FIG. 33A).

Aspect 84. The multimeric polypeptide of aspect 80, wherein the IgG1 Fc polypeptide comprises an L234F substitution, an L235E substitution, and a P331S (L14F, L15E, and P111S substitutions based on the amino acid numbering depicted in FIG. 33A).

Aspect 85. The multimeric polypeptide of any one of aspects 80-84, wherein the second polypeptide comprises two copies of the variant IL-2 polypeptide.

Aspect 86. The multimeric polypeptide of any one of aspects 80-85, wherein the first polypeptide comprises a peptide linker between the epitope and the β2M polypeptide.

Aspect 87. The multimeric polypeptide of any one of aspects 80-86, wherein the second polypeptide comprises a peptide linker between one or more of:
a) a first copy of the variant IL-2 polypeptide and a second copy of the variant IL-2 polypeptide;
b) the variant IL-2 polypeptide and the MHC heavy chain polypeptide; and
c) between the MHC heavy chain polypeptide and the IgG1 Fc polypeptide.

Aspect 88. The multimeric polypeptide of aspect 86 or aspect 87, wherein the peptide linker is selected from (GGGGS)$_3$, (GGGGS)$_4$, and AAAGG.

Aspect 89. A multimeric polypeptide comprising:
a) a first polypeptide comprising, in order from N-terminus to C-terminus:
i) an epitope;
ii) a β2-microglobulin polypeptide comprising the amino acid sequence depicted in FIG. 34A; and
b) a second polypeptide comprising, in order from N-terminus to C-terminus:
i) a variant IL-2 polypeptide comprising the amino acid sequence depicted in FIG. 34B;
ii) a major histocompatibility complex (MHC) heavy chain polypeptide comprising the amino acid sequence depicted in FIG. 34C; and
iii) an IgG1 Fc polypeptide comprising one or more amino acid substitutions selected from N297A, L234A, L235A, L234F, L235E, and P331S (N77A, L14A, L15A, L14F, L15E, and P111S, respectively, based on the amino acid numbering depicted in FIG. 33A).

Aspect 90. The multimeric polypeptide of aspect 89, wherein the IgG1 Fc polypeptide comprises an N297A substitution (N77A based on the amino acid numbering depicted in FIG. 33A).

Aspect 91. The multimeric polypeptide of aspect 89, wherein the IgG1 Fc polypeptide comprises an L234A substitution and an L235A substitution (L14A and L15A based on the amino acid numbering depicted in FIG. 33A).

Aspect 92. The multimeric polypeptide of aspect 89, wherein the IgG1 Fc polypeptide comprises an L234F substitution and an L235E substitution (L14F and L15E based on the amino acid numbering depicted in FIG. 33A).

Aspect 93. The multimeric polypeptide of aspect 89, wherein the IgG1 Fc polypeptide comprises an L234F substitution, an L235E substitution, and a P331S substitution (L14F, L15E, and P111S based on the amino acid numbering depicted in FIG. 33A).

Aspect 94. The multimeric polypeptide of any one of aspects 89-93, wherein the second polypeptide comprises two copies of the variant IL-2 polypeptide.

Aspect 95. The multimeric polypeptide of any one of aspects 89-94, wherein the first polypeptide comprises a peptide linker between the epitope and the β2M polypeptide.

Aspect 96. The multimeric polypeptide of any one of aspects 89-95, wherein the second polypeptide comprises a peptide linker between one or more of:
a) a first copy of the variant IL-2 polypeptide and a second copy of the variant IL-2 polypeptide;
b) the variant IL-2 polypeptide and the MHC heavy chain polypeptide; and
c) between the MHC heavy chain polypeptide and the IgG1 Fc polypeptide.

Aspect 97. The multimeric polypeptide of aspect 95 or aspect 96, wherein the peptide linker is selected from (GGGGS)$_3$, (GGGGS)$_4$, and AAAGG.

Aspect 98. A multimeric polypeptide comprising:
a) a first polypeptide comprising, in order from N-terminus to C-terminus:
i) an epitope comprising the amino acid sequence YMLDLQPETT (SEQ ID NO:77);
ii) a β2-microglobulin polypeptide comprising the amino acid sequence depicted in FIG. 34A; and
b) a second polypeptide comprising, in order from N-terminus to C-terminus:
i) a variant IL-2 polypeptide comprising the amino acid sequence depicted in FIG. 34B;
ii) a major histocompatibility complex (MHC) heavy chain polypeptide comprising the amino acid sequence depicted in FIG. 34C; and
iii) an IgG1 Fc polypeptide comprising the amino acid sequence depicted in FIG. 33A, 33B, 33C, or 33D.

Aspect 99. The multimeric polypeptide of aspect 98, wherein the IgG1 Fc polypeptide comprises the amino acid sequence depicted in FIG. 33B.

Aspect 100. The multimeric polypeptide of aspect 98, wherein the IgG1 Fc polypeptide comprises the amino acid sequence depicted in FIG. 33C.

Aspect 101. The multimeric polypeptide of aspect 98, wherein the IgG1 Fc polypeptide comprises the amino acid sequence depicted in FIG. 33D.

Aspect 102. The multimeric polypeptide of any one of aspects 98-101, wherein the second polypeptide comprises two copies of the variant IL-2 polypeptide.

Aspect 103. The multimeric polypeptide of any one of aspects 98-102, wherein the first polypeptide comprises a peptide linker between the epitope and the β2M polypeptide.

Aspect 104. The multimeric polypeptide of any one of aspects 98-103, wherein the second polypeptide comprises a peptide linker between one or more of:
a) a first copy of the variant IL-2 polypeptide and a second copy of the variant IL-2 polypeptide;

b) the variant IL-2 polypeptide and the MHC heavy chain polypeptide; and c) between the MHC heavy chain polypeptide and the IgG1 Fc polypeptide.

Aspect 105. The multimeric polypeptide of aspect 103 or aspect 104, wherein the peptide linker is selected from (GGGGS)$_3$, (GGGGS)$_4$, and AAAGG.

Aspect 106. A multimeric polypeptide comprising:
a) a first polypeptide comprising the amino acid sequence depicted in FIG. 31;
b) a second polypeptide comprising the amino acid sequence depicted in FIG. 22.

Aspect 107. A multimeric polypeptide comprising:
a) a first polypeptide comprising the amino acid sequence depicted in FIG. 31;
b) a second polypeptide comprising the amino acid sequence depicted in FIG. 25.

Aspect 108. A multimeric polypeptide comprising:
a) a first polypeptide comprising the amino acid sequence depicted in FIG. 31;
b) a second polypeptide comprising the amino acid sequence depicted in FIG. 28.

Aspect 109. A pharmaceutical composition comprising:
a) a multimeric polypeptide according to any one of aspects 80-108; and
b) a pharmaceutically acceptable excipient.

Aspect 110. One or more nucleic acids comprising nucleotide sequences encoding the first and/or the second polypeptide of the multimeric polypeptide according to any one of aspects 80-108.

Aspect 111. The one or more nucleic acids of aspect 110, wherein the nucleic acid(s) is/are present in recombinant expression vectors.

Aspect 112. A method of selectively activating an epitope-specific T cell, the method comprising contacting the T cell with the multimeric polypeptide of any one of aspects 80-108, wherein said contacting selectively activates the epitope-specific T cell.

Aspect 113. The method of aspect 112, wherein said contacting is in vitro.

Aspect 114. The method of aspect 112, wherein said contacting is in vivo.

Aspect 115. A method comprising administering to an individual an effective amount of:
a) the multimeric polypeptide of any one of aspects 80-108; or
b) one or more recombinant expression vectors comprising nucleotide sequences encoding the multimeric polypeptide of any one of aspects 80-108; or
c) one or more mRNAs comprising nucleotide sequences encoding the multimeric polypeptide of any one of aspects 80-108, wherein said administering induces a T cell response to epitope in the individual.

Aspect 116. The method of aspect 115, wherein said administering is subcutaneous.

Aspect 117. The method of aspect 115, wherein said administering is intravenous.

Aspect 118. The method of aspect 115, wherein said administering is systemic.

Aspect 119. The method of aspect 115, wherein said administering is intramuscular.

Aspect 120. The method of aspect 115, wherein said administering is distal to a treatment site.

Aspect 121. The method of aspect 115, wherein said administering is local.

Aspect 122. The method of aspect 115, wherein said administering is at or near a treatment site.

Aspect A. A method of modulating an immune response an individual in need thereof, the method comprising administering to the individual a multimeric polypeptide and an immune checkpoint inhibitor,
wherein the multimeric polypeptide comprises:
a) a first polypeptide comprising, in order from N-terminus to C-terminus:
 i) an epitope;
 ii) a first major histocompatibility complex (MHC) polypeptide; and
b) a second polypeptide comprising, in order from N-terminus to C-terminus:
 i) a second MHC polypeptide; and
 ii) optionally an immunoglobulin (Ig) Fc polypeptide or a non-Ig scaffold,
wherein the multimeric polypeptide comprises one or more immunomodulatory polypeptides, wherein the one or more immunomodulatory polypeptides is:
 A) at the C-terminus of the first polypeptide;
 B) at the N-terminus of the second polypeptide;
 C) at the C-terminus of the second polypeptide; or
 D) at the C-terminus of the first polypeptide and at the N-terminus of the second polypeptide; and
wherein said administering modulates the immune response in the individual.

Aspect B. A treatment method comprising administering to an individual a multimeric polypeptide and an immune checkpoint inhibitor,
wherein the multimeric polypeptide comprises:
a) a first polypeptide comprising, in order from N-terminus to C-terminus:
 i) an epitope;
 ii) a first major histocompatibility complex (MHC) polypeptide; and
b) a second polypeptide comprising, in order from N-terminus to C-terminus:
 i) a second MHC polypeptide; and
 ii) optionally an immunoglobulin (Ig) Fc polypeptide or a non-Ig scaffold,
wherein the multimeric polypeptide comprises one or more immunomodulatory polypeptides, wherein the one or more immunomodulatory polypeptides is:
 A) at the C-terminus of the first polypeptide;
 B) at the N-terminus of the second polypeptide;
 C) at the C-terminus of the second polypeptide; or
 D) at the C-terminus of the first polypeptide and at the N-terminus of the second polypeptide; and
wherein said administering treats the individual.

Aspect C. A method of treating cancer in an individual, the method comprising administering to the individual a multimeric polypeptide and an immune checkpoint inhibitor,
wherein the multimeric polypeptide comprises:
a) a first polypeptide comprising, in order from N-terminus to C-terminus:
 i) an epitope;
 ii) a first major histocompatibility complex (MHC) polypeptide; and
b) a second polypeptide comprising, in order from N-terminus to C-terminus:
 i) a second MHC polypeptide; and
 ii) optionally an immunoglobulin (Ig) Fc polypeptide or a non-Ig scaffold,
wherein the multimeric polypeptide comprises one or more immunomodulatory polypeptides, wherein the one or more immunomodulatory polypeptides is:

A) at the C-terminus of the first polypeptide;
B) at the N-terminus of the second polypeptide;
C) at the C-terminus of the second polypeptide; or
D) at the C-terminus of the first polypeptide and at the N-terminus of the second polypeptide; and
wherein said administering treats the cancer in the individual.

Aspect D. A treatment method comprising administering to an individual a multimeric polypeptide, where the individual is undergoing treatment with an immune checkpoint inhibitor,
wherein the multimeric polypeptide comprises:
a) a first polypeptide comprising, in order from N-terminus to C-terminus:
 i) an epitope;
 ii) a first major histocompatibility complex (MHC) polypeptide; and
b) a second polypeptide comprising, in order from N-terminus to C-terminus:
 i) a second MHC polypeptide; and
 ii) optionally an immunoglobulin (Ig) Fc polypeptide or a non-Ig scaffold,
wherein the multimeric polypeptide comprises one or more immunomodulatory polypeptides, wherein the one or more immunomodulatory polypeptides is:
A) at the C-terminus of the first polypeptide;
B) at the N-terminus of the second polypeptide;
C) at the C-terminus of the second polypeptide; or
D) at the C-terminus of the first polypeptide and at the N-terminus of the second polypeptide; and
wherein said administering treats the individual.

Aspect E. The method of any one of Aspects A-D, wherein the multimeric polypeptide comprises:
a) a first polypeptide comprising, in order from N-terminus to C-terminus:
 i) an epitope;
 ii) a first MHC polypeptide; and
 iii) an immunomodulatory domain; and
b) a second polypeptide comprising, in order from N-terminus to C-terminus:
 i) a second MHC polypeptide; and
 ii) an Ig Fc polypeptide.

Aspect F. The method of any one of Aspects A-D, wherein the multimeric polypeptide comprises:
a) a first polypeptide comprising, in order from N-terminus to C-terminus:
 i) an epitope; and
 ii) a first MHC polypeptide; and
b) a second polypeptide comprising, in order from N-terminus to C-terminus:
 i) an immunomodulatory domain;
 iii) a second MHC polypeptide; and
 ii) an immunoglobulin (Ig) Fc polypeptide.

Aspect G. The method of any one of Aspects A-D, wherein the multimeric polypeptide comprises:
a) a first polypeptide comprising, in order from N-terminus to C-terminus:
 i) an epitope; and
 ii) a first MHC polypeptide; and
b) a second polypeptide comprising, in order from N-terminus to C-terminus:
 i) a second MHC polypeptide; and
 ii) an Ig Fc polypeptide; and
 iii) an immunomodulatory domain.

Aspect H. The method of any one of Aspects A-D, wherein the multimeric polypeptide comprises:
a) a first polypeptide comprising, in order from N-terminus to C-terminus:
 i) an epitope; and
 ii) a first MHC polypeptide; and
b) a second polypeptide comprising, in order from N-terminus to C-terminus:
 i) a second MHC polypeptide; and
 ii) an immunomodulatory domain.

Aspect I. The method of any one of Aspects A-D, wherein the multimeric polypeptide comprises:
a) a first polypeptide comprising, in order from N-terminus to C-terminus:
 i) an epitope; and
 ii) a first MHC polypeptide; and
b) a second polypeptide comprising, in order from N-terminus to C-terminus:
 i) an immunomodulatory domain; and
 ii) a second MHC polypeptide.

Aspect J. The method of any one of Aspects A-D, wherein the multimeric polypeptide comprises:
a) a first polypeptide comprising, in order from N-terminus to C-terminus:
 i) an epitope;
 ii) a first MHC polypeptide; and
 iii) an immunomodulatory domain; and
b) a second polypeptide comprising, in order from N-terminus to C-terminus:
 i) a second MHC polypeptide.

Aspect K. The method of any one of Aspects A-D, wherein the non-Ig scaffold of the multimeric polypeptide is an XTEN polypeptide, a transferrin polypeptide, an Fc receptor polypeptide, an elastin-like polypeptide, a silk-like polypeptide, or a silk-elastin-like polypeptide.

Aspect L. The method of any one of aspects A-K, wherein the first MHC polypeptide of the multimeric polypeptide is a β2-microglobulin polypeptide; and wherein the second MHC polypeptide is an MHC class I heavy chain polypeptide.

Aspect M. The method of aspect L, wherein the β2-microglobulin polypeptide of the multimeric polypeptide comprises an amino acid sequence having at least 85% amino acid sequence identity to one of the amino acid sequences set forth in FIG. 6.

Aspect N. The method of aspect L, wherein the MHC class I heavy chain polypeptide of the multimeric polypeptide is an HLA-A, an HLA-B, or an HLA-C heavy chain.

Aspect O. The method of aspect 11, wherein the MHC class I heavy chain polypeptide comprises an amino acid sequence having at least 85% amino acid sequence identity to the amino acid sequence set forth in one of FIG. 5A-5C.

Aspect P. The method of any one of aspects A-K, wherein the first MHC polypeptide of the multimeric polypeptide is an MHC Class II alpha chain polypeptide; and wherein the second MHC polypeptide is an MHC class II beta chain polypeptide.

Aspect Q. The method of any one of aspects A-P, wherein the epitope is a T-cell epitope.

Aspect R. The method of any one of aspects A-J, wherein multimeric polypeptide of the multimeric polypeptide comprises an Fc polypeptide, and wherein the Ig Fc polypeptide is an IgG1 Fc polypeptide, an IgG2 Fc polypeptide, an IgG3 Fc polypeptide, an IgG4 Fc polypeptide, an IgA Fc polypeptide, or an IgM Fc polypeptide.

Aspect S. The method of aspect R, wherein the Ig Fc polypeptide comprises an amino acid sequence having at least 85% amino acid sequence identity to an amino acid sequence depicted in FIG. 4A-4C.

Aspect T. The method of any one of aspects A-S, wherein the first polypeptide and the second polypeptide of the multimeric polypeptide are non-covalently associated.

Aspect U. The method of any one of aspects A-S, wherein the first polypeptide and the second polypeptide of the multimeric polypeptide are covalently linked.

Aspect V. The method of aspect U, wherein the covalent linkage is via a disulfide bond.

Aspect W. The method of aspect V, wherein the first MHC polypeptide or a linker between the epitope and the first MHC polypeptide of the multimeric polypeptide comprises an amino acid substitution to provide a first Cys residue, and the second MHC polypeptide of the multimeric polypeptide comprises an amino acid substitution to provide a second Cys residue, and wherein the disulfide linkage is between the first and the second Cys residues.

Aspect X. The method of any one of aspects A-K, wherein the multimeric polypeptide comprises a linker between the epitope and the first MHC polypeptide, between the immunomodulatory polypeptide and the MHC polypeptide, or between the MHC polypeptide and the Ig Fc.

Aspect Y. The method of any one of aspects A-K, wherein the immunomodulatory polypeptide of the multimeric polypeptide is selected from a 4-1BBL polypeptide, a B7-1 polypeptide; a B7-2 polypeptide, an ICOS-L polypeptide, an OX-40L polypeptide, a CD80 polypeptide, a CD86 polypeptide, a PD-L1 polypeptide, a FasL polypeptide, and a PD-L2 polypeptide.

Aspect Z. The method of any one of aspects A-Y, wherein the multimeric polypeptide comprises 2 or more immunomodulatory polypeptides.

Aspect AA. The method of aspect Z, wherein the 2 or more immunomodulatory polypeptides are in tandem.

Aspect BB. The method of any one of aspects A-Z and AA, wherein the immunomodulatory polypeptide is selected from a 4-1BBL polypeptide, a CD80 polypeptide, a CD86 polypeptide, an IL-2 polypeptide, a B7-1 polypeptide; a B7-2 polypeptide, an ICOS-L polypeptide, an OX-40L polypeptide, a CD86 polypeptide, a PD-L1 polypeptide, a FasL polypeptide, and a PD-L2 polypeptide.

Aspect CC. The method of any one of aspects A-Z and AA-BB, wherein the immunomodulatory polypeptide is a variant immunomodulatory polypeptide has one or more amino acid substitutions relative to the naturally occurring form of the immunomodulatory polypeptide, and wherein the variant immunomodulatory polypeptide exhibits reduced binding affinity to a co-modulatory polypeptide to which the naturally occurring form of the immunomodulatory polypeptide binds.

Aspect DD. The method of any one of aspects A-Z and AA-BB, wherein the immunomodulatory polypeptide is a variant IL-2 polypeptide comprising an amino acid sequence having at least 85% amino acid sequence identity to set forth in SEQ ID NO:1, wherein the variant IL-2 polypeptide has one or more amino acid substitutions relative to set forth in SEQ ID NO:1, and wherein the variant IL-2 polypeptide exhibits reduced binding affinity to an IL-2 receptor (IL2R) comprising alpha, beta, and gamma polypeptides having amino acid sequences depicted in FIG. 3A-3C, compared to the binding affinity of the IL-2 amino acid sequence set forth in one of SEQ ID NO:1 for the IL2R.

Aspect EE. The method of aspect DD, wherein the variant IL-2 polypeptide comprises a substitution of one or more of E15, H16, D20, F42, Y45, and Q126.

Aspect FF. The method of aspect EE, wherein the variant IL-2 polypeptide comprises:
 a) substitutions of F42 and D20;
 b) substitutions of F42 and H16;
 c) substitutions of F42, D20, and Y45; or
 d) substitutions of F42, H16, and Q126.

Aspect GG. The method of any one of aspects A-Z and AA-FF, wherein the multimeric polypeptide comprises an Ig Fc polypeptide comprising one or more amino acid substitutions selected from N297A, L234A, L235A, L234F, L235E, and P331S.

Aspect HH. The method of aspect GG, wherein the Ig Fc polypeptide comprises:
 a) an N297A substitution;
 b) an L234A substitution and an L235A substitution;
 c) an L234F substitution and an L235E substitution; or
 d) an L234F substitution, an L235E substitution, and a P331S substitution.

Aspect II. The method of any one of aspects A-Z and AA-HH, wherein the epitope of the multimeric polypeptide comprises the amino acid sequence YMLDLQPETT (SEQ ID NO:77).

Aspect JJ. The method of any one of aspects A-Z and AA-HH, wherein the β2-microglobulin polypeptide of the multimeric polypeptide comprises the amino acid sequence depicted in FIG. 34A.

Aspect KK. The method of any one of aspects A-Z and AA-JJ, wherein the major histocompatibility complex (MHC) heavy chain polypeptide of the multimeric polypeptide comprises the amino acid sequence depicted in FIG. 34C.

Aspect LL. The method of any one of aspects A-Z and AA-KK, wherein the immune checkpoint inhibitor is an antibody specific for the immune checkpoint inhibitor.

Aspect MM. The method of aspect LL, wherein the antibody is a monoclonal antibody.

Aspect NN. The method of aspect KK or aspect LL, wherein the antibody comprises at least one humanized light chain and/or heavy chain framework region.

Aspect OO. The method of aspect LL, wherein the antibody comprises an Fc polypeptide, and wherein the Ig Fc polypeptide is an IgG1 Fc polypeptide, an IgG2 Fc polypeptide, an IgG3 Fc polypeptide, an IgG4 Fc polypeptide, an IgA Fc polypeptide, or an IgM Fc polypeptide.

Aspect PP. The method of aspect LL, wherein the antibody is an Fv fragment, a nanobody, or a Fab fragment.

Aspect QQ. The method of any one of aspects LL-PP, wherein the immune checkpoint inhibitor is an antibody specific for an immune checkpoint inhibitor selected from CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, CD96, TIGIT, CD122, PD-1, PD-L1 and PD-L2.

Aspect RR. The method of any one of aspects LL-PP, wherein the immune checkpoint inhibitor is an antibody specific for PD1.

Aspect SS. The method of aspect RR, wherein the antibody is pembrolizumab, nivolumab, pidilizumab, or BMS-39886.

Aspect TT. The method of any one of aspects LL-PP, wherein the immune checkpoint inhibitor is an antibody specific for PD-L1.

Aspect UU. The method of aspect TT, wherein the antibody is durvalumab, atezolizumab, KN035, or avelumab.

Aspect VV. The method of any one of aspects LL-PP, wherein the immune checkpoint inhibitor is an antibody specific for CTLA4.

Aspect WW. The method of aspect VV, wherein the antibody is ipilimumab or tremelimumab.

Aspect XX. The method of any one of aspects A-Z and AA-WW, wherein the multimeric polypeptide and the immune checkpoint inhibitor are administered by the same route of administration.

Aspect YY. The method of any one of aspects A-Z and AA-WW, wherein the multimeric polypeptide and the immune checkpoint inhibitor are administered by different routes of administration.

Aspect ZZ. The method of any one of aspects A-Z and AA-YY, wherein the multimeric polypeptide is administered by a route of administration selected from subcutaneous, intravenous, peritumoral, and intramuscular.

Aspect AAA. The method of any one of aspects A-Z and AA-YY, wherein the immune checkpoint inhibitor is administered by a route of administration selected from subcutaneous, intravenous, peritumoral, and intramuscular.

Aspect BBB. The method of any one of aspects A-Z, AA-ZZ, and AAA, wherein the individual is a human.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); kiloDalton(s), kDa; i.m., intramuscular (ly); i.p., intraperitoneal(ly); s.c., subcutaneous(ly); and the like.

Example 1: Production of IL-2/synTac

Figure 7B:
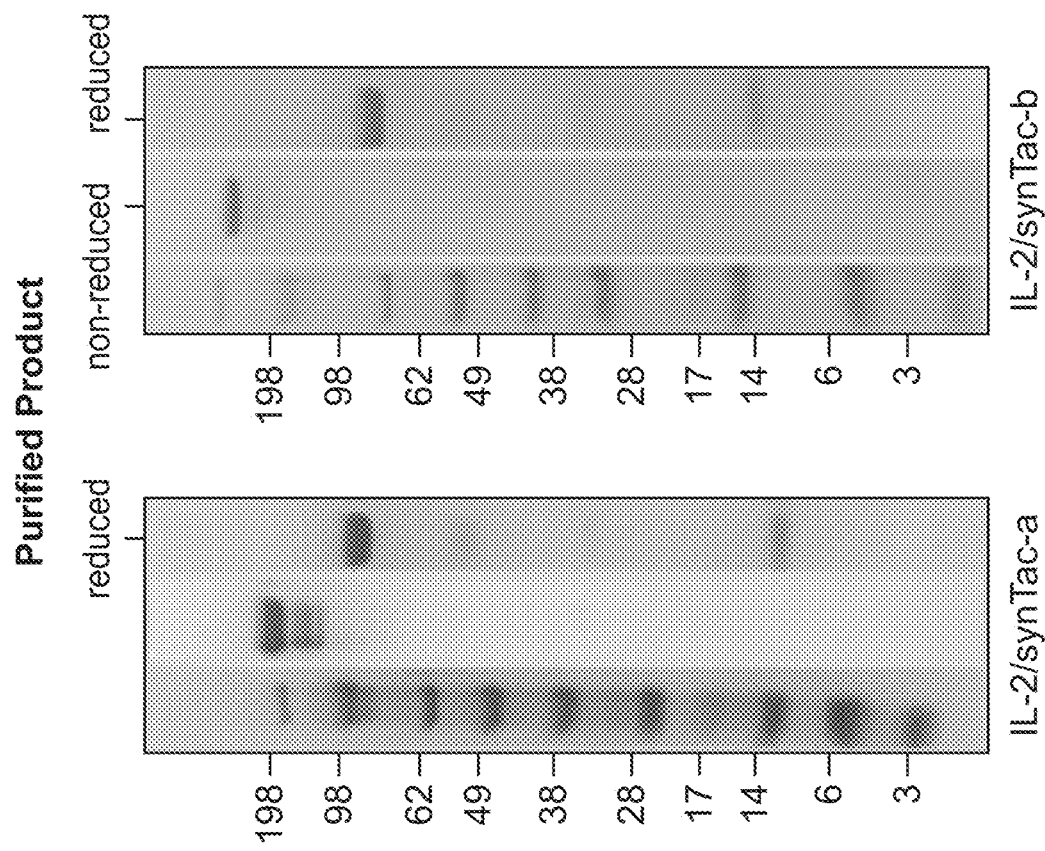
FIG. 7A-7B depict production of IL-2/synTacs ("Cue-IL-2-a" and Cue-IL-2-b") of the present disclosure following transient transfection.
Figure 7A:
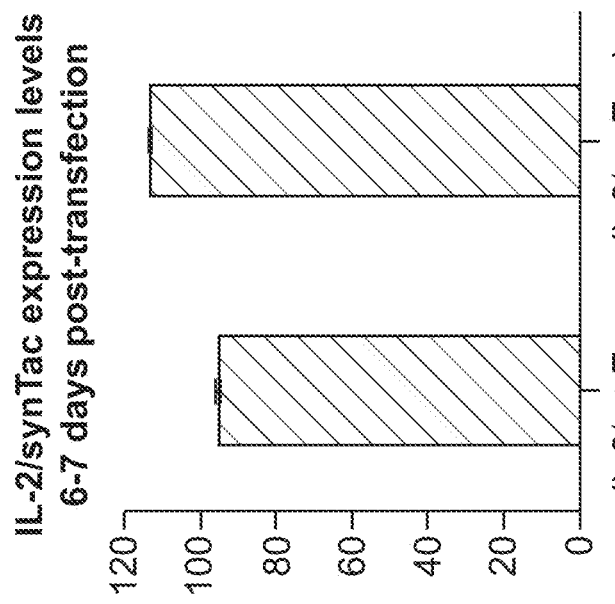

Production of IL-2/synTac by transiently transfected mammalian cells was analyzed. As shown in FIG. 7A, production levels (in mg/L culture medium) of two different IL-2/synTacs, 6-7 days following transient transfection of the cells, was greater than 90 mg/L.

The IL-2/synTacs produced by the mammalian cells was purified, and subjected to reducing and non-reducing polyacrylamide gel electrophoresis. The results are depicted in FIG. 7B. Sizes are given in kDa.

IL-2/synTacs were generated, in which the IL-2 polypeptide was in the "light chain" (i.e., the polypeptide comprising MHC Class I light chain; e.g., β2M) or in the "heavy chain" (i.e., the polypeptide comprising MHC Class I heavy chain). Expression levels and stability of the IL-2/synTacs were analyzed.

The synTacs were produced in mammalian cells. As shown in FIG. 8A, the IL-2/synTac comprising IL-2 on the heavy chain was produced at levels about 25-fold higher than the level of the IL-2/synTac comprising IL-2 on the light chain.

The IL-2/synTacs produced by mammalian cells were subjected to reducing and non-reducing polyacrylamide gel electrophoresis; and the gels were stained with Coomassie blue. As shown in FIG. 8B, the IL-2/synTac comprising IL-2 on the heavy chain was more stable than the IL-2/synTac comprising IL-2 on the light chain. Sizes are given in kDa.

Figure 9:
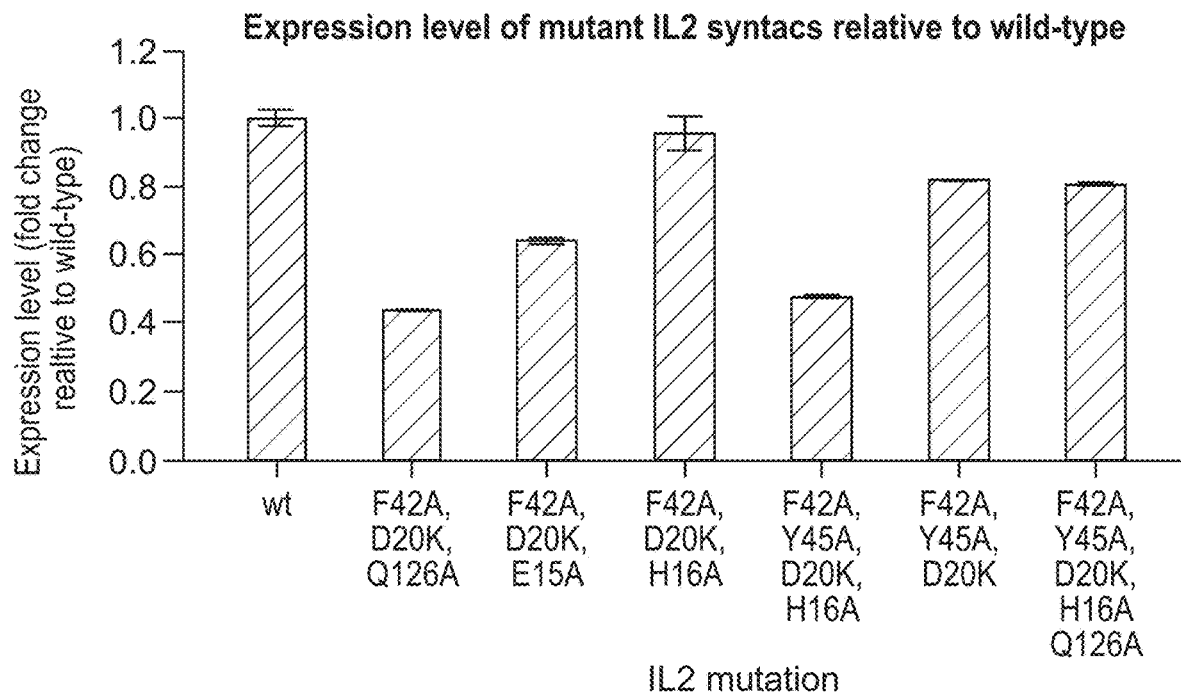
FIG. 9 depicts the expression level of IL-2/syn-Tacs, in which the IL-2 is wild-type (wt), or comprises various combinations of F42A, D20K, Q126A, E15A, Y45A, and H16A.

Expression levels of IL-2/synTacs comprising variant IL-2 were assessed. FIG. 9 depicts the expression level of IL-2/syn-Tacs, in which the IL-2 is wild-type (wt), or comprises various combinations of F42A, D20K, Q126A, E15A, Y45A, and H16A. The expression levels are expressed as percent change relative to expression levels of a synTac with wild-type IL-2.

Figure 10:
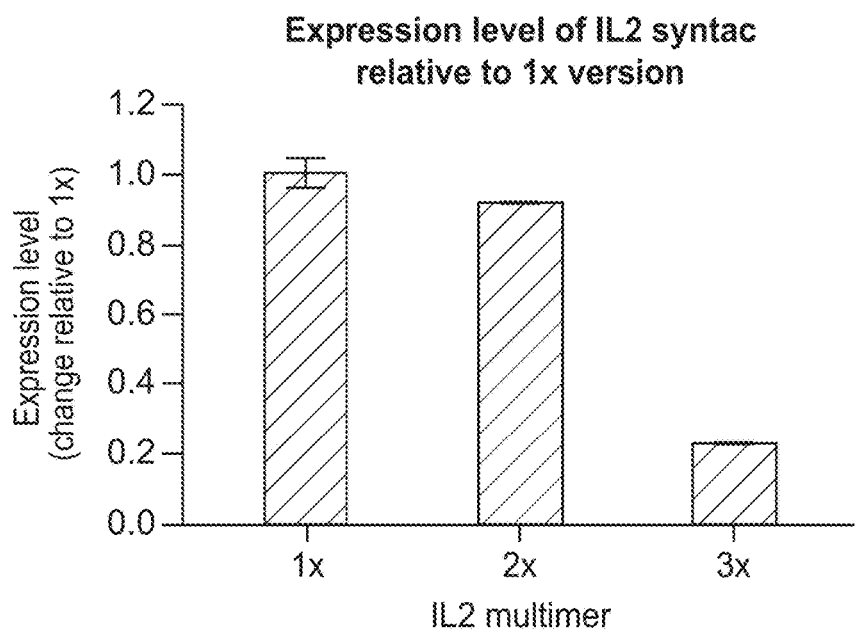
FIG. 10 depicts expression of IL-2/synTacs of the present disclosure, in which the IL-2 is present in one copy (1×), two copies (2×) or three copies (3×) in the synTac.

The effect of the copy number of IL-2 in an IL-2/synTac on expression levels was evaluated. IL-2/synTacs comprising one copy (1×), two copies (2×) or three copies (3×) in the synTac. The various IL-2/synTacs were produced in mammalian cells, and expression levels were assayed. The data are depicted in FIG. 10. IL-2/synTacs with one or two copies of IL-2 exhibit similar expression levels, while an IL-2/synTac with three copies of IL-2 exhibited lower expression levels. Expression levels are expressed as fold change relative to the expression level of the IL-2/synTac with a single copy of IL-2.

Example 2: In Vitro Activity of IL-2/synTac

To achieve maximal specificity of targeting through a T-cell receptor, the affinity of the co-stimulatory polypeptide for its ligand should be lower than the affinity of MHC for the TCR. The peptide/MHC affinity for TCR can be about 10 µM.

An IL-2/synTac was generated, comprising two copies of a variant IL-2 comprising F42A and H16A substitutions. Costimulatory signaling induced by the IL-2/synTac was tested on antigen-specific CD8$^+$ T cells and non-specific CD8$^+$ T cells. Antigen-specific CD8$^+$ T cells and non-specific CD8$^+$ T cells were contacted with various concentrations of the IL-2/synTac.

Figure 11:
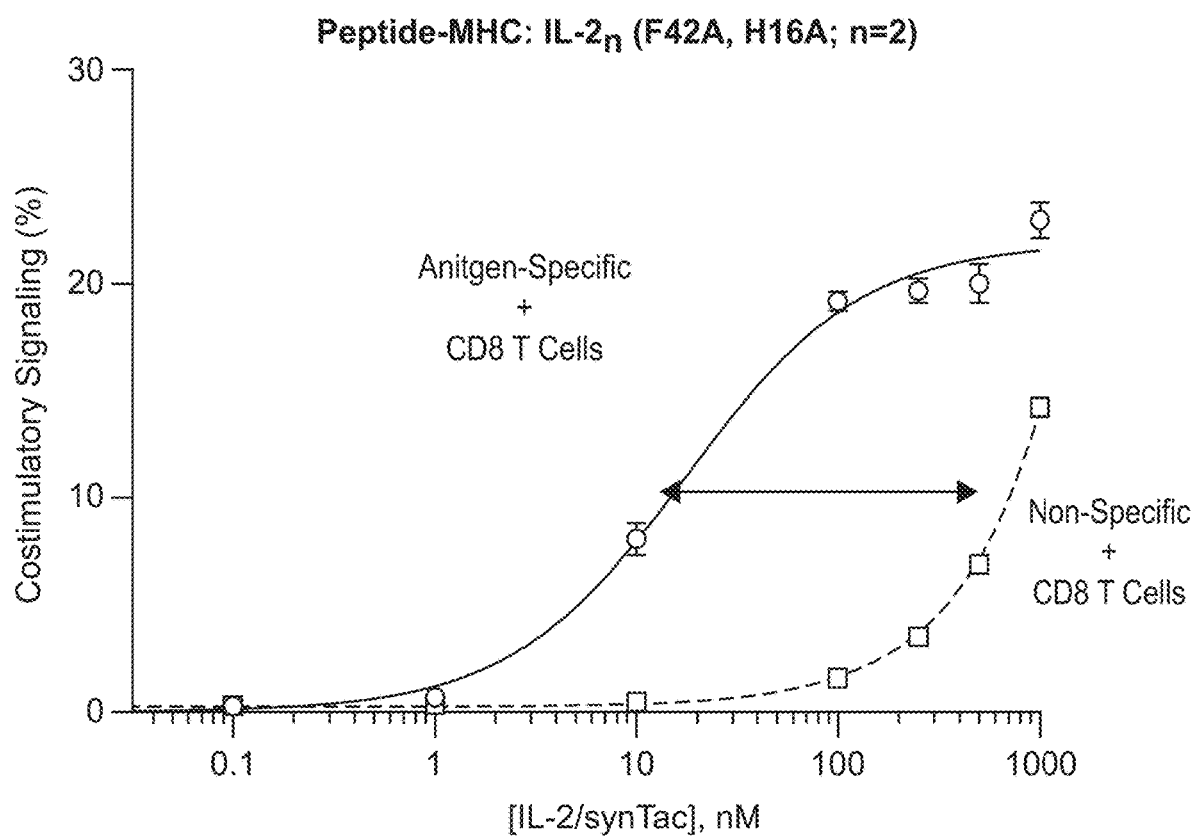
FIG. 11 depicts in vitro stimulation of antigen-specific CD8$^+$ T cells and non-specific CD8$^+$ T cells by an IL-2/synTac of the present disclosure, where the IL-2 variant comprising F42A and H16A substitutions is present in the synTac in two copies.

As shown in FIG. 11, the IL-2/synTac induced costimulatory signaling in antigen-specific CD8$^+$ T cells at a much lower concentration than in non-specific CD8$^+$ T cells.

Selectivity of IL-2/synTac binding was tested. CD8$^+$ T cells were isolated from spleens of LCMV or OT1 mice. The CD8$^+$ T cells were incubated with IL-2/synTacs at various concentrations, and allowed to bind for 20 minutes. The IL-2/synTacs comprise IgG2a Fc. Binding of IL-2/synTacs to the CD8$^+$ T cells was detected using phycoerythrin (PE)-labeled anti-IgG2a antibody. PE fluorescence was detected using flow cytometry to determine the percent of cells bound to IL-2/synTac.

As shown in FIG. 12, IL-2/synTac binds in an antigen-specific manner to LCMV CD8$^+$ T cells, but does not exhibit significant binding to OT1 CD8$^+$ T cells. Thus, IL-2/synTac selectively binds to CD8$^+$ T cells specific for the epitope present in the IL-2/synTac.

It was determined whether an IL-2/synTac selectively activates target T cells. CD8$^+$ T cells were isolated from spleens of LCMV or OT1 mice. The IL-2/synTacs used included either the F42A single amino acid substitution, or the F42A and H16A substitutions. The CD8$^+$ T cells were stimulated with IL-2/synTacs at various concentrations for 20 minutes. The cells were then stained with PE-labelled anti-phospho-STAT5 antibody. PE fluorescence was detected using flow cytometry to determine the percent of cells that are phospho-STAT5 positive, where phospho-STAT5 is a marker of activation.

Figure 13:
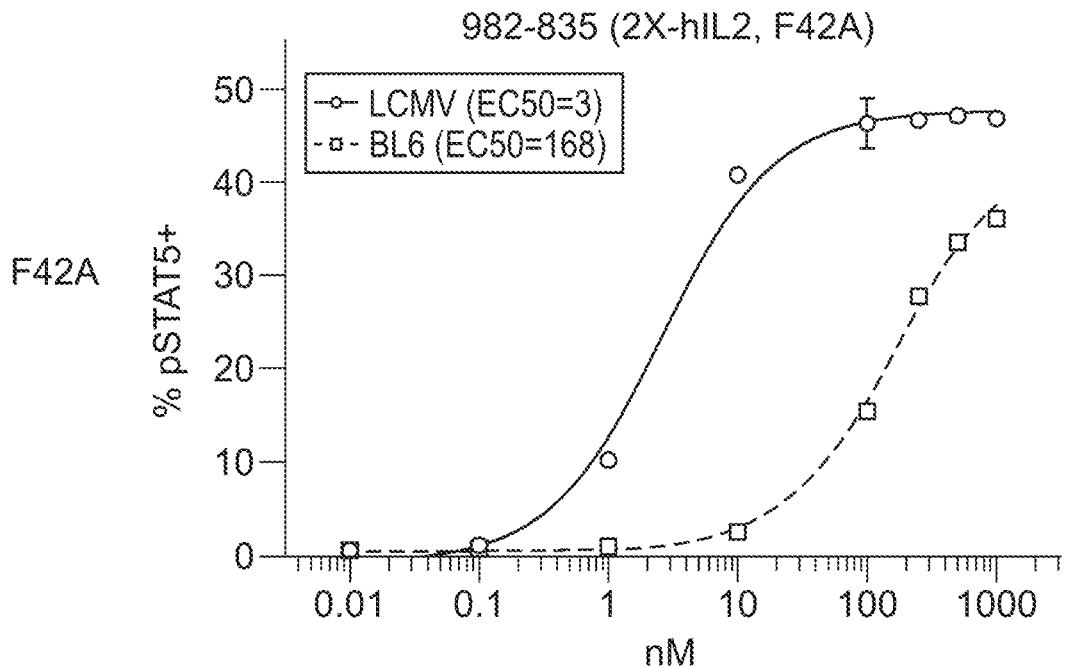
FIG. 13 depicts IL-2/synTac-mediated signaling in antigen-specific (LCMV) or non-specific (BL6) CD8$^+$ T cells.
Figure 14C:
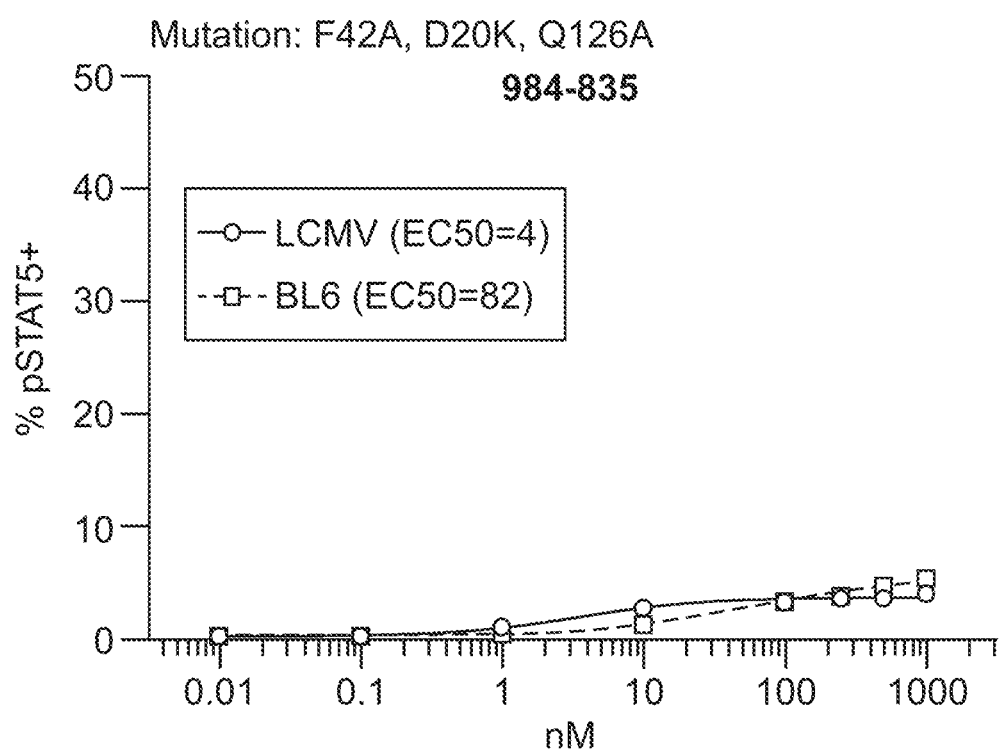
Figure 14E:
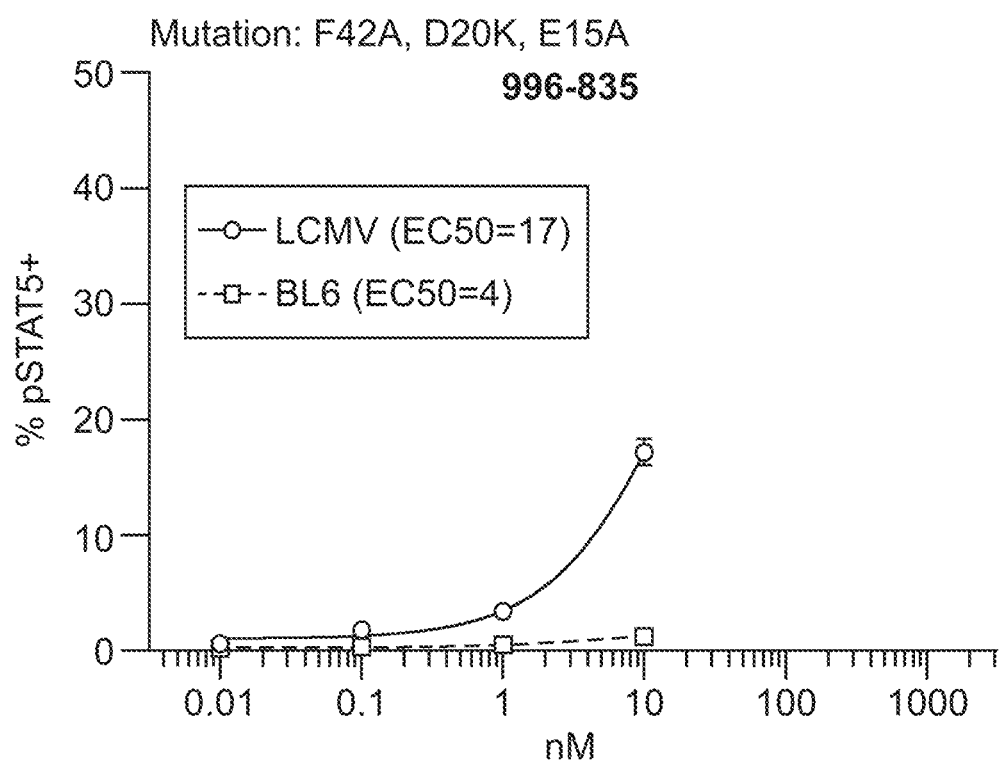

As shown in FIG. 13, IL-2/synTac induced CD8+ stimulation (as indicated by the % phospho-STAT5-positive cells) in antigen-specific (LCMV) CD8+ T cells at much lower concentrations than in non-specific (BL6) CD8+ T cells.

The specific activity of various IL-2/synTacs was analyzed. IL-2/synTacs comprising a single copy of IL-2, two copies of IL-2, or three copies of IL-2, where the IL-2 comprised various combinations of F42A, D20K, Q126A, E15A, H16A, and Y45A substitutions, were tested at various concentrations for stimulation of CD8+ antigen-specific (LCMV) or non-specific (BL6) cells. The percent phospho-signal transducer and activator of transcription 5 (pSTAT5)-positive was determined. The data are depicted in FIG. 14A-14F.

Example 3: In Vivo Activity of IL-2/synTac

The in vivo activity of IL-2/synTac was tested. The in vivo fold change in antigen-specific CD8+ T cells was tested, following administration of phosphate buffered saline (PBS), recombinant IL-2 (rIL-2), or an IL-2/synTac of the present disclosure. The data are shown in FIG. 15, left panel. The data indicate that IL-2/synTac is 10 times more potent than rIL-2.

The in vivo specificity of IL-2/synTac was tested. Antigen-specific and non-antigen-specific responses following administration of PBS, rIL-2, or IL-2/synTac was assessed. The data are expressed as percent of lymph node cells that were antigen-specific or antigen non-specific following administration of PBS, rIL-2, or IL-2/synTac. As depicted in FIG. 15, right panel, IL-2/synTac induced an antigen-specific response (expressed as % maximum dilution of carboxyfluorescein succinimidyl ester (CFSE), an index of T cell proliferation). In contrast, the response induced by rIL-2 was not antigen-specific.

Figure 16A:
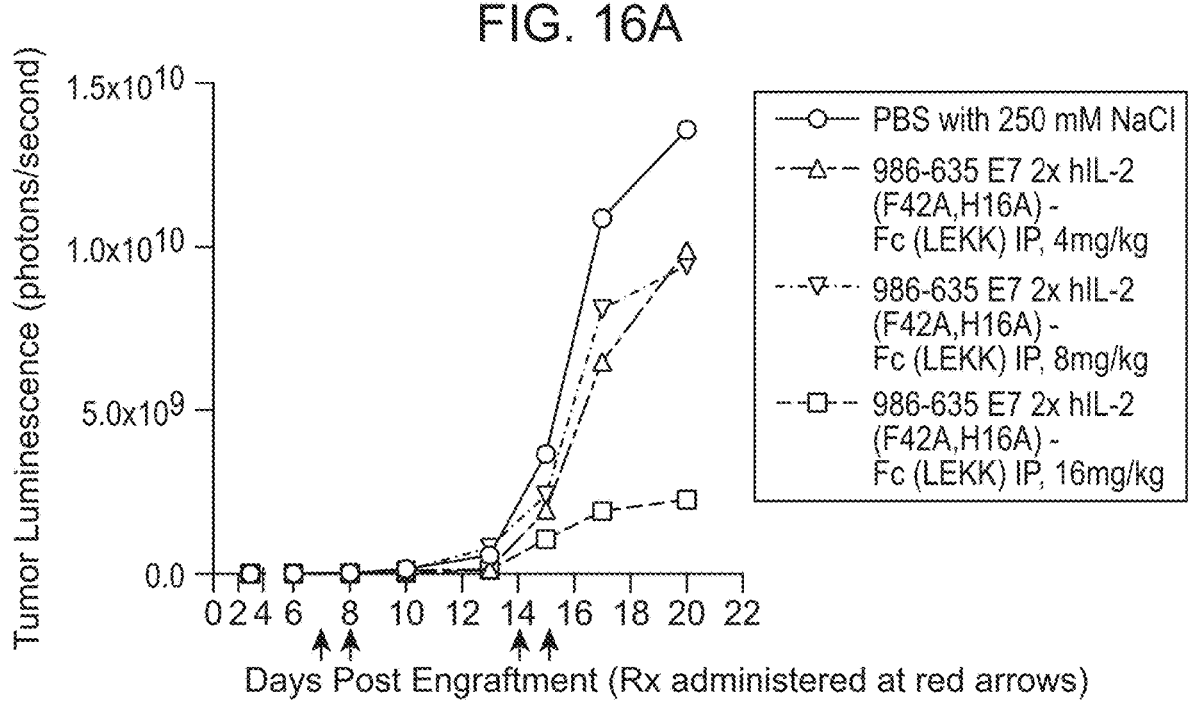
FIG. 16A-16B depict dose escalation (FIG. 16A) and route of administration (FIG. 16B) effects.

A dose response assay was conducted. IL-2/synTac (F42A, H16A) was administered intraperitoneally at concentrations of 4 mg/kg, 8 mg/kg, and 16 mg/kg. The results are shown in FIG. 16A. As shown in FIG. 16A, IL-2/synTac administered at 4 mg/kg or 8 mg/kg gave similar results; IL-2/synTac administered at 16 mg/kg induced the most potent immunostimulatory activity.

Figure 16B:
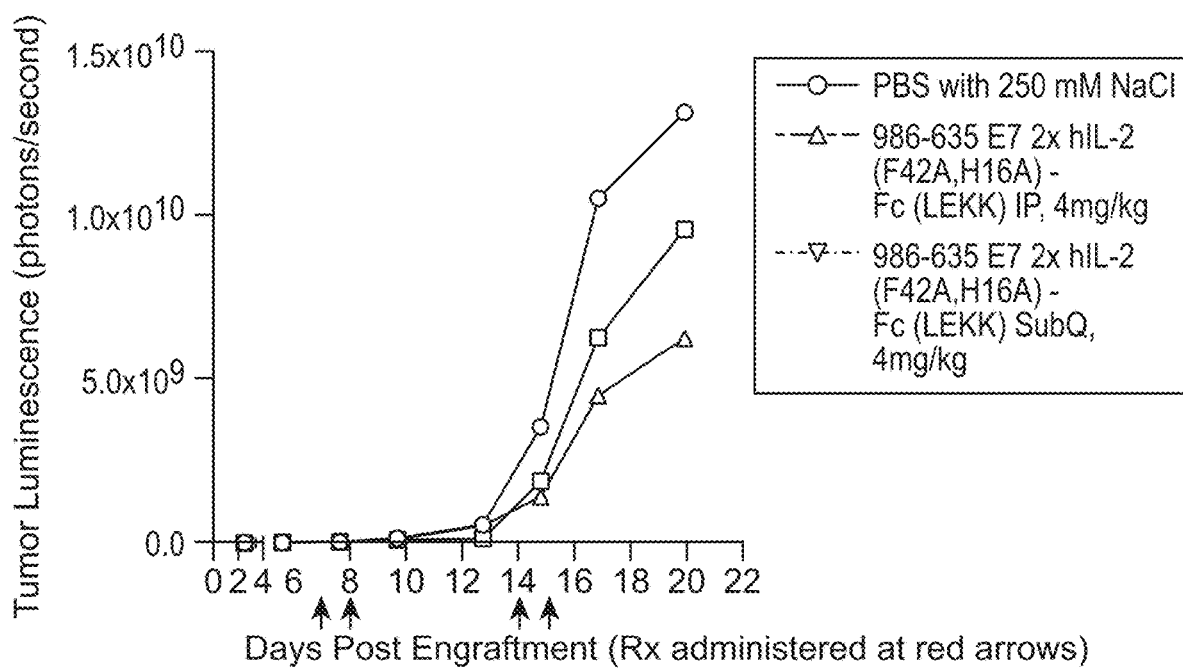

The effect of route of administration of IL-2/synTac was tested. IL-2/synTac (F42A, H16A) was administered at 4 mg/kg, either subcutaneously (SubQ) or intraperitoneally (IP). As shown in FIG. 16B, subcutaneous administration resulted in a more potent immunostimulatory activity than IP administration.

Figure 17A:
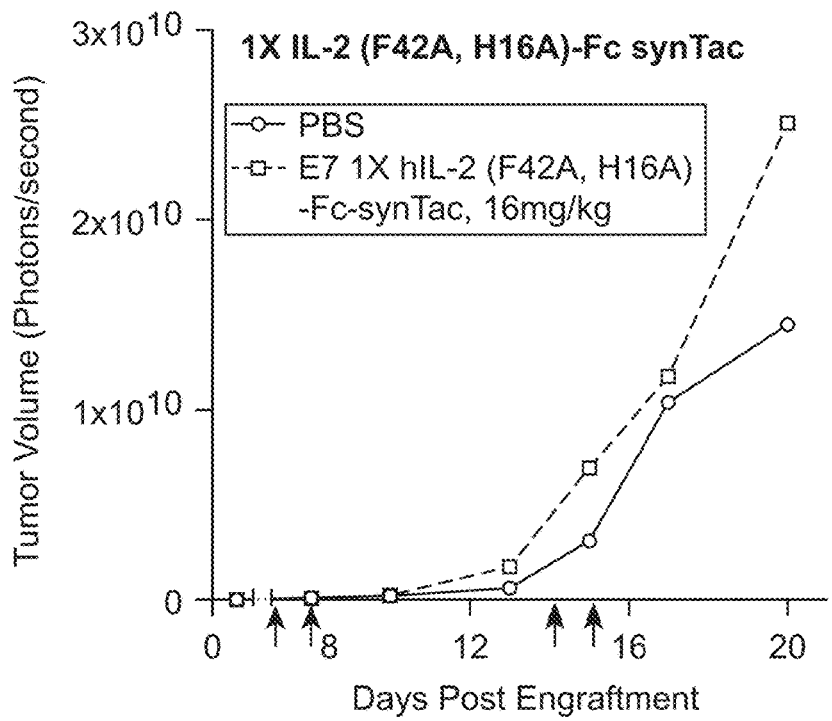
FIG. 17A-17B depict the effect of IL-2 copy number on in vivo efficacy against a tumor.
Figure 17B:
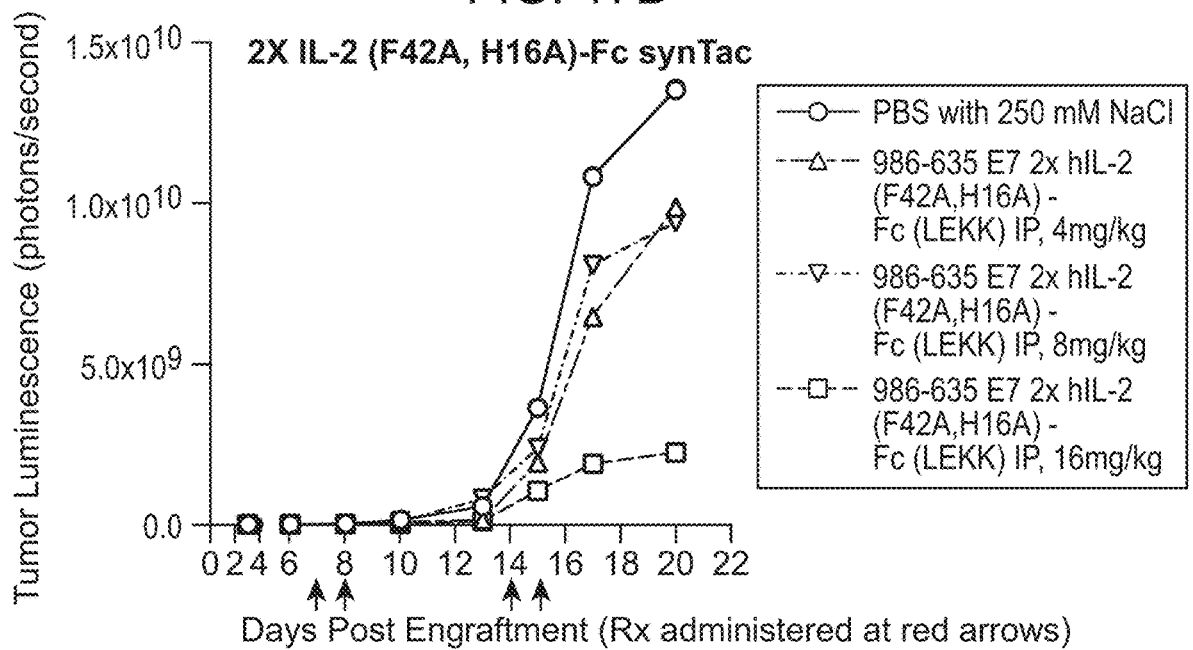

The effect of IL-2 copy number on efficacy was determined. IL-2/synTacs comprising a single copy of IL-2 (F42A, H16A) or two copies of IL-2 (F42A, H16A) were injected into mice with tumors bearing an HPV E7 epitope. The epitope included in the IL-2/synTacs was the HPV E7 epitope. As shown in FIGS. 17A and 17B, an IL-2/synTac comprising two copies of IL-2(F42A, H16A) were more effective at reducing tumor size than an IL-2/synTac comprising only a single copy of IL-2(F42A, H16A).

Example 4: PK/PD and Stability Studies of IL-2/synTac

Figure 18:
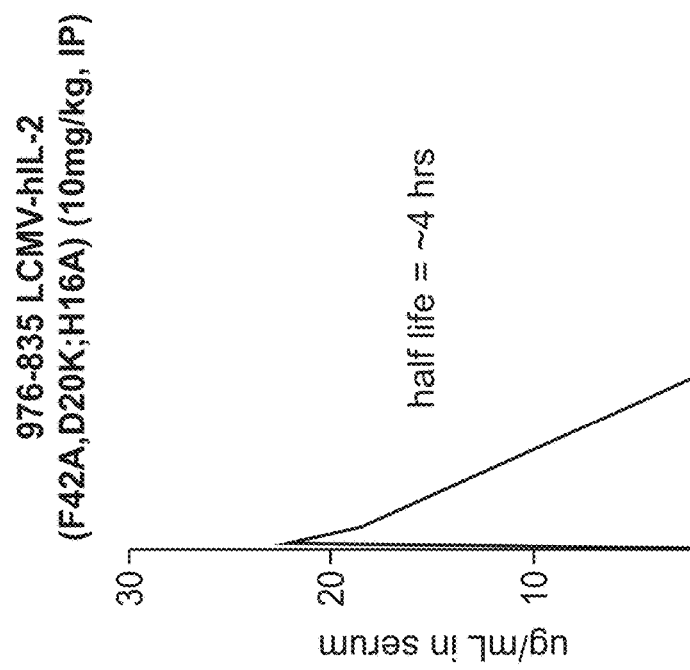
FIG. 18 depicts the serum half-life of an IL-2/synTac of the present disclosure, following intraperitoneal administration of the IL-2/synTac in an amount of 10 mg/kg.

Pharmacokinetic (PK) analysis of IL-2/synTac was carried out. IL-2/synTac (F42A, D20K, H16A) was administered IP at 10 mg/kg. At various time points post-administration, serum samples were obtained and the level of IL-2/synTac was measured in the serum samples. As shown in FIG. 18, the serum half-life of the IL-2/synTac was about 4 hours.

Figure 19:
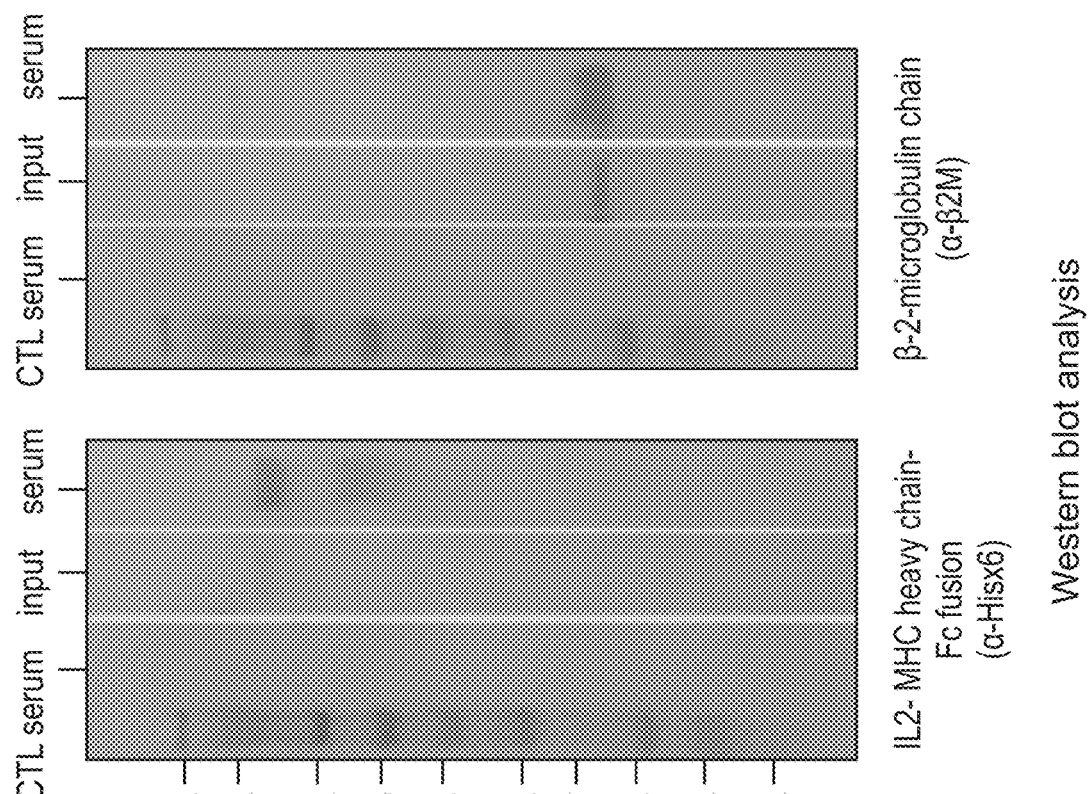
FIG. 19 depicts stability of an IL-2/synTac of the present disclosure 2 hours following intraperitoneal administration of the IL-2/synTac in an amount of 10 mg/kg.

IL-2/synTac was injected IP into a C57BL/6 mouse at 10 mg/kg, and serum was collected two hours after injections. The IL-2/synTac included a His$_6$ tag. 100 ng of the input protein, or the equivalent of 40 µl of serum, was subjected to sodium dodecyl sulfate-polyacrylamide gel electrophoresis (SDS-PAGE), and probed with an anti-(His)$_6$ antibody or an anti-β-2M antibody. The results, depicted in FIG. 19, show that IL-2/synTac remains stable and intact for at least 2 hours in vivo.

Figure 20:
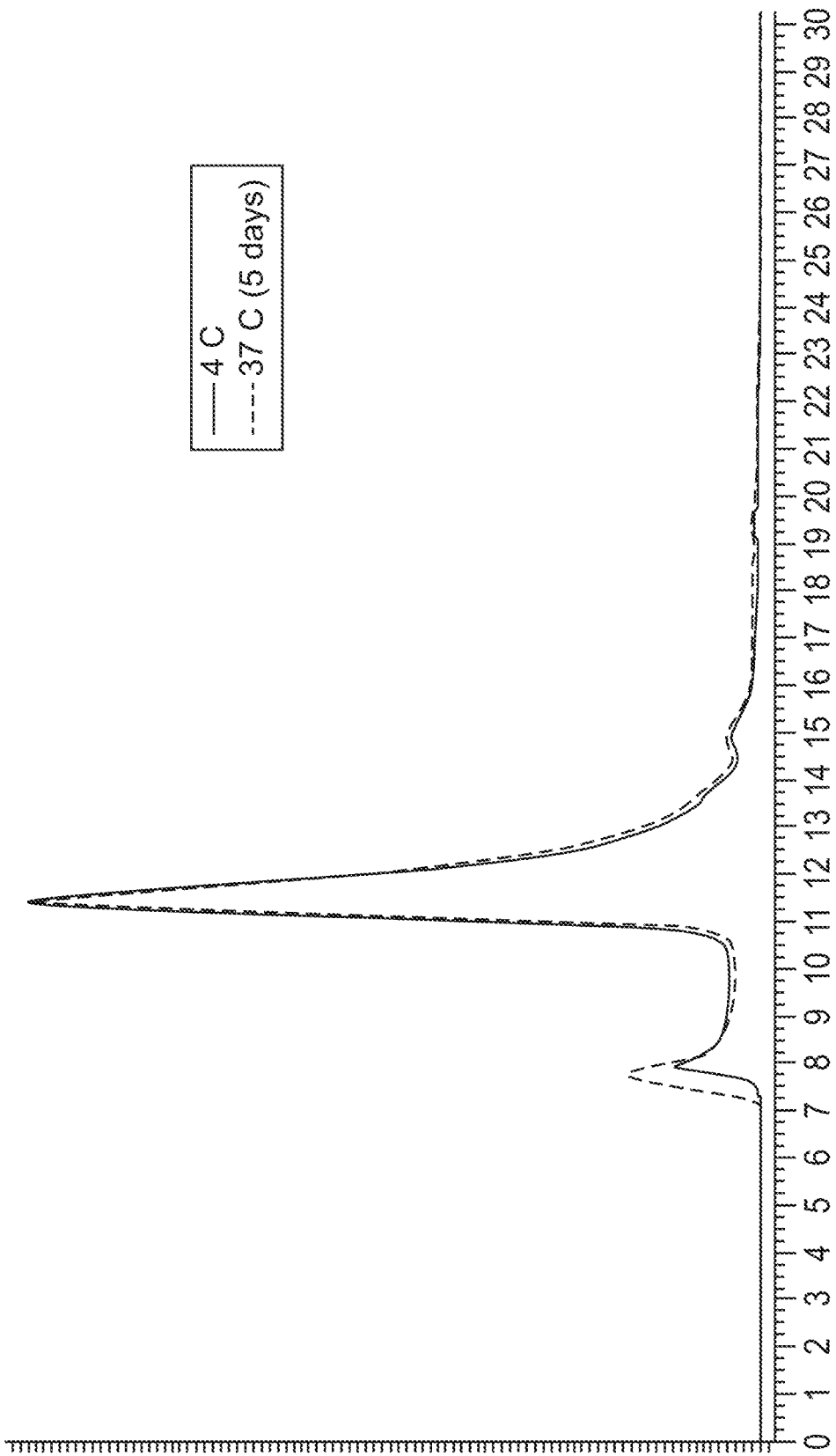
FIG. 20 depicts size exclusion chromatography data on an IL-2/synTac of the present disclosure after keeping the IL-2/synTac at 4° C. or 37° C. for 5 days.
Figure 38A:
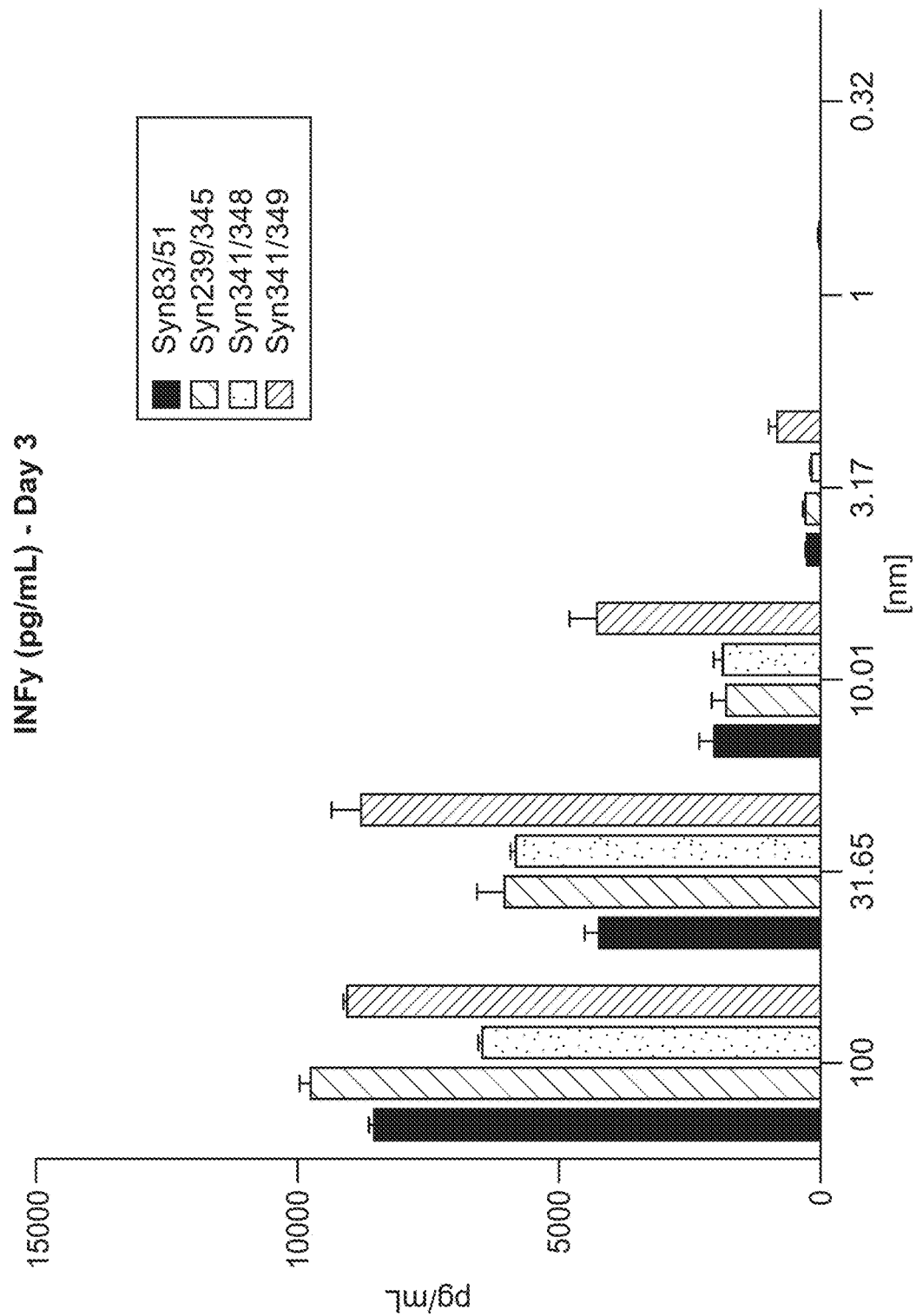
Figure 45:
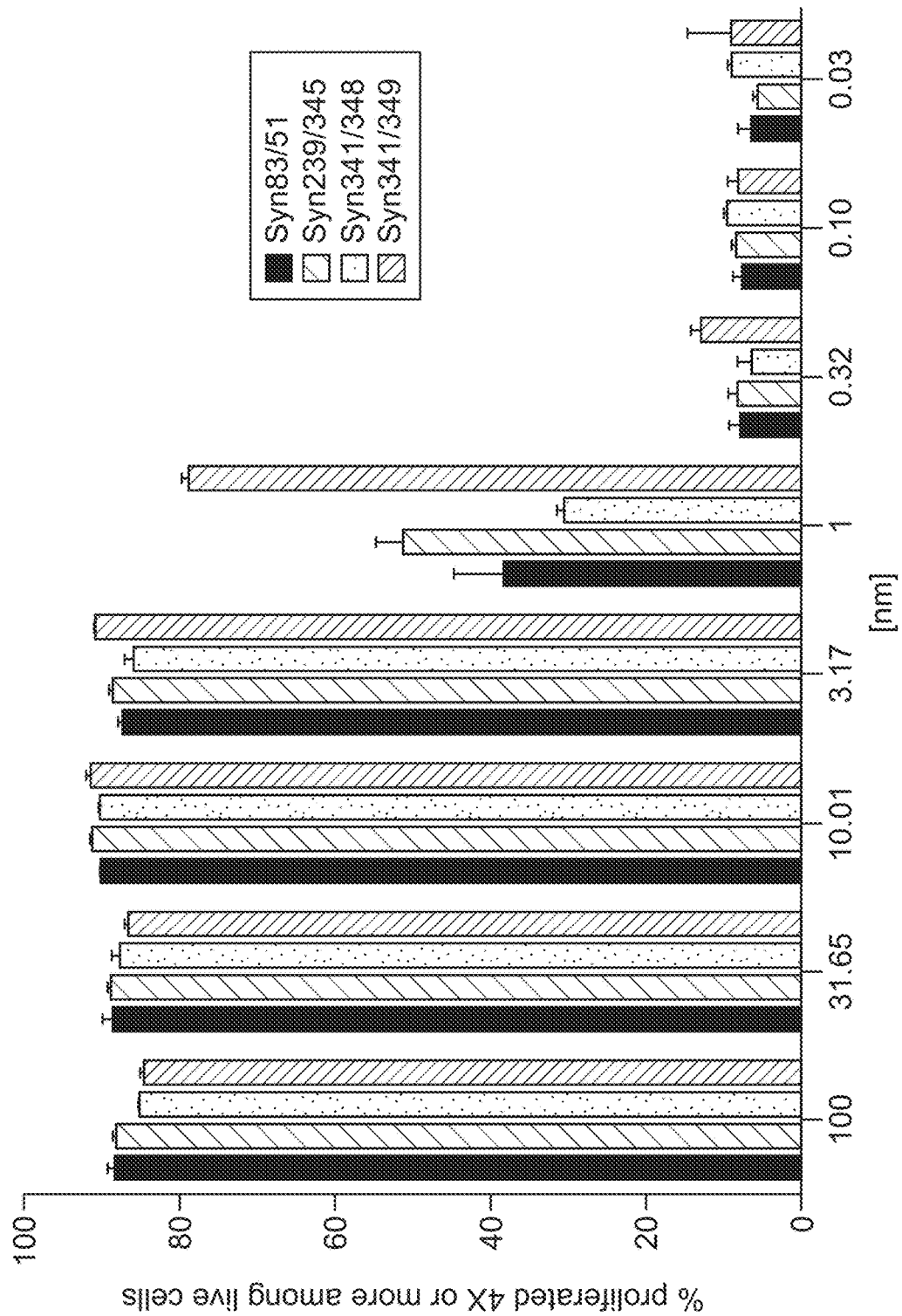
FIG. 45 depicts proliferation of target cells contacted with a synTac polypeptide according to an embodiment of the present disclosure.
Figure 46:
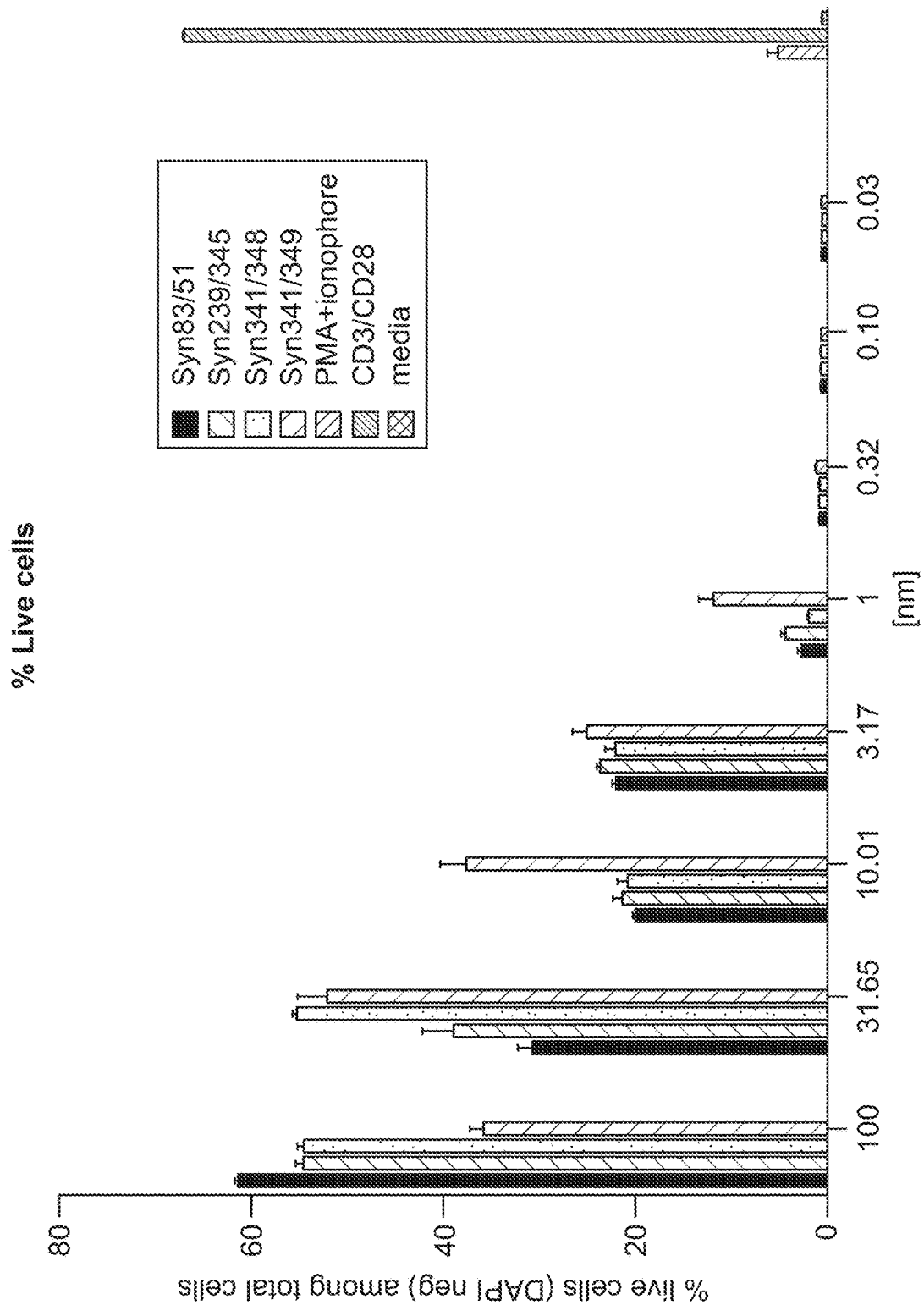
FIG. 46 depicts viability of target cells contacted with a synTac polypeptide according to an embodiment of the present disclosure.

IL-2/synTac was kept at 4° C. or 37° C. for 5 days. 0.5 mg of each sample (at 10 mg/ml) was analyzed by size exclusion chromatography. As shown in FIG. 20, IL-2/synTac is stable and intact for at least 5 days at 4° C. or 37° C.

Example 5: Effect of an IL-2/synTac and an Anti-PD1 Antibody on Tumor Volume

As shown in FIG. 35, administration of an IL-2/synTac and an anti-PD1 antibody to a mouse having a tumor reduced tumor volume.

Example 6: Generation and Characterization of synTac Polypeptides with Variant 4-1BBL synTac polypeptides were synthesized and characterized. The following synTac polypeptides were tested for activity on ovalbumin (OVA)-specific T cells:

1) Syn83/51. The light chain of Syn83/51 comprises: a) an OVA T-cell epitope; b) amino acids 50-254 of a wild-type 4-1BBL polypeptide; and c) β2M; and the heavy chain of Syn83/51 comprises: a) MHC heavy chain; and b) Ig Fc.

2) Syn239/345. The light chain of Syn239/345 comprises: a) an OVA T-cell epitope; b) a trimer of amino acids 80-254 of wild-type 4-1BBL; and c) β2M; and the heavy chain of Syn239/345 comprises: a) MHC heavy chain; and b) IgG2a Fc.

3) Syn341/348. The light chain of Syn341/348 comprises: a) an OVA T-cell epitope; b) a trimer of wild-type 4-1BBL; and c) β2M; and the heavy chain of Syn239/345 comprises: a) MHC heavy chain; and b) IgG2a Fc. In Syn341/348 the first unit of the 4-1BBL trimer comprises amino acids 50-254 of wild-type 4-1BBL; the second and third units of the 4-1BBL trimer comprise amino acids 80 to 254 of wild-type 4-1BBL.

4) Syn341/349. The light chain of Syn341/349 comprises: an OVA T-cell epitope; b) a trimer of amino acids 80-254 of 4-1BBL comprising a K127A substitution in each unit of the trimer, with a linker GlySerSerSerSer between the first and second units and between the second and third units of the trimer; and c) β2M; and the heavy chain of Syn239/345 comprises: a) MHC heavy chain; and b) IgG2a Fc.

The resulting synTac heterodimers were cultured in vitro with ovalbumin-specific T cells for 3 days or 5 days, at concentrations of 0, 1, 3.17, 10.01, 31.65, and 100 nM synTac. Controls included: a) medium alone; b) phorbol 12-myristate 13-acetate (PMA) and the ionophore A23187; and c) an anti-CD3 antibody and an anti-CD28 antibody.

After 3 days, and after 5 days, the concentration of IFN-γ, IL-2, IL-6, TNF, IL-10, IL-17A, and IL-4 in the culture medium was determined. In addition, the viability of the OVA-specific T cells, and the proliferation of the OVA-specific T cells, was determined.

The data are depicted in FIGS. 38-46.

As shown in FIG. 38 through FIG. 46, Syn 341/349 induces production of IL-2 (a cellular fitness cytokine); induces production of cytotoxic cytokines TNFα and IFN-γ; and also induces proliferation and enhances viability of epitope-specific T cells.

Example 7: Production of synTacs in CHO Cells

SynTacs comprising wild-type (wt) 4-1BBL, or comprising 4-1BBL with amino acid substitutions as set out in FIG. 47 were transiently expressed in CHO cells. The amount of synTac produced was determined. The amounts produced are provided in FIG. 47.

Example 8: In Vivo Effect of a 4-1BBL synTac

Figure 48:
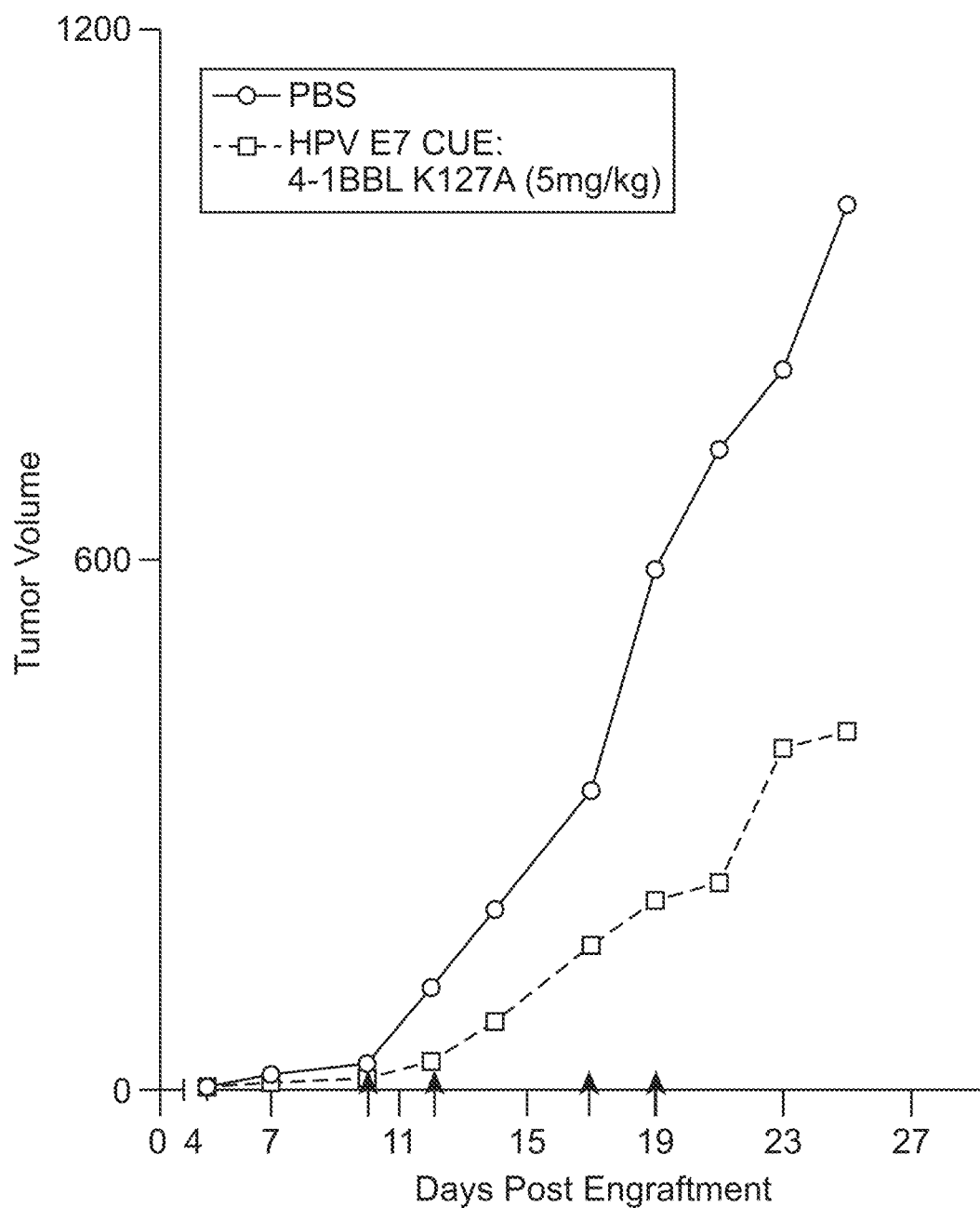
FIG. 48 depicts the in vivo effect of a synTac polypeptide of the present disclosure on tumor volume.

A synTac comprising a human papilloma virus (HPV) E7 antigenic peptide and a 4-1BBL K127A variant of the present disclosure (referred to as "CUE:4-1BBL (K127A)" in FIG. 48) was administered at 5 mg/kg by intraperitoneal (IP) injection into mice bearing flank engrafted HPV+ TC-1 lung carcinoma. As a control, phosphate buffered saline (PBS) was administered to mice bearing the same tumor. As shown in FIG. 48, tumor volume was decreased in mice treated with CUE:4-1BBL (K127A), compared to mice treated with PBS.

Example 9: In Vivo Effects of Co-Administration of a 4-1BBL synTac and an Immune Checkpoint Inhibitor As depicted in FIG. 49, co-administration of a 4-1BBL synTac of the present disclosure and an anti-PD1 antibody reduced tumor volume in a mouse tumor model, and increased the percent of tumor infiltrating lymphocytes (TILs) that were granzyme B+.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

SEQUENCE LISTING

```
Sequence total quantity: 216
SEQ ID NO: 1            moltype = AA  length = 133
FEATURE                 Location/Qualifiers
source                  1..133
                        mol_type = protein
                        organism = Homo sapiens
SEQUENCE: 1
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                    133

SEQ ID NO: 2            moltype = AA  length = 133
FEATURE                 Location/Qualifiers
VARIANT                 42
                        note = Xaa is any amino acid other than a phenylalanine
source                  1..133
                        mol_type = protein
                        organism = synthetic construct
SEQUENCE: 2
APTSSSTKKT QLQLEHLLLD LQMILNGINN YKNPKLTRML TXKFYMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                    133

SEQ ID NO: 3            moltype = AA  length = 133
FEATURE                 Location/Qualifiers
VARIANT                 20
                        note = Xaa is any amino acid other than an aspartic acid
source                  1..133
                        mol_type = protein
                        organism = synthetic construct
SEQUENCE: 3
APTSSSTKKT QLQLEHLLLX LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                    133

SEQ ID NO: 4            moltype = AA  length = 133
FEATURE                 Location/Qualifiers
VARIANT                 15
                        note = Xaa is any amino acid other than a glutamic acid
source                  1..133
                        mol_type = protein
                        organism = synthetic construct
SEQUENCE: 4
APTSSSTKKT QLQLXHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                    133
```

```
SEQ ID NO: 5              moltype = AA  length = 133
FEATURE                   Location/Qualifiers
VARIANT                   16
                          note = Xaa is any amino acid other than a histidine
source                    1..133
                          mol_type = protein
                          organism = synthetic construct
SEQUENCE: 5
APTSSSTKKT QLQLEXLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 6              moltype = AA  length = 133
FEATURE                   Location/Qualifiers
VARIANT                   45
                          note = Xaa is any amino acid other than a tyrosine
source                    1..133
                          mol_type = protein
                          organism = synthetic construct
SEQUENCE: 6
APTSSSTKKT QLQLEHLLLD LQMILNGINN YKNPKLTRML TFKFXMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 7              moltype = AA  length = 133
FEATURE                   Location/Qualifiers
VARIANT                   126
                          note = Xaa is any amino acid other than a glutamine
source                    1..133
                          mol_type = protein
                          organism = synthetic construct
SEQUENCE: 7
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCXSIIS TLT                                                     133

SEQ ID NO: 8              moltype = AA  length = 133
FEATURE                   Location/Qualifiers
VARIANT                   16
                          note = Xaa is any amino acid other than a histidine
VARIANT                   42
                          note = Xaa is any amino acid other than a phenylalanine
source                    1..133
                          mol_type = protein
                          organism = synthetic construct
SEQUENCE: 8
APTSSSTKKT QLQLEXLLLD LQMILNGINN YKNPKLTRML TXKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 9              moltype = AA  length = 133
FEATURE                   Location/Qualifiers
VARIANT                   20
                          note = Xaa is any amino acid other than an aspartic acid
VARIANT                   42
                          note = Xaa is any amino acid other than a phenylalanine
source                    1..133
                          mol_type = protein
                          organism = synthetic construct
SEQUENCE: 9
APTSSSTKKT QLQLEHLLLX LQMILNGINN YKNPKLTRML TXKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 10             moltype = AA  length = 133
FEATURE                   Location/Qualifiers
VARIANT                   15
                          note = Xaa is any amino acid other than a glutamic acid
VARIANT                   20
                          note = Xaa is any amino acid other than an aspartic acid
VARIANT                   42
                          note = Xaa is any amino acid other than a phenylalanine
source                    1..133
                          mol_type = protein
                          organism = synthetic construct
SEQUENCE: 10
APTSSSTKKT QLQLXHLLLX LQMILNGINN YKNPKLTRML TXKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133
```

```
SEQ ID NO: 11            moltype = AA   length = 133
FEATURE                  Location/Qualifiers
VARIANT                  16
                         note = Xaa is any amino acid other than a histidine
VARIANT                  20
                         note = Xaa is any amino acid other than an aspartic acid
VARIANT                  42
                         note = Xaa is any amino acid other than a phenylalanine
source                   1..133
                         mol_type = protein
                         organism = synthetic construct
SEQUENCE: 11
APTSSSTKKT QLQLEXLLLX LQMILNGINN YKNPKLTRML TXKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 12            moltype = AA   length = 133
FEATURE                  Location/Qualifiers
VARIANT                  20
                         note = Xaa is any amino acid other than an aspartic acid
VARIANT                  42
                         note = Xaa is any amino acid other than a phenylalanine
VARIANT                  126
                         note = Xaa is any amino acid other than a glutamine
source                   1..133
                         mol_type = protein
                         organism = synthetic construct
SEQUENCE: 12
APTSSSTKKT QLQLEHLLLX LQMILNGINN YKNPKLTRML TXKFYMPKKA TELKHLQCLE    60
EELKPLEEVL NLAQSKNFHL RPRDLISNIN VIVLELKGSE TTFMCEYADE TATIVEFLNR   120
WITFCXSIIS TLT                                                     133

SEQ ID NO: 13            moltype = AA   length = 133
FEATURE                  Location/Qualifiers
VARIANT                  20
                         note = Xaa is any amino acid other than an aspartic acid
VARIANT                  42
                         note = Xaa is any amino acid other than a phenylalanine
VARIANT                  45
                         note = Xaa is any amino acid other than a tyrosine
source                   1..133
                         mol_type = protein
                         organism = synthetic construct
SEQUENCE: 13
APTSSSTKKT QLQLEHLLLX LQMILNGINN YKNPKLTRML TXKFXMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 14            moltype = AA   length = 133
FEATURE                  Location/Qualifiers
VARIANT                  16
                         note = Xaa is any amino acid other than a histidine
VARIANT                  20
                         note = Xaa is any amino acid other than an aspartic acid
VARIANT                  42
                         note = Xaa is any amino acid other than a phenylalanine
VARIANT                  45
                         note = Xaa is any amino acid other than a tyrosine
source                   1..133
                         mol_type = protein
                         organism = synthetic construct
SEQUENCE: 14
APTSSSTKKT QLQLEXLLLX LQMILNGINN YKNPKLTRML TXKFXMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 15            moltype = AA   length = 133
FEATURE                  Location/Qualifiers
VARIANT                  20
                         note = Xaa is any amino acid other than an aspartic acid
VARIANT                  42
                         note = Xaa is any amino acid other than a phenylalanine
VARIANT                  45
                         note = Xaa is any amino acid other than a tyrosine
VARIANT                  126
                         note = Xaa is any amino acid other than a glutamine
source                   1..133
                         mol_type = protein
```

```
                         organism = synthetic construct
SEQUENCE: 15
APTSSSTKKT QLQLEHLLLX LQMILNGINN YKNPKLTRML TXKFXMPKKA TELKHLQCLE    60
EELKPLEEVL NLAQSKNFHL RPRDLISNIN VIVLELKGSE TTFMCEYADE TATIVEFLNR   120
WITFCXSIIS TLT                                                     133

SEQ ID NO: 16            moltype = AA  length = 133
FEATURE                  Location/Qualifiers
VARIANT                  16
                         note = Xaa is any amino acid other than a histidine
VARIANT                  20
                         note = Xaa is any amino acid other than an aspartic acid
VARIANT                  42
                         note = Xaa is any amino acid other than a phenylalanine
VARIANT                  45
                         note = Xaa is any amino acid other than a tyrosine
VARIANT                  126
                         note = Xaa is any amino acid other than a glutamine
source                   1..133
                         mol_type = protein
                         organism = synthetic construct
SEQUENCE: 16
APTSSSTKKT QLQLEXLLLX LQMILNGINN YKNPKLTRML TXKFXMPKKA TELKHLQCLE    60
EELKPLEEVL NLAQSKNFHL RPRDLISNIN VIVLELKGSE TTFMCEYADE TATIVEFLNR   120
WITFCXSIIS TLT                                                     133

SEQ ID NO: 17            moltype = AA  length = 133
FEATURE                  Location/Qualifiers
VARIANT                  16
                         note = Xaa is any amino acid other than a histidine
VARIANT                  42
                         note = Xaa is any amino acid other than a phenylalanine
VARIANT                  126
                         note = Xaa is any amino acid other than a glutamine
source                   1..133
                         mol_type = protein
                         organism = synthetic construct
SEQUENCE: 17
APTSSSTKKT QLQLEXLLLD LQMILNGINN YKNPKLTRML TXKFYMPKKA TELKHLQCLE    60
EELKPLEEVL NLAQSKNFHL RPRDLISNIN VIVLELKGSE TTFMCEYADE TATIVEFLNR   120
WITFCXSIIS TLT                                                     133

SEQ ID NO: 18            moltype = AA  length = 272
FEATURE                  Location/Qualifiers
source                   1..272
                         mol_type = protein
                         organism = Homo sapiens
SEQUENCE: 18
MDSYLLMWGL LTFIMVPGCQ AELCDDDPPE IPHATFKAMA YKEGTMLNCE CKRGFRRIKS    60
GSLYMLCTGN SSHSSWDNQC QCTSSATRNT TKQVTPQPEE QKERKTTEMQ SPMQPVDQAS   120
LPGHCREPPP WENEATERIY HFVVGQMVYY QCVQGYRALH RGPAESVCKM THGKTRWTQP   180
QLICTGEMET SQFPGEEKPQ ASPEGRPESE TSCLVTTTDF QIQTEMAATM ESIFTTEYQ    240
VAVAGCVFLL ISVLLLSGLT WQRRQRKSRR TI                                272

SEQ ID NO: 19            moltype = AA  length = 551
FEATURE                  Location/Qualifiers
source                   1..551
                         mol_type = protein
                         organism = Homo sapiens
SEQUENCE: 19
MAAPALSWRL PLLILLLPLA TSWASAAVNG TSQFTCFYNS RANISCVWSQ DGALQDTSCQ    60
VHAWPDRRRW NQTCELLPVS QASWACNLIL GAPDSQKLTT VDIVTLRVLC REGVRWRVMA   120
IQDFKPFENL RLMAPISLQV VHVETHRCNI SWEISQASHY FERHLEFEAR TLSPGHTWEE   180
APLLTLKQKQ EWICLETLTP DTQYEFQVRV KPLQGEFTTW SPWSQPLAFR TKPAALGKDT   240
IPWLGHLLVG LSGAFGFIIL VYLLINCRNT GPWLKKVLKC NTPDPSKFFS QLSSEHGGDV   300
QKWLSSPFPS SSFSPGGLAP EISPLEVLER DKVTQLLLQQ DKVPEPASLS SNHSLTSCFT   360
NQGYFFHLP DALEIEACQV YFTYDPYSEE DPDEGVAGAP TGSSPQPLQP LSGEDDAYCT   420
FPSRDDLLLF SPSLLGGPSP PSTAPGGSGA GEERMPPSLQ ERVPRDWDPQ PLGPPTPGVP   480
DLVDFQPPPE LVLREAGEEV PDAGPREGVS FPWSRPPGQG EFRALNARLP LNTDAYLSLQ   540
ELQGQDPTHL V                                                       551

SEQ ID NO: 20            moltype = AA  length = 369
FEATURE                  Location/Qualifiers
source                   1..369
                         mol_type = protein
                         organism = Homo sapiens
SEQUENCE: 20
MLKPSLPFTS LLFLQLPLLG VGLNTTILTP NGNEDTTADF FLTTMPTDSL SVSTLPLPEV    60
QCFVFNVEYM NCTWNSSSEP QPTNLTLHYW YKNSDNDKVQ KCSHYLFSEE ITSGCQLQKK   120
```

```
EIHLYQTFVV QLQDPREPRR QATQMLKLQN LVIPWAPENL TLHKLSESQL ELNWNNRFLN    180
HCLEHLVQYR TDWDHSWTEQ SVDYRHKFSL PSVDGQKRYT FRVRSRFNPL CGSAQHWSEW    240
SHPIHWGSNT SKENPFLFAL EAVVISVGSM GLIISLLCVY FWLERTMPRI PTLKNLEDLV    300
TEYHGNFSAW SGVSKGLAES LQPDYSERLC LVSEIPPKGG ALGEGPGASP CNQHSPYWAP    360
PCYTLKPET                                                            369

SEQ ID NO: 21             moltype = AA  length = 227
FEATURE                   Location/Qualifiers
source                    1..227
                          mol_type = protein
                          organism = Homo sapiens
SEQUENCE: 21
DKTHTCPPCP APELLGGPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALPA PIEKTISKAK    120
GQPREPQVYT LPPSRDELTK NQVSLTCLVK GFYPSDIAVE WESNGQPENN YKTTPPVLDS    180
DGSFFLYSKL TVDKSRWQQG NVFSCSVMHE ALHNHYTQKS LSLSPGK                  227

SEQ ID NO: 22             moltype = AA  length = 325
FEATURE                   Location/Qualifiers
source                    1..325
                          mol_type = protein
                          organism = Homo sapiens
SEQUENCE: 22
STKGPSVFPL APCSRSTSES TAALGCLVKD YFPEPVTVSW NSGALTSGVH TFPAVLQSSG     60
LYSLSSVVTV PSSNFGTQTY TCNVDHKPSN TKVDKTVERK CCVECPPCPA PPVAGPSVFL    120
FPPKPKDTLM ISRTPEVTCV VVDVSHEDPE VQFNWYVDGV EVHNAKTKPR EEQFNSTFRV    180
VSVLTVVHQD WLNGKEYKCK VSNKGLPAPI EKTISKTKGQ PREPQVYTLP PSREEMTKNQ    240
VSLTCLVKGF YPSDIAVEWE SNGQPENNYK TTPPMLDSDG SFFLYSKLTV DKSRWQQGNV    300
FSCSVMHEAL HNHYTQKSLS LSPGK                                          325

SEQ ID NO: 23             moltype = AA  length = 246
FEATURE                   Location/Qualifiers
source                    1..246
                          mol_type = protein
                          organism = Homo sapiens
SEQUENCE: 23
HKPSNTKVDK RVELKTPLGD TTHTCPPCPA PELLGGPSVF LFPPKPKDTL MISRTPEVTC     60
VVVDVSHEDP EVKFNWYVDG VEVHNAKTKP REEQYNSTYR VVSVLTVLHQ DWLNGKEYKC    120
KVSNKALPAP IEKTISKAKG QPREPQVYTL PPSRDELTKN QVSLTCLVKG FYPSDIAVEW    180
ESNGQPENNY KTTPPVLDSD GSFFLYSKLT VDKSRWQQGN VFSCSVMHEA LHNHYTQKSL    240
SLSPGK                                                               246

SEQ ID NO: 24             moltype = AA  length = 383
FEATURE                   Location/Qualifiers
source                    1..383
                          mol_type = protein
                          organism = Homo sapiens
SEQUENCE: 24
PTKAPDVFPI ISGCRHPKDN SPVVLACLIT GYHPTSVTVT WYMGTQSQPQ RTFPEIQRRD     60
SYYMTSSQLS TPLQQWRQGE YKCVVQHTAS KSKKEIFRWP ESPKAQASSV PTAQPQAEGS    120
LAKATTAPAT TRNTGRGGEE KKKEKEKEEQ EERETKTPEC PSHTQPLGVY LLTPAVQDLW    180
LRDKATFTCF VVGSDLKDAH LTWEVAGKVP TGGVEEGLLE RHSNGSQSQH SRLTLPRSLW    240
NAGTSVTCTL NHPSLPPQRL MALREPAAQA PVKLSLNLLA SSDPPEAASW LLCEVSGFSP    300
PNILLMWLED QREVNTSGFA PARPPPQPRS TTFWAWSVLR VPAPPSPQPA TYTCVVSHED    360
SRTLLNASRS LEVSYVTDHG PMK                                            383

SEQ ID NO: 25             moltype = AA  length = 276
FEATURE                   Location/Qualifiers
source                    1..276
                          mol_type = protein
                          organism = Homo sapiens
SEQUENCE: 25
VTSTLTIKZS DWLGESMFTC RVDHRGLTFQ QNASSMCVPD QDTAIRVFAI PPSFASIFLT     60
KSTKLTCLVT DLTTYBSVTI SWTREENGAV KTHTNISESH PNATFSAVGE ASICEDBDWS    120
GERFTCTVTH TDLPSPLKQT ISRPKGVALH RPBVYLLPPA RZZLNLRESA TITCLVTGFS    180
PADVFVEWMQ RGEPLSPQKY VTSAPMPEPQ APGRYFAHSI LTVSEEEWNT GGTYTCVVAH    240
EALPNRVTER TVDKSTGKPT LYNVSLVMSD TAGTCY                              276

SEQ ID NO: 26             moltype = AA  length = 353
FEATURE                   Location/Qualifiers
source                    1..353
                          mol_type = protein
                          organism = Homo sapiens
SEQUENCE: 26
ASPTSPKVFP LSLCSTQPDG NVVIACLVQG FFPQEPLSVT WSESGQGVTA RNFPPSQDAS     60
GDLYTTSSQL TLPATQCLAG KSVTCHVKHY TNPSQDVTVP CPVPSTPPTP SPSTPPTPSP    120
SCCHPRLSLH RPALEDLLLG SEANLTCTLT GLRDASGVTF TWTPSSGKSA VQGPPERDLC    180
GCYSVSSVLP GCAEPWNHGK TFTCTAAYPE SKTPLTATLS KSGNTFRPEV HLLPPPSEEL    240
ALNELVTLTC LARGFSPKDV LVRWLQGSQE LPREKYLTWA SRQEPSQGTT TFAVTSILRV    300
```

```
AAEDWKKGDT FSCMVGHEAL PLAFTQKTID RLAGKPTHVN VSVVMAEVDG TCY          353

SEQ ID NO: 27             moltype = AA  length = 222
FEATURE                   Location/Qualifiers
source                    1..222
                          mol_type = protein
                          organism = Homo sapiens
SEQUENCE: 27
ADPCDSNPRG VSAYLSRPSP FDLFIRKSPT ITCLVVDLAP SKGTVNLTWS RASGKPVNHS    60
TRKEEKQRNG TLTVTSTLPV GTRDWIEGET YQCRVTHPHL PRALMRSTTK TSGPRAAPEV   120
YAFATPEWPG SRDKRTLACL IQNFMPEDIS VQWLHNEVQL PDARHSTTQP RKTKGSGFFV   180
FSRLEVTRAE WEQKDEFICR AVHEAASPSQ TVQRAVSVNP GK                     222

SEQ ID NO: 28             moltype = AA  length = 327
FEATURE                   Location/Qualifiers
source                    1..327
                          mol_type = protein
                          organism = Homo sapiens
SEQUENCE: 28
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPSCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                      327

SEQ ID NO: 29             moltype = AA  length = 365
FEATURE                   Location/Qualifiers
source                    1..365
                          mol_type = protein
                          organism = Homo sapiens
SEQUENCE: 29
MAVMAPRTLL LLLSGALALT QTWAGSHSMR YFFTSVSRPG RGEPRFIAVG YVDDTQFVRF    60
DSDAASQKME PRAPWIEQEG PEYWDQETRN MKAHSQTDRA NLGTLRGYYN QSEDGSHTIQ   120
IMYGCDVGPD GRFLRGYRQD AYDGKDYIAL NEDLRSWTAA DMAAQITKRK WEAVHAAEQR   180
RVYLEGRCVD GLRRYLENGK ETLQRTDPPK THMTHHPISD HEATLRCWAL GFYPAEITLT   240
WQRDGEDQTQ DTELVETRPA GDGTFQKWAA VVVPSGEEQR YTCHVQHEGL PKPLTLRWEL   300
SSQPTIPIVG IIAGLVLLGA VITGAVVAAV MWRRKSSDRK GGSYTQAASS DSAQGSDVSL   360
TACKV                                                              365

SEQ ID NO: 30             moltype = AA  length = 362
FEATURE                   Location/Qualifiers
source                    1..362
                          mol_type = protein
                          organism = Homo sapiens
SEQUENCE: 30
MLVMAPRTVL LLLSAALALT ETWAGSHSMR YFYTSVSRPG RGEPRFISVG YVDDTQFVRF    60
DSDAASPREE PRAPWIEQEG PEYWDRNTQI YKAQAQTDRE SLRNLRGYYN QSEAGSHTLQ   120
SMYGCDVGPD GRLLRGHDQY AYDGKDYIAL NEDLRSWTAA DTAAQITQRK WEAAREAEQR   180
RAYLEGECVE WLRRYLENGK DKLERADPPK THVTHHPISD HEATLRCWAL GFYPAEITLT   240
WQRDGEDQTQ DTELVETRPA GDRTFQKWAA VVVPSGEEQR YTCHVQHEGL PKPLTLRWEP   300
SSQSTVPIVG IVAGLAVLAV VVIGAVVAAV MCRRKSSGGK GGSYSQAACS DSAQGSDVSL   360
TA                                                                 362

SEQ ID NO: 31             moltype = AA  length = 366
FEATURE                   Location/Qualifiers
source                    1..366
                          mol_type = protein
                          organism = Homo sapiens
SEQUENCE: 31
MRVMAPRALL LLLSGGLALT ETWACSHSMR YFDTAVSRPG RGEPRFISVG YVDDTQFVRF    60
DSDAASPRGE PRAPWVEQEG PEYWDRETQN YKRQAQADRV SLRNLRGYYN QSEDGSHTLQ   120
RMYGCDLGPD GRLLRGYDQS AYDGKDYIAL NEDLRSWTAA DTAAQITQRK LEAARAAEQL   180
RAYLEGTCVE WLRRYLENGK ETLQRAEPPK THVTHHPLSD HEATLRCWAL GFYPAEITLT   240
WQRDGEDQTQ DTELVETRPA GDGTFQKWAA VVVPSGQEQR YTCHMQHEGL QEPLTLSWEP   300
SSQPTIPIMG IVAGLAVLVV LAVLGAVVTA MMCRRKSSGG KGGSCSQAAC SNSAQGSDES   360
LITCKA                                                             366

SEQ ID NO: 32             moltype = AA  length = 833
FEATURE                   Location/Qualifiers
source                    1..833
                          mol_type = protein
                          organism = Homo sapiens
SEQUENCE: 32
MYRMQLLSCI ALSLALVTNS APTSSSTKKT QLQLEALLLD LQMILNGINN YKNPKLTRML    60
TAKFYMPKKA TELKHLQCLE EELKPLEEVL NLAQSKNPHL RPRDLISNIN VIVLELKGSE   120
TTFMCEYADE TATIVEFLNR WITFCQSIIS TLTGGGGSGG GGSGGGGSGG GGSAPTSSST   180
KKTQLQLEAL LLDLQMILNG INNYKNPKLT RMLTAKFYMP KKATELKHLQ CLEEELKPLE   240
EVLNLAQSKN FHLRPRDLIS NINVIVLELK GSETTFMCEY ADETATIVEF LNRWITFCQS   300
```

```
IISTLTGGGG SGGGGSGGGG SGGGGSGSHS MRYFFTSVSR PGRGEPRFIA VGYVDDTQFV   360
RFDSDAASQR MEPRAPWIEQ EGPEYWDGET RKVKAHSQTH RVDLGTLRGA YNQSEAGSHT   420
VQRMYGCDVG SDWRFLRGYH QYAYDGKDYI ALKEDLRSWT AADMAAQTTK HKWEAAHVAE   480
QLRAYLEGTC VEWLRRYLEN GKETLQRTDA PKTHMTHHAV SDHEATLRCW ALSFYPAEIT   540
LTWQRDGEDQ TQDTELVETR PCGDGTFQKW AAVVVPSGQE QRYTCHVQHE GLPKPLTLRW   600
EAAAGGDKTH TCPPCPAPEL LGGPSVFLFP PKPKDTLMIS RTPEVTCVVV DVSHEDPEVK   660
FNWYVDGVEV HNAKTKPREE QYASTYRVVS VLTVLHQDWL NGKEYKCKVS NKALPAPIEK   720
TISKAKGQPR EPQVYTLPPS REEMTKNQVS LTCLVKGFYP SDIAVEWESN GQPENNYKTT   780
PPVLDSDGSF FLYSKLTVDK SRWQQGNVFS CSVMHEALHN HYTQKSLSLS PGK          833

SEQ ID NO: 33           moltype = AA   length = 813
FEATURE                 Location/Qualifiers
source                  1..813
                        mol_type = protein
                        organism = Homo sapiens
SEQUENCE: 33
APTSSSTKKT QLQLEALLLD LQMILNGINN YKNPKLTRML TAKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTGGGGSGG GGSGGGGSGG GGSAPTSSST KKTQLQLEAL LLDLQMILNG   180
INNYKNPKLT RMLTAKFYMP KKATELKHLQ CLEEELKPLE EVLNLAQSKN FHLRPRDLIS   240
NINVIVLELK GSETTFMCEY ADETATIVEF LNRWITFCQS IISTLTGGGG SGGGGSGGGG   300
SGGGGSGSHS MRYFFTSVSR PGRGEPRFIA VGYVDDTQFV RFDSDAASQR MEPRAPWIEQ   360
EGPEYWDGET RKVKAHSQTH RVDLGTLRGA YNQSEAGSHT VQRMYGCDVG SDWRFLRGYH   420
QYAYDGKDYI ALKEDLRSWT AADMAAQTTK HKWEAAHVAE QLRAYLEGTC VEWLRRYLEN   480
GKETLQRTDA PKTHMTHHAV SDHEATLRCW ALSFYPAEIT LTWQRDGEDQ TQDTELVETR   540
PCGDGTFQKW AAVVVPSGQE QRYTCHVQHE GLPKPLTLRW EAAAGGDKTH TCPPCPAPEL   600
LGGPSVFLFP PKPKDTLMIS RTPEVTCVVV DVSHEDPEVK FNWYVDGVEV HNAKTKPREE   660
QYASTYRVVS VLTVLHQDWL NGKEYKCKVS NKALPAPIEK TISKAKGQPR EPQVYTLPPS   720
REEMTKNQVS LTCLVKGFYP SDIAVEWESN GQPENNYKTT PPVLDSDGSF FLYSKLTVDK   780
SRWQQGNVFS CSVMHEALHN HYTQKSLSLS PGK                                813

SEQ ID NO: 34           moltype = DNA   length = 2505
FEATURE                 Location/Qualifiers
source                  1..2505
                        mol_type = other DNA
                        organism = synthetic construct
SEQUENCE: 34
atgtacagga tgcaactcct gtcttgcatt gcactaagtc ttgcacttgt cacaaacagt    60
gcacctactt caagttctac aaagaaaaca cagctacaac tggaggcatt actgctggat   120
ttacagatga ttttgaatgg aattaataat tacaagaatc ccaaactcac caggatgctc   180
acagcaaagt tttacatgcc caagaaggcc acagaactga acatcttca gtgtctagaa    240
gaagaactca aacctctgga ggaagtgcta aatttagctc aaagcaaaaa ctttcactta   300
agacccaggg acttaatcag caatatcaac gtaatagttc tggaactaaa gggatctgaa   360
acaacattca tgtgtgaata tgctgatgag acagcaacca ttgtagaatt tctgaacaga   420
tggattacct tttgtcaaag catcatctca cactgactgg aggcggagg atctggtggt    480
ggaggttctg gtggtggggg atctggaggc ggaggatctg cacctacttc aagttctaca   540
aagaaaacac agctacaact ggaggcatta ctgctggatt tacagatgat tttgaatgga   600
attaataatt acaagaatcc caaactcacc aggatgctca cagcaaagtt ttacatgccc   660
aagaaggcca cagaactgaa catcttcag tgtctagaag aagaactcaa acctctggag    720
gaagtgctaa atttagctca aagcaaaaac tttcacttaa gacccaggga cttaatcagc   780
aatatcaacg taatagttct ggaactaaag gatctgaaac aacattcat gtgtgaattt    840
gctgatgaga cagcaaccat tgtagaattt ctgaacagat ggattacctt ttgtcaaagc   900
atcatctcaa cactgactgg aggcggagga tctggtggtg gaggttctgg tggtggggga   960
tctggaggcg gaggatctgg ctctcactcc atgaggtatt tcttcacatc cgtgtcccgg  1020
cccggccgcg gggagcccg cttcatcgca gtgggctacg tggacgacac gcagttcgtg    1080
cggttcgaca gcgacgccgc gagccagagg atggagccgc gggcgccgtg gatagagcag   1140
gagggtccgg agtattggga cggggagaca cggaaagtga aggcccactc acagactcac   1200
cgagtggacc tggggaccct gcgcggcgcc tacaaccaga gcgaggccgg ttctcacacc   1260
gtccagagga tgtatggctg cgacgtgggg tcggactggc gcttcctccg cgggtaccac   1320
cagtacgcct acgacggcaa ggattacatc gccctgaaag aggacctgcg ctcttggacc   1380
gcggcggaca tggcagctca gaccaccaag cacaagtggg aggcggccca tgtggcggag   1440
cagttgagag cctacctgga gggcacgtgc gtggagtggc tccgcagata cctggagaac   1500
gggaaggaga cgctgcagcg cacggacgcc cccaaaacgc atatgactca ccacgctgtc   1560
tctgaccatg aagccaccct gaggtgctgg gccctgtctt ctacccctgc ggagatcaca   1620
ctgacctggc agcgggatgg ggaggaccag acccaggaca cggagctcgt ggagaccagg   1680
ccttgcggga tggaaccttt ccagaagtgg cggctgtgg tggtgccttc tggacaggag    1740
cagagataca ccctgccatg tgcagcatga ggtttgccca gcccctcac cctgagatgt    1800
gaggcagctg cgggtggcga caaaactcac acatgcccag cctgaactc ctgggggac     1860
cgtcagtctt cctcttccc ccaaacccaa ggacaccctc atgatctcc cggaccctg      1920
aggtcacatg cgtggtggtg gacgtgagcc acgaagaccc tgaggtcaag ttcaactggt   1980
acgtggacgg cgtggaggtg cataatgcca agacaaagcc gcgggaggag cagtacgcaa   2040
gcacgtaccg tgtggtcagc gtcctcaccg tcctgcacca ggactggctg                2100
aatggcaagg agtacaagtg caaggtctcc aacaaagccc tcccagcccc catcgagaaa   2160
accatctcca aagccaaagg tgcccccga acccaggtgt acaccctgcc cccatccc       2220
cgggaggaga tgaccaagaa ccaggtcagc ctgacctgcc tggtcaaagg cttctatccc   2280
agcgacatcg ccgtggagtg ggagagcaat gggcagccgg agaacaacta caagaccacg   2340
cctcccgtgc tggactccga cggctccttc ttcctctaca gcaagctcac cgtggacaag   2400
agcagatggc agcaggggaa cgtcttctca tgctccgtga tgcacgaggc tctgcacaac   2460
cactacacgc agaagtccct ctccctgtct ccgggtaaat agtga                    2505
```

```
SEQ ID NO: 35             moltype = AA   length = 833
FEATURE                   Location/Qualifiers
source                    1..833
                          mol_type = protein
                          organism = Homo sapiens
SEQUENCE: 35
MYRMQLLSCI ALSLALVTNS APTSSSTKKT QLQLEALLLD LQMILNGINN YKNPKLTRML   60
TAKFYMPKKA TELKHLQCLE EELKPLEEVL NLAQSKNFHL RPRDLISNIN VIVLELKGSE  120
TTFMCEYADE TATIVEFLNR WITFCQSIIS TLTGGGGSGG GGSGGGGSGG GGSAPTSSST  180
KKTQLQLEAL LLDLQMILNG INNYKNPKLT RMLTAKFYMP KKATELKHLQ CLEEELKPLE  240
EVLNLAQSKN FHLRPRDLIS NINVIVLELK GSETTFMCEY ADETATIVEF LNRWITFCQS  300
IISTLTGGGG SGGGGSGGGG SGGGGSGSHS MRYFFTSVSR PGRGEPRFIA VGYVDDTQFV  360
RFDSDAASQR MEPRAPWIEQ EGPEYWDGET RKVKAHSQTH RVDLGTLRGA YNQSEAGSHT  420
VQRMYGCDVG SDWRFLRGYH QYAYDGKDYI ALKEDLRSWT AADMAAQTTK HKWEAAHVAE  480
QLRAYLEGTC VEWLRRYLEN GKETLQRTDA PKTHMTHHAV SDHEATLRCW ALSFYPAEIT  540
LTWQRDGEDQ TQDTELVETR PCGDGTFQKW AAVVVPSGQE QRYTCHVQHE GLPKPLTLRW  600
EAAAGGDKTH TCPPCPAPEA AGGPSVFLFP PKPKDTLMIS RTPEVTCVVV DVSHEDPEVK  660
FNWYVDGVEV HNAKTKPREE QYNSTYRVVS VLTVLHQDWL NGKEYKCKVS NKALPAPIEK  720
TISKAKGQPR EPQVYTLPPS REEMTKNQVS LTCLVKGFYP SDIAVEWESN GQPENNYKTT  780
PPVLDSDGSF FLYSKLTVDK SRWQQGNVFS CSVMHEALHN HYTQKSLSLS PGK         833

SEQ ID NO: 36             moltype = AA   length = 813
FEATURE                   Location/Qualifiers
source                    1..813
                          mol_type = protein
                          organism = Homo sapiens
SEQUENCE: 36
APTSSSTKKT QLQLEALLLD LQMILNGINN YKNPKLTRML TAKFYMPKKA TELKHLQCLE   60
EELKPLEEVL NLAQSKNFHL RPRDLISNIN VIVLELKGSE TTFMCEYADE TATIVEFLNR  120
WITFCQSIIS TLTGGGGSGG GGSGGGGSGG GGSAPTSSST KKTQLQLEAL LLDLQMILNG  180
INNYKNPKLT RMLTAKFYMP KKATELKHLQ CLEEELKPLE EVLNLAQSKN PHLRPRDLIS  240
NINVIVLELK GSETTFMCEY ADETATIVEF LNRWITFCQS IISTLTGGGG SGGGGSGGGG  300
SGGGGSGSHS MRYFFTSVSR PGRGEPRFIA VGYVDDTQFV RFDSDAASQR MEPRAPWIEQ  360
EGPEYWDGET RKVKAHSQTH RVDLGTLRGA YNQSEAGSHT VQRMYGCDVG SDWRFLRGYH  420
QYAYDGKDYI ALKEDLRSWT AADMAAQTTK HKWEAAHVAE QLRAYLEGTC VEWLRRYLEN  480
GKETLQRTDA PKTHMTHHAV SDHEATLRCW ALSFYPAEIT LTWQRDGEDQ TQDTELVETR  540
PCGDGTFQKW AAVVVPSGQE QRYTCHVQHE GLPKPLTLRW EAAAGGDKTH TCPPCPAPEA  600
AGGPSVFLFP PKPKDTLMIS RTPEVTCVVV DVSHEDPEVK FNWYVDGVEV HNAKTKPREE  660
QYNSTYRVVS VLTVLHQDWL NGKEYKCKVS NKALPAPIEK TISKAKGQPR EPQVYTLPPS  720
REEMTKNQVS LTCLVKGFYP SDIAVEWESN GQPENNYKTT PPVLDSDGSF FLYSKLTVDK  780
SRWQQGNVFS CSVMHEALHN HYTQKSLSLS PGK                               813

SEQ ID NO: 37             moltype = DNA   length = 2505
FEATURE                   Location/Qualifiers
source                    1..2505
                          mol_type = other DNA
                          organism = synthetic construct
SEQUENCE: 37
atgtacagga tgcaactcct gtcttgcatt gcactaagtc ttgcacttgt cacaaacagt    60
gcacctactt caagttctac aaagaaaaca cagctacaac tggaggcatt actgctggat   120
ttacagatga ttttgaatgg aattaataat tacaagaatc ccaaactcac caggatgctc   180
acagcaaagt tttacatgcc caagaaggcc acagaactga acatcttca gtgtctagaa    240
gaagaactca aacctctgga ggaagtgcta aatttagctc aaagcaaaaa ctttcactta   300
agacccaggg acttaatcag caatatcaac gtaatagttc tggaactaaa gggatctgaa   360
acaacattca tgtgtgaata tgctgatgag acagcaacca ttgtagaatt tctgaacaga   420
tggattacct tttgtcaaag catcatctca cactgactgg aggcggagga tctggtggt    480
ggaggttctg gtggtggggg atctggaggc ggaggatctg cacctacttc aagttctaca   540
aagaaaacac agctacaact ggaggcatta ctgctggatt tacagatgat tttgaatgga   600
attaataatt acaagaatcc caaactcacc aggatgctca cagcaaagtt ttacatgccc   660
aagaaggcca cagaactgaa acatcttcag tgtctagaag aagaactcaa acctctggag   720
gaagtgctaa atttagctca aagcaaaaac tttcacttaa gacccaggga cttaatcagc   780
aatatcaacg taatagttct ggaactaaag ggatctgaaa caacattcat gtgtgaatat   840
gctgatgaga cagcaaccat tgtagaattt ctgaacagat ggattacctt ttgtcaaagc   900
atcatctcaa cactgactgg aggcggagga tctggtggtg gaggttctgg tggtggggga   960
tctggaggcg gaggatctgg ctctcactcc atgaggtatt tcttcacatc cgtgtcccgg  1020
cccgccgcg gggagcccg cttcatcgca gtgggctacg tggacgacac gcagttcgtg   1080
cggttcgaca gcgacgccgc gagccagagg atggagccgc gggccgtg gatagagcag   1140
gagggtccgg agtattggga cggggagaca cggaaagtga aggccacac acagactgag  1200
cgagtggacc tggggaccct gcgcggcgcc tacaaccaga agcaggccgg ttctcacacc  1260
gtccagagga tgtatggctg cgacgtgggg tcggactggc gcttcctccg gggtaccac   1320
cagtacgcct acgacggcaa ggattacatc gccctgaaag aggacctgcg ctcttggacc  1380
gcggcggaca tggcagctca gaccaccaag cacaagtggg aggcggccca tgtggcggag  1440
cagttgaggg cctacctgga gggcacgtgc gtggagtggc tccgcagata ccttgagaac  1500
gggaaggaga cgctgcagcg cacggacgcc cccaaaacgc atatgactca ccacgctgtc  1560
tctgaccatg aagccaccct gaggtgctgg gccctgagct tctacccgc ggagatcaca   1620
ctgacctggc agcgggatgg ggaggaccag acccaggaca cggagctcgt ggagaccagg  1680
ccttgcgggg atggaacctt ccagaagtgg gcggctgtgg tggtgccttc tggacaggag  1740
cagagataca cctgccatgt gcagcatgag ggtttgccca gcccctcac cctgagatgg  1800
```

```
gaggcagctg cgggtggcga caaaactcac acatgcccac cgtgcccagc acctgaagcc   1860
gccgggggac cgtcagtctt cctcttcccc ccaaaaccca aggacaccct catgatctcc   1920
cggacccctg aggtcacatg cgtggtggtg gacgtgagcc acgaagaccc tgaggtcaag   1980
ttcaactggt acgtggacgg cgtggaggtg cataatgcca agacaaagcc gcgggaggag   2040
cagtacaaca gcacgtaccg tgtggtcagc gtcctcaccg tcctgcacca ggactggctg   2100
aatggcaagg agtacaagtg caaggtctcc aacaaagccc tcccagcccc catcgagaaa   2160
accatctcca aagccaaagg gcagccccga gaaccacagg tgtacaccct gcccccatcc   2220
cgggaggaga tgaccaagaa ccaggtcagc ctgacctgcc tggtcaaagg cttctatccc   2280
agcgacatcg ccgtggagtg ggagagcaat gggcagccgg agaacaacta caagaccacg   2340
cctcccgtgc tggactccga cggctccttc ttcctctaca gcaagctcac cgtggacaag   2400
agcagatggc agcaggggaa cgtcttctca tgctccgtga tgcacgaggc tctgcacaac   2460
cactacacg agaagtccct ctccctgtct ccgggtaaat agtga              2505

SEQ ID NO: 38            moltype = AA   length = 833
FEATURE                  Location/Qualifiers
source                   1..833
                         mol_type = protein
                         organism = Homo sapiens
SEQUENCE: 38
MYRMQLLSCI ALSLALVTNS APTSSSTKKT QLQLEALLLD LQMILNGINN YKNPKLTRML    60
TAKFYMPKKA TELKHLQCLE EELKPLEEVL NLAQSKNFHL RPRDLISNIN VIVLELKGSE   120
TTFMCEYADE TATIVEFLNR WITFCQSIIS TLTGGGSGG GSGGGGSGG GGSAPTSSST    180
KKTQLQLEAL LLDLQMILNG INNYKNPKLT RMLTAKFYMP KKATELKHLQ CLEEELKPLE   240
EVLNLAQSKN FHLRPRDLIS NINVIVLELK GSETTFMCEY ADETATIVEF LNRWITFCQS   300
IISTLTGGGG SGGGGSGGGG SGGGGSGSHS MRYFFTSVSR PGRGEPRFIA VGYVDDTQFV   360
RFDSDAASQR MEPRAPWIEQ EGPEYWDGET RKVKAHSQTH RVDLGTLRGA YNQSEAGSHT   420
VQRMYGCDVG SDWRFLRGYH QYAYDGKDYI ALKEDLRSWT AADMAAQTTK HKWEAAHVAE   480
QLRAYLEGTC VEWLRRYLEN GKETLQRTDA PKTHMTHHAV SDHEATLRCW ALSFYPAEIT   540
LTWQRDGEDQ TQDTELVETR PCGDGTFQKW AAVVVPSGQE QRYTCHVQHE GLPKPLTLRW   600
EAAAGGDKTH TCPPCPAPEF EGGPSVFLFP PKPKDTLMIS RTPEVTCVVV DVSHEDPEVK   660
FNWYVDGVEV HNAKTKPREE QYNSTYRVVS VLTVLHQDWL NGKEYKCKVS NKALPASIEK   720
TISKAKGQPR EPQVYTLPPS REEMTKNQVS LTCLVKGFYP SDIAVEWESN GQPENNYKTT   780
PPVLDSDGSF FLYSKLTVDK SRWQQGNVFS CSVMHEALHN HYTQKSLSLS PGK          833

SEQ ID NO: 39            moltype = AA   length = 813
FEATURE                  Location/Qualifiers
source                   1..813
                         mol_type = protein
                         organism = Homo sapiens
SEQUENCE: 39
APTSSSTKKT QLQLEALLLD LQMILNGINN YKNPKLTRML TAKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTGGGSGG GSGGGGSGG GGSAPTSSST KKTQLQLEAL LLDLQMILNG    180
INNYKNPKLT RMLTAKFYMP KKATELKHLQ CLEEELKPLE EVLNLAQSKN FHLRPRDLIS   240
NINVIVLELK GSETTFMCEY ADETATIVEF LNRWITFCQS IISTLTGGGG SGGGGSGGGG   300
SGGGGSGSHS MRYFFTSVSR PGRGEPRFIA VGYVDDTQFV RFDSDAASQR MEPRAPWIEQ   360
EGPEYWDGET RKVKAHSQTH RVDLGTLRGA YNQSEAGSHT VQRMYGCDVG SDWRFLRGYH   420
QYAYDGKDYI ALKEDLRSWT AADMAAQTTK HKWEAAHVAE QLRAYLEGTC VEWLRRYLEN   480
GKETLQRTDA PKTHMTHHAV SDHEATLRCW ALSFYPAEIT LTWQRDGEDQ TQDTELVETR   540
PCGDGTFQKW AAVVVPSGQE QRYTCHVQHE GLPKPLTLRW EAAAGGDKTH TCPPCPAPEF   600
EGGPSVFLFP PKPKDTLMIS RTPEVTCVVV DVSHEDPEVK FNWYVDGVEV HNAKTKPREE   660
QYNSTYRVVS VLTVLHQDWL NGKEYKCKVS NKALPASIEK TISKAKGQPR EPQVYTLPPS   720
REEMTKNQVS LTCLVKGFYP SDIAVEWESN GQPENNYKTT PPVLDSDGSF FLYSKLTVDK   780
SRWQQGNVFS CSVMHEALHN HYTQKSLSLS PGK                                813

SEQ ID NO: 40            moltype = DNA   length = 2505
FEATURE                  Location/Qualifiers
source                   1..2505
                         mol_type = other DNA
                         organism = synthetic construct
SEQUENCE: 40
atgtacagga tgcaactcct gtcttgcatt gcactaagtc ttgcacttgt cacaaacagt    60
gcacctactt caagttctac aaagaaaaca cagctacaac tggaggcatt actgctggat   120
ttacagatga ttttgaatgg aattaataat tacaagaatc ccaaactcac caggatgctc   180
acagcaaagt tttacatgcc caagaaggcc acagaactga acatcttcca gtgtctagaa   240
gaagaactca aacctctgga ggaagtgcta aatttagctc aaagcaaaaa ctttcactta   300
agacccagga acttaatcag caatatcaac gtaatagttc tggaactaaa gggatctgaa   360
acaacattca tgtgtgaata tgctgatgag acagcaacca tgtagaatt tctgaacaga   420
tggattacct tttgtcaaag catcatctca acactgactg gaggcggagg atctggtggt   480
ggaggttctg gtggtggggg atctggaggc ggaggatctg cacctacttc aagttctaca   540
aagaaaacac agctacaact ggaggcatta ctgctggatt tacagatgat tttgaatgga   600
attaataatt acaagaatcc caaactcacc aggatgctca cagcaaagtt ttacatgccc   660
aagaaggcca cagaactgaa catcttcagt gtctagaag aagaactcaa acctctggag   720
gaagtgctaa atttagctca aagcaaaaac tttcacttaa gacccaggga cttaatcagc   780
aatatcaacg taatagttct ggaactaaag gatctgaaa caacattcat gtgtgaatat   840
gctgatgaga cagcaaccat gtagaaaatt ctgaacagat ggattacct tttgtcaaagc   900
atcatctcaa cactgactgg aggcggagga tctggtggtg gaggttctgg tggtggggga   960
tctggaggcg gaggatctgg ctctcactcc atgaggtatt tcttcacatc cgtgtcccgg  1020
cccgccgcg gggagcccg cttcatcgca gtgggctacg tggacgacac gcagttcgtg  1080
```

```
cggttcgaca gcgacgccgc gagccagagg atggagccgc gggcgccgtg gatagagcag    1140
gagggtccgg agtattggga cggggagaca cggaaagtga aggcccactc acagactcac    1200
cgagtggacc tggggaccct gcgcggcgcc tacaaccaga gcgaggccgg ttctcacacc    1260
gtccagagga tgtatggctg cgacgtgggg tcggactggc gcttcctccg cgggtaccac    1320
cagtacgcct acgacggcaa ggattacatc gccctgaaag aggacctgcg ctcttggacc    1380
gcggcggaca tggcagctca gaccaccaag cacaagtggg aggcggccca tgtggcggaa    1440
cagttgagag cctacctgga gggcacgtgc gtggagtggc tccgcagata cctggagaac    1500
gggaaggaga cgctgcagcg cacggacgcc cccaaaacgc atatgactca ccacgctgtc    1560
tctgaccatg aagccaccct gaggtgctgg gcccctgagct tctaccctgc ggagatcaca    1620
ctgacctggc agcgggatgg ggaggaccag acccaggaca cggagctcgt ggagaccagg    1680
ccttgcgggg atggaacctt ccagaagtgg cggctgtgg tggtgccttc tggacaggag    1740
cagagataca cctgccatgt gcagcatgag ggtttgccca gcccctcac cctgagatgg    1800
gaggcagctg cgggtggcga caaaactcac acatgcccac cgtgcccagc acctgaattc    1860
gaggggggac cgtcagtctt cctcttcccc ccaaaaccca aggacaccct catgatctcc    1920
cggacccctg aggtcacatg cgtggtggtg gacgtgagcc acgaagaccc tgaggtcaag    1980
ttcaactggt acgtggacgg cgtggaggtg cataatgcca agacaaagcc gcgggaggag    2040
cagtacaaca gcacgtaccg tgtggtcagc gtcctcaccg tcctgcacca ggactggctg    2100
aatggcaagg agtacaagtg caaggtctcc aacaaagccc tcccagccag catcgagaaa    2160
accatctcca aagccaaagg gcagccccga gaaccacagg tgtacaccct gcccccatcc    2220
cgggaggaga tgaccaagaa ccaggtcagc ctgacctgcc tggtcaaagg cttctatccc    2280
agcgacatcg ccgtggagtg ggagagcaat gggcagccgg agaacaacta caagaccacg    2340
cctcccgtgc tggactccga cggctccttc ttcctctaca gcgtggacaa    2400
gagcagatgg cagcagggga cgtcttctca tgctccgtga tgcacgaggc tctgcacaac    2460
cactacacgc agaagtccct ctccctgtct ccgggtaaat agtga                    2505

SEQ ID NO: 41         moltype = AA   length = 144
FEATURE               Location/Qualifiers
source                1..144
                      mol_type = protein
                      organism = synthetic construct
SEQUENCE: 41
MSRSVALAVL ALLSLSGLEA YMLDLQPETT GGGGSGGGGS GGGGSIQRTP KIQVYSCHPA    60
ENGKSNFLNC YVSGFHPSDI EVDLLKNGER IEKVEHSDLS FSKDWSFYLL YYTEFTPTEK    120
DEYACRVNHV TLSQPKIVKW DRDM                                           144

SEQ ID NO: 42         moltype = AA   length = 248
FEATURE               Location/Qualifiers
source                1..248
                      mol_type = protein
                      organism = synthetic construct
SEQUENCE: 42
YMLDLQPETT GGGGSGGGGS GGGGSIQYML DLQPETTGGG GSGGGGSGGG GSIQRTPKIQ    60
VYSCHPAENG KSNFLNCYVS GFHPSDIEVD LLKNGERIEK VEHSDLSFSK DWSFYLLYYT    120
EFTPTEKDEY ACRVNHVTLS QPKIVKWDRD MRTPKIQVYS CHPAENGKSN FLNCYVSGFH    180
PSDIEVDLLK NGERIEKVEH SDLSFSKDWS FYLLYYTEFT PTEKDEYACR VNHVTLSQPK    240
IVKWDRDM                                                             248

SEQ ID NO: 43         moltype = DNA  length = 438
FEATURE               Location/Qualifiers
source                1..438
                      mol_type = other DNA
                      organism = synthetic construct
SEQUENCE: 43
atgtctcgct ccgtggcctt agctgtgctc gcgctactct ctctttctgg cctggaggcc    60
tacatgctcg atttgcagcc cgaaacgacg gtggaggtg gttctggagg aggcggttcg    120
ggcggaggtg gtagtatcca gcgtactcca aagattcagg tttactcatg ccatccagca    180
gagaatggaa agtcaaattt cctgaattgc tatgtgtctg gtttcatcc atccgacatt    240
gaagttgact tactgaagaa tggagagaga attgaaaaag tggagcattc agacttgtct    300
ttcagcaagg actggtcttt ctatctcttg tattatactg aattcacccc cactgaaaaa    360
gatgagtatg cctgccgtgt gaaccacgtg actttgtcac agcccaagat agttaagtgg    420
gatcgagaca tgtagtga                                                  438

SEQ ID NO: 44         moltype = AA   length = 227
FEATURE               Location/Qualifiers
source                1..227
                      mol_type = protein
                      organism = Homo sapiens
SEQUENCE: 44
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK    120
GQPREPQVYT LPPSREEMTK NQVSLTCLVK GFYPSDIAVE WESNGQPENN YKTTPPVLDS    180
DGSFFLYSKL TVDKSRWQQG NVFSCSVMHE ALHNHYTQKS LSLSPGK                  227

SEQ ID NO: 45         moltype = AA   length = 227
FEATURE               Location/Qualifiers
source                1..227
                      mol_type = protein
                      organism = Homo sapiens
SEQUENCE: 45
```

```
DKTHTCPPCP APEFEGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA SIEKTISKAK   120
GQPREPQVYT LPPSREEMTK NQVSLTCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 46            moltype = AA  length = 227
FEATURE                  Location/Qualifiers
source                   1..227
                         mol_type = protein
                         organism = Homo sapiens
SEQUENCE: 46
DKTHTCPPCP APELLGGPSV FLFPPKPKDT LMISRTPEVT CVVVDVSHED PEVKFNWYVD    60
GVEVHNAKTK PREEQYASTY RVVSVLTVLH QDWLNGKEYK CKVSNKALPA PIEKTISKAK   120
GQPREPQVYT LPPSREEMTK NQVSLTCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 47            moltype = AA  length = 227
FEATURE                  Location/Qualifiers
source                   1..227
                         mol_type = protein
                         organism = Homo sapiens
SEQUENCE: 47
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSREEMTK NQVSLTCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 48            moltype = AA  length = 99
FEATURE                  Location/Qualifiers
source                   1..99
                         mol_type = protein
                         organism = synthetic construct
SEQUENCE: 48
IQRTPKIQVY SCHPAENGKS NFLNCYVSGF HPSDIEVDLL KNGERIEKVE HSDLSFSKDW    60
SFYLLYYTEF TPTEKDEYAC RVNHVTLSQP KIVKWDRDM                          99

SEQ ID NO: 49            moltype = AA  length = 133
FEATURE                  Location/Qualifiers
source                   1..133
                         mol_type = protein
                         organism = Homo sapiens
SEQUENCE: 49
APTSSSTKKT QLQLEALLLD LQMILNGINN YKNPKLTRML TAKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                     133

SEQ ID NO: 50            moltype = AA  length = 275
FEATURE                  Location/Qualifiers
source                   1..275
                         mol_type = protein
                         organism = Homo sapiens
SEQUENCE: 50
GSHSMRYFFT SVSRPGRGEP RFIAVGYVDD TQFVRFDSDA ASQRMEPRAP WIEQEGPEYW    60
DGETRKVKAH SQTHRVDLGT LRGAYNQSEA GSHTVQRMYG CDVGSDWRFL RGYHQYAYDG   120
KDYIALKEDL RSWTAADMAA QTTKHKWEAA HVAEQLRAYL EGTCVEWLRR YLENGKETLQ   180
RTDAPKTHMT HHAVSDHEAT LRCWALSFYP AEITLTWQRD GEDQTQDTEL VETRPCGDGT   240
FQKWAAVVVP SGQEQRYTCH VQHEGLPKPL TLRWE                             275

SEQ ID NO: 51            moltype = AA  length = 447
FEATURE                  Location/Qualifiers
source                   1..447
                         mol_type = protein
                         organism = synthetic construct
SEQUENCE: 51
QVQLVQSGVE VKKPGASVKV SCKASGYTFT NYYMWVRQA PGQGLEWMGG INPSNGGTNF     60
NEKFKNRVTL TTDSSTTTAY MELKSLQFDD TAVYYCARRD YRFDMGFDYW GQTTVTVSS    120
ASTKGPSVFP LAPCSRSTSE STAALGCLVK DYFPEPVTVS WNSGALTSGV HTFPAVLQSS   180
GLYSLSSVVT VPSSSLGTKT YTCNVDHKPS NTKVDKRVES KYGPPCPPCP APEFLGGPSV   240
FLFPPKPKDT LMISRTPEVT CVVVDVSQED PEVQFNWYVD GVEVHNAKTK PREEQFNSTY   300
RVVSVLTVLH QDWLNGKEYK CKVSNKGLPS SIEKTISKAK GQPREPQVYT LPPSQEEMTK   360
NQVSLTCLVK GFYPSDIAVE WESNGQPENN YKTTPPVLDS DGSFFLYSRL TVDKSRWQEG   420
NVFSCSVMHE ALHNHYTQKS LSLSLGK                                      447

SEQ ID NO: 52            moltype = AA  length = 218
FEATURE                  Location/Qualifiers
source                   1..218
                         mol_type = protein
                         organism = synthetic construct
SEQUENCE: 52
```

```
EIVLTQSPAT LSLSPGERAT LSCRASKGVS TSGYSYLHWY QQKPGQAPRL LIYLASYLES   60
GVPARFSGSG SGTDFTLTIS SLEPEDFAVY YCQHSRDLPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 53           moltype = AA   length = 440
FEATURE                 Location/Qualifiers
source                  1..440
                        mol_type = protein
                        organism = Homo sapiens
SEQUENCE: 53
QVQLVESGGG VVQPGRSLRL DCKASGITFS NSGMHWVRQA PGKGLEWVAV IWYDGSKRYY   60
ADSVKGRFTI SRDNSKNTLF LQMNSLRAED TAVYYCATND DYWGQGTLVT VSSASTKGPS  120
VFPLAPCSRS TSESTAALGC LVKDYFPEPV TVSWNSGALT SGVHTFPAVL QSSGLYSLSS  180
VVTVPSSSLG TKTYTCNVDH KPSNTKVDKR VESKYGPPCP PCPAPEFLGG PSVFLFPPKP  240
KDTLMISRTP EVTCVVVDVS QEDPEVQFNW YVDGVEVHNA KTKPREEQFN STYRVVSVLT  300
VLHQDWLNGK EYKCKVSNKG LPSSIEKTIS KAKGQPREPQ VYTLPPSQEE MTKNQVSLTC  360
LVKGFYPSDI AVEWESNGQP ENNYKTTPPV LDSDGSFFLY SRLTVDKSRW QEGNVFSCSV  420
MHEALHNHYT QKSLSLSLGK                                              440

SEQ ID NO: 54           moltype = AA   length = 214
FEATURE                 Location/Qualifiers
source                  1..214
                        mol_type = protein
                        organism = synthetic construct
SEQUENCE: 54
EIVLTQSPAT LSLSPGERAT LSCRASQSVS SYLAWYQQKP GQAPRLLIYD ASNRATGIPA   60
RFSGSGSGTD FTLTISSLEP EDFAVYYCQQ SSNWPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 55           moltype = AA   length = 448
FEATURE                 Location/Qualifiers
source                  1..448
                        mol_type = protein
                        organism = Homo sapiens
SEQUENCE: 55
QVQLVESGGG VVQPGRSLRL SCAASGFTFS SYTMHWVRQA PGKGLEWVTF ISYDGNNKYY   60
ADSVKGRFTI SRDNSKNTLY LQMNSLRAED TAIYYCARTG WLGPFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                     448

SEQ ID NO: 56           moltype = AA   length = 215
FEATURE                 Location/Qualifiers
source                  1..215
                        mol_type = protein
                        organism = Homo sapiens
SEQUENCE: 56
EIVLTQSPGT LSLSPGERAT LSCRASQSVG SSYLAWYQQK PGQAPRLLIY GAFSRATGIP   60
DRFSGSGSGT DFTLTISRLE PEDFAVYYCQ QYGSSPWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 57           moltype = AA   length = 448
FEATURE                 Location/Qualifiers
source                  1..448
                        mol_type = protein
                        organism = Homo sapiens
SEQUENCE: 57
EVQLVESGGG LVQPGGSLRL SCAASGFTFS DSWIHWVRQA PGKGLEWVAW ISPYGGSTYY   60
ADSVKGRFTI SADTSKNTAY LQMNSLRAED TAVYYCARRH WPGGFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYAST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                     448

SEQ ID NO: 58           moltype = AA   length = 214
FEATURE                 Location/Qualifiers
source                  1..214
                        mol_type = protein
                        organism = synthetic construct
SEQUENCE: 58
DIQMTQSPSS LSASVGDRVT ITCRASQDVS TAVAWYQQKP GKAPKLLIYS ASFLYSGVPS   60
```

```
RFSGSGSGTD FTLTISSLQP EDFATYYCQQ YLYHPATFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 59           moltype = AA   length = 276
FEATURE                 Location/Qualifiers
source                  1..276
                        mol_type = protein
                        organism = Homo sapiens
SEQUENCE: 59
GSHSMRYFFT SVSRPGRGEP RFIAVGYVDD TQFVRFDSDA ASQRMEPRAP WIEQEGPEYW    60
DGETRKVKAH SQTHRVDLGT LRGYYNQSEA GSHTVQRMYG CDVGSDWRFL RGYHQYAYDG    120
KDYIALKEDL RSWTAADMAA QTTKHKWEAA HVAEQLRAYL EGTCVEWLRR YLENGKETLQ    180
RTDAPKTHMT HHAVSDHEAT LRCWALSFYP AEITLTWQRD GEDQTQDTEL VETRPAGDGT    240
FQKWAAVVVP SGQEQRYTCH VQHEGLPKPL TLRWEP                              276

SEQ ID NO: 60           moltype = AA   length = 274
FEATURE                 Location/Qualifiers
source                  1..274
                        mol_type = protein
                        organism = Mus musculus
SEQUENCE: 60
GPHSLRYFVT AVSRPGLGEP RFIAVGYVDD TQFVRFDSDA DNPRFEPRAP WMEQEGPEYW    60
EEQTQRAKSD EQWFRVSLRT AQRYYNQSKG GSHTFQRMFG CDVGSDWRLL RGYQQFAYDG    120
RDYIALNEDL KTWTAADTAA LITRRKWEQA GDAEYYRAYL EGECVEWLRR YLELGNETLL    180
RTDSPKAHVT YHPRSQVDVT LRCWALGFYP ADITLTWQLN GEDLTQDMEL VETRPAGDGT    240
FQKWAAVVVP LGKEQNYTCH VHHKGLPEPL TLRW                                274

SEQ ID NO: 61           moltype = AA   length = 99
FEATURE                 Location/Qualifiers
source                  1..99
                        mol_type = protein
                        organism = synthetic construct
SEQUENCE: 61
IQRTPKIQVY SRHPAENGKS NFLNCYVSGF HPSDIEVDLL KNGERIEKVE HSDLSFSKDW    60
SFYLLYYTEF TPTEKDEYAC RVNHVTLSQP KIVKWDRDM                           99

SEQ ID NO: 62           moltype = AA   length = 276
FEATURE                 Location/Qualifiers
source                  1..276
                        mol_type = protein
                        organism = Homo sapiens
SEQUENCE: 62
GSHSMRYFFT SVSRPGRGEP RFIAVGYVDD TQFVRFDSDA ASQRMEPRAP WIEQEGPEYW    60
DGETRKVKAH SQTHRVDLGT LRGYYNQSEA GSHTVQRMYG CDVGSDWRFL RGYHQYAYDG    120
KDYIALKEDL RSWTAADMAA QTTKHKWEAA HVAEQLRAYL EGTCVEWLRR YLENGKETLQ    180
RTDAPKTHMT HHAVSDHEAT LRCWALSFYP AEITLTWQRD GEDQTQDTEL VETRPCGDGT    240
FQKWAAVVVP SGQEQRYTCH VQHEGLPKPL TLRWEP                              276

SEQ ID NO: 63           moltype = AA   length = 5
FEATURE                 Location/Qualifiers
source                  1..5
                        mol_type = protein
                        organism = synthetic construct
SEQUENCE: 63
GSGGS                                                                5

SEQ ID NO: 64           moltype = AA   length = 4
FEATURE                 Location/Qualifiers
source                  1..4
                        mol_type = protein
                        organism = synthetic construct
SEQUENCE: 64
GGGS                                                                 4

SEQ ID NO: 65           moltype = AA   length = 4
FEATURE                 Location/Qualifiers
source                  1..4
                        mol_type = protein
                        organism = synthetic construct
SEQUENCE: 65
GGSG                                                                 4

SEQ ID NO: 66           moltype = AA   length = 5
FEATURE                 Location/Qualifiers
source                  1..5
                        mol_type = protein
                        organism = synthetic construct
SEQUENCE: 66
```

```
GGSGG                                                                            5

SEQ ID NO: 67            moltype = AA  length = 5
FEATURE                  Location/Qualifiers
source                   1..5
                         mol_type = protein
                         organism = synthetic construct
SEQUENCE: 67
GSGSG                                                                            5

SEQ ID NO: 68            moltype = AA  length = 5
FEATURE                  Location/Qualifiers
source                   1..5
                         mol_type = protein
                         organism = synthetic construct
SEQUENCE: 68
GSGGG                                                                            5

SEQ ID NO: 69            moltype = AA  length = 5
FEATURE                  Location/Qualifiers
source                   1..5
                         mol_type = protein
                         organism = synthetic construct
SEQUENCE: 69
GGGSG                                                                            5

SEQ ID NO: 70            moltype = AA  length = 5
FEATURE                  Location/Qualifiers
source                   1..5
                         mol_type = protein
                         organism = synthetic construct
SEQUENCE: 70
GSSSG                                                                            5

SEQ ID NO: 71            moltype = AA  length = 5
FEATURE                  Location/Qualifiers
source                   1..5
                         mol_type = protein
                         organism = synthetic construct
SEQUENCE: 71
GSSSS                                                                            5

SEQ ID NO: 72            moltype = AA  length = 5
FEATURE                  Location/Qualifiers
source                   1..5
                         mol_type = protein
                         organism = synthetic construct
SEQUENCE: 72
GGGGS                                                                            5

SEQ ID NO: 73            moltype = AA  length = 5
FEATURE                  Location/Qualifiers
source                   1..5
                         mol_type = protein
                         organism = synthetic construct
SEQUENCE: 73
AAAGG                                                                            5

SEQ ID NO: 74            moltype = AA  length = 15
FEATURE                  Location/Qualifiers
source                   1..15
                         mol_type = protein
                         organism = synthetic construct
SEQUENCE: 74
GCGASGGGGS GGGGS                                                                 15

SEQ ID NO: 75            moltype = AA  length = 9
FEATURE                  Location/Qualifiers
source                   1..9
                         mol_type = protein
                         organism = synthetic construct
SEQUENCE: 75
LLMGTLGIV                                                                        9

SEQ ID NO: 76            moltype = AA  length = 8
FEATURE                  Location/Qualifiers
source                   1..8
                         mol_type = protein
                         organism = synthetic construct
```

| | | |
|---|---|---|
| SEQUENCE: 76 TLGIVCPI | | 8 |
| SEQ ID NO: 77 FEATURE source | moltype = AA  length = 10 Location/Qualifiers 1..10 mol_type = protein organism = synthetic construct | |
| SEQUENCE: 77 YMLDLQPETT | | 10 |
| SEQ ID NO: 78 FEATURE source | moltype = AA  length = 9 Location/Qualifiers 1..9 mol_type = protein organism = synthetic construct | |
| SEQUENCE: 78 YMLDLQPET | | 9 |
| SEQ ID NO: 79 FEATURE source | moltype = AA  length = 9 Location/Qualifiers 1..9 mol_type = protein organism = synthetic construct | |
| SEQUENCE: 79 YPYDVPDYA | | 9 |
| SEQ ID NO: 80 FEATURE source | moltype = AA  length = 8 Location/Qualifiers 1..8 mol_type = protein organism = synthetic construct | |
| SEQUENCE: 80 DYKDDDDK | | 8 |
| SEQ ID NO: 81 FEATURE source | moltype = AA  length = 10 Location/Qualifiers 1..10 mol_type = protein organism = synthetic construct | |
| SEQUENCE: 81 EQKLISEEDL | | 10 |
| SEQ ID NO: 82 FEATURE source | moltype = AA  length = 5 Location/Qualifiers 1..5 mol_type = protein organism = synthetic construct | |
| SEQUENCE: 82 HHHHH | | 5 |
| SEQ ID NO: 83 FEATURE source | moltype = AA  length = 6 Location/Qualifiers 1..6 mol_type = protein organism = synthetic construct | |
| SEQUENCE: 83 HHHHHH | | 6 |
| SEQ ID NO: 84 FEATURE source | moltype = AA  length = 8 Location/Qualifiers 1..8 mol_type = protein organism = synthetic construct | |
| SEQUENCE: 84 WSHPQFEK | | 8 |
| SEQ ID NO: 85 FEATURE source | moltype = AA  length = 5 Location/Qualifiers 1..5 mol_type = protein organism = synthetic construct | |
| SEQUENCE: 85 RYIRS | | 5 |
| SEQ ID NO: 86 FEATURE source | moltype = AA  length = 4 Location/Qualifiers 1..4 mol_type = protein | |

```
                        organism = synthetic construct
SEQUENCE: 86
FHHT                                                                              4

SEQ ID NO: 87           moltype = AA   length = 17
FEATURE                 Location/Qualifiers
source                  1..17
                        mol_type = protein
                        organism = synthetic construct
SEQUENCE: 87
WEAAAREACC RECCARA                                                               17

SEQ ID NO: 88           moltype = AA   length = 8
FEATURE                 Location/Qualifiers
source                  1..8
                        mol_type = protein
                        organism = synthetic construct
SEQUENCE: 88
LEVLFQGP                                                                          8

SEQ ID NO: 89           moltype = AA   length = 4
FEATURE                 Location/Qualifiers
source                  1..4
                        mol_type = protein
                        organism = synthetic construct
SEQUENCE: 89
LVPR                                                                              4

SEQ ID NO: 90           moltype = AA   length = 7
FEATURE                 Location/Qualifiers
source                  1..7
                        mol_type = protein
                        organism = synthetic construct
SEQUENCE: 90
ENLYTQS                                                                           7

SEQ ID NO: 91           moltype = AA   length = 22
FEATURE                 Location/Qualifiers
source                  1..22
                        mol_type = protein
                        organism = synthetic construct
SEQUENCE: 91
GSGATNFSLL KQAGDVEENP GP                                                         22

SEQ ID NO: 92           moltype = AA   length = 21
FEATURE                 Location/Qualifiers
source                  1..21
                        mol_type = protein
                        organism = synthetic construct
SEQUENCE: 92
GSGEGRGSLL TCGDVEENPG P                                                          21

SEQ ID NO: 93           moltype = AA   length = 23
FEATURE                 Location/Qualifiers
source                  1..23
                        mol_type = protein
                        organism = synthetic construct
SEQUENCE: 93
GSGQCTNYAL LKLAGDVESN PGP                                                        23

SEQ ID NO: 94           moltype = AA   length = 25
FEATURE                 Location/Qualifiers
source                  1..25
                        mol_type = protein
                        organism = synthetic construct
SEQUENCE: 94
GSGVKQTLNF DLLKLAGDVE SNPGP                                                      25

SEQ ID NO: 95           moltype = AA   length = 119
FEATURE                 Location/Qualifiers
source                  1..119
                        mol_type = protein
                        organism = Homo sapiens
SEQUENCE: 95
MSRSVALAVL ALLSLSGLEA IQRTPKIQVY SRHPAENGKS NFLNCYVSGF HPSDIEVDLL                 60
KNGERIEKVE HSDLSFSKDW SFYLLYYTEF TPTEKDEYAC RVNHVTLSQP KIVKWDRDM                 119

SEQ ID NO: 96           moltype = AA   length = 119
FEATURE                 Location/Qualifiers
```

```
source                   1..119
                         mol_type = protein
                         organism = Macaca mulatta
SEQUENCE: 96
MSRSVALAVL ALLSLSGLEA IQRTPKIQVY SRHPPENGKP NFLNCYVSGF HPSDIEVDLL    60
KNGEKMGKVE HSDLSFSKDW SFYLLYYTEF TPNEKDEYAC RVNHVTLSGP RTVKWDRDM    119

SEQ ID NO: 97            moltype = AA  length = 118
FEATURE                  Location/Qualifiers
source                   1..118
                         mol_type = protein
                         organism = Bos taurus
SEQUENCE: 97
MARFVALVLL GLLSLSGLDA IQRPPKIQVY SRHPPEDGKP NYLNCYVYGF HPPQIEIDLL    60
KNGEKIKSEQ SDLSFSKDWS FYLLSHAEFT PNSKDQYSCR VKHVTLEQPR IVKWDRDL    118

SEQ ID NO: 98            moltype = AA  length = 119
FEATURE                  Location/Qualifiers
source                   1..119
                         mol_type = protein
                         organism = Mus musculus
SEQUENCE: 98
MARSVTLVFL VLVSLTGLYA IQKTPQIQVY SRHPPENGKP NILNCYVTQF HPPHIEIQML    60
KNGKKIPKVE MSDMSFSKDW SFYILAHTEF TPTETDTYAC RVKHASMAEP KTVYWDRDM    119

SEQ ID NO: 99            moltype = AA  length = 254
FEATURE                  Location/Qualifiers
source                   1..254
                         mol_type = protein
                         organism = Homo sapiens
SEQUENCE: 99
MEYASDASLD PEAPWPPAPR ARACRVLPWA LVAGLLLLLL LAAACAVFLA CPWAVSGARA    60
SPGSAASPRL REGPELSPDD PAGLLDLRQG MFAQLVAQNV LLIDGPLSWY SDPGLAGVSL   120
TGGLSYKEDT KELVVAKAGV YYVFFQLELR RVVAGEGSGS VSLALHLQPL RSAAGAAALA   180
LTVDLPPASS EARNSAFGFQ GRLLHLSAGQ RLGVHLHTEA RARHAWQLTQ GATVLGLFRV   240
TPEIPAGLPS PRSE                                                    254

SEQ ID NO: 100           moltype = AA  length = 174
FEATURE                  Location/Qualifiers
VARIANT                  47
                         note = Xaa is any amino acid other than a lysine
source                   1..174
                         mol_type = protein
                         organism = synthetic construct
SEQUENCE: 100
PAGLLDLRQG MFAQLVAQNV LLIDGPLSWY SDPGLAGVSL TGGLSYXEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATVLGLFRV TPEIPAGLPS PRSE         174

SEQ ID NO: 101           moltype = AA  length = 174
FEATURE                  Location/Qualifiers
source                   1..174
                         mol_type = protein
                         organism = synthetic construct
SEQUENCE: 101
PAGLLDLRQG MFAQLVAQNV LLIDGPLSWY SDPGLAGVSL TGGLSYAEDT KELVVAKAGV    60
YVFFQLELR RVVAGEGSGS VSLALHLQPL RSAAGAAALA LTVDLPPASS EARNSAFGFQ    120
GRLLHLSAGQ RLGVHLHTEA RARHAWQLTQ GATVLGLFRV TPEIPAGLPS PRSE         174

SEQ ID NO: 102           moltype = AA  length = 174
FEATURE                  Location/Qualifiers
VARIANT                  147
                         note = Xaa is any amino acid other than a glutamine
source                   1..174
                         mol_type = protein
                         organism = synthetic construct
SEQUENCE: 102
PAGLLDLRQG MFAQLVAQNV LLIDGPLSWY SDPGLAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWXLTQ GATVLGLFRV TPEIPAGLPS PRSE         174

SEQ ID NO: 103           moltype = AA  length = 174
FEATURE                  Location/Qualifiers
VARIANT                  11
                         note = Xaa is any amino acid other than a methionine
source                   1..174
                         mol_type = protein
                         organism = synthetic construct
SEQUENCE: 103
```

```
PAGLLDLRQG XFAQLVAQNV LLIDGPLSWY SDPGLAGVSL TGGLSYKEDT KELVVAKAGV   60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 104          moltype = AA  length = 174
FEATURE                 Location/Qualifiers
VARIANT                 12
                        note = Xaa is any amino acid other than a phenylalanine
source                  1..174
                        mol_type = protein
                        organism = synthetic construct
SEQUENCE: 104
PAGLLDLRQG MXAQLVAQNV LLIDGPLSWY SDPGLAGVSL TGGLSYKEDT KELVVAKAGV   60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 105          moltype = AA  length = 174
FEATURE                 Location/Qualifiers
VARIANT                 14
                        note = Xaa is any amino acid other than a glutamine
source                  1..174
                        mol_type = protein
                        organism = synthetic construct
SEQUENCE: 105
PAGLLDLRQG MFAXLVAQNV LLIDGPLSWY SDPGLAGVSL TGGLSYKEDT KELVVAKAGV   60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 106          moltype = AA  length = 174
FEATURE                 Location/Qualifiers
VARIANT                 15
                        note = Xaa is any amino acid other than a leucine
source                  1..174
                        mol_type = protein
                        organism = synthetic construct
SEQUENCE: 106
PAGLLDLRQG MFAQXVAQNV LLIDGPLSWY SDPGLAGVSL TGGLSYKEDT KELVVAKAGV   60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 107          moltype = AA  length = 174
FEATURE                 Location/Qualifiers
VARIANT                 16
                        note = Xaa is any amino acid other than a valine
source                  1..174
                        mol_type = protein
                        organism = synthetic construct
SEQUENCE: 107
PAGLLDLRQG MFAQLXAQNV LLIDGPLSWY SDPGLAGVSL TGGLSYKEDT KELVVAKAGV   60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 108          moltype = AA  length = 174
FEATURE                 Location/Qualifiers
VARIANT                 18
                        note = Xaa is any amino acid other than a glutamine
source                  1..174
                        mol_type = protein
                        organism = synthetic construct
SEQUENCE: 108
PAGLLDLRQG MFAQLVAXNV LLIDGPLSWY SDPGLAGVSL TGGLSYKEDT KELVVAKAGV   60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 109          moltype = AA  length = 174
FEATURE                 Location/Qualifiers
VARIANT                 19
                        note = Xaa is any amino acid other than a asparagine
source                  1..174
                        mol_type = protein
                        organism = synthetic construct
SEQUENCE: 109
PAGLLDLRQG MFAQLVAQXV LLIDGPLSWY SDPGLAGVSL TGGLSYKEDT KELVVAKAGV   60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 110          moltype = AA  length = 174
FEATURE                 Location/Qualifiers
VARIANT                 20
```

```
                        note = Xaa is any amino acid other than a valine
source                  1..174
                        mol_type = protein
                        organism = synthetic construct
SEQUENCE: 110
PAGLLDLRQG MFAQLVAQNX LLIDGPLSWY SDPGLAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATVLGLFRV TPEIPAGLPS PRSE         174

SEQ ID NO: 111          moltype = AA   length = 174
FEATURE                 Location/Qualifiers
VARIANT                 21
                        note = Xaa is any amino acid other than a leucine
source                  1..174
                        mol_type = protein
                        organism = synthetic construct
SEQUENCE: 111
PAGLLDLRQG MFAQLVAQNV XLIDGPLSWY SDPGLAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATVLGLFRV TPEIPAGLPS PRSE         174

SEQ ID NO: 112          moltype = AA   length = 174
FEATURE                 Location/Qualifiers
VARIANT                 22
                        note = Xaa is any amino acid other than a leucine
source                  1..174
                        mol_type = protein
                        organism = synthetic construct
SEQUENCE: 112
PAGLLDLRQG MFAQLVAQNV LXIDGPLSWY SDPGLAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATVLGLFRV TPEIPAGLPS PRSE         174

SEQ ID NO: 113          moltype = AA   length = 174
FEATURE                 Location/Qualifiers
VARIANT                 23
                        note = Xaa is any amino acid other than a isoleucine
source                  1..174
                        mol_type = protein
                        organism = synthetic construct
SEQUENCE: 113
PAGLLDLRQG MFAQLVAQNV LLXDGPLSWY SDPGLAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATVLGLFRV TPEIPAGLPS PRSE         174

SEQ ID NO: 114          moltype = AA   length = 174
FEATURE                 Location/Qualifiers
VARIANT                 24
                        note = Xaa is any amino acid other than a aspartic acid
source                  1..174
                        mol_type = protein
                        organism = synthetic construct
SEQUENCE: 114
PAGLLDLRQG MFAQLVAQNV LLIXGPLSWY SDPGLAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATVLGLFRV TPEIPAGLPS PRSE         174

SEQ ID NO: 115          moltype = AA   length = 174
FEATURE                 Location/Qualifiers
VARIANT                 25
                        note = Xaa is any amino acid other than a glycine
source                  1..174
                        mol_type = protein
                        organism = synthetic construct
SEQUENCE: 115
PAGLLDLRQG MFAQLVAQNV LLIDXPLSWY SDPGLAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATVLGLFRV TPEIPAGLPS PRSE         174

SEQ ID NO: 116          moltype = AA   length = 174
FEATURE                 Location/Qualifiers
VARIANT                 26
                        note = Xaa is any amino acid other than a proline
source                  1..174
                        mol_type = protein
                        organism = synthetic construct
SEQUENCE: 116
PAGLLDLRQG MFAQLVAQNV LLIDGXLSWY SDPGLAGVSL TGGLSYKEDT KELVVAKAGV    60
YYVFFQLELR RVVAGEGSGS VSLALHLQPL RSAAGAAALA LTVDLPPASS EARNSAFGFQ   120
```

```
GRLLHLSAGQ RLGVHLHTEA RARHAWQLTQ GATVLGLFRV TPEIPAGLPS PRSE         174

SEQ ID NO: 117           moltype = AA   length = 174
FEATURE                  Location/Qualifiers
VARIANT                  27
                         note = Xaa is any amino acid other than a leucine
source                   1..174
                         mol_type = protein
                         organism = synthetic construct
SEQUENCE: 117
PAGLLDLRQG MFAQLVAQNV LLIDGPXSWY SDPGLAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATVLGLFRV TPEIPAGLPS PRSE         174

SEQ ID NO: 118           moltype = AA   length = 174
FEATURE                  Location/Qualifiers
VARIANT                  28
                         note = Xaa is any amino acid other than a serine
source                   1..174
                         mol_type = protein
                         organism = synthetic construct
SEQUENCE: 118
PAGLLDLRQG MFAQLVAQNV LLIDGPLXWY SDPGLAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATVLGLFRV TPEIPAGLPS PRSE         174

SEQ ID NO: 119           moltype = AA   length = 174
FEATURE                  Location/Qualifiers
VARIANT                  29
                         note = Xaa is any amino acid other than a Tryptophan
source                   1..174
                         mol_type = protein
                         organism = synthetic construct
SEQUENCE: 119
PAGLLDLRQG MFAQLVAQNV LLIDGPLSXY SDPGLAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATVLGLFRV TPEIPAGLPS PRSE         174

SEQ ID NO: 120           moltype = AA   length = 174
FEATURE                  Location/Qualifiers
VARIANT                  30
                         note = Xaa is any amino acid other than a tyrosine
source                   1..174
                         mol_type = protein
                         organism = synthetic construct
SEQUENCE: 120
PAGLLDLRQG MFAQLVAQNV LLIDGPLSWX SDPGLAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATVLGLFRV TPEIPAGLPS PRSE         174

SEQ ID NO: 121           moltype = AA   length = 174
FEATURE                  Location/Qualifiers
VARIANT                  31
                         note = Xaa is any amino acid other than a Serine
source                   1..174
                         mol_type = protein
                         organism = synthetic construct
SEQUENCE: 121
PAGLLDLRQG MFAQLVAQNV LLIDGPLSWY XDPGLAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATVLGLFRV TPEIPAGLPS PRSE         174

SEQ ID NO: 122           moltype = AA   length = 174
FEATURE                  Location/Qualifiers
VARIANT                  32
                         note = Xaa is any amino acid other than a Aspartic acid
source                   1..174
                         mol_type = protein
                         organism = synthetic construct
SEQUENCE: 122
PAGLLDLRQG MFAQLVAQNV LLIDGPLSWY SXPGLAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATVLGLFRV TPEIPAGLPS PRSE         174

SEQ ID NO: 123           moltype = AA   length = 174
FEATURE                  Location/Qualifiers
VARIANT                  33
                         note = Xaa is any amino acid other than a Proline
source                   1..174
```

```
                        mol_type = protein
                        organism = synthetic construct
SEQUENCE: 123
PAGLLDLRQG MFAQLVAQNV LLIDGPLSWY SDXGLAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATVLGLFRV TPEIPAGLPS PRSE         174

SEQ ID NO: 124          moltype = AA  length = 174
FEATURE                 Location/Qualifiers
VARIANT                 34
                        note = Xaa is any amino acid other than a glycine
source                  1..174
                        mol_type = protein
                        organism = synthetic construct
SEQUENCE: 124
PAGLLDLRQG MFAQLVAQNV LLIDGPLSWY SDPXLAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATVLGLFRV TPEIPAGLPS PRSE         174

SEQ ID NO: 125          moltype = AA  length = 174
FEATURE                 Location/Qualifiers
VARIANT                 35
                        note = Xaa is any amino acid other than a Leucine
source                  1..174
                        mol_type = protein
                        organism = synthetic construct
SEQUENCE: 125
PAGLLDLRQG MFAQLVAQNV LLIDGPLSWY SDPGXAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATVLGLFRV TPEIPAGLPS PRSE         174

SEQ ID NO: 126          moltype = AA  length = 174
FEATURE                 Location/Qualifiers
VARIANT                 37
                        note = Xaa is any amino acid other than a Glycine
source                  1..174
                        mol_type = protein
                        organism = synthetic construct
SEQUENCE: 126
PAGLLDLRQG MFAQLVAQNV LLIDGPLSWY SDPGLAXVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATVLGLFRV TPEIPAGLPS PRSE         174

SEQ ID NO: 127          moltype = AA  length = 174
FEATURE                 Location/Qualifiers
VARIANT                 38
                        note = Xaa is any amino acid other than a Valine
source                  1..174
                        mol_type = protein
                        organism = synthetic construct
SEQUENCE: 127
PAGLLDLRQG MFAQLVAQNV LLIDGPLSWY SDPGLAGXSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATVLGLFRV TPEIPAGLPS PRSE         174

SEQ ID NO: 128          moltype = AA  length = 174
FEATURE                 Location/Qualifiers
VARIANT                 39
                        note = Xaa is any amino acid other than a Serine
source                  1..174
                        mol_type = protein
                        organism = synthetic construct
SEQUENCE: 128
PAGLLDLRQG MFAQLVAQNV LLIDGPLSWY SDPGLAGVXL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATVLGLFRV TPEIPAGLPS PRSE         174

SEQ ID NO: 129          moltype = AA  length = 174
FEATURE                 Location/Qualifiers
VARIANT                 40
                        note = Xaa is any amino acid other than a Leucine
source                  1..174
                        mol_type = protein
                        organism = synthetic construct
SEQUENCE: 129
PAGLLDLRQG MFAQLVAQNV LLIDGPLSWY SDPGLAGVSX TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATVLGLFRV TPEIPAGLPS PRSE         174
```

-continued

```
SEQ ID NO: 130          moltype = AA  length = 174
FEATURE                 Location/Qualifiers
VARIANT                 41
                        note = Xaa is any amino acid other than a Threonine
source                  1..174
                        mol_type = protein
                        organism = synthetic construct
SEQUENCE: 130
PAGLLDLRQG MFAQLVAQNV LLIDGPLSWY SDPGLAGVSL XGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATVLGLFRV TPEIPAGLPS PRSE         174

SEQ ID NO: 131          moltype = AA  length = 174
FEATURE                 Location/Qualifiers
VARIANT                 42
                        note = Xaa is any amino acid other than a Glycine
source                  1..174
                        mol_type = protein
                        organism = synthetic construct
SEQUENCE: 131
PAGLLDLRQG MFAQLVAQNV LLIDGPLSWY SDPGLAGVSL TXGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATVLGLFRV TPEIPAGLPS PRSE         174

SEQ ID NO: 132          moltype = AA  length = 174
FEATURE                 Location/Qualifiers
VARIANT                 43
                        note = Xaa is any amino acid other than a Glycine
source                  1..174
                        mol_type = protein
                        organism = synthetic construct
SEQUENCE: 132
PAGLLDLRQG MFAQLVAQNV LLIDGPLSWY SDPGLAGVSL TGXLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATVLGLFRV TPEIPAGLPS PRSE         174

SEQ ID NO: 133          moltype = AA  length = 174
FEATURE                 Location/Qualifiers
VARIANT                 44
                        note = Xaa is any amino acid other than a Leucine
source                  1..174
                        mol_type = protein
                        organism = synthetic construct
SEQUENCE: 133
PAGLLDLRQG MFAQLVAQNV LLIDGPLSWY SDPGLAGVSL TGGXSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATVLGLFRV TPEIPAGLPS PRSE         174

SEQ ID NO: 134          moltype = AA  length = 174
FEATURE                 Location/Qualifiers
VARIANT                 45
                        note = Xaa is any amino acid other than a Serine
source                  1..174
                        mol_type = protein
                        organism = synthetic construct
SEQUENCE: 134
PAGLLDLRQG MFAQLVAQNV LLIDGPLSWY SDPGLAGVSL TGGLXYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATVLGLFRV TPEIPAGLPS PRSE         174

SEQ ID NO: 135          moltype = AA  length = 174
FEATURE                 Location/Qualifiers
VARIANT                 46
                        note = Xaa is any amino acid other than a Tyrosine
source                  1..174
                        mol_type = protein
                        organism = synthetic construct
SEQUENCE: 135
PAGLLDLRQG MFAQLVAQNV LLIDGPLSWY SDPGLAGVSL TGGLSXKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATVLGLFRV TPEIPAGLPS PRSE         174

SEQ ID NO: 136          moltype = AA  length = 174
FEATURE                 Location/Qualifiers
VARIANT                 48
                        note = Xaa is any amino acid other than a Glutamic Acid
source                  1..174
                        mol_type = protein
                        organism = synthetic construct
```

```
SEQUENCE: 136
PAGLLDLRQG MFAQLVAQNV LLIDGPLSWY SDPGLAGVSL TGGLSYKXDT KELVVAKAGV   60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 137          moltype = AA   length = 174
FEATURE                 Location/Qualifiers
VARIANT                 49
                        note = Xaa is any amino acid other than a Aspartic acid
source                  1..174
                        mol_type = protein
                        organism = synthetic construct
SEQUENCE: 137
PAGLLDLRQG MFAQLVAQNV LLIDGPLSWY SDPGLAGVSL TGGLSYKEXT KELVVAKAGV   60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 138          moltype = AA   length = 174
FEATURE                 Location/Qualifiers
VARIANT                 50
                        note = Xaa is any amino acid other than a Threonine
source                  1..174
                        mol_type = protein
                        organism = synthetic construct
SEQUENCE: 138
PAGLLDLRQG MFAQLVAQNV LLIDGPLSWY SDPGLAGVSL TGGLSYKEDX KELVVAKAGV   60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 139          moltype = AA   length = 174
FEATURE                 Location/Qualifiers
VARIANT                 51
                        note = Xaa is any amino acid other than a Lysine
source                  1..174
                        mol_type = protein
                        organism = synthetic construct
SEQUENCE: 139
PAGLLDLRQG MFAQLVAQNV LLIDGPLSWY SDPGLAGVSL TGGLSYKEDT XELVVAKAGV   60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 140          moltype = AA   length = 174
FEATURE                 Location/Qualifiers
VARIANT                 52
                        note = Xaa is any amino acid other than a Glutamic acid
source                  1..174
                        mol_type = protein
                        organism = synthetic construct
SEQUENCE: 140
PAGLLDLRQG MFAQLVAQNV LLIDGPLSWY SDPGLAGVSL TGGLSYKEDT KXLVVAKAGV   60
YYVFFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 141          moltype = AA   length = 174
FEATURE                 Location/Qualifiers
VARIANT                 64
                        note = Xaa is any amino acid other than a Phenylalanine
source                  1..174
                        mol_type = protein
                        organism = synthetic construct
SEQUENCE: 141
PAGLLDLRQG MFAQLVAQNV LLIDGPLSWY SDPGLAGVSL TGGLSYKEDT KELVVAKAGV   60
YYVXFQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 142          moltype = AA   length = 174
FEATURE                 Location/Qualifiers
VARIANT                 65
                        note = Xaa is any amino acid other than a Phenylalanine
source                  1..174
                        mol_type = protein
                        organism = synthetic construct
SEQUENCE: 142
PAGLLDLRQG MFAQLVAQNV LLIDGPLSWY SDPGLAGVSL TGGLSYKEDT KELVVAKAGV   60
YYVFXQLELR RVVAGEGSGS VSLALHLQPL RSAAGAAALA LTVDLPPASS EARNSAFGFQ  120
GRLLHLSAGQ RLGVHLHTEA RARHAWQLTQ GATVLGLFRV TPEIPAGLPS PRSE        174

SEQ ID NO: 143          moltype = AA   length = 174
FEATURE                 Location/Qualifiers
```

| | |
|---|---|
| VARIANT | 66 |
| | note = Xaa is any amino acid other than a Glutamine |
| source | 1..174 |
| | mol_type = protein |
| | organism = synthetic construct |

SEQUENCE: 143
PAGLLDLRQG MFAQLVAQNV LLIDGPLSWY SDPGLAGVSL TGGLSYKEDT KELVVAKAGV 60
YYVFFXLELR RVVAGEGSGS VSLALHLQPL RSAAGAAALA LTVDLPPASS EARNSAFGFQ 120
GRLLHLSAGQ RLGVHLHTEA RARHAWQLTQ GATVLGLFRV TPEIPAGLPS PRSE 174

| | |
|---|---|
| SEQ ID NO: 144 | moltype = AA length = 174 |
| FEATURE | Location/Qualifiers |
| VARIANT | 67 |
| | note = Xaa is any amino acid other than a Leucine |
| source | 1..174 |
| | mol_type = protein |
| | organism = synthetic construct |

SEQUENCE: 144
PAGLLDLRQG MFAQLVAQNV LLIDGPLSWY SDPGLAGVSL TGGLSYKEDT KELVVAKAGV 60
YYVFFQXELR RVVAGEGSGS VSLALHLQPL RSAAGAAALA LTVDLPPASS EARNSAFGFQ 120
GRLLHLSAGQ RLGVHLHTEA RARHAWQLTQ GATVLGLFRV TPEIPAGLPS PRSE 174

| | |
|---|---|
| SEQ ID NO: 145 | moltype = AA length = 174 |
| FEATURE | Location/Qualifiers |
| VARIANT | 68 |
| | note = Xaa is any amino acid other than a Glutamic acid |
| source | 1..174 |
| | mol_type = protein |
| | organism = synthetic construct |

SEQUENCE: 145
PAGLLDLRQG MFAQLVAQNV LLIDGPLSWY SDPGLAGVSL TGGLSYKEDT KELVVAKAGV 60
YYVFFQLXLR RVVAGEGSGS VSLALHLQPL RSAAGAAALA LTVDLPPASS EARNSAFGFQ 120
GRLLHLSAGQ RLGVHLHTEA RARHAWQLTQ GATVLGLFRV TPEIPAGLPS PRSE 174

| | |
|---|---|
| SEQ ID NO: 146 | moltype = AA length = 174 |
| FEATURE | Location/Qualifiers |
| VARIANT | 69 |
| | note = Xaa is any amino acid other than a Leucine |
| source | 1..174 |
| | mol_type = protein |
| | organism = synthetic construct |

SEQUENCE: 146
PAGLLDLRQG MFAQLVAQNV LLIDGPLSWY SDPGLAGVSL TGGLSYKEDT KELVVAKAGV 60
YYVFFQLEXR RVVAGEGSGS VSLALHLQPL RSAAGAAALA LTVDLPPASS EARNSAFGFQ 120
GRLLHLSAGQ RLGVHLHTEA RARHAWQLTQ GATVLGLFRV TPEIPAGLPS PRSE 174

| | |
|---|---|
| SEQ ID NO: 147 | moltype = AA length = 174 |
| FEATURE | Location/Qualifiers |
| VARIANT | 70 |
| | note = Xaa is any amino acid other than a Arginine |
| source | 1..174 |
| | mol_type = protein |
| | organism = synthetic construct |

SEQUENCE: 147
PAGLLDLRQG MFAQLVAQNV LLIDGPLSWY SDPGLAGVSL TGGLSYKEDT KELVVAKAGV 60
YYVFFQLELX RVVAGEGSGS VSLALHLQPL RSAAGAAALA LTVDLPPASS EARNSAFGFQ 120
GRLLHLSAGQ RLGVHLHTEA RARHAWQLTQ GATVLGLFRV TPEIPAGLPS PRSE 174

| | |
|---|---|
| SEQ ID NO: 148 | moltype = AA length = 174 |
| FEATURE | Location/Qualifiers |
| VARIANT | 71 |
| | note = Xaa is any amino acid other than a Arginine |
| source | 1..174 |
| | mol_type = protein |
| | organism = synthetic construct |

SEQUENCE: 148
PAGLLDLRQG MFAQLVAQNV LLIDGPLSWY SDPGLAGVSL TGGLSYKEDT KELVVAKAGV 60
YYVFFQLELR XVVAGEGSGS VSLALHLQPL RSAAGAAALA LTVDLPPASS EARNSAFGFQ 120
GRLLHLSAGQ RLGVHLHTEA RARHAWQLTQ GATVLGLFRV TPEIPAGLPS PRSE 174

| | |
|---|---|
| SEQ ID NO: 149 | moltype = AA length = 174 |
| FEATURE | Location/Qualifiers |
| VARIANT | 72 |
| | note = Xaa is any amino acid other than a Valine |
| source | 1..174 |
| | mol_type = protein |
| | organism = synthetic construct |

SEQUENCE: 149
PAGLLDLRQG MFAQLVAQNV LLIDGPLSWY SDPGLAGVSL TGGLSYKEDT KELVVAKAGV 60

```
YVVFFQLELR RXVAGEGSGS VSLALHLQPL RSAAGAAALA LTVDLPPASS EARNSAFGFQ    120
GRLLHLSAGQ RLGVHLHTEA RARHAWQLTQ GATVLGLFRV TPEIPAGLPS PRSE          174

SEQ ID NO: 150          moltype = AA  length = 174
FEATURE                 Location/Qualifiers
VARIANT                 73
                        note = Xaa is any amino acid other than a Valine
source                  1..174
                        mol_type = protein
                        organism = synthetic construct
SEQUENCE: 150
PAGLLDLRQG MFAQLVAQNV LLIDGPLSWY SDPGLAGVSL TGGLSYKEDT KELVVAKAGV    60
YVVFFQLELR RVXAGEGSGS VSLALHLQPL RSAAGAAALA LTVDLPPASS EARNSAFGFQ    120
GRLLHLSAGQ RLGVHLHTEA RARHAWQLTQ GATVLGLFRV TPEIPAGLPS PRSE          174

SEQ ID NO: 151          moltype = AA  length = 174
FEATURE                 Location/Qualifiers
VARIANT                 75
                        note = Xaa is any amino acid other than a Glycine
source                  1..174
                        mol_type = protein
                        organism = synthetic construct
SEQUENCE: 151
PAGLLDLRQG MFAQLVAQNV LLIDGPLSWY SDPGLAGVSL TGGLSYKEDT KELVVAKAGV    60
YVVFFQLELR RVVAXEGSGS VSLALHLQPL RSAAGAAALA LTVDLPPASS EARNSAFGFQ    120
GRLLHLSAGQ RLGVHLHTEA RARHAWQLTQ GATVLGLFRV TPEIPAGLPS PRSE          174

SEQ ID NO: 152          moltype = AA  length = 174
FEATURE                 Location/Qualifiers
VARIANT                 76
                        note = Xaa is any amino acid other than a Glutamic acid
source                  1..174
                        mol_type = protein
                        organism = synthetic construct
SEQUENCE: 152
PAGLLDLRQG MFAQLVAQNV LLIDGPLSWY SDPGLAGVSL TGGLSYKEDT KELVVAKAGV    60
YVVFFQLELR RVVAGXGSGS VSLALHLQPL RSAAGAAALA LTVDLPPASS EARNSAFGFQ    120
GRLLHLSAGQ RLGVHLHTEA RARHAWQLTQ GATVLGLFRV TPEIPAGLPS PRSE          174

SEQ ID NO: 153          moltype = AA  length = 174
FEATURE                 Location/Qualifiers
VARIANT                 77
                        note = Xaa is any amino acid other than a Glycine
source                  1..174
                        mol_type = protein
                        organism = synthetic construct
SEQUENCE: 153
PAGLLDLRQG MFAQLVAQNV LLIDGPLSWY SDPGLAGVSL TGGLSYKEDT KELVVAKAGV    60
YVVFFQLELR RVVAGEXSGS VSLALHLQPL RSAAGAAALA LTVDLPPASS EARNSAFGFQ    120
GRLLHLSAGQ RLGVHLHTEA RARHAWQLTQ GATVLGLFRV TPEIPAGLPS PRSE          174

SEQ ID NO: 154          moltype = AA  length = 174
FEATURE                 Location/Qualifiers
VARIANT                 78
                        note = Xaa is any amino acid other than a Serine
source                  1..174
                        mol_type = protein
                        organism = synthetic construct
SEQUENCE: 154
PAGLLDLRQG MFAQLVAQNV LLIDGPLSWY SDPGLAGVSL TGGLSYKEDT KELVVAKAGV    60
YVVFFQLELR RVVAGEGXGS VSLALHLQPL RSAAGAAALA LTVDLPPASS EARNSAFGFQ    120
GRLLHLSAGQ RLGVHLHTEA RARHAWQLTQ GATVLGLFRV TPEIPAGLPS PRSE          174

SEQ ID NO: 155          moltype = AA  length = 174
FEATURE                 Location/Qualifiers
VARIANT                 104
                        note = Xaa is any amino acid other than a Aspartic acid
source                  1..174
                        mol_type = protein
                        organism = synthetic construct
SEQUENCE: 155
PAGLLDLRQG MFAQLVAQNV LLIDGPLSWY SDPGLAGVSL TGGLSYKEDT KELVVAKAGV    60
YVVFFQLELR RVVAGEGSGS VSLALHLQPL RSAAGAAALA LTVXLPPASS EARNSAFGFQ    120
GRLLHLSAGQ RLGVHLHTEA RARHAWQLTQ GATVLGLFRV TPEIPAGLPS PRSE          174

SEQ ID NO: 156          moltype = AA  length = 174
FEATURE                 Location/Qualifiers
VARIANT                 105
                        note = Xaa is any amino acid other than a Leucine
```

```
                        source          1..174
                                        mol_type = protein
                                        organism = synthetic construct
SEQUENCE: 156
PAGLLDLRQG MFAQLVAQNV LLIDGPLSWY SDPGLAGVSL TGGLSYKEDT KELVVAKAGV    60
YYVFFQLELR RVVAGEGSGS VSLALHLQPL RSAAGAAALA LTVDXPPASS EARNSAFGFQ   120
GRLLHLSAGQ RLGVHLHTEA RARHAWQLTQ GATVLGLFRV TPEIPAGLPS PRSE         174

SEQ ID NO: 157          moltype = AA  length = 174
FEATURE                 Location/Qualifiers
VARIANT                 106
                        note = Xaa is any amino acid other than a Proline
source                  1..174
                        mol_type = protein
                        organism = synthetic construct
SEQUENCE: 157
PAGLLDLRQG MFAQLVAQNV LLIDGPLSWY SDPGLAGVSL TGGLSYKEDT KELVVAKAGV    60
YYVFFQLELR RVVAGEGSGS VSLALHLQPL RSAAGAAALA LTVDLXPASS EARNSAFGFQ   120
GRLLHLSAGQ RLGVHLHTEA RARHAWQLTQ GATVLGLFRV TPEIPAGLPS PRSE         174

SEQ ID NO: 158          moltype = AA  length = 174
FEATURE                 Location/Qualifiers
VARIANT                 107
                        note = Xaa is any amino acid other than a Proline
source                  1..174
                        mol_type = protein
                        organism = synthetic construct
SEQUENCE: 158
PAGLLDLRQG MFAQLVAQNV LLIDGPLSWY SDPGLAGVSL TGGLSYKEDT KELVVAKAGV    60
YYVFFQLELR RVVAGEGSGS VSLALHLQPL RSAAGAAALA LTVDLPXASS EARNSAFGFQ   120
GRLLHLSAGQ RLGVHLHTEA RARHAWQLTQ GATVLGLFRV TPEIPAGLPS PRSE         174

SEQ ID NO: 159          moltype = AA  length = 174
FEATURE                 Location/Qualifiers
VARIANT                 109
                        note = Xaa is any amino acid other than a Serine
source                  1..174
                        mol_type = protein
                        organism = synthetic construct
SEQUENCE: 159
PAGLLDLRQG MFAQLVAQNV LLIDGPLSWY SDPGLAGVSL TGGLSYKEDT KELVVAKAGV    60
YYVFFQLELR RVVAGEGSGS VSLALHLQPL RSAAGAAALA LTVDLPPAXS EARNSAFGFQ   120
GRLLHLSAGQ RLGVHLHTEA RARHAWQLTQ GATVLGLFRV TPEIPAGLPS PRSE         174

SEQ ID NO: 160          moltype = AA  length = 174
FEATURE                 Location/Qualifiers
VARIANT                 110
                        note = Xaa is any amino acid other than a Serine
source                  1..174
                        mol_type = protein
                        organism = synthetic construct
SEQUENCE: 160
PAGLLDLRQG MFAQLVAQNV LLIDGPLSWY SDPGLAGVSL TGGLSYKEDT KELVVAKAGV    60
YYVFFQLELR RVVAGEGSGS VSLALHLQPL RSAAGAAALA LTVDLPPASX EARNSAFGFQ   120
GRLLHLSAGQ RLGVHLHTEA RARHAWQLTQ GATVLGLFRV TPEIPAGLPS PRSE         174

SEQ ID NO: 161          moltype = AA  length = 174
FEATURE                 Location/Qualifiers
VARIANT                 111
                        note = Xaa is any amino acid other than a Glutamic acid
source                  1..174
                        mol_type = protein
                        organism = synthetic construct
SEQUENCE: 161
PAGLLDLRQG MFAQLVAQNV LLIDGPLSWY SDPGLAGVSL TGGLSYKEDT KELVVAKAGV    60
YYVFFQLELR RVVAGEGSGS VSLALHLQPL RSAAGAAALA LTVDLPPASS XARNSAFGFQ   120
GRLLHLSAGQ RLGVHLHTEA RARHAWQLTQ GATVLGLFRV TPEIPAGLPS PRSE         174

SEQ ID NO: 162          moltype = AA  length = 174
FEATURE                 Location/Qualifiers
VARIANT                 113
                        note = Xaa is any amino acid other than a Arginine
source                  1..174
                        mol_type = protein
                        organism = synthetic construct
SEQUENCE: 162
PAGLLDLRQG MFAQLVAQNV LLIDGPLSWY SDPGLAGVSL TGGLSYKEDT KELVVAKAGV    60
YYVFFQLELR RVVAGEGSGS VSLALHLQPL RSAAGAAALA LTVDLPPASS EAXNSAFGFQ   120
GRLLHLSAGQ RLGVHLHTEA RARHAWQLTQ GATVLGLFRV TPEIPAGLPS PRSE         174
```

```
SEQ ID NO: 163         moltype = AA   length = 174
FEATURE                Location/Qualifiers
VARIANT                114
                       note = Xaa is any amino acid other than a Asparagine
source                 1..174
                       mol_type = protein
                       organism = synthetic construct
SEQUENCE: 163
PAGLLDLRQG MFAQLVAQNV LLIDGPLSWY SDPGLAGVSL TGGLSYKEDT KELVVAKAGV   60
YYVFFQLELR RVVAGEGSGS VSLALHLQPL RSAAGAAALA LTVDLPPASS EARXSAFGFQ  120
GRLLHLSAGQ RLGVHLHTEA RARHAWQLTQ GATVLGLFRV TPEIPAGLPS PRSE        174

SEQ ID NO: 164         moltype = AA   length = 174
FEATURE                Location/Qualifiers
VARIANT                115
                       note = Xaa is any amino acid other than a Serine
source                 1..174
                       mol_type = protein
                       organism = synthetic construct
SEQUENCE: 164
PAGLLDLRQG MFAQLVAQNV LLIDGPLSWY SDPGLAGVSL TGGLSYKEDT KELVVAKAGV   60
YYVFFQLELR RVVAGEGSGS VSLALHLQPL RSAAGAAALA LTVDLPPASS EARNXAFGFQ  120
GRLLHLSAGQ RLGVHLHTEA RARHAWQLTQ GATVLGLFRV TPEIPAGLPS PRSE        174

SEQ ID NO: 165         moltype = AA   length = 174
FEATURE                Location/Qualifiers
VARIANT                117
                       note = Xaa is any amino acid other than a Phenylalanine
source                 1..174
                       mol_type = protein
                       organism = synthetic construct
SEQUENCE: 165
PAGLLDLRQG MFAQLVAQNV LLIDGPLSWY SDPGLAGVSL TGGLSYKEDT KELVVAKAGV   60
YYVFFQLELR RVVAGEGSGS VSLALHLQPL RSAAGAAALA LTVDLPPASS EARNSAXGFQ  120
GRLLHLSAGQ RLGVHLHTEA RARHAWQLTQ GATVLGLFRV TPEIPAGLPS PRSE        174

SEQ ID NO: 166         moltype = AA   length = 174
FEATURE                Location/Qualifiers
VARIANT                130
                       note = Xaa is any amino acid other than a Glutamine
source                 1..174
                       mol_type = protein
                       organism = synthetic construct
SEQUENCE: 166
PAGLLDLRQG MFAQLVAQNV LLIDGPLSWY SDPGLAGVSL TGGLSYKEDT KELVVAKAGV   60
YYVFFQLELR RVVAGEGSGS VSLALHLQPL RSAAGAAALA LTVDLPPASS EARNSAFGFQ  120
GRLLHLSAGX RLGVHLHTEA RARHAWQLTQ GATVLGLFRV TPEIPAGLPS PRSE        174

SEQ ID NO: 167         moltype = AA   length = 174
FEATURE                Location/Qualifiers
VARIANT                131
                       note = Xaa is any amino acid other than a Asparagine
source                 1..174
                       mol_type = protein
                       organism = synthetic construct
SEQUENCE: 167
PAGLLDLRQG MFAQLVAQNV LLIDGPLSWY SDPGLAGVSL TGGLSYKEDT KELVVAKAGV   60
YYVFFQLELR RVVAGEGSGS VSLALHLQPL RSAAGAAALA LTVDLPPASS EARNSAFGFQ  120
GRLLHLSAGQ XLGVHLHTEA RARHAWQLTQ GATVLGLFRV TPEIPAGLPS PRSE        174

SEQ ID NO: 168         moltype = AA   length = 174
FEATURE                Location/Qualifiers
VARIANT                132
                       note = Xaa is any amino acid other than a Leucine
source                 1..174
                       mol_type = protein
                       organism = synthetic construct
SEQUENCE: 168
PAGLLDLRQG MFAQLVAQNV LLIDGPLSWY SDPGLAGVSL TGGLSYKEDT KELVVAKAGV   60
YYVFFQLELR RVVAGEGSGS VSLALHLQPL RSAAGAAALA LTVDLPPASS EARNSAFGFQ  120
GRLLHLSAGQ RXGVHLHTEA RARHAWQLTQ GATVLGLFRV TPEIPAGLPS PRSE        174

SEQ ID NO: 169         moltype = AA   length = 174
FEATURE                Location/Qualifiers
VARIANT                133
                       note = Xaa is any amino acid other than a Glycine
source                 1..174
                       mol_type = protein
```

```
                                  organism = synthetic construct
SEQUENCE: 169
PAGLLDLRQG MFAQLVAQNV LLIDGPLSWY SDPGLAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLXVHLHTEA RARHAWQLTQ GATVLGLFRV TPEIPAGLPS PRSE         174

SEQ ID NO: 170               moltype = AA  length = 174
FEATURE                      Location/Qualifiers
VARIANT                      134
                             note = Xaa is any amino acid other than a Valine
source                       1..174
                             mol_type = protein
                             organism = synthetic construct
SEQUENCE: 170
PAGLLDLRQG MFAQLVAQNV LLIDGPLSWY SDPGLAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGXHLHTEA RARHAWQLTQ GATVLGLFRV TPEIPAGLPS PRSE         174

SEQ ID NO: 171               moltype = AA  length = 174
FEATURE                      Location/Qualifiers
VARIANT                      135
                             note = Xaa is any amino acid other than a Histidine
source                       1..174
                             mol_type = protein
                             organism = synthetic construct
SEQUENCE: 171
PAGLLDLRQG MFAQLVAQNV LLIDGPLSWY SDPGLAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVXLHTEA RARHAWQLTQ GATVLGLFRV TPEIPAGLPS PRSE         174

SEQ ID NO: 172               moltype = AA  length = 174
FEATURE                      Location/Qualifiers
VARIANT                      136
                             note = Xaa is any amino acid other than a Leucine
source                       1..174
                             mol_type = protein
                             organism = synthetic construct
SEQUENCE: 172
PAGLLDLRQG MFAQLVAQNV LLIDGPLSWY SDPGLAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHXHTEA RARHAWQLTQ GATVLGLFRV TPEIPAGLPS PRSE         174

SEQ ID NO: 173               moltype = AA  length = 174
FEATURE                      Location/Qualifiers
VARIANT                      137
                             note = Xaa is any amino acid other than a Histidine
source                       1..174
                             mol_type = protein
                             organism = synthetic construct
SEQUENCE: 173
PAGLLDLRQG MFAQLVAQNV LLIDGPLSWY SDPGLAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLXTEA RARHAWQLTQ GATVLGLFRV TPEIPAGLPS PRSE         174

SEQ ID NO: 174               moltype = AA  length = 174
FEATURE                      Location/Qualifiers
VARIANT                      138
                             note = Xaa is any amino acid other than a Threonine
source                       1..174
                             mol_type = protein
                             organism = synthetic construct
SEQUENCE: 174
PAGLLDLRQG MFAQLVAQNV LLIDGPLSWY SDPGLAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHXEA RARHAWQLTQ GATVLGLFRV TPEIPAGLPS PRSE         174

SEQ ID NO: 175               moltype = AA  length = 174
FEATURE                      Location/Qualifiers
VARIANT                      139
                             note = Xaa is any amino acid other than a Glutamic acid
source                       1..174
                             mol_type = protein
                             organism = synthetic construct
SEQUENCE: 175
PAGLLDLRQG MFAQLVAQNV LLIDGPLSWY SDPGLAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTXA RARHAWQLTQ GATVLGLFRV TPEIPAGLPS PRSE         174

SEQ ID NO: 176               moltype = AA  length = 174
```

| FEATURE | Location/Qualifiers |
|---|---|
| VARIANT | 141 |
| | note = Xaa is any amino acid other than Arginine |
| source | 1..174 |
| | mol_type = protein |
| | organism = synthetic construct |

SEQUENCE: 176
PAGLLDLRQG MFAQLVAQNV LLIDGPLSWY SDPGLAGVSL TGGLSYKEDT KELVVAKAGV 60
YYVFFQLELR RVVAGEGSGS VSLALHLQPL RSAAGAAALA LTVDLPPASS EARNSAFGFQ 120
GRLLHLSAGQ RLGVHLHTEA XARHAWQLTQ GATVLGLFRV TPEIPAGLPS PRSE 174

| SEQ ID NO: 177 | moltype = AA length = 174 |
|---|---|
| FEATURE | Location/Qualifiers |
| VARIANT | 143 |
| | note = Xaa is any amino acid other than a Arginine |
| source | 1..174 |
| | mol_type = protein |
| | organism = synthetic construct |

SEQUENCE: 177
PAGLLDLRQG MFAQLVAQNV LLIDGPLSWY SDPGLAGVSL TGGLSYKEDT KELVVAKAGV 60
YYVFFQLELR RVVAGEGSGS VSLALHLQPL RSAAGAAALA LTVDLPPASS EARNSAFGFQ 120
GRLLHLSAGQ RLGVHLHTEA RAXHAWQLTQ GATVLGLFRV TPEIPAGLPS PRSE 174

| SEQ ID NO: 178 | moltype = AA length = 174 |
|---|---|
| FEATURE | Location/Qualifiers |
| VARIANT | 144 |
| | note = Xaa is any amino acid other than a Histidine |
| source | 1..174 |
| | mol_type = protein |
| | organism = synthetic construct |

SEQUENCE: 178
PAGLLDLRQG MFAQLVAQNV LLIDGPLSWY SDPGLAGVSL TGGLSYKEDT KELVVAKAGV 60
YYVFFQLELR RVVAGEGSGS VSLALHLQPL RSAAGAAALA LTVDLPPASS EARNSAFGFQ 120
GRLLHLSAGQ RLGVHLHTEA RARXAWQLTQ GATVLGLFRV TPEIPAGLPS PRSE 174

| SEQ ID NO: 179 | moltype = AA length = 174 |
|---|---|
| FEATURE | Location/Qualifiers |
| VARIANT | 146 |
| | note = Xaa is any amino acid other than a Tryptophan |
| source | 1..174 |
| | mol_type = protein |
| | organism = synthetic construct |

SEQUENCE: 179
PAGLLDLRQG MFAQLVAQNV LLIDGPLSWY SDPGLAGVSL TGGLSYKEDT KELVVAKAGV 60
YYVFFQLELR RVVAGEGSGS VSLALHLQPL RSAAGAAALA LTVDLPPASS EARNSAFGFQ 120
GRLLHLSAGQ RLGVHLHTEA RARHAXQLTQ GATVLGLFRV TPEIPAGLPS PRSE 174

| SEQ ID NO: 180 | moltype = AA length = 174 |
|---|---|
| FEATURE | Location/Qualifiers |
| VARIANT | 148 |
| | note = Xaa is any amino acid other than a Leucine |
| source | 1..174 |
| | mol_type = protein |
| | organism = synthetic construct |

SEQUENCE: 180
PAGLLDLRQG MFAQLVAQNV LLIDGPLSWY SDPGLAGVSL TGGLSYKEDT KELVVAKAGV 60
YYVFFQLELR RVVAGEGSGS VSLALHLQPL RSAAGAAALA LTVDLPPASS EARNSAFGFQ 120
GRLLHLSAGQ RLGVHLHTEA RARHAWQXTQ GATVLGLFRV TPEIPAGLPS PRSE 174

| SEQ ID NO: 181 | moltype = AA length = 174 |
|---|---|
| FEATURE | Location/Qualifiers |
| VARIANT | 149 |
| | note = Xaa is any amino acid other than a Threonine |
| source | 1..174 |
| | mol_type = protein |
| | organism = synthetic construct |

SEQUENCE: 181
PAGLLDLRQG MFAQLVAQNV LLIDGPLSWY SDPGLAGVSL TGGLSYKEDT KELVVAKAGV 60
YYVFFQLELR RVVAGEGSGS VSLALHLQPL RSAAGAAALA LTVDLPPASS EARNSAFGFQ 120
GRLLHLSAGQ RLGVHLHTEA RARHAWQLXQ GATVLGLFRV TPEIPAGLPS PRSE 174

| SEQ ID NO: 182 | moltype = AA length = 174 |
|---|---|
| FEATURE | Location/Qualifiers |
| VARIANT | 150 |
| | note = Xaa is any amino acid other than a Glutamine |
| source | 1..174 |
| | mol_type = protein |
| | organism = synthetic construct |

SEQUENCE: 182

```
PAGLLLDLRQG MFAQLVAQNV LLIDGPLSWY SDPGLAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTX GATVLGLFRV TPEIPAGLPS PRSE         174

SEQ ID NO: 183          moltype = AA   length = 174
FEATURE                 Location/Qualifiers
VARIANT                 151
                        note = Xaa is any amino acid other than a Glycine
source                  1..174
                        mol_type = protein
                        organism = synthetic construct
SEQUENCE: 183
PAGLLLDLRQG MFAQLVAQNV LLIDGPLSWY SDPGLAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ XATVLGLFRV TPEIPAGLPS PRSE         174

SEQ ID NO: 184          moltype = AA   length = 174
FEATURE                 Location/Qualifiers
VARIANT                 153
                        note = Xaa is any amino acid other than a Threonine
source                  1..174
                        mol_type = protein
                        organism = synthetic construct
SEQUENCE: 184
PAGLLLDLRQG MFAQLVAQNV LLIDGPLSWY SDPGLAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GAXVLGLFRV TPEIPAGLPS PRSE         174

SEQ ID NO: 185          moltype = AA   length = 174
FEATURE                 Location/Qualifiers
VARIANT                 154
                        note = Xaa is any amino acid other than a Valine
source                  1..174
                        mol_type = protein
                        organism = synthetic construct
SEQUENCE: 185
PAGLLLDLRQG MFAQLVAQNV LLIDGPLSWY SDPGLAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATXLGLFRV TPEIPAGLPS PRSE         174

SEQ ID NO: 186          moltype = AA   length = 255
FEATURE                 Location/Qualifiers
source                  1..255
                        mol_type = protein
                        organism = Homo sapiens
SEQUENCE: 186
MGNSCYNIVA TLLLVLNFER TRSLQDPCSN CPAGTFCDNN RNQICSPCPP NSFSSAGGQR    60
TCDICRQCKG VFRTRKECSS TSNAECDCTP GFHCLGAGCS MCEQDCKQGQ ELTKKGCKDC   120
CFGTFNDQKR GICRPWTNCS LDGKSVLVNG TKERDVVCGP SPADLSPGAS SVTPPAPARE   180
PGHSPQIISF FLALTSTALL FLLFFLTLRF SVVKRGRKKL LYIFKQPFMR PVQTTQEEDG   240
CSCRFPEEEE GGCEL                                                    255

SEQ ID NO: 187          moltype = AA   length = 290
FEATURE                 Location/Qualifiers
source                  1..290
                        mol_type = protein
                        organism = Mus musculus
SEQUENCE: 187
MRIFAGIIFT ACCHLLRAFT ITAPKDLYVV EYGSNVTMEC RFPVERELDL LALVVYWEKE    60
DEQVIQFVAG EEDLKPQHSN FRGRASLPKD QLLKGNAALQ ITDVKLQDAG VYCCIISYGG   120
ADYKRITLKV NAPYRKINQR ISVDPATSEH ELICQAEGYP EAEVIWTNSD HQPVSGKRSV   180
TTSRTEGMLL NVTSSLRVNA TANDVFYCTF WRSQPGQNHT AELIIPELPA THPPQNRTHW   240
VLLGSILLFL IVVSTVLLFL RKQVRMLDVE KCGVEDTSSK NRNDTQFEET              290

SEQ ID NO: 188          moltype = AA   length = 290
FEATURE                 Location/Qualifiers
source                  1..290
                        mol_type = protein
                        organism = Homo sapiens
SEQUENCE: 188
MRIFAVFIFM TYWHLLNAFT VTVPKDLYVV EYGSNMTIEC KFPVEKQLDL AALIVYWEME    60
DKNIIQFVHG EEDLKVQHSS YRQRARLLKD QLSLGNAALQ ITDVKLQDAG VYRCMISYGG   120
ADYKRITVKV NAPYNKINQR ILVVDPVTSE HELTCQAEGY PKAEVIWTSS DHQVLSGKTT   180
TTNSKREEKL FNVTSTLRIN TTTNEIFYCT FRRLDPEENH TAELVIPELP LAHPPNERTH   240
LVILGAILLC LGVALTFIFR LRKGRMMDVK KCGIQDTNSK KQSDTHLEET              290

SEQ ID NO: 189          moltype = AA   length = 208
FEATURE                 Location/Qualifiers
source                  1..208
```

```
                        mol_type = protein
                        organism = synthetic construct
SEQUENCE: 189
VIHVTKEVKE VATLSCGHNV SVEELAQTRI YWQKEKKMVL TMMSGDMNIW PEYKNRTIFD    60
ITNNLSIVIL ALRPSDEGTY ECVVLKYEKD APKREHLAEV TLSVKADFPT PSISDFEIPT   120
SNIRRIICST SGGFPEPHLS WLENGEELNA INTTVSQDPE TELYAVSSKL DFNMTTNHSF   180
MCLIKYGHLR VNQTFNWNTT KQEHFPDN                                     208

SEQ ID NO: 190          moltype = AA  length = 302
FEATURE                 Location/Qualifiers
source                  1..302
                        mol_type = protein
                        organism = Homo sapiens
SEQUENCE: 190
MRLGSPGLLF LLFSSLRADT QEKEVRAMVG SDVELSCACP EGSRFDLNDV YVYWQTSESK    60
TVVTYHIPQN SSLENVDSRY RNRALMSPAG MLRGDFSLRL FNVTPQDEQK FHCLVLSQSL   120
GFQEVLSVEV TLHVAANFSV PVVSAPHSPS QDELTFTCTS INGYPRPNVY WINKTDNSLL   180
DQALQNDTVF LNMRGLYDVV SVLRIARTPS VNIGCCIENV LLQQNLTVGS QTGNDIGERD   240
KITENPVSTG EKNAATWSIL AVLCLLVVVA VAIGWVCRDR CLQHSYAGAW AVSPETELTG   300
HV                                                                 302

SEQ ID NO: 191          moltype = AA  length = 183
FEATURE                 Location/Qualifiers
source                  1..183
                        mol_type = protein
                        organism = Homo sapiens
SEQUENCE: 191
MERVQPLEEN VGNAARPRFE RNKLLLVASV IQGLGLLLCF TYICLHFSAL QVSHRYPRIQ    60
SIKVQFTEYK KEKGFILTSQ KEDEIMKVQN NSVIINCDGF YLISLKGYFS QEVNISLHYQ   120
KDEEPLFQLK KVRSVNSLMV ASLTYKDKVY LNVTTDNTSL DDFHVNGGEL ILIHQNPGEF   180
CVL                                                                183

SEQ ID NO: 192          moltype = AA  length = 273
FEATURE                 Location/Qualifiers
source                  1..273
                        mol_type = protein
                        organism = Homo sapiens
SEQUENCE: 192
MIFLLLMLSL ELQLHQIAAL FTVTVPKELY IIEHGSNVTL ECNFDTGSHV NLGAITASLQ    60
KVENDTSPHR ERATLLEEQL PLGKASFHIP QVQVRDEGQY QCIIIYGVAW DYKYLTLKVK   120
ASYRKINTHI LKVPETDEVE LTCQATGYPL AEVSWPNVSV PANTSHSRTP EGLYQVTSVL   180
RLKPPPGRNF SCVFWNTHVR ELTLASIDLQ SQMEPRTHPT WLLHIFIPFC IIAFIFIATV   240
IALRKQLCQK LYSSKDTTKR PVTTTKREVN SAI                                273

SEQ ID NO: 193          moltype = AA  length = 329
FEATURE                 Location/Qualifiers
source                  1..329
                        mol_type = protein
                        organism = Homo sapiens
SEQUENCE: 193
MDPQCTMGLS NILFVMAFLL SGAAPLKIQA YFNETADLPC QFANSQNQSL SELVVFWQDQ    60
ENLVLNEVYL GKEKFDSVHS KYMGRTSFDS DSWTLRLHNL QIKDKGLYQC IIHHKKPTGM   120
IRIHQMNSEL SVLANFSQPE IVPISNITEN VYINLTCSSI HGYPEPKKMS VLLRTKNSTI   180
EYDGIMQKSQ DNVTELYDVS ISLSVSFPDV TSNMTIFCIL ETDKTRLLSS PFSIELEDPQ   240
PPPDHIPWIT AVLPTVIICV MVFCLILWKW KKKKRPRNSY KCGTNTMERE ESEQTKKREK   300
IHIPERSDEA QRVFKSSKTS SCDKSDTCF                                    329

SEQ ID NO: 194          moltype = AA  length = 281
FEATURE                 Location/Qualifiers
source                  1..281
                        mol_type = protein
                        organism = Homo sapiens
SEQUENCE: 194
MQQPFNYPYP QIYWVDSSAS SPWAPPGTVL PCPTSVPRRP GQRRPPPPPP PPLPPPPPP     60
PPLPPLPLPP LKKRGNHSTG LCLLVMFFMV LVALVGLGLG MFQLFHLQKE LAELRESTSQ   120
MHTASSLEKQ IGHPSPPPEK KELRKVAHLT GKSNSRSMPL EWEDTYGIVL LSGVKYKKGG   180
LVINETGLYF VYSKVYFRGQ SCNNLPLSHK VYMRNSKYPQ DLVMMEGKMM SYCTTGQMWA   240
RSSYLGAVFN LTSADHLYVN VSELSLVNFE ESQTFFGLYK L                       281

SEQ ID NO: 195          moltype = AA  length = 119
FEATURE                 Location/Qualifiers
source                  1..119
                        mol_type = protein
                        organism = Pan troglodytes
SEQUENCE: 195
MSRSVALAVL ALLSLSGLEA IQRTPKIQVY SRHPAENGKS NFLNCYVSGF HPSDIEVDLL    60
KNGERIEKVE HSDLSFSKDW SFYLLYYTEF TPTEKDEYAC RVNHVTLSQP KIVKWDRDM    119

SEQ ID NO: 196          moltype = AA  length = 276
```

```
FEATURE              Location/Qualifiers
source               1..276
                     mol_type = protein
                     organism = synthetic construct
SEQUENCE: 196
GSHSMRYFFT SVSRPGRGEP RFIAVGYVDD TQFVRFDSDA ASQRMEPRAP WIEQEGPEYW    60
DGETRKVKAH SQTHRVDLGT LRGCYNQSEA GSHTVQRMYG CDVGSDWRFL RGYHQYAYDG   120
KDYIALKEDL RSWTAADMCA QTTKHKWEAA HVAEQLRAYL EGTCVEWLRR YLENGKETLQ   180
RTDAPKTHMT HHAVSDHEAT LRCWALSFYP AEITLTWQRD GEDQTQDTEL VETRPAGDGT   240
FQKWAAVVVP SGQEQRYTCH VQHEGLPKPL TLRWEP                             276

SEQ ID NO: 197       moltype = AA   length = 275
FEATURE              Location/Qualifiers
source               1..275
                     mol_type = protein
                     organism = synthetic construct
SEQUENCE: 197
GSHSMRYFYT SVSRPGRGEP RFIAVGYVDD TQFVRFDSDA ASQRMEPRAP WIEQEGPEYW    60
DQETRNVKAQ SQTDRVDLGT LRGYYNQSED GSHTIQIMYG CDVGPDGRFL RGYRQDAYDG   120
KDYIALNEDL RSWTAADMAA QITKRKWEAA HAAEQQRAYL EGTCVEWLRR YLENGKETLQ   180
RTDPPKTHMT HHPISDHEAT LRCWALGFYP AEITLTWQRD GEDQTQDTEL VETRPAGDGT   240
FQKWAAVVVP SGEEQRYTCH VQHEGLPKPL TLRWE                              275

SEQ ID NO: 198       moltype = AA   length = 275
FEATURE              Location/Qualifiers
source               1..275
                     mol_type = protein
                     organism = synthetic construct
SEQUENCE: 198
GSHSMRYFYT SVSRPGRGEP RFIAVGYVDD TQFVRFDSDA ASQRMEPRAP WIEQEGPEYW    60
DQETRNVKAQ SQTDRVDLGT LRGAYNQSED GSHTIQIMYG CDVGPDGRFL RGYRQDAYDG   120
KDYIALNEDL RSWTAADMAA QITKRKWEAA HAAEQQRAYL EGTCVEWLRR YLENGKETLQ   180
RTDPPKTHMT HHPISDHEAT LRCWALGFYP AEITLTWQRD GEDQTQDTEL VETRPCGDGT   240
FQKWAAVVVP SGEEQRYTCH VQHEGLPKPL TLRWE                              275

SEQ ID NO: 199       moltype = AA   length = 276
FEATURE              Location/Qualifiers
source               1..276
                     mol_type = protein
                     organism = synthetic construct
SEQUENCE: 199
GSHSMRYFYT SVSRPGRGEP RFISVGYVDD TQFVRFDSDA ASPREEPRAP WIEQEGPEYW    60
DRNTQIYKAQ AQTDRESLRN LRGYYNQSEA GSHTLQSMYG CDVGPDGRLL RGHDQYAYDG   120
KDYIALNEDL RSWTAADTAA QITQRKWEAA REAEQRRAYL EGECVEWLRR YLENGKDKLE   180
RADPPKTHVT HHPISDHEAT LRCWALGFYP AEITLTWQRD GEDQTQDTEL VETRPAGDRT   240
FQKWAAVVVP SGEEQRYTCH VQHEGLPKPL TLRWEP                             276

SEQ ID NO: 200       moltype = AA   length = 276
FEATURE              Location/Qualifiers
source               1..276
                     mol_type = protein
                     organism = synthetic construct
SEQUENCE: 200
GSHSMRYFYT SVSRPGRGEP RFISVGYVDD TQFVRFDSDA ASPREEPRAP WIEQEGPEYW    60
DRNTQIYKAQ AQTDRESLRN LRGAYNQSEA GSHTLQSMYG CDVGPDGRLL RGHDQYAYDG   120
KDYIALNEDL RSWTAADTAA QITQRKWEAA REAEQRRAYL EGECVEWLRR YLENGKDKLE   180
RADPPKTHVT HHPISDHEAT LRCWALGFYP AEITLTWQRD GEDQTQDTEL VETRPCGDRT   240
FQKWAAVVVP SGEEQRYTCH VQHEGLPKPL TLRWEP                             276

SEQ ID NO: 201       moltype = AA   length = 276
FEATURE              Location/Qualifiers
source               1..276
                     mol_type = protein
                     organism = synthetic construct
SEQUENCE: 201
GSHSMRYFYT SVSRPGRGEP RFISVGYVDD TQFVRFDSDA ASPREEPRAP WIEQEGPEYW    60
DRNTQIYKAQ AQTDRESLRN LRGCYNQSEA GSHTLQSMYG CDVGPDGRLL RGHDQYAYDG   120
KDYIALNEDL RSWTAADTCA QITQRKWEAA REAEQRRAYL EGECVEWLRR YLENGKDKLE   180
RADPPKTHVT HHPISDHEAT LRCWALGFYP AEITLTWQRD GEDQTQDTEL VETRPAGDRT   240
FQKWAAVVVP SGEEQRYTCH VQHEGLPKPL TLRWEP                             276

SEQ ID NO: 202       moltype = AA   length = 276
FEATURE              Location/Qualifiers
source               1..276
                     mol_type = protein
                     organism = synthetic construct
SEQUENCE: 202
CSHSMRYFDT AVSRPGRGEP RFISVGYVDD TQFVRFDSDA ASPRGEPRAP WVEQEGPEYW    60
DRETQNYKRQ AQADRVSLRN LRGYYNQSED GSHTLQRMYG CDLGPDGRLL RGYDQSAYDG   120
```

```
KDYIALNEDL RSWTAADTAA QITQRKLEAA RAAEQLRAYL EGTCVEWLRR YLENGKETLQ  180
RAEPPKTHVT HHPLSDHEAT LRCWALGFYP AEITLTWQRD GEDQTQDTEL VETRPAGDGT  240
FQKWAAVVVP SGQEQRYTCH MQHEGLQEPL TLSWEP                            276

SEQ ID NO: 203          moltype = AA  length = 276
FEATURE                 Location/Qualifiers
source                  1..276
                        mol_type = protein
                        organism = synthetic construct
SEQUENCE: 203
CSHSMRYFDT AVSRPGRGEP RFISVGYVDD TQFVRFDSDA ASPRGEPRAP WVEQEGPEYW  60
DRETQNYKRQ AQADRVSLRN LRGAYNQSED GSHTLQRMYG CDLGPDGRLL RGYDQSAYDG  120
KDYIALNEDL RSWTAADTAA QITQRKLEAA RAAEQLRAYL EGTCVEWLRR YLENGKETLQ  180
RAEPPKTHVT HHPLSDHEAT LRCWALGFYP AEITLTWQRD GEDQTQDTEL VETRPCGDGT  240
FQKWAAVVVP SGQEQRYTCH MQHEGLQEPL TLSWEP                            276

SEQ ID NO: 204          moltype = AA  length = 276
FEATURE                 Location/Qualifiers
source                  1..276
                        mol_type = protein
                        organism = synthetic construct
SEQUENCE: 204
CSHSMRYFDT AVSRPGRGEP RFISVGYVDD TQFVRFDSDA ASPRGEPRAP WVEQEGPEYW  60
DRETQNYKRQ AQADRVSLRN LRGCYNQSED GSHTLQRMYG CDLGPDGRLL RGYDQSAYDG  120
KDYIALNEDL RSWTAADTCA QITQRKLEAA RAAEQLRAYL EGTCVEWLRR YLENGKETLQ  180
RAEPPKTHVT HHPLSDHEAT LRCWALGFYP AEITLTWQRD GEDQTQDTEL VETRPAGDGT  240
FQKWAAVVVP SGQEQRYTCH MQHEGLQEPL TLSWEP                            276

SEQ ID NO: 205          moltype = AA  length = 5
FEATURE                 Location/Qualifiers
source                  1..5
                        mol_type = protein
                        organism = synthetic construct
SEQUENCE: 205
GGGGS                                                              5

SEQ ID NO: 206          moltype = AA  length = 10
FEATURE                 Location/Qualifiers
source                  1..10
                        mol_type = protein
                        organism = synthetic construct
SEQUENCE: 206
GGGGSGGGGS                                                         10

SEQ ID NO: 207          moltype = AA  length = 15
FEATURE                 Location/Qualifiers
source                  1..15
                        mol_type = protein
                        organism = synthetic construct
SEQUENCE: 207
GGGGSGGGGS GGGGS                                                   15

SEQ ID NO: 208          moltype = AA  length = 20
FEATURE                 Location/Qualifiers
source                  1..20
                        mol_type = protein
                        organism = synthetic construct
SEQUENCE: 208
GGGGSGGGGS GGGGSGGGGS                                              20

SEQ ID NO: 209          moltype = AA  length = 25
FEATURE                 Location/Qualifiers
source                  1..25
                        mol_type = protein
                        organism = synthetic construct
SEQUENCE: 209
GGGGSGGGGS GGGGSGGGGS GGGGS                                        25

SEQ ID NO: 210          moltype = AA  length = 5
FEATURE                 Location/Qualifiers
source                  1..5
                        mol_type = protein
                        organism = synthetic construct
SEQUENCE: 210
GSGGS                                                              5

SEQ ID NO: 211          moltype = AA  length = 4
FEATURE                 Location/Qualifiers
source                  1..4
```

```
                        mol_type = protein
                        organism = synthetic construct
SEQUENCE: 211
GGGS                                                                         4

SEQ ID NO: 212          moltype = AA   length = 5
FEATURE                 Location/Qualifiers
VARIANT                 4
                        note = Xaa is any amino acid other than proline
source                  1..5
                        mol_type = protein
                        organism = synthetic construct
SEQUENCE: 212
VPGXG                                                                        5

SEQ ID NO: 213          moltype = AA   length = 174
FEATURE                 Location/Qualifiers
source                  1..174
                        mol_type = protein
                        organism = synthetic construct
SEQUENCE: 213
PAGLLDLRQG MFAQLVAQNV LLIDGPLSWY SDPGLAGVSL TGGLSYKEDT KELVVAKAGV    60
YYVFFQLELR RVVAGEGSGS VSLALHLQPL RSAAGAAALA LTVDLPPASS EARNSAFGFQ   120
GRLLHLSAGQ RLGVHLHTEA RARHAWQLTQ GATVLGLFRV TPEIPAGLPS PRSE          174

SEQ ID NO: 214          moltype = AA   length = 175
FEATURE                 Location/Qualifiers
source                  1..175
                        mol_type = protein
                        organism = synthetic construct
SEQUENCE: 214
DPAGLLDLRQ GMFAQLVAQN VLLIDGPLSW YSDPGLAGVS LTGGLSYKED TKELVVAKAG    60
VYYVFFQLEL RRVVAGEGSG SVSLALHLQP LRSAAGAAAL ALTVDLPPAS SEARNSAFGF   120
QGRLLHLSAG QRLGVHLHTE ARARHAWQLT QGATVLGLFR VTPEIPAGLP SPRSE         175

SEQ ID NO: 215          moltype = AA   length = 167
FEATURE                 Location/Qualifiers
source                  1..167
                        mol_type = protein
                        organism = synthetic construct
SEQUENCE: 215
DPAGLLDLRQ GMFAQLVAQN VLLIDGPLSW YSDPGLAGVS LTGGLSYKED TKELVVAKAG    60
VYYVFFQLEL RRVVAGEGSG SVSLALHLQP LRSAAGAAAL ALTVDLPPAS SEARNSAFGF   120
QGRLLHLSAG QRLGVHLHTE ARARHAWQLT QGATVLGLFR VTPEIPA                 167

SEQ ID NO: 216          moltype = AA   length = 127
FEATURE                 Location/Qualifiers
source                  1..127
                        mol_type = protein
                        organism = synthetic construct
SEQUENCE: 216
QVQLQESGGG LVQPGGSLRL SCAASGKMSS RRCMAWFRQA PGKERERVAK LLTTSGSTYL    60
ADSVKGRFTI SQNNAKSTVY LQMNSLKPED TAMYYCAADS FEDPTCTLVT SSGAFQYWGQ   120
GTQVTVS                                                             127
```

What is claimed is:

1. A method of treating an individual having a cancer that expresses an HPV16 E7 antigen, the method comprising administering to the individual a combination of (i) an effective amount of an immune checkpoint inhibitor that targets PD-1, wherein the immune checkpoint inhibitor is an anti-PD-1 antibody, and (ii) an effective amount of a protein that is a homodimer of two multimeric polypeptides, wherein each multimeric polypeptide comprises:
   a) a first polypeptide comprising from N-terminus to C-terminus:
      i) an HPV16 E7 epitope comprising amino acid sequence YMLDLQPETT (SEQ ID NO:77);
      ii) a linker comprising amino acid sequence GGGG-SGGGGSGGGGS (SEQ ID NO:207); and
      iii) a β2-microglobulin (β2M) polypeptide comprising the amino acid sequence set forth in SEQ ID NO:48; and
   b) a second polypeptide comprising:
      i) two copies of an IL-2 polypeptide, each copy comprising the amino acid sequence set forth in SEQ ID NO:49;
      ii) a second MHC polypeptide, wherein the second MHC polypeptide is an MHC class I heavy chain polypeptide comprising the amino acid sequence as set forth in SEQ ID NO:50; and
      iii) an immunoglobulin (Ig) Fc polypeptide, and
   wherein the multimeric polypeptides are joined to each other by one or more disulfide bonds that join the Ig Fc polypeptide of one multimeric polypeptide to the Ig Fc polypeptide of the other multimeric polypeptide, and
   wherein the immune checkpoint inhibitor and the protein are administered at the same time or at different times.

2. A method of treating according to claim 1, wherein the Ig Fc polypeptide comprises an amino acid sequence having at least about 95% amino acid sequence identity to SEQ ID NO:21, and wherein the Ig Fc polypeptide comprises an L14A substitution and an L15A substitution based on the amino acid numbering depicted in SEQ ID NO:44;

wherein each multimeric polypeptide comprises a disulfide bond joining the Cys residue at amino acid 12 of the β2M polypeptide and the Cys residue at amino acid 236 of the class I MHC heavy chain polypeptide, and wherein the second polypeptide comprises a peptide linker between one or more of:
a) a first copy of the IL-2 polypeptide and a second copy of the IL-2 polypeptide;
b) one of the two copies of the IL-2 polypeptide and the MHC class I heavy chain polypeptide; and
c) the MHC class I heavy chain polypeptide and the Ig Fc polypeptide.

3. A method according to claim 1, wherein the cancer is a head and neck cancer.

4. A method according to claim 2, wherein the cancer is a head and neck cancer.

5. A method according to claim 1, wherein the cancer is a cervical cancer, or a genitoanal cancer.

6. A method according to claim 2, wherein the cancer is a cervical cancer, or a genitoanal cancer.

7. A method according to claim 1, wherein the individual has become refractory to a prior treatment for the cancer or has failed to respond to a prior treatment for the cancer.

8. A method according to claim 2, wherein the individual has become refractory to a prior treatment for the cancer or has failed to respond to a prior treatment for the cancer.

9. A method according to claim 1, wherein the protein is administered in an amount of administered in an amount of from 1 mg/kg to 5 mg/kg of body weight.

10. A method according to claim 2, wherein the protein is administered in an amount of administered in an amount of from 1 mg/kg to 5 mg/kg of body weight.

11. A method according to claim 3, wherein the protein is administered in an amount of administered in an amount of from 1 mg/kg to 5 mg/kg of body weight.

12. A method according to claim 4, wherein the protein is administered in an amount of administered in an amount of from 1 mg/kg to 5 mg/kg of body weight.

13. A method according to claim 5, wherein the protein is administered in an amount of administered in an amount of from 1 mg/kg to 5 mg/kg of body weight.

14. A method according to claim 6, wherein the protein is administered in an amount of administered in an amount of from 1 mg/kg to 5 mg/kg of body weight.

15. A method according to claim 1, wherein the immune checkpoint inhibitor is nivolumab.

16. A method according to claim 2, wherein the immune checkpoint inhibitor is nivolumab.

17. A method according to claim 3, wherein the immune checkpoint inhibitor is nivolumab.

18. A method according to claim 4, wherein the immune checkpoint inhibitor is nivolumab.

19. A method according to claim 5, wherein the immune checkpoint inhibitor is nivolumab.

20. A method according to claim 6, wherein the immune checkpoint inhibitor is nivolumab.

21. A method according to claim 7, wherein the immune checkpoint inhibitor is nivolumab.

22. A method according to claim 8, wherein the immune checkpoint inhibitor is nivolumab.

23. A method according to claim 9, wherein the immune checkpoint inhibitor is nivolumab.

24. A method according to claim 10, wherein the immune checkpoint inhibitor is nivolumab.

25. A method according to claim 11, wherein the immune checkpoint inhibitor is nivolumab.

26. A method according to claim 12, wherein the immune checkpoint inhibitor is nivolumab.

27. A method according to claim 13, wherein the immune checkpoint inhibitor is nivolumab.

28. A method according to claim 14, wherein the immune checkpoint inhibitor is nivolumab.

\* \* \* \* \*